(12) United States Patent
Rozamus et al.

(10) Patent No.: US 10,934,317 B2
(45) Date of Patent: Mar. 2, 2021

(54) CRYSTALLINE FORMS OF 5-CHLORO-N4-[-2-(DIMETHYL PHOSPHORYL) PHENYL]-N2-{2-METHOXY-4-[4-(4-METHYL PIPERAZIN-1-YL) PIPERIDIN-1-YL] PHENYL} PYRIMIDINE-2,4-DIAMINE

(71) Applicant: ARIAD Pharmaceuticals, Inc., Cambridge, MA (US)

(72) Inventors: Leonard W. Rozamus, Andover, MA (US); Pradeep Sharma, Westford, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/429,988

(22) Filed: Jun. 3, 2019

(65) Prior Publication Data
US 2020/0010493 A1 Jan. 9, 2020

Related U.S. Application Data

(62) Division of application No. 15/520,694, filed as application No. PCT/US2015/056701 on Oct. 21, 2015, now Pat. No. 10,385,078.

(60) Provisional application No. 62/066,849, filed on Oct. 21, 2014.

(51) Int. Cl.
C07F 9/6558 (2006.01)
C07D 239/48 (2006.01)

(52) U.S. Cl.
CPC ........ C07F 9/65583 (2013.01); C07D 239/48 (2013.01); C07B 2200/13 (2013.01)

(58) Field of Classification Search
CPC ............................ C07D 239/48; C07F 9/65583
See application file for complete search history.

(56) References Cited

U.S. PATENT DOCUMENTS

| | | | | |
|---|---|---|---|---|
| 3,686,168 A * | 8/1972 | Timreck | ............... | C07D 499/00 540/320 |
| 4,432,987 A * | 2/1984 | Barth | ................... | C07D 499/00 514/193 |
| 5,721,359 A * | 2/1998 | Dunn | ................... | C07D 501/00 540/227 |
| 7,145,002 B2 * | 12/2006 | Brands | ................. | C07D 477/20 540/350 |
| 2011/0224182 A1 * | 9/2011 | Bullock | ................... | C07J 53/00 514/182 |
| 2012/0202776 A1 * | 8/2012 | Wang | ................... | C07F 9/65586 514/81 |

FOREIGN PATENT DOCUMENTS

| | | |
|---|---|---|
| CA | 2450961 C | 3/2010 |
| CA | 2463146 C | 1/2011 |
| WO | WO 1999/003854 A1 | 1/1999 |
| WO | WO 1999/018097 A1 | 4/1999 |
| WO | WO 2005/016894 A1 | 2/2005 |
| WO | WO 2009/143389 A1 | 11/2009 |
| WO | WO 2012/082972 A1 | 6/2012 |

OTHER PUBLICATIONS

Katayama (PNAS, (2011), pp. 7535-7540, vol. 108 (18)).*
Morissette et al. (Advanced Drug Delivery Reviews, 56, (2004) p. 275-300)—provided in parent case.*
Solomon et al., "Current Status of Targeted Therapy for Anaplastic Lymphoma Kinase-Rearranged Non-Small Cell Lung Cancer", Clinical Pharmacology & Therapeutics, 2014, 95(1):15-23.
Caira, "Crystalline Polymorphism of Organic Compounds", Topics in Current Chemistry, 1998, 198:163-208.
Shaw et al., "Ceritinib in ALK-Rearranged Non-Small-Cell Lung Cancer", New Eng. J. Med., 2014, 370:1189-97.
Brittain, "Polymorphism in Pharmaceutical Solids", 2nd Edition, 2009, pp. 1-4, 15-19, and 318-435.
Byrn et al., "Pharmaceutical Solids: A Strategic Approach to Regulatory Considerations," *Pharmaceutical Research*, 1995, 12(7):945-954.
Morissette et al. "High-throughput crystallization: polymorphs, salts, co-crystals and solvates of pharmaceutical solids", Advanced Drug Delivery Reviews, 2004, 56:275-300.
Brittain, "Polymorphism in Pharmaceutical Solids", 1999, pp. 235-238.
Braga et al., "Crystal Polymorphism and Multiple Crystal Forms," *Struct. Bond.* 132:25-50 (2009).
Hilfker et al., "Relevance of Solid-State Properties for Pharmaceutical Products", Polymorphism in the Pharmaceutical Industry, 2006, pp. 1-19.
Bavin, "Polymorphism in Process Development", *Chemistry & Industry*, 1989, (16), pp. 527-529.
Ashizawa edited, Science of polymorphism and crystallization in pharmaceutical products:, Maruzen Planet Co., Sep. 20, 2002, pp. 312-317.
Shioji, Manufacturing technology of solid formulation, Jan. 27, 2003, CMC Publishing CO., LTD., p. 9, 12, and 13.

* cited by examiner

*Primary Examiner* — Valerie Rodriguez-Garcia
(74) *Attorney, Agent, or Firm* — Honigman LLP; Lucy X. Yang; Jonathan P. O'Brien

(57) ABSTRACT

Crystalline forms of brigatinib, pharmaceutical compositions comprising the same, and methods of their preparation and use of the same are disclosed herein.

13 Claims, 50 Drawing Sheets

CRYSTALLINE FORMS OF 5-CHLORO-N4-[-2-(DIMETHYLPHOSPHORYL) PHENYL]-N2-{2-METHOXY-4-[4-(4-METHYL PIPERAZIN-1-YL) PIPERIDIN-1-YL] PHENYL} PYRIMIDINE-2,4-DIAMINE

This application is a divisional application of U.S. application Ser. No. 15/520,694, which is a national phase entry pursuant to 35 U.S.C. § 371 of International Application No. PCT/US2015/056701, filed Oct. 21, 2015, which claims priority to U.S. Provisional Application No. 62/066,849, file Oct. 21, 2014, the entireties of which are incorporated herein by reference.

This application is directed to novel crystalline forms of 5-chloro-N4-[2-(dimethylphosphoryl)phenyl]-N2-{2-methoxy-4-[4-(4-methylpiperazin-1-yl)piperidin-1-yl]pheny}pyrimidine-2,4-diamine (also referred to as, "AP26113" and "brigatinib"), compositions comprising such crystalline forms, and methods of their preparation and use.

Brigatinib has the chemical formula $C_{29}H_{39}ClN_7O_2P$ which corresponds to a formula weight of 584.09 g/mol. Its chemical structure is shown below:

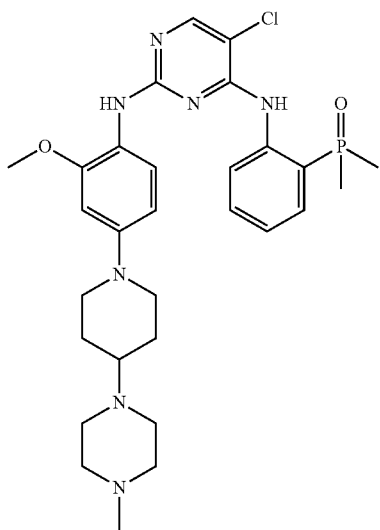

Brigatinib is a multi-targeted tyrosine-kinase inhibitor useful for the treatment of non-small cell lung cancer (NSCLC) and other diseases. It is a potent inhibitor of ALK (anaplastic lymphoma kinase) and is in clinical development for the treatment of adult patients with ALK-driven NSCLC. Crizotinib (XALKORI®) is an FDA approved drug for first-line treatment of ALK-positive NSCLC. "Despite initial responses to crizotinib, the majority of patients have a relapse within 12 months, owing to the development of resistance." Shaw et al., *New Eng. J. Med.* 370:1189-97 2014. Thus, a growing population of cancer patients are in need of new and effective therapies for ALK-positive cancers.

Brigatinib is also potentially useful for treating other diseases or conditions in which ALK or other protein kinases inhibited by brigatinib are implicated. Such kinases and their associated disorders or conditions are disclosed in WO 2009/143389, both of which are hereby incorporated herein by reference for all purposes.

Knowledge of the potential polymorphic forms of active pharmaceutical ingredients (API) such as brigatinib can be useful in the development of drugs, as is knowledge of characteristics of those polymorphs. Not knowing the specific polymorphic form present or desired in the API can result in inconsistent manufacturing of the API, thus results with the drug can potentially vary between various lots of the API. In addition, knowledge of the polymorphic forms of an API informs and permits long term systematic stability determination of the API. Once a specific polymorphic form is selected for pharmaceutical development, a method for reproducibly preparing that polymorphic form can be useful. It is also useful for there to be a process for making APIs such as brigatinib at or above a specified level of chemical and/or polymorphic purity.

The chemical structure of brigatinib was first disclosed in WO 2009/143389, which is also owned by Applicant (ARIAD Pharmaceuticals, Inc.) and is hereby incorporated herein by reference in its entirety for all purposes. Example 122 of WO 2009/143389 discloses the synthesis of brigatinib and states that the product was obtained as an off-white solid but does not provide further characterization, such as chemical purity or solid form. Example 122 does not state to what degree, if any, its product was crystalline.

Provided herein are certain crystalline and other polymorphic forms of brigatinib, certain of which are suitable for pharmaceutical formulation development.

In some embodiments, the present disclosure relates to crystalline brigatinib. In some embodiments, the present disclosure relates to substantially pure crystalline brigatinib.

In one embodiment, the present disclosure is directed to polymorphs of brigatinib. The polymorphs of brigatinib are herein designated as Form A, Form B, Form C, Form D, Form E, Form F, Form G, Form H, Form J, and Form K.

In another embodiment, the present disclosure is directed to substantially pure crystalline forms of brigatinib. The substantially pure crystalline forms of brigatinib are herein designated as Form A, Form B, Form C, Form D, Form E, Form F, Form G, Form H, Form J, and Form K.

In another embodiment, the present disclosure is directed to pharmaceutical compositions consisting essentially of a crystalline form of brigatinib disclosed herein and at least one additional component chosen from pharmaceutically acceptable carriers, pharmaceutically acceptable vehicles, and pharmaceutically acceptable excipients. In another embodiment, the present disclosure is directed to pharmaceutical compositions consisting of at least one polymorph of brigatinib disclosed herein and at least one additional component chosen from pharmaceutically acceptable carriers, pharmaceutically acceptable vehicles, and pharmaceutically acceptable excipients.

In another embodiment, the present disclosure is directed to a method of treating a disorder and/or condition in a subject that responds to the inhibition of a protein kinase by administering to the subject a polymorph of brigatinib disclosed herein. In certain embodiments, at least one of the disorders and/or conditions is non-small cell lung cancer (NSCLC).

In another embodiment, the present disclosure is directed to a method of treating a disorder and/or condition in a subject that responds to the inhibition of a protein kinase by administering to the subject a substantially pure crystalline form of brigatinib disclosed herein. In certain embodiments, at least one of the disorders and/or conditions is NSCLC when the protein kinase is ALK or a mutant form thereof.

BRIEF DESCRIPTION OF THE DRAWINGS

The following drawings form part of the present specification and are included to further demonstrate certain embodiments of the present disclosure. The disclosure may be understood by reference to one or more of these drawings in combination with the detailed description of embodiments disclosed herein.

Figure 1:
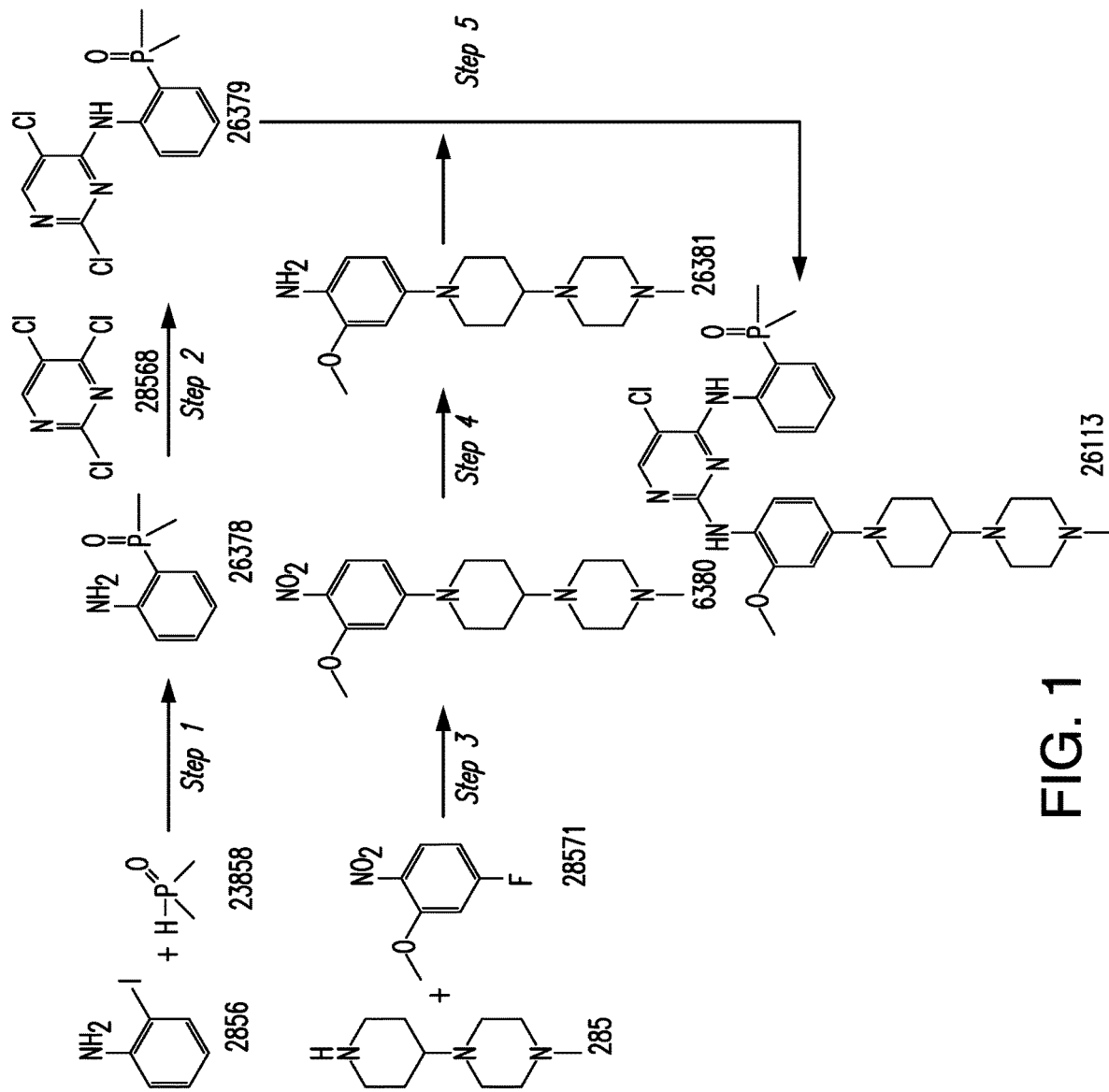
FIG. 1 is a synthetic scheme for brigatinib.

While polymorphism classically refers to the ability of a compound to crystallize into more than one crystalline form (having identical chemical structure), the term "pseudopolymorphism" is typically applied to solvate and hydrate crystalline forms. For purposes of this disclosure, however, both true polymorphs as well as pseudopolymorphs (i.e., hydrate and solvate forms) are included in the scope of the term "crystalline forms" and "polymorphic forms." In addition, "amorphous" refers to a non-crystalline solid state.

It should be there can be variation in the angle of peaks (XRPD maxima values) in XRPD diffractograms. Those of ordinary skill in the art are aware that a variance in 2–θ peak position may be observed, such as for example a variance of ±0.2° 2θ or a variance of ±0.3° 2θ. Furthermore, those of ordinary skill in the art would recognize that the relative intensities (expressed in counts) of peaks can vary between samples, for example, due to preferred orientation. See, e.g., U.S. Pharmacopeia <941> X-Ray Diffraction. Accordingly, crystalline forms disclosed herein have X-ray powder diffraction patterns substantially as shown in certain figures, e.g., Forms A-H respectively have X-ray powder diffraction patterns substantially as shown in the FIGS. 2, 14, 18, 19, and 21-25. Of course, those of ordinary skill in the art would recognize that any additional component(s) in an XRPD sample can give contribute peaks to the XRPD pattern observed for the sample which peaks can mask or overlap (either partially or completely) peaks attributable to the crystalline form(s) of brigatinib in the XRPD sample.

As used herein, the terms "isolated" and "substantially pure" mean that more than 50%, such as more than 60%, such as more than 70%, such as more than 80%, such as more than 85%, such as more than 90%, such as more than 95%, such as more than 99%, such as more than 99.5%, such as more than 99.8%, or such as more than 99.9% of the brigatinib present in a sample is of a single crystalline form (as can be determined by a method in accordance with the art). For example, some embodiments of the invention is substantially pure crystalline brigatinib Form A. In some embodiments, the substantially pure crystalline form of brigatinib contains less than 5%, such as less than 1%, such as less than 0.5%, such as less than 0.2%, or such as less than 0.1% of any other solid form of brigatinib (as can be determined by a method in accordance with the art, such as XPRD analysis, for example).

As used herein, when used with reference to the chemical purity of a compound such as brigatinib, "pure" means that more than 90%, such as more than 95%, such as more than 99%, such as more than 99.5%, such as more than 99.8%, or such as more than 99.9% of the sum of all chemical(s) present in the selected material, e.g., in a sample of API, is the brigatinib molecule (as can be determined by a method in accordance with the art).

The following abbreviations for solvents may be used herein:
DCM Dichloromethane
DMA N,N-Dimethylacetamide
DMF N,N-Dimethylformamide
DMSO Dimethylsulfoxide
EtOAc Ethyl acetate
EtOH Ethanol
IPA Isopropyl alcohol
LiHDMS lithium bis(trimethylsilyl)amide
MeCN Acetonitrile
MeOH Methanol
NMP N-Methylpyrrolidine
TFE 2,2,2-Trifluoroethanol
THE Tetrahydrofuran
2-methylTHF 2-Methyltetrahydrofuran Other abbreviations (alphabetical order) that may be used herein include:
Am Amorphous
API Active Pharmaceutical Ingredient
AS Anti-solvent
DSC Differential Scanning Calorimetry
DVS Dynamic Vapor Sorption
HPLC High-Performance Liquid Chromatography
IDR Intrinsic Dissolution Rate
MS Mass Spectroscopy
NSCLC Non-Small Cell Lung Cancer
psi pounds per square inch
QSA Quantitative Solubility Assessment
RH Relative Humidity
S Solvent
SDTA Single Differential Thermal Analysis
SGF Simulated Gastric Fluid
SM Starting Material
TGA Thermogravimetric Analysis
TGMS Thermogravimetric Analysis Coupled with Mass Spectroscopy
VH-XRPD Variable humidity X-Ray Powder Diffraction
VT-XRPD Variable temperature X-Ray Powder Diffraction Xantphos 4,5-bis(diphenylphosphino)-9,9-dimethylxanthene XRPD X-Ray Powder Diffraction A "subject" to which/whom administration is contemplated includes, but is not limited to, a human (i.e., a male or female of any age group, e.g., a pediatric subject (e.g., infant, child, adolescent) or adult subject (e.g., young adult, middle-aged adult or senior adult)), another primate (e.g., cynomolgus monkeys, rhesus monkeys), a mammal, including, but is not limited to, cattle, pigs, horses, sheep, goats, cats, and/or dogs; and/or birds, including, but is not limited to, chickens, ducks, geese, quail, and/or turkeys.

XRPD patterns disclosed herein were obtained using the Crystallics T2 high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings.

Data collection was carried out at room temperature using monochromatic CuKα radiation in the 2θ region between 1.5° and 41.5°. The diffraction pattern of each well was collected in two 2θ ranges (1.5°≤2θ≤21.5° for the first frame, and 19.5°≤2θ≤41.5° for the second) with an exposure time of 90 seconds for each frame. No background subtraction or curve smoothing was applied to the XRPD patterns in the Figures.

The carrier material used during XRPD analysis was transparent to X-rays.

High resolution X-ray powder diffraction patterns disclosed herein were collected on a D8 Advance system in the Brag-Brentano geometry equipped with LynxEye solid state detector. The radiation used for collecting the data was CuKα1 (λ=1.54056 Å) monochromatized by germanium crystal. The patterns were collected in the range of 4-41.5° 2θ, with a step in the range of 0.016° 2θ without further processing. All patterns were taken at room temperature, approximately 295 K. The material was placed in a boron glass capillary of 0.3 mm diameter. For variable humidity and variable temperature experiments disclosed herein, an ANSYCO HT chamber was used. The material was placed on a fixed sample holder that was mounted inside the chamber. The humidity was applied locally and varied from 10% to 80% (dew point). The temperature variation rate was 10° C./min.

The step used during the experiments were 0.016, 0.017 or 0.064° 2θ/sec.

Melting properties disclosed herein were obtained from DSC thermograms, recorded with a heat flux DSC822e instrument (Mettler-Toledo GmbH, Switzerland). The DSC822e was calibrated for temperature and enthalpy with a small piece of indium (m.p.=156.6° C.; □Hf=28.45 J·g$^{-1}$). Samples were sealed in standard 40 μL aluminum pans, pin-holed and heated in the DSC from 25° C. to 300° C., at a heating rate of 10° C. min$^{-1}$. Dry N$_2$ gas, at a flow rate of 50 mL min$^{-1}$ was used to purge the DSC equipment during measurement.

Mass loss due to solvent or water loss from the various crystal samples disclosed herein was determined by TGA/SDTA. Monitoring the sample weight, during heating in a TGA/SDTA851e instrument (Mettler-Toledo GmbH, Switzerland), resulted in a weight vs. temperature curve. The TGA/SDTA851e was calibrated for temperature with indium and aluminum. Samples were weighed into 100 μL aluminum crucibles and sealed. The seals were pin-holed and the crucibles heated in the TGA from 25 to 300° C. at a heating rate of 10° C. min$^{-1}$. Dry N$_2$ gas was used for purging.

The gases evolved from the TGA samples were analyzed by a quadrupole mass spectrometer Omnistar GSD 301 T2 (Pfeiffer Vacuum GmbH, Germany), which analyses masses in the range of 0-200 amu.

Digital images disclosed herein were automatically collected for all the wells of each well-plate, employing a Philips PCVC 840K CCD camera controlled by Avantium Photoslider software.

HPLC analysis disclosed herein was performed using an Agilent 1200SL HPLC system equipped with UV and MS detectors following the conditions presented below:

HPLC Equipment: LC-MS
Manufacturer: Agilent
HPLC: Agilent 1200
UV-detector: Agilent DAD
MS-detector: Agilent 1100 API-ES MSD VL-type
Column: Waters Sunfire C18 (100×4.6 mm; 3.5 μm).
Column temp: 30° C.
Mobile phase: Gradient mode
Mobile phase A: 1000/1; H$_2$O/TFA (v/v)
Mobile phase B: 1000/5/1; ACN/MeOH/TFA (v/v)
Flow: 10 mL/min

|  | Time [min]: | % A: | % B: |
|---|---|---|---|
| Gradient program: | 0 | 98 | 2 |
|  | 5 | 98 | 2 |
|  | 9 | 86 | 14 |
|  | 22 | 73 | 27 |
|  | 30 | 50 | 50 |
|  | 30.10 | 98 | 2 |

Posttime: 7
UV-Detector: DAD
Range: 200-400 nm
Wavelength: 244 nm
Slit Width: 4 nm
Time: 0-30 min
MS-Detector: MSD
Scan: positive
Mass Range: 70-1000 amu
Fragmentator: 70
Time: 0-30 min
Autosampler:
Temperature: Not controlled
Injection mode: loop
Injection volume: 5 μL
Needle wash: 2/3; ACN/H$_2$O (v/v)
Dilution solvent: 0.1% TFA water/CAN Compound integrity disclosed herein is expressed as a "peak-area %" for each peak (other than the peak due to injection), which is calculated by dividing the area of each peak in the chromatogram ("peak-area") by the total peak-area ("total-area") and multiplying by 100%, as follows:

$$\text{peak-area \%} = \frac{\text{peak-area}}{\text{total-area}} * 100\%$$

The peak-area percentage of the compound of interest may be employed as an indication of the purity of the component in the sample.

Mass spectrometry disclosed herein was performed using a Finnigan ion-trap Mass Spectrometer Model LTQ XL. Samples were infused through a syringe pump into an atmospheric pressure electrospray ionization (ESI) probe.

Fragmentation of the ions was achieved using collisional activation, and mass spectral data were collected in full scan (MS1) and multilevel MS modes (MS2 and MS3). The structures of the product ions were deduced using established fragmentation rules and through use of Mass Frontier software (High Chem Ltd., Slovak Republic, version 5.1.0.3).

I. POLYMORPHIC FORMS OF BRIGATINIB

Through analyses disclosed herein, ten polymorphic forms of brigatinib were identified. The ten new polymorphic forms are referred to herein as Form A, Form B, Form C, Form D, Form E, Form F, Form G, Form H, Form J, and Form K. In general, crystalline forms of brigatinib have physical properties (such as high stability, etc.) that are advantageous for the commercial preparation of solid dosage forms as compared to amorphous brigatinib. The distinction between crystalline brigatinib and amorphous brigatinib can be readily seen with the same type of physical chemical data (e.g., DSC, XRPD, thermal analysis) that is used to distinguish the individual crystalline forms of brigatinib disclosed herein.

Form A:

Form A was the predominant crystalline form identified in the experiments disclosed herein. Form A can be obtained from the the final synthetic step in the synthesis of brigatinib shown in FIG. 1, for example, by elevating the temperature of crystallization to 60° C. and adding a NaOH solution at a slow rate. Form A is anhydrous and not hygroscopic. Form A did not convert into other forms via solvent-mediated or solid-solid transition or exposure to elevated temperature, elevated humidity, mechanical pressure, or grinding as disclosed herein.

The chemical and crystal structures of Form A have been unambiguously established by a combination of nuclear magnetic resonance spectroscopy (NMR), mass spectrometry (MS), and X-ray powder diffraction (XRPD), single crystal X-ray crystallography with confirmatory data from elemental analysis (EA) and Fourier transform infra-red (FT-IR) spectroscopy.

In some embodiments, the present disclosure relates to crystalline Form A of brigatinib. In some embodiments, the present disclosure relates to crystalline Form A of brigatinib, wherein the crystalline Form A of brigatinib is substantially pure. In some embodiments, the crystalline Form A is anhydrous.

Figure 2:
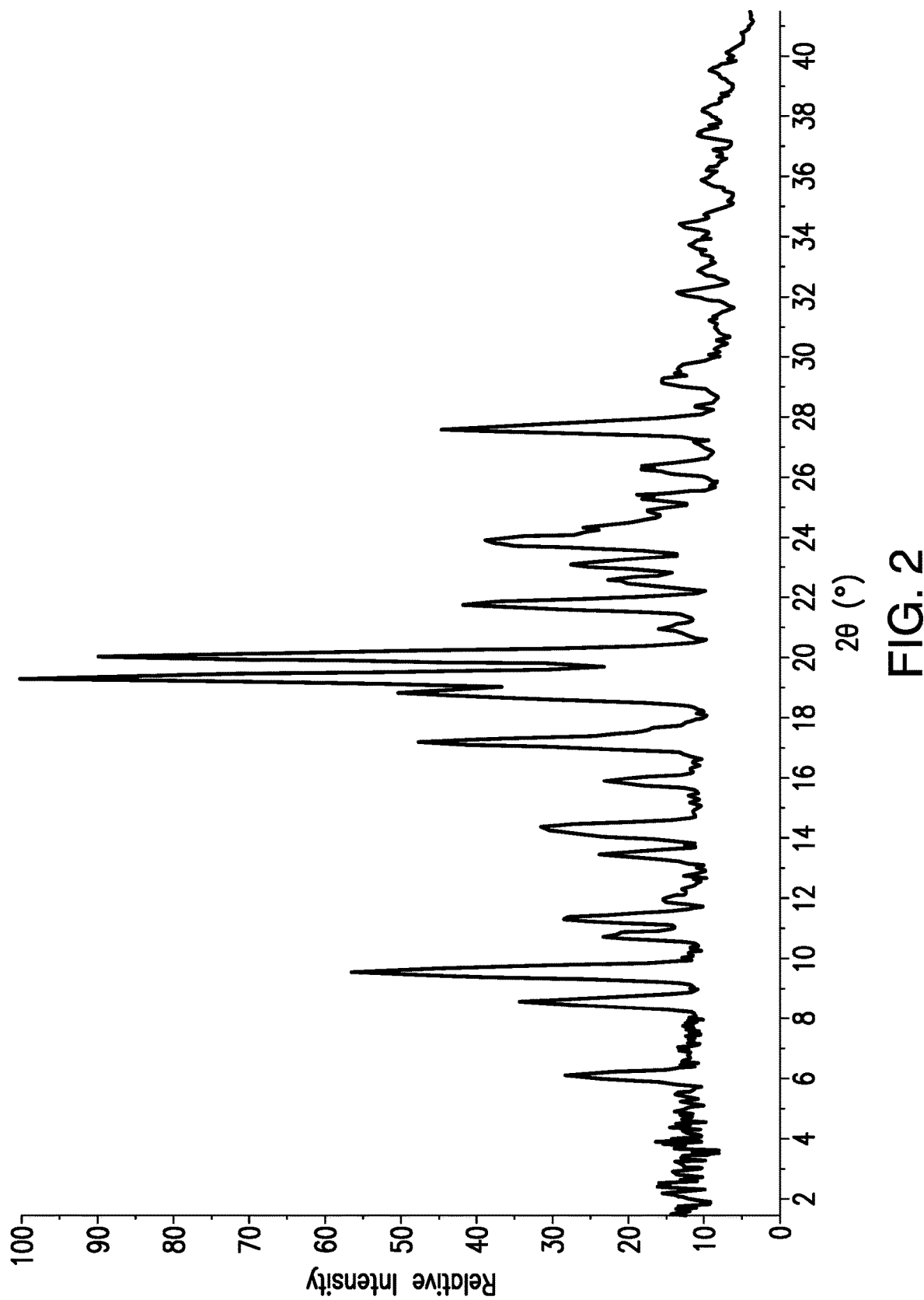
FIG. 2 is an X-Ray Powder Diffraction (XRPD) pattern obtained from a sample of brigatinib Form A. Relative Intensity (in counts) is shown on the vertical axis and angle (in degrees two theta (° 2θ)) is shown on the horizontal axis.

Samples of Form A were analyzed by X-ray powder diffraction (XRPD). In some embodiments, the present disclosure relates to crystalline Form A having an x-ray powder diffraction pattern substantially as shown in FIG. 2.

In some embodiments, the XRPD pattern of crystalline Form A has at least one, at least two, at least three, at least four, at least five, at least six, at least seven, at least eight, at least nine, at least ten, at least eleven, at least twelve, at least thirteen, at least fourteen, at least fifteen, at least sixteen, or at least seventeen peaks expressed in degrees two-theta chosen from 6.1, 8.6, 9.6, 10.8, 11.3, 13.5, 14.3, 15.9, 17.2, 18.9, 19.4, 20.1, 21.8, 22.6, 23.1, 23.9, and 27.7. As previously noted, in some embodiments, a variance of ±0.3° 2θ may be observed in one or more 2-θ peak positions.

In some embodiments, the XRPD pattern of crystalline Form A has at least one, at least two, at least three, at least four, at least five, at least six, at least seven, at least eight, at least nine, at least ten, at least eleven, at least twelve, at least thirteen, at least fourteen, at least fifteen, at least sixteen, or at least seventeen peaks expressed in degrees two-theta chosen from 6.1, 8.58, 9.58, 10.78, 11.34, 13.46, 14.34, 15.9, 17.22, 18.86, 19.38, 20.1, 21.82, 22.58, 23.14, 23.86, and 27.66. A variance of ±0.30° 2θ may be observed in one or more 2-θ peak positions in some embodiments.

In some embodiments, the present disclosure relates to the crystalline Form A having an x-ray powder diffraction pattern with at least one, at least two, at least three, at least four, at least five, or at least six peaks expressed in degrees two-theta chosen from 9.6, 17.2, 19.4, 20.1, 23.1, and 27.7. In some embodiments, a variance of ±0.3° 2θ may be observed in one or more 2-θ peak positions.

In some embodiments, the present disclosure relates to the crystalline Form A having an x-ray powder diffraction pattern with at least one, at least two, at least three, at least four, at least five, or at least six peaks expressed in degrees two-theta chosen from 9.58, 17.22, 19.38, 20.1, 23.14, and 27.66. In some embodiments, a variance of ±0.30° 2θ may be observed in one or more 2-θ peak positions.

Figure 3:
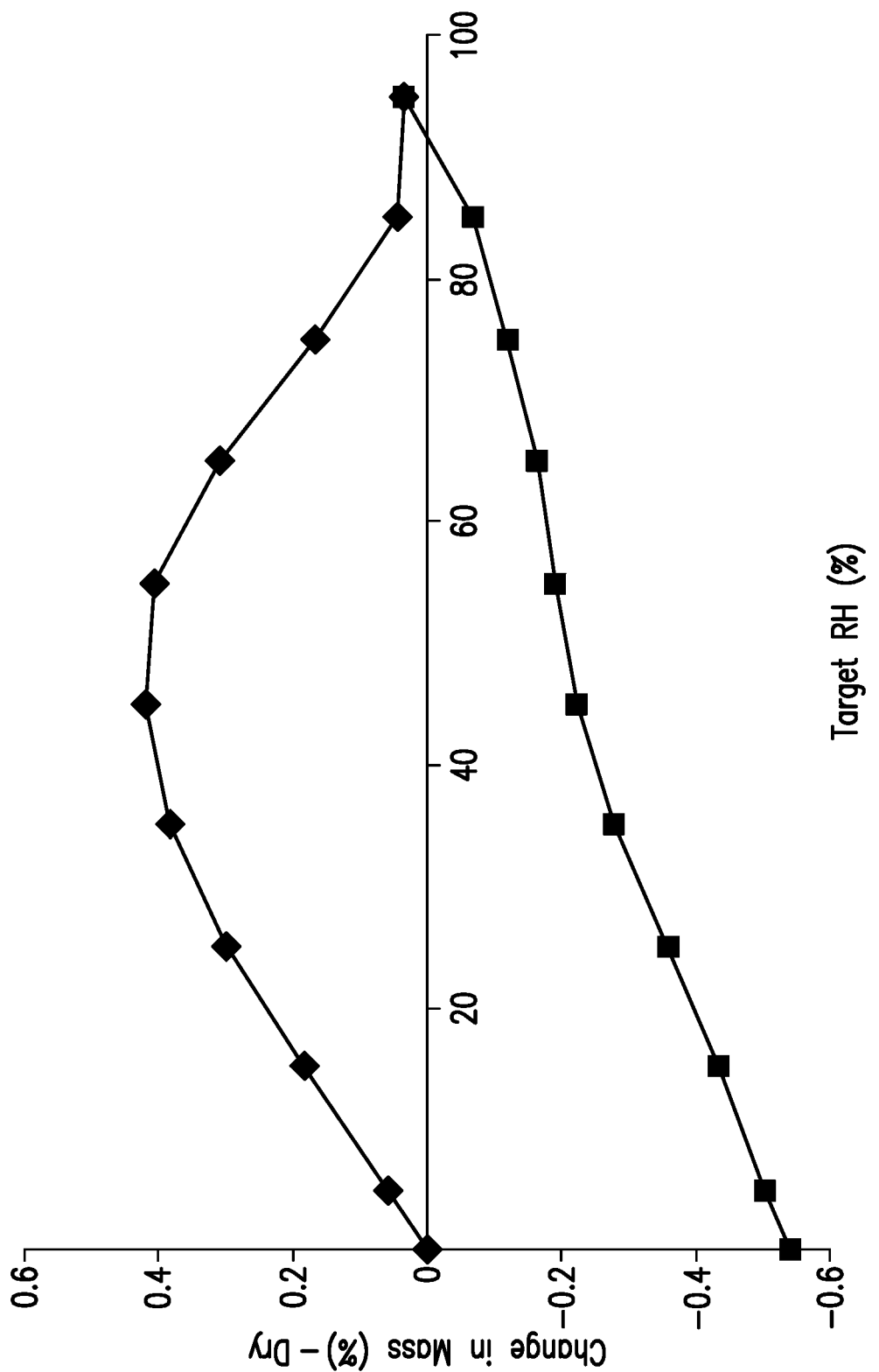
FIG. 3 is a sorption-desorption plot of the dynamic vapor sorption (DVS) experiment of a sample of brigatinib Form A. Change in mass (%) is shown on the vertical axis and Target RH (%) is shown on the horizontal axis.

In a differential vapor sorption (DVS) experiment with Form A, the sample was first dried at Q % RH for 6 hours. Then, the relative humidity was cycled from 5% to 95% RH (sorption), then to 5% RH (desorption) at a constant temperature of 25° C., with a hold time of 60 minutes per step. As shown in FIG. 3, these results demonstrate that Form A is not hygroscopic.

Figure 4:
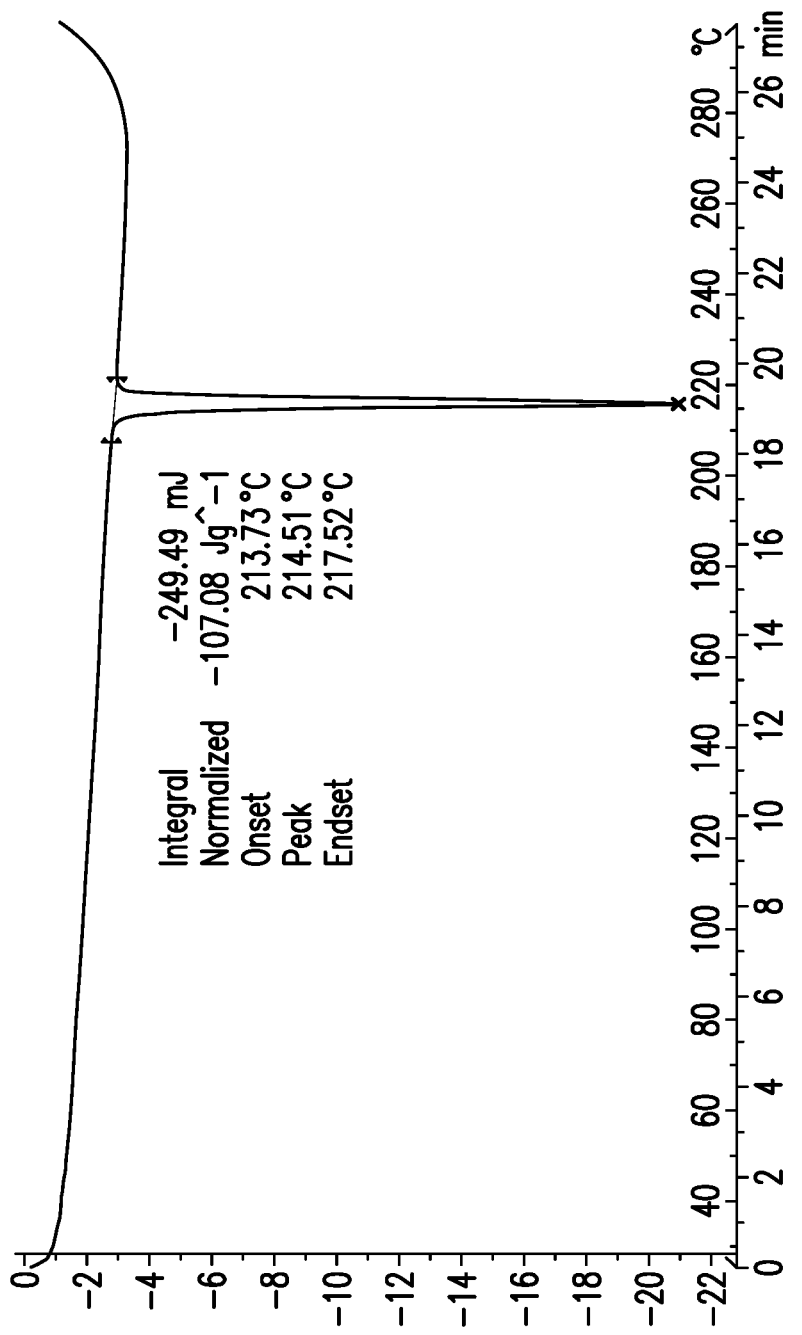
FIG. 4 is a differential scanning calorimetry (DSC) scan obtained from a sample of Form A of brigatinib. Heat flow (mW) is shown on the vertical axis and temperature (° C.) is shown on the horizontal axis.

With reference to FIG. 4, the melting point of Form A was determined by differential scanning calorimetry (DSC). A sample of Form A was analyzed in a pin-holed 40 μL aluminum pan in the temperature range of 25° C. to 300° C. at a heating rate of 10° C./min. An endothermic peak at 214.5° C. was observed. Accordingly, in some embodiments, the present disclosure relates to crystalline Form A having an onset melting temperature of 214.5° C. In some embodiments, the onset melting temperature of crystalline Form A is 214° C. In some embodiments, the onset melting temperature of crystalline Form A is 215° C.

Figure 5A:
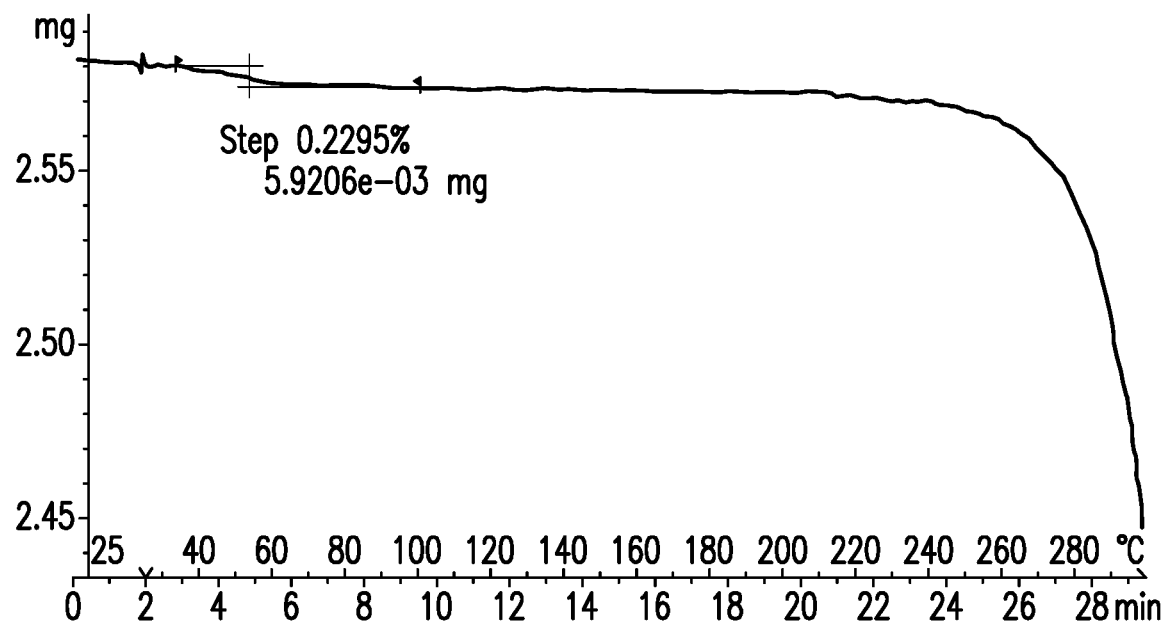
FIG. 5A is a thermogravimetric analysis/single differential thermal analysis thermogram (TGA/SDTA) for a sample of brigatinib Form A.
Figure 5B:
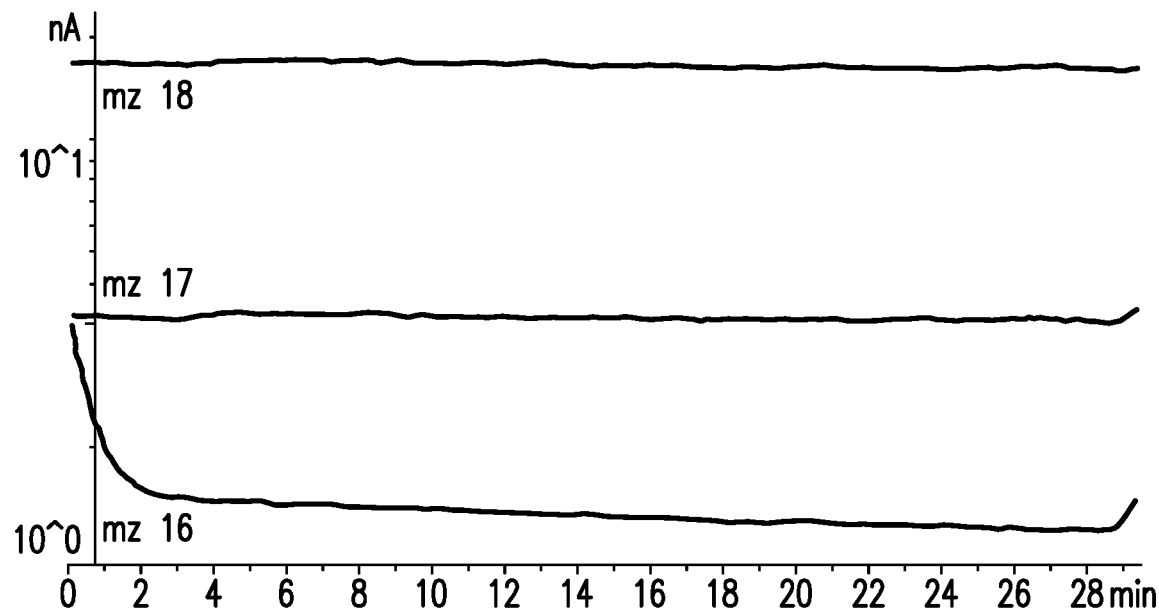
FIG. 5B is a thermogravimetric mass spectrometry (TGMS) thermogram for a sample of brigatinib Form A.

With reference to FIG. 5, thermogravimetric analysis/single differential thermal analysis (TGA/SDTA) and thermogravimetric mass spectrometry (TGMS) were performed on Form A. The sample, contained in a pin-holed crucible, was heated in the TGA instrument from 25° C. to 300° C. at a heating rate of 10° C. min-, with dry $N_2$ gas used for purging. Gases evolved from the TGA were analyzed using a quadrupole mass spectrometer. The TGA/TGMS experiment indicated that a mass loss of 0.23% (water) was observed over a temperature range of 30° C.-100° C.y.

Elemental analysis was performed on a Form A sample for hydrogen, carbon, nitrogen, chlorine, phosphorous and oxygen. The results are shown in Table 1 and confirm the molecular formula of brigatinib as $C_{29}H_{40}ClN_7O_2P$. The determined elemental composition is consistent with the molecular formula of brigatinib.

TABLE 1

Elemental Analysis Results

| Element | Actual | Theoretical |
|---|---|---|
| hydrogen | 7.01% | 6.73% |
| carbon | 58.88% | 59.63% |
| nitrogen | 16.73% | 16.79% |
| chlorine | 5.86% | 6.07% |
| phosphorous | 5.14% | 5.30% |
| oxygen | 6.38% | 5.48% |

Figure 6:
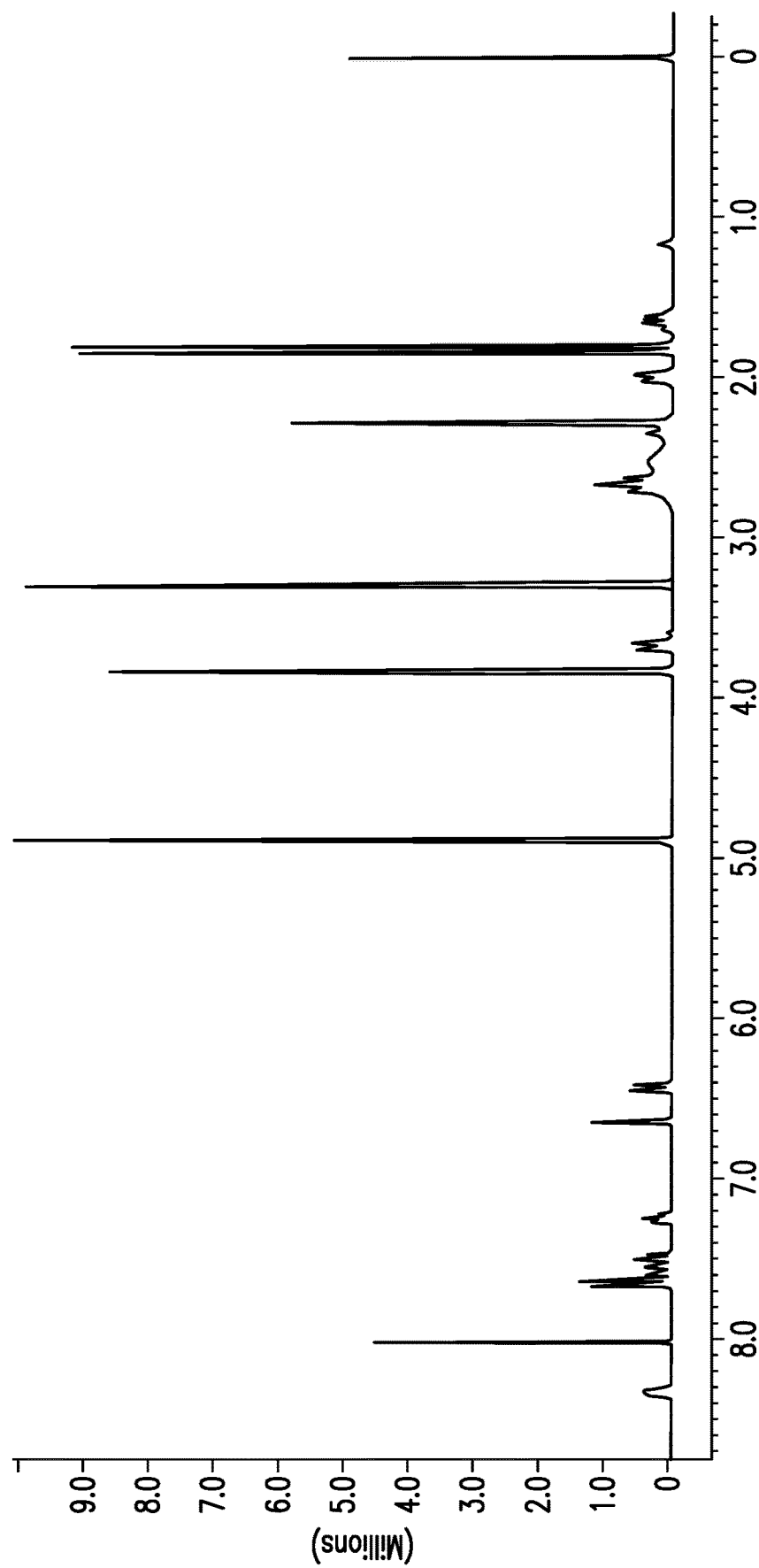
FIG. 6. is an $^1$H-NMR spectrum obtained for a sample of brigatinib dissolved in $CD_3OD$. Normalized intensity is shown on the vertical axis and chemical shift (ppm) is shown on the horizontal axis.
Figure 7:
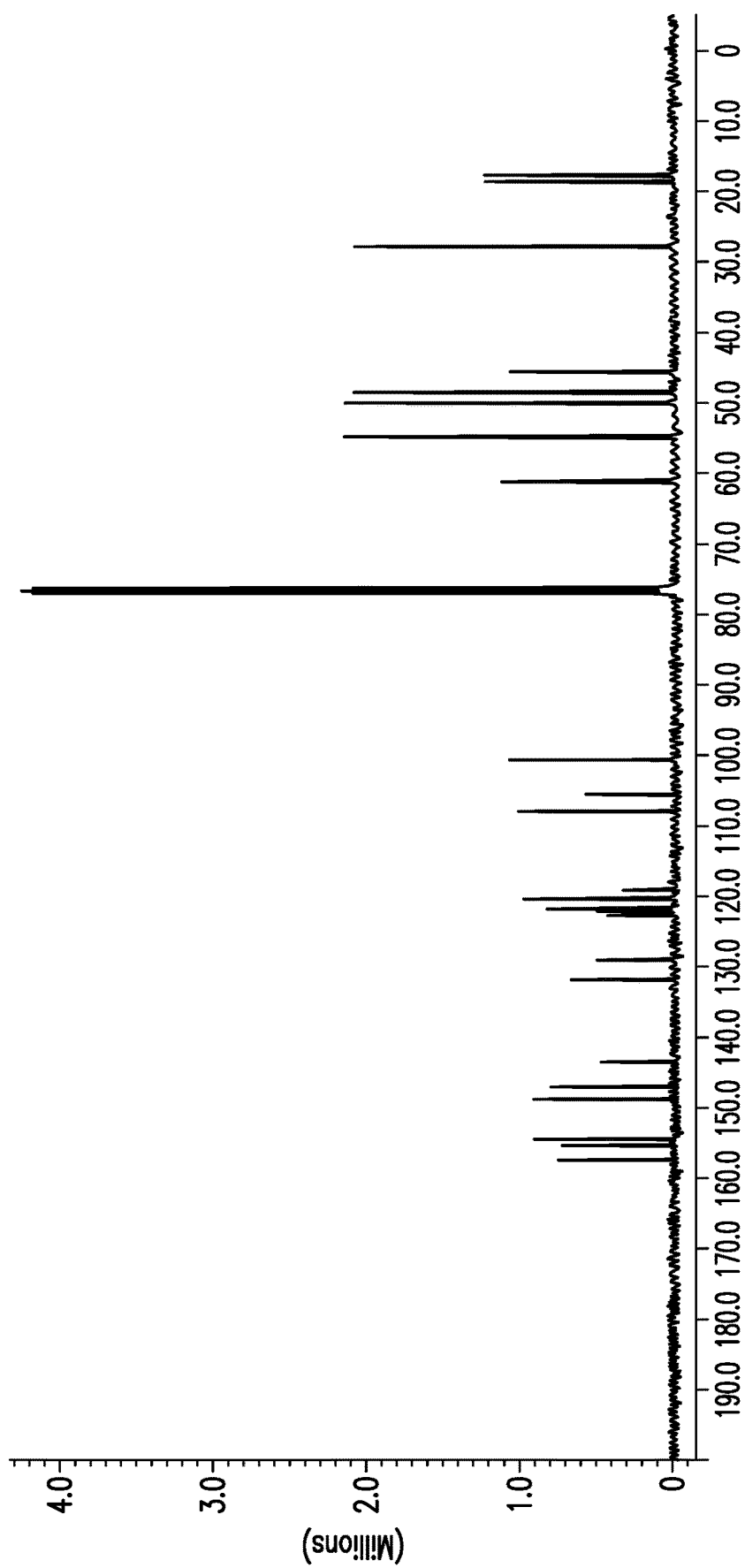
FIG. 7 is a $^{13}$C-NMR spectrum obtained for a sample of brigatinib dissolved in $CDCl_3$. Normalized intensity is shown on the vertical axis and chemical shift (ppm) is shown on the horizontal axis.

Solution phase NMR studies were performed on Form A to obtain a complete assignment of $^1$H, $^{13}$C and $^{31}$P resonances, and hence to confirm the chemical formula of brigatinib. $^1$H NMR analyses were performed on a sample of Form A dissolved in $CD_3OD$ solvent, while $^{13}$C-NMR analyses were performed on a sample of Form A dissolved in $CDCl_3$ solvent. FIG. 6 provides the 1D $^1$H-NMR spectra of Form A. FIG. 7 shows the 1D $^{13}$C-NMR spectra of Form A.

Table 2 summarizes the relevant chemical shift data of Form A obtained from the $^1$H, and $^{13}$C-NMR experiments. The number of signals and their relative intensity (integrals) confirm the number of protons and carbons in the structure of Form A of brigatinib. The $^{31}$P-NMR chemical shift for the single phosphorous atom in brigatinib was 43.6 ppm. These $^1$H and $^{13}$C-NMR chemical shift data are reported according to the atom numbering scheme shown immediately below:

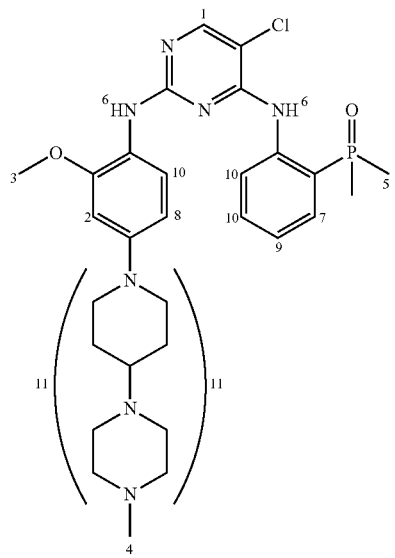

$^1$H-NMR Assignments

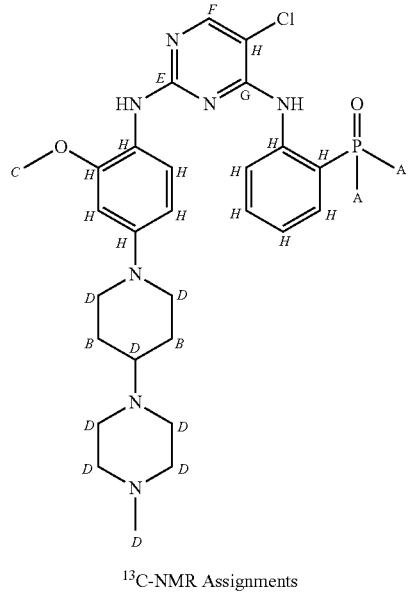

$^{13}$C-NMR Assignments

TABLE 2

$^1$H and $^{13}$C Chemical Shift Data (in ppm) of Form A of Brigatinib

| $^1$H Atom Number | $^1$H, ppm | $^{13}$C Atom Letter | $^{13}$C, ppm |
|---|---|---|---|
| 1 | 1H, 8.0 | A | 18-19 |
| 2 | 1H, 6.65 | B | 28.1 |
| 3 | 3H, 3.8 | C | 61.6 |
| 4 | 3H, 2.3 | D | 46-56 |
| 5 | 6H, 1.8-1.9 | E | 157.7 |
| 6 | 2H, 3.66-3.70 | F | 154.8 |
| 7 | 1H, 8.3 | G | 155.8 |
| 8 | 1H, 6.5 | H | 101-149 |
| 9 | 1H, 7.2 | — | — |
| 10 | 3H, 7.5-7.7 | — | — |
| 11 | 17H, 1.0-3.0, unassigned | — | — |

Figure 8:
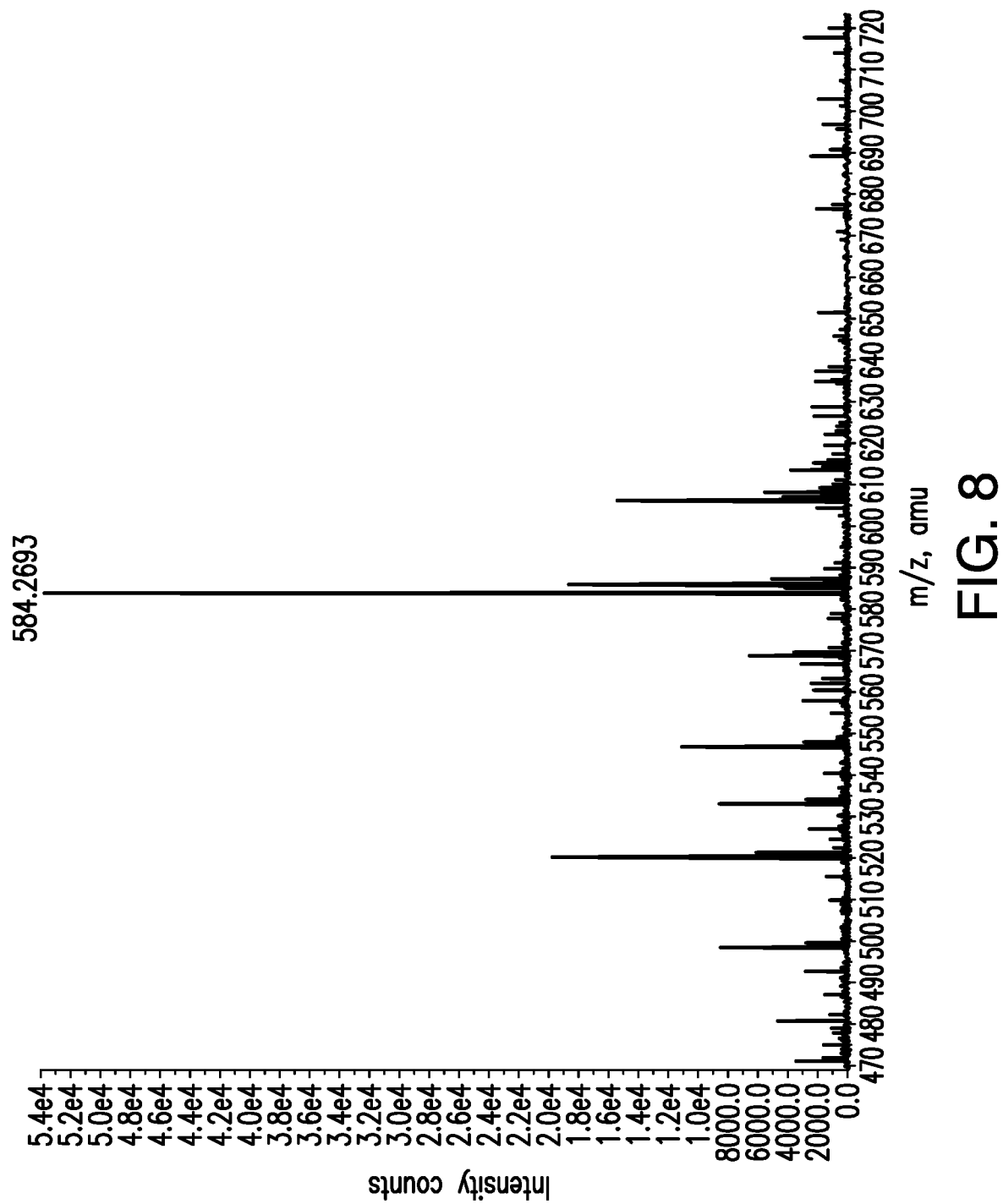
FIG. 8 is a mass spectral fragmentation pattern of a sample of brigatinib Form A. Relative abundance is shown on the vertical axis and atomic weight (m/z) is shown on the horizontal axis.
Figure 9A:
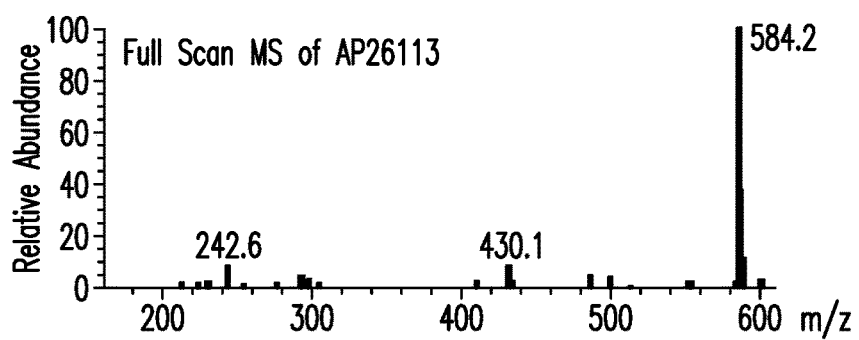
FIGS. 9A-9E depict the fragmentation pattern of ions of a sample of brigatinib Form A using collisional activation, measured using an electrospray time of flight mass spectrometer. Relative abundance is shown on the vertical axis and atomic weight (m/z) is shown on the horizontal axis.
Figure 9B:
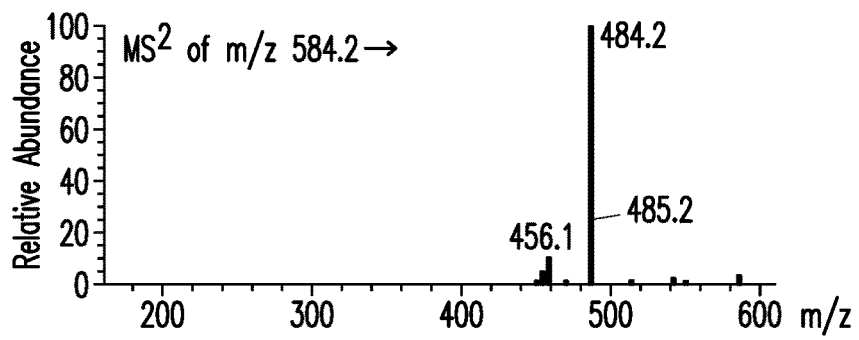
Figure 9C:
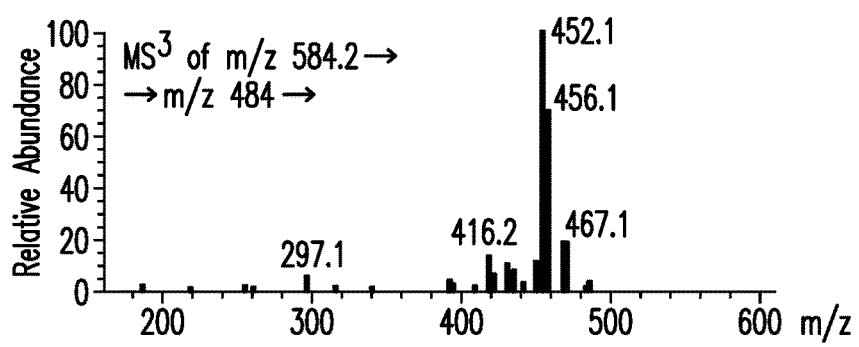
Figure 9D:
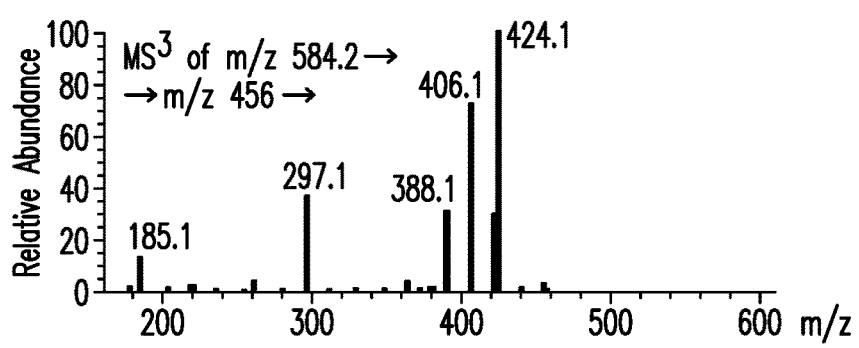
Figure 9E:
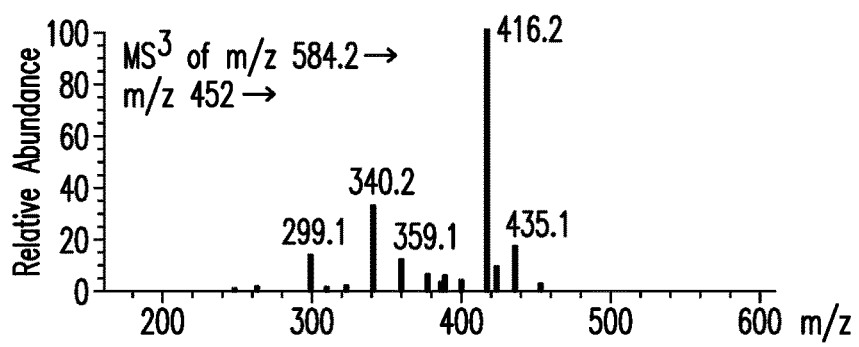

With reference to FIG. 8, mass spectral experiments of Form A were carried out using an Agilent electrospray time of flight mass spectrometer (Model 6210) operating in positive ion mode using flow injection sample introduction. Samples of Form A were dissolved in methanol/water and were analyzed and the mass observed was m/z 584.263 (M+H$^+$) with the calculated exact mass being 584.2664 (M+H$^+$). The observed molecular mass is consistent with the elemental composition calculated from the molecular formula of brigatinib.

Using the Finnigan ion-trap mass spectrometer described above, fragmentation of the ions was achieved using collisional activation, and mass spectral data were collected in full scan (MS1) and multilevel MS modes (MS2 and MS3) as shown in FIG. 9. The structures of the product ions were deduced using established fragmentation rules and through use of Mass Frontier software (High Chem Ltd., Slovak Republic, version 5.1.0.3) as shown in Table 3. The proposed structures of the key product ions were consistent with the structure of brigatinib as shown in Table 4.

TABLE 3

Mass Spectral Product Ions of Brigatinib

| Experiment | Ion Selected for Collisional Activation | Key Product Ions (m/z) |
|---|---|---|
| MS | Full Scan | 584 (M + H$^+$) molecular ion |
| MS$^2$ (MS/MS) | 584 | 484, 456, 452 |
| MS$^3$ (MS/MS/MS) | 484 | 467, 456, 452, 448, 430, 416, 315, 297, 219 |
| MS$^3$ (MS/MS/MS) | 456 | 424, 420, 406, 388, 379, 297, 262, 185, 160 |
| MS$^3$ (MS/MS/MS) | 452 | 435, 416, 387, 340, 299 |

TABLE 4

Mass Spectral Data of Product Ions of Brigatinib

| m/z of the Product Ion | Proposed Structure of the Ion | amu Difference from Precursor Ion | Chemical Groups Lost from Precursor Ion |
|---|---|---|---|
| | MS Experiment - Molecular Ion m/z 584 | | |
| 584 | 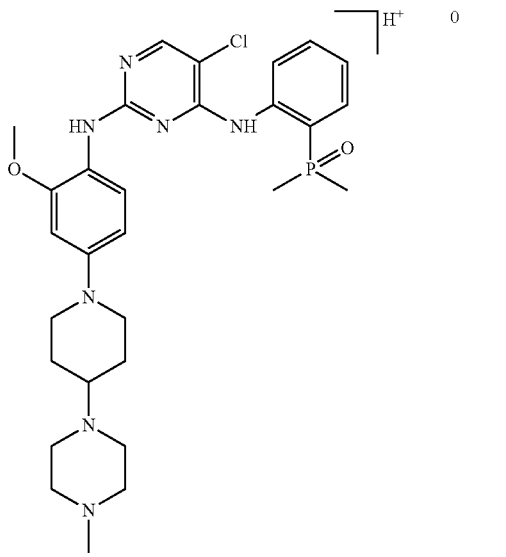 | 0 | Molecular ion MH+, Calculation based on the nominal monoisotopic molecular weight with 35Cl atom. |
| | MS² Experiment - Product Ions of the Molecular Ion m/z 584 | | |
| 484 | 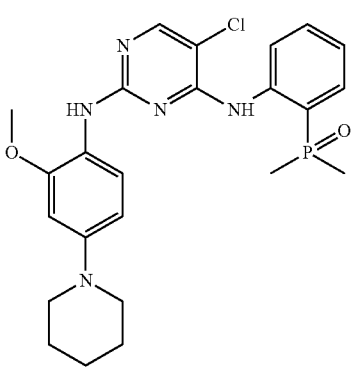 | 100 | N-methyl piperazine |
| 456 | 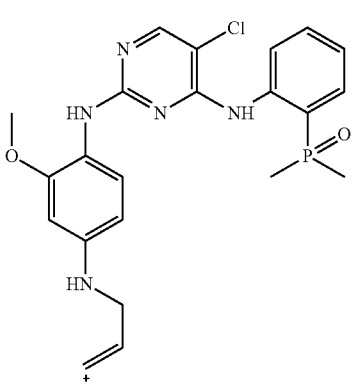 | 128 | N-methyl piperazine and ethylene |

TABLE 4-continued

Mass Spectral Data of Product Ions of Brigatinib

| m/z of the Product Ion | Proposed Structure of the Ion | amu Difference from Precursor Ion | Chemical Groups Lost from Precursor Ion |
|---|---|---|---|
| 452 | (structure) | 132 (100 + 32) | N-methyl piperazine and CH₃OH |

MS³ Experiment - Product Ions of the Precursor Ion m/z 484

| m/z of the Product Ion | Proposed Structure of the Ion | amu Difference from Precursor Ion | Chemical Groups Lost from Precursor Ion |
|---|---|---|---|
| 467 | (structure) | 17 | •OH |
| 456 | Identical to that produced in MS² experiment m/z 584 → | 28 | C₂H₄ |
| 452 | Identical to that produced in MS² experiment m/z 584 → | 32 | CH₃OH |
| 448 | (structure) | 36 | HCl |

TABLE 4-continued

Mass Spectral Data of Product Ions of Brigatinib

| m/z of the Product Ion | Proposed Structure of the Ion | amu Difference from Precursor Ion | Chemical Groups Lost from Precusor Ion |
|---|---|---|---|
| 430 | | 54 | C₄H₆ |
| 416 | | 68 (32 + 36) | CH₃OH, HCl |
| 315 | | 169 | 2-dimethyl phosphoryl aniline |
| 297 | | 187 | C₁₂H₁₃NO |

TABLE 4-continued

Mass Spectral Data of Product Ions of Brigatinib

| m/z of the Product Ion | Proposed Structure of the Ion | amu Difference from Precursor Ion | Chemical Groups Lost from Precusor Ion |
|---|---|---|---|
| 219 | (structure) | 265 | $C_{12}H_{13}NO$, $(CH_3)_2PO$* |

MS³ Experiment - Product Ions of the Precursor Ion m/z 456

| | | | |
|---|---|---|---|
| 424 | (structure) | 32 | $CH_3OH$ |
| 420 | (structure) | 36 | HCl |
| 406 | (structure) | 50 | *HNCl |

TABLE 4-continued

Mass Spectral Data of Product Ions of Brigatinib

| m/z of the Product Ion | Proposed Structure of the Ion | amu Difference from Precursor Ion | Chemical Groups Lost from Precursor Ion |
|---|---|---|---|
| 388 | | 68 | HCl, CH$_3$OH |
| 379 | | 77 | (CH$_3$)$_2$PO* |
| 297 | | 159 | C$_{10}$H$_9$NO |
| 262 | | 194 | C$_{10}$H$_9$NOCl |
| 185 | | 271 | C$_{10}$H$_9$NO, HCl, (CH$_3$)(CH$_2$) PO |

TABLE 4-continued
Mass Spectral Data of Product Ions of Brigatinib
| m/z of the Product Ion | Proposed Structure of the Ion | amu Difference from Precursor Ion | Chemical Groups Lost from Precusor Ion |
|---|---|---|---|
| 160 | 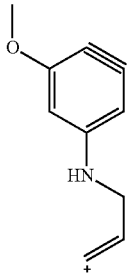 | 296 | $C_{12}H_{14}N_4OPCl$ |
MS³ Experiment - Product Ions of the Precursor Ion m/z 452
| | | | |
|---|---|---|---|
| 435 | 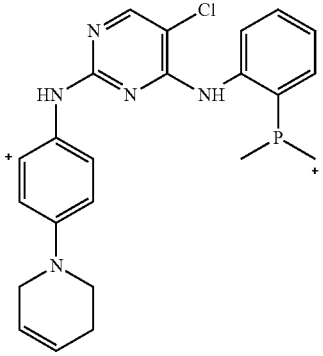 | 17 | *OH |
| 416 | 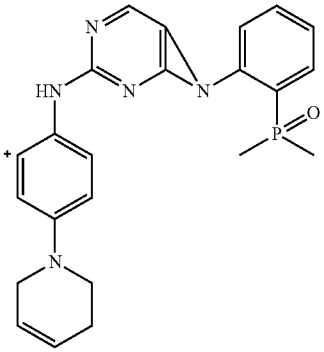 [SMILES: CP(C)(=O)c1ccccc1N1c2cnc(NC3=CC=C(N4CC=CCC4)C=[C+]3)nc21] | 36 | HCl |
| 387 | 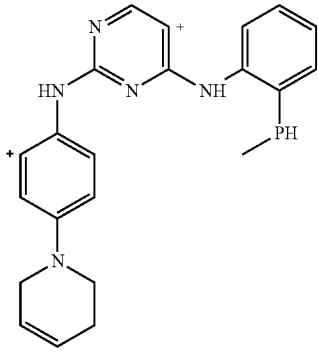 | 65 | *Cl, $CH_2O$ |

TABLE 4-continued

Mass Spectral Data of Product Ions of Brigatinib

| m/z of the Product Ion | Proposed Structure of the Ion | amu Difference from Precursor Ion | Chemical Groups Lost from Precursor Ion |
|---|---|---|---|
| 340 | | 112 | HCl, $(CH_2)_2PO^*$ |
| 299 | | 153 | 2-dimethyl phosphoryl phenyl |

Figure 10:
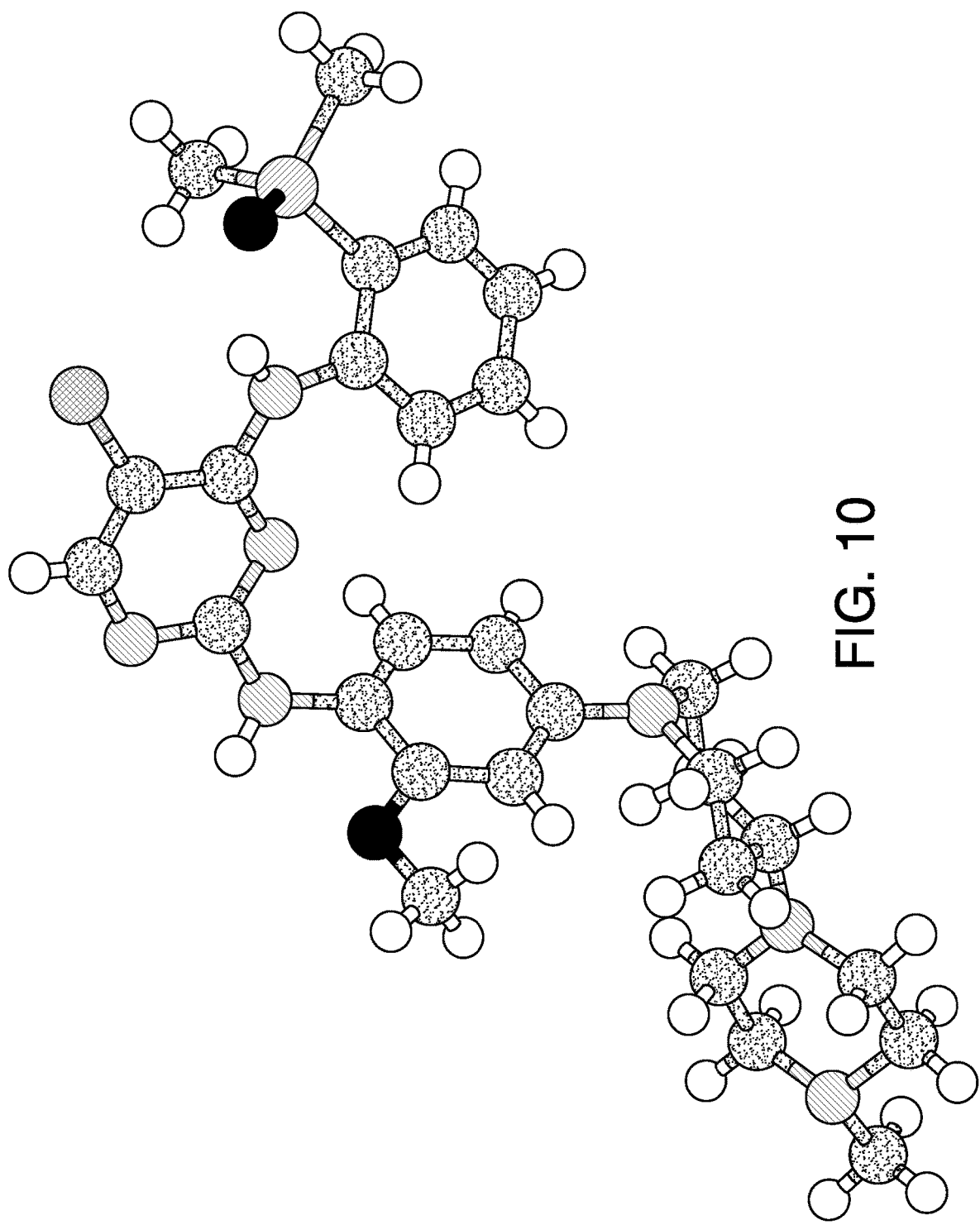
FIG. 10 is a crystal structure of brigatinib Form A, as determined by single-crystal X-Ray diffraction.

Single-crystal X-ray diffraction was employed to solve the crystal structure of Form A of brigatinib. Crystals of brigatinib Form A were obtained from MOH-toluene, the structure of Form A brigatinib is shown in FIG. 10, and crystallographic parameters are summarized in Table 5. The structure is composed of hydrogen-bonded dimers. Based on this structure solution, it was determined that Form A is unsolvated. Some disorder in the crystal is associated with the terminal N-methyl piperidine moiety of brigatinib.

TABLE 5

Crystal Data and Structure Refinement for Brigatinib Form A

| Parameter | Value |
|---|---|
| Empirical formula | $C_{29}H_{39}ClN_7O_2P$ |
| FW | 584.11 |
| Space group | P −1 (No. 2) |
| Unit cell dimensions: | |
| a [Å] | 9.5619(11) |
| b [Å] | 10.8027(13) |
| c [Å] | 14.9715(17) |
| α [°] | 75.685(5) |
| β [°] | 79.835(6) |
| γ [°] | 74.187(5) |
| V [Å$^3$] | 1431.8(3) |
| Z | 2 |
| $D_c$ [g/cm$^3$] | 1.355 |
| Crystal size [mm$^3$] | 0.20 × 0.20 × 0.02 |
| Temperature (K) | 150 |
| Radiation (wavelength, Å) | Cu K$_\alpha$(1.54184) |

TABLE 5-continued

Crystal Data and Structure Refinement for Brigatinib Form A

| Parameter | Value |
|---|---|
| Monochromator | confocal optics |
| Linear abs coef, mm−1 | 2.035 |
| Absorption correction applied | empirical |
| Transmission factors: min. max | 0.79, 0.96 |
| Diffractometer | Rigaku RAPID-II |
| h, k, l range | −11 to 9 −12 to 12 −17 to 17 |
| 2θ range, deg | 13.49-133.23 |
| Mosaicity, deg | 0.93 |
| Programs used | SHELXTL |
| $F_{000}$ | 620.0 |
| Weighting | $1/[\sigma^2(Fo^2) + (0.0806P)^2 + 0.0000P]$ where $P = (Fo^2 + 2Fc^2)/3$ |
| Data collected | 20289 |
| Unique Data | 4179 |
| $R_{int}$ | 0.079 |
| Data used in refinement | 4179 |
| Cutoff used in R-factor calculations | $F_o^2 > 2.0\sigma(F_o^2)$ |
| Data with I > 2.0σ(I) | 2420 |
| Refined extinction coef | 0.0034 |
| Number of variables | 419 |
| Largest shift/esd in final cycle | 0.00 |
| R ($F_o$) | 0.063 |
| Rw ($F_o^2$) | 0.139 |
| Goodness of fit | 1.010 |

The % transmittance FT-IR spectrum of brigatinib Form A is shown in Table 6, with a summary of selected IR band assignments provided in Table 6. Data was collected on a Form A sample within a potassium bromide salt plate.

TABLE 6

Selected IR Band Assignment of Brigatinib

| Assignment | Frequency (cm$^{-1}$) |
|---|---|
| Stretches for benzene and aliphatic and aromatic amines | 3241.0, 3165.1 |
| Stretches for alkane bonds | 2980.0 to 2793.2 |
| 1,2 and 1,2,4 substituted benzene | 1616.4 to 1417.6 |
| Aromatic nitrogen | 1441.1 to 1219.8 |
| Aromatic ester | 1354.6 to 1278.0 |
| Aromatic chlorine | 1307.4 to 1196.1 |
| Phosphoryl group | 1163.6 to 1135.0 |
| Alkane stretches | 1094.9 to 794.6 |
| 1,2 and 1,2,4 substituted benzene | 867.4 |
| Aliphatic secondary amines | 768.6 to 716.8 |

In some embodiments, the present disclosure relates to crystalline Form A having an FT-IR spectrum with any at least one of the following frequency bands:

| Frequency (cm$^{-1}$) |
|---|
| 3241.0, 3165.1 |
| 2980.0 to 2793.2 |
| 1616.4 to 1417.6 |
| 1441.1 to 1219.8 |
| 1354.6 to 1278.0 |
| 1307.4 to 1196.1 |
| 1163.6 to 1135.0 |
| 1094.9 to 794.6 |
| 867.4 |
| 768.6 to 716.8 |

Form B:

Form B is hygroscopic. Form B can be obtained, for example, indirectly from dehydration of hydrated Forms C and D. A mixture of Forms A, B, and C can form through vapor diffusion onto solids using water as the solvent. None of the direct crystallization experiments disclosed herein afforded Form B.

Form B can convert to the hydrated Forms C and D depending, for example, on the humidity level (e.g., above 60% RH at 30° C.). That conversion was determined to be reversible. Form B converts irreversibly via solid-solid transition to Form A at about 150° C. at ambient humidity as evidenced by XRPD. Form B also transforms to Form A upon slurrying in aqueous media at high temperature, for example, at least 37° C. The solubility of Form B could not be determined via slurries as Form B converted either to Forms D and/or C (at 25° C.) or Form A (at 37° C.).

Figure 11:
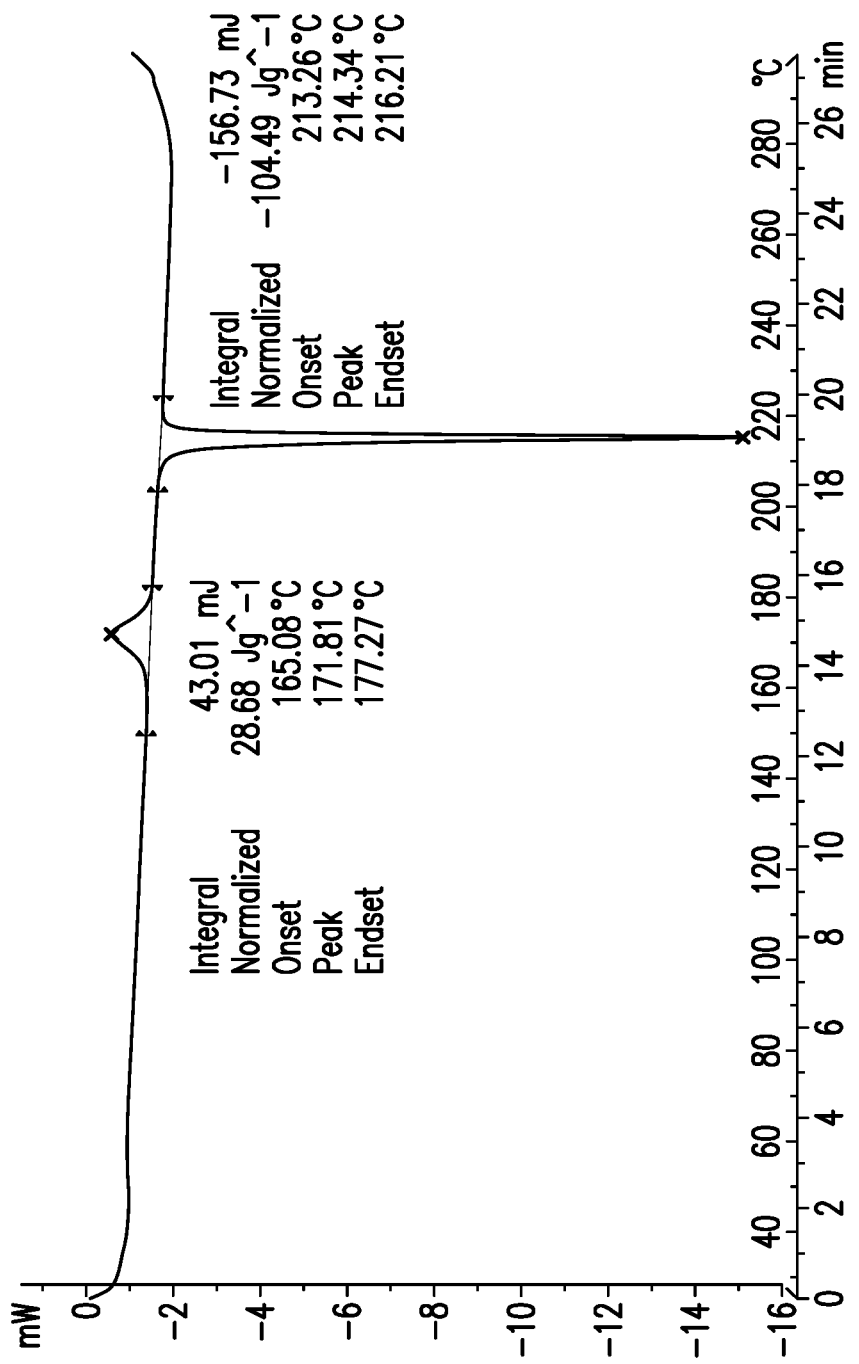
FIG. 11 is a differential scanning calorimetry (DSC) scan obtained from a sample of brigatinib Form B. Heat flow (mW) is shown on the vertical axis and temperature (° C.) is shown on the horizontal axis.

In the DSC thermogram shown in FIG. 11, a minor endotherm was observed up to approximately 50° C., corresponding to water loss of some small quantity of Form C present in the sample. Thereafter, Form B transformed via solid-solid transition (exotherm shown at 171.8° C.) to Form A, which then melted (endotherm shown at 214.3° C.). That series of events was confirmed by VT-XRPD experiments on Form B.

Figure 12:
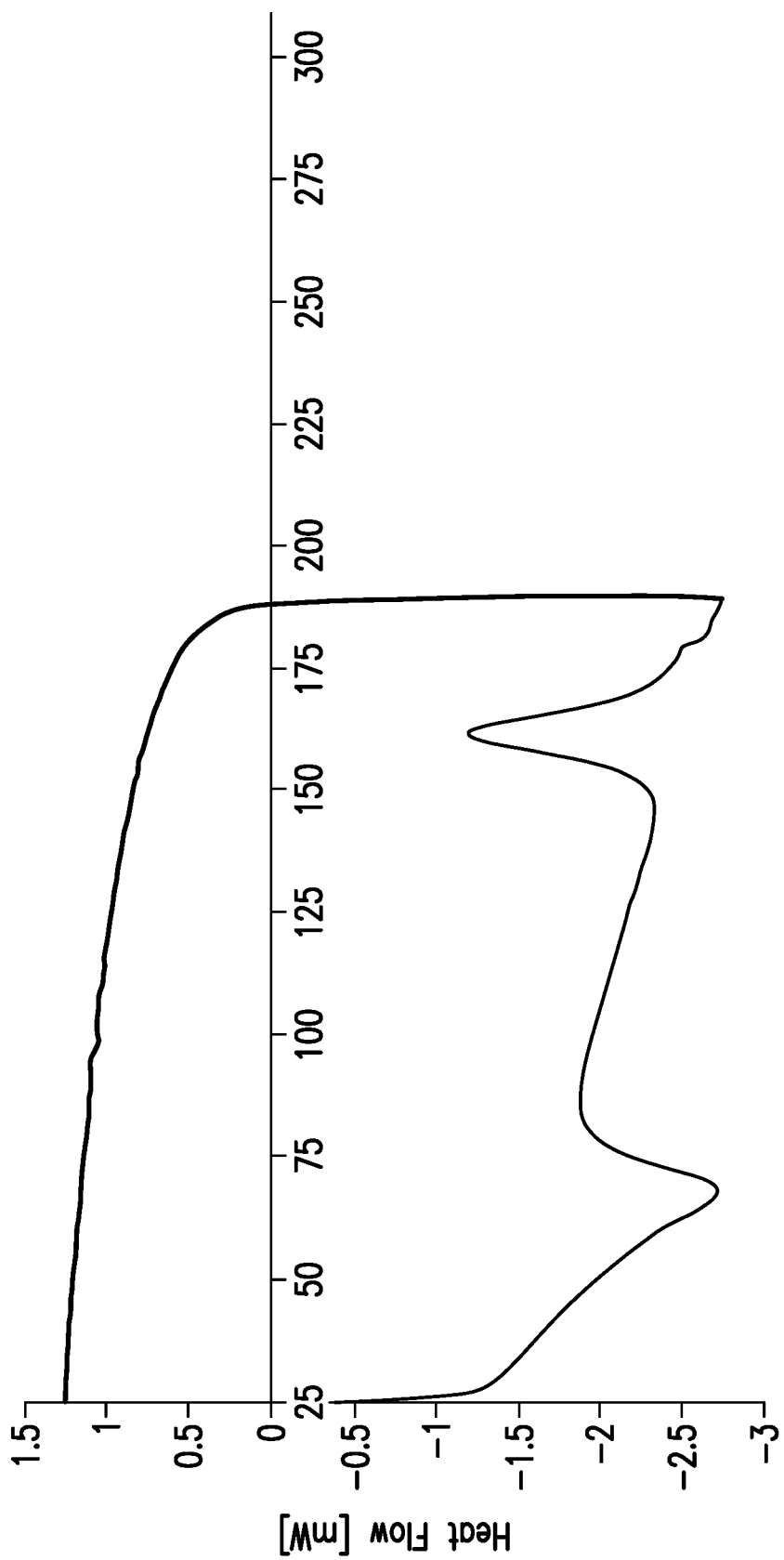
FIG. 12 is a cyclic differential scanning calorimetry (DSC) scan of a sample of brigatinib Form B; heating to 190° C. at 10° C./min and cooling to 25° C. at the same rate. Heat flow (mW) is shown on the vertical axis and temperature (° C.) is shown on the horizontal axis.
Figure 13A:
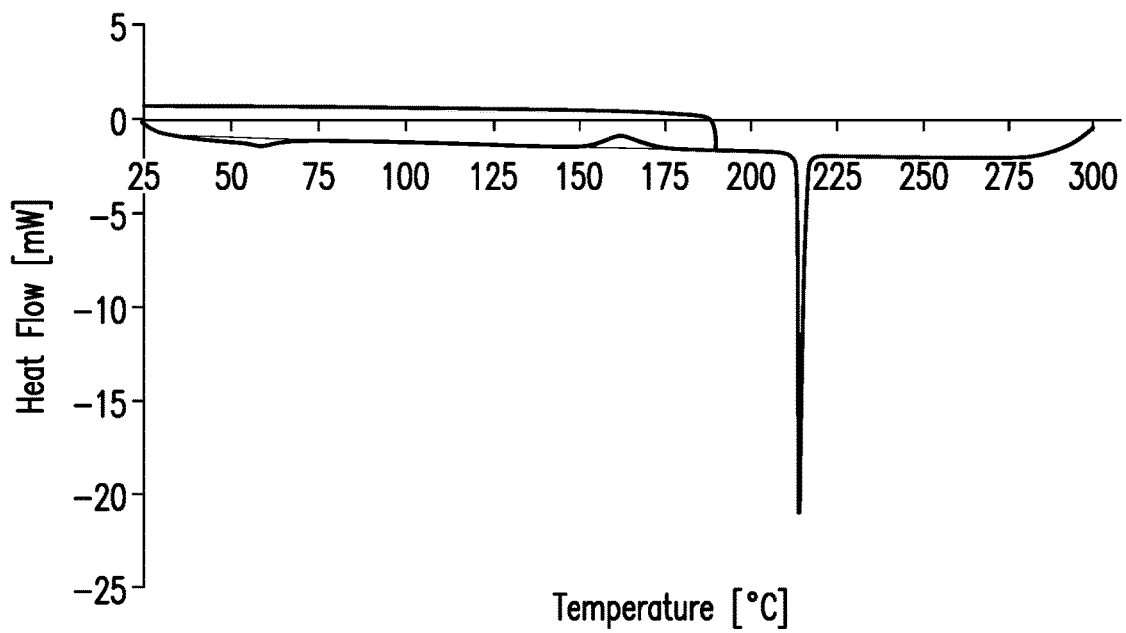
FIG. 13A is a cyclic differential scanning calorimetry (DSC) scan of a sample of brigatinib Form B; heating to 190° C. at 10° C./min, cooling to 25° C. at the same rate, followed by a second heating to 300° C. at the same rate. Heat flow (mW) is plotted on the vertical axis and temperature (° C.) is plotted on the horizontal axis.
Figure 13B:
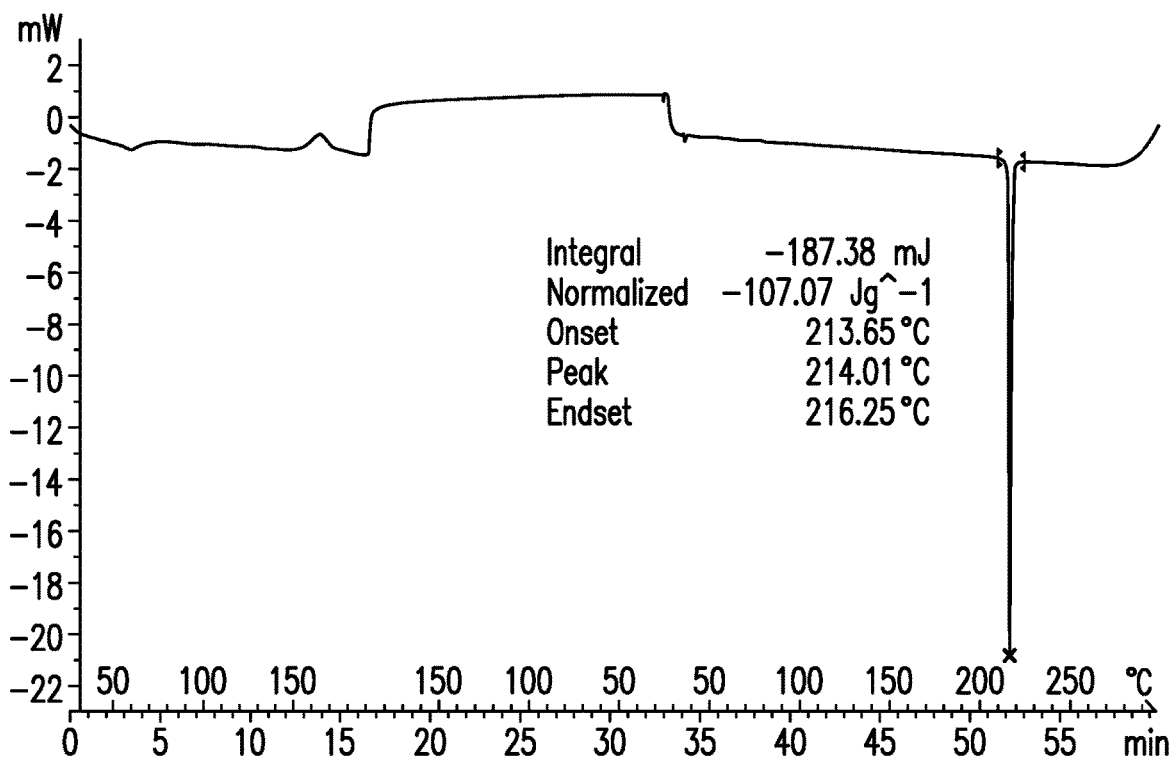
FIG. 13B is a cyclic differential scanning calorimetry (DSC) scan of a sample of brigatinib Form B; heating to 190° C. at 10° C./min, cooling to 25° C. at the same rate, followed by a second heating to 300° C. at the same rate. Heat flow (mW) is plotted on the vertical axis and time (min) is plotted on the horizontal axis.
Figure 13C:
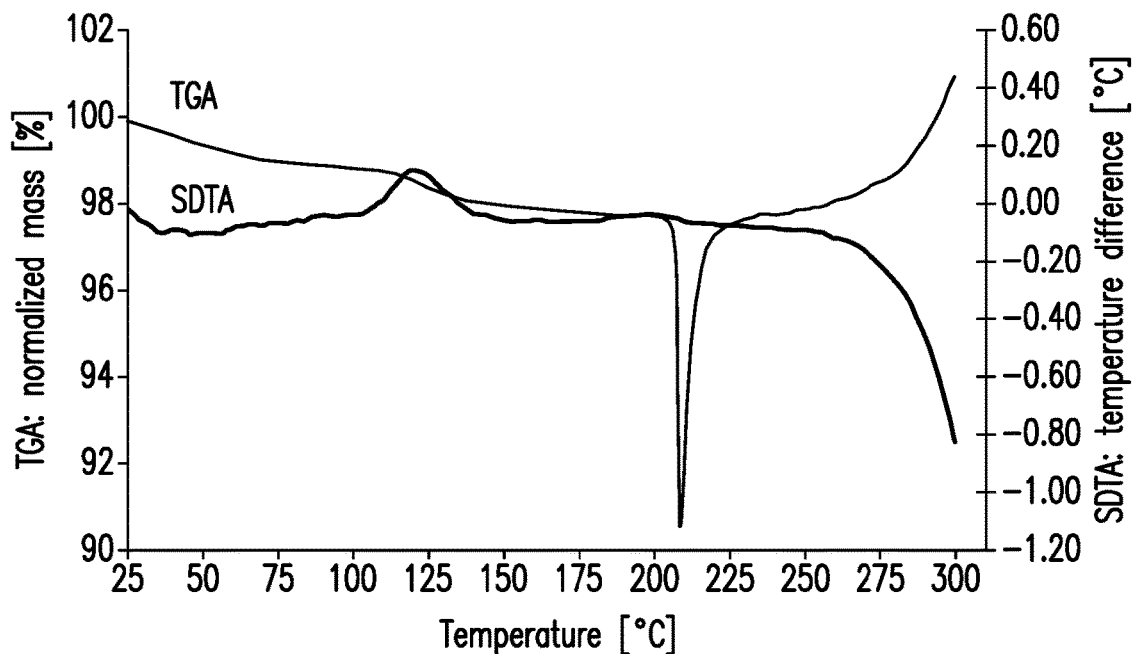
FIG. 13C is a thermogravimetric analysis/single differential thermal analysis thermogram (TGA/SDTA) for a sample of brigatinib Form B.
Figure 13D:
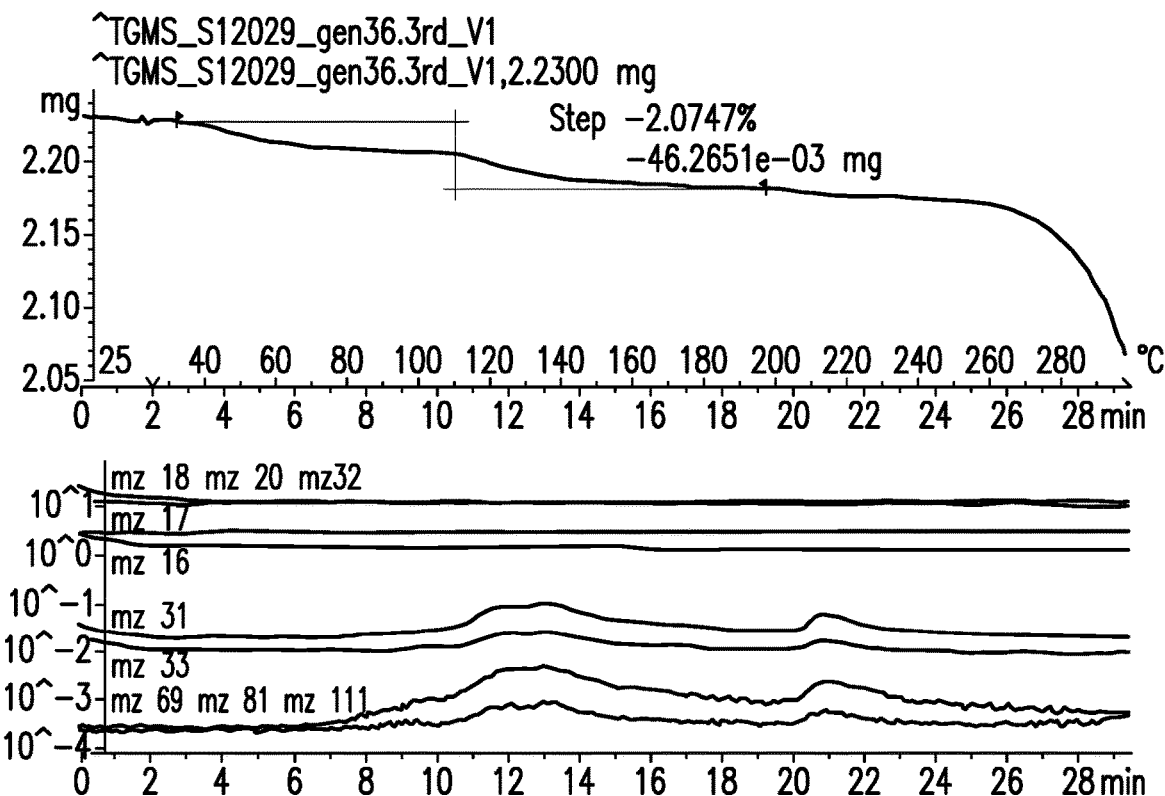
FIG. 13D is a thermogravimetric mass spectrometry (TGMS) thermogram for a sample of brigatinib Form B.

Two cyclic DSC experiments using Form B were performed. In the first experiment, the temperature was elevated by 10° C./min to 190° C. and subsequently decreased by 10° C./min to 25° C. as shown in FIG. 12. The endotherm at around 70° C. in FIG. 12 can be attributed to the presence of a small quantity of Form C and its water loss. The exotherm at 161° C. can be attributed to the solid-solid transformation of Form B to Form A. XRPD analysis of the solids at the end of the cyclic DSC experiments confirmed that the solid had transformed to Form A.

The second cyclic DSC experiment was performed with the following thermal profile: heating by 10° C./min to 190° C., cooling by 10° C./min to 25° C.; second heating by 10° C./min to 300° C. The obtained thermogram is shown in FIG. 13. The top thermogram is plotted vs. time and the bottom thermogram is plotted vs. temperature. For the first heating and cooling segments, the behavior was as described above for the first cyclic DSC experiment. Upon the second heating, only the melting of Form A was observed at $T_{peak}$=214.0° C.

In some embodiments, the present disclosure relates to crystalline Form B of brigatinib. In some embodiments, the present disclosure relates to crystalline Form B of brigatinib, wherein the crystalline Form B of brigatinib is substantially pure.

Figure 14:
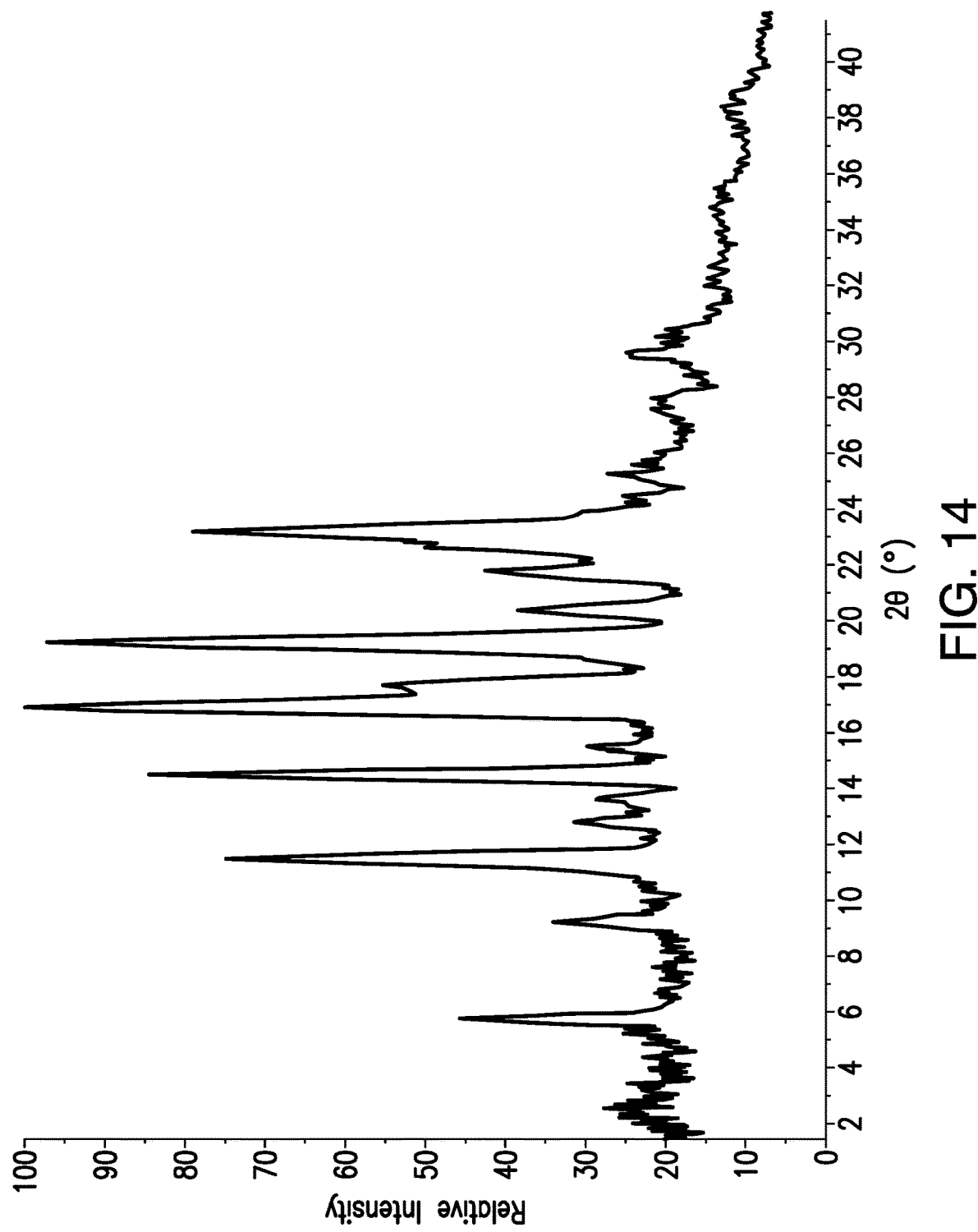
FIG. 14 is a X-Ray Powder Diffraction (XRPD) pattern obtained from a sample of brigatinib Form B. Relative Intensity (in counts) is shown on the vertical axis and the angle (in degrees two theta (°2θ)) is shown on the horizontal axis.

Samples of Form B were analyzed by X-ray powder diffraction (XRPD). In some embodiments, the present disclosure relates to crystalline Form B having an x-ray powder diffraction pattern substantially as shown in FIG. 14.

In some embodiments, the XRPD pattern of crystalline Form B has at least one, at least two, at least three, at least four, at least five, at least six, at least seven, at least eight, at least nine, at least ten, at least eleven, at least twelve, or at least thirteen peaks expressed in degrees two-theta chosen from 5.7, 9.2, 11.5, 12.8, 14.5, 15.5, 16.9, 17.7, 19.2, 20.4, 21.8, 23.2, and 29.5. In some embodiments, a variance of ±0.3° 2θ may be observed in one or more 2-θ peak positions.

In some embodiments, the XRPD pattern of crystalline Form B has at least one, at least two, at least three, at least four, at least five, at least six, at least seven, at least eight, at least nine, at least ten, at least eleven, at least twelve, or at least thirteen peaks expressed in degrees two-theta chosen from 5.74, 9.22, 11.46, 12.82, 14.5, 15.46, 16.94, 17.66, 19.22, 20.38, 21.78, 23.18, and 29.54. In some embodiments, a variance of ±0.30° 2θ may be observed in one or more 2-θ peak positions.

In some embodiments, the present disclosure is related to crystalline Form B having an x-ray powder diffraction pattern with at least two peaks expressed in degrees two-theta chosen from 11.5, 14.5, 16.9, 19.2 and 23.2. In some embodiments, a variance of ±0.3° 2θ may be observed in one or more 2-θ peak positions.

In some embodiments, the present disclosure is related to crystalline Form B having an x-ray powder diffraction pattern with at least two peaks expressed in degrees two-theta chosen from 11.46, 14.5, 16.94, 19.22 and 23.18. In certain embodiments, th In some embodiments, a variance of ±0.30° 2θ may be observed in one or more 2-θ peak positions.

Form C:

Form C can be obtained, for example, from either partial dehydration of hepta-hydrated Form D or by hydration of Form B. Form C is a hydrate that dehydrates to Form B upon exposure to relative humidity levels below 25% RH at 30° C. Form C converts to Form D upon exposure to 90% RH at 30° C. These conversions are reversible with hysteresis. Upon temperature increase at ambient humidity, Form C dehydrates to Form B, which converts irreversibly via solid-solid transition to Form A as measured by XRPD. No direct crystallization experiment as described herein afforded Form C.

Figure 15:
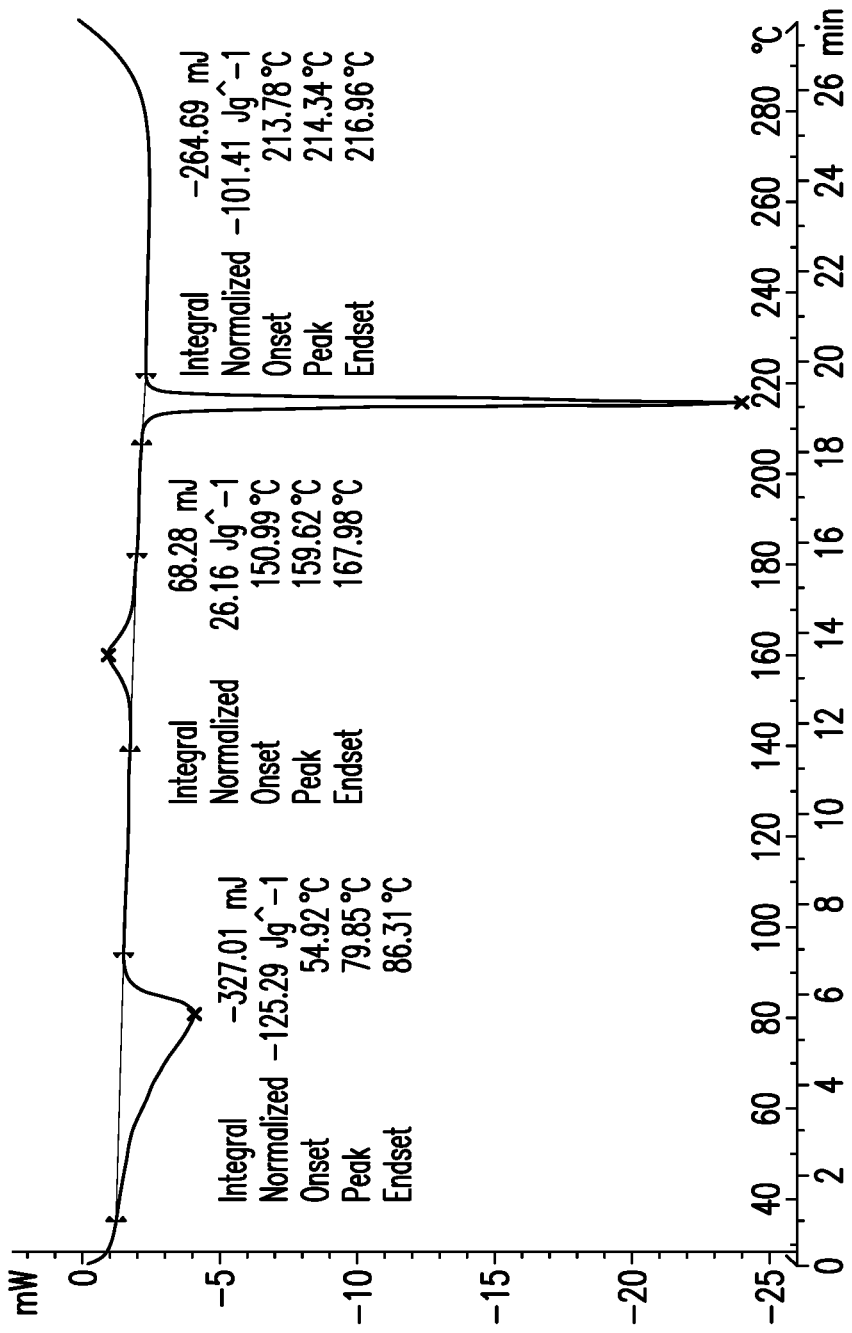
FIG. 15 is a differential scanning calorimetry (DSC) scan obtained from a sample of brigatinib Form C. Heat flow (mW) is shown on the vertical axis and temperature (° C.) is shown on the horizontal axis.

The DSC thermogram in FIG. 15 shows an endotherm that corresponds to water loss (as confirmed by TGMS) by which the solid form converted to Form B. Form B converted via solid-solid transition (exotherm at 159.6° C.) to Form A, which in turn melted (endotherm at 214.3° C.). That series of events was confirmed by VT-XRPD experiments on Form C.

Figure 16A:
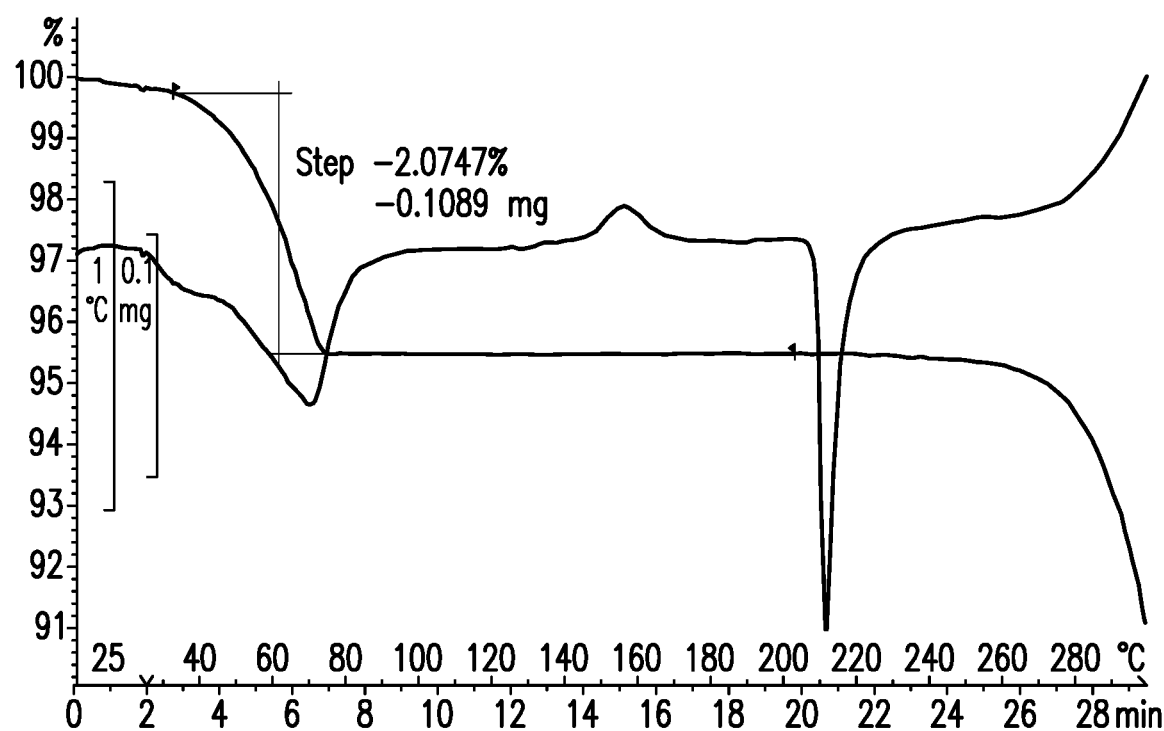
FIG. 16A is a thermogravimetric analysis/single differential thermal analysis (TGA/SDTA) thermogram of a sample of brigatinib Form C. A water mass loss of 4.25% was observed up to about 75° C., corresponding to 1.44 water molecules.
Figure 16B:
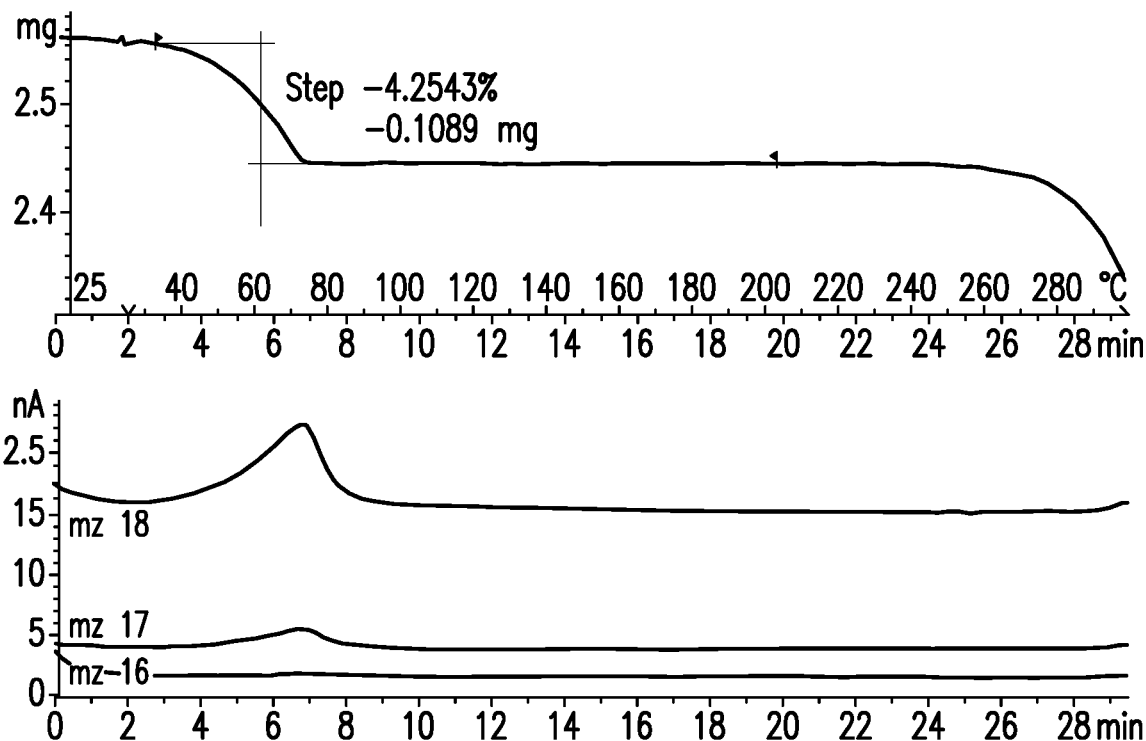
FIG. 16B is a thermogravimetric mass spectrometry (TGMS) thermogram of a sample of brigatinib Form C. A water mass loss of 4.25% was observed up to about 75° C., corresponding to 1.44 water molecules.
Figure 17A:
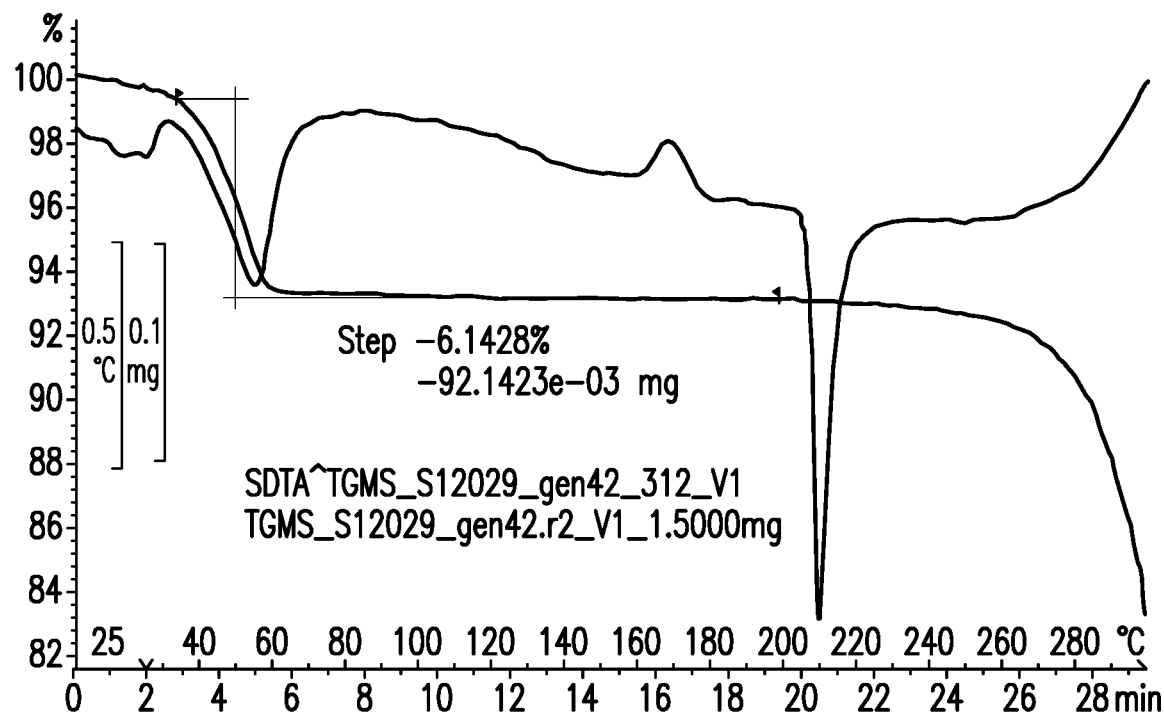
FIG. 17A is a thermogravimetric analysis/single differential thermal analysis (TGA/SDTA) thermogram of a sample of brigatinib Form C. A water mass loss of 6.14% was observed up to about 75° C., corresponding to 2.12 water molecules.
Figure 17B:
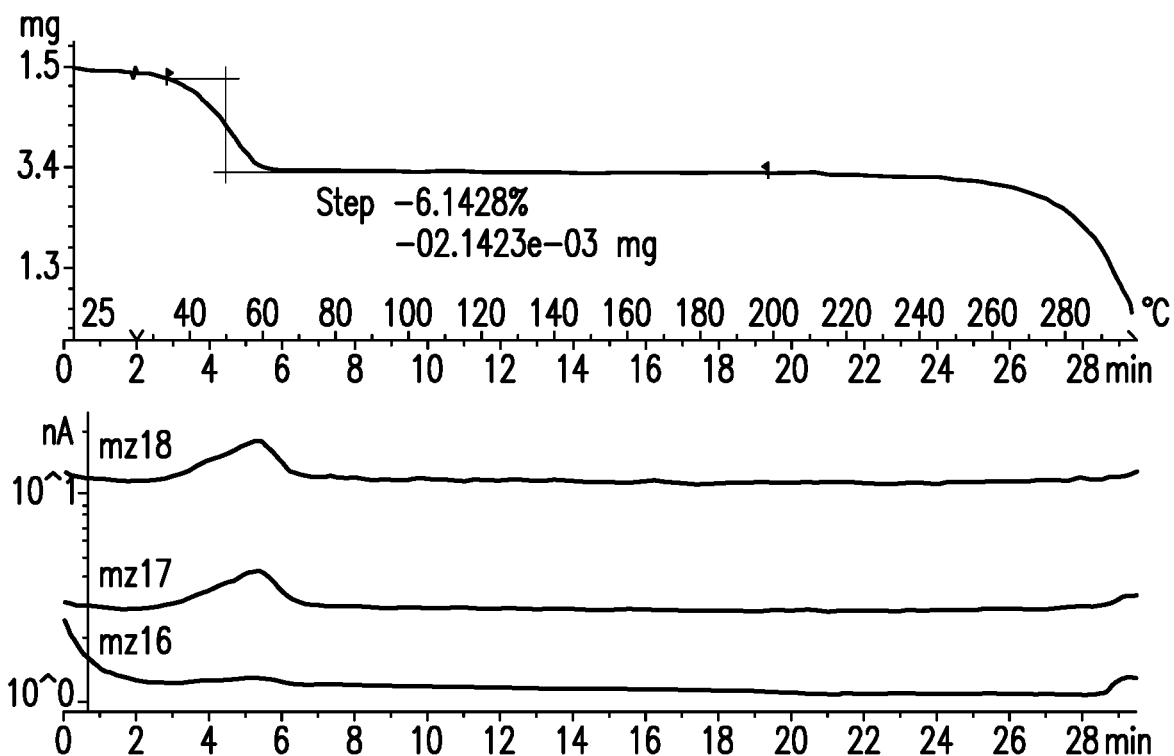
FIG. 17B is a thermogravimetric mass spectrometry (TGMS) thermogram of a sample of brigatinib Form C. A water mass loss of 6.14% was observed up to about 75° C., corresponding to 2.12 water molecules.

Two TGMS thermograms from different samples of Form C are shown in FIGS. 16A/B and FIGS. 17A/B, each containing a TGA/SDTA plot on top and TGMS plot at bottom. These thermograms show water mass losses of 4.25% and 6.14% respectively. The corresponding numbers of water molecules are 1.44 and 2.12, suggesting a degree of hydration of 2.

Form C can be obtained as a mixture of Forms A, B, and C through vapor diffusion onto solids using water as solvent. A mixture of Forms A and C can be obtained by cooling crystallization with hot filtration using as solvent systems any one of acetone/water (50/50), water/methanol (50/50), and water/1,4-dioxane (50/50). Another route to formation of Form C is evaporation from acetone/water (50/50) solvent.

In some embodiments, the present disclosure relates to crystalline Form C of brigatinib. In some embodiments, the present disclosure relates to crystalline Form C of brigatinib, wherein the crystalline Form C of brigatinib is substantially pure.

Figure 18:
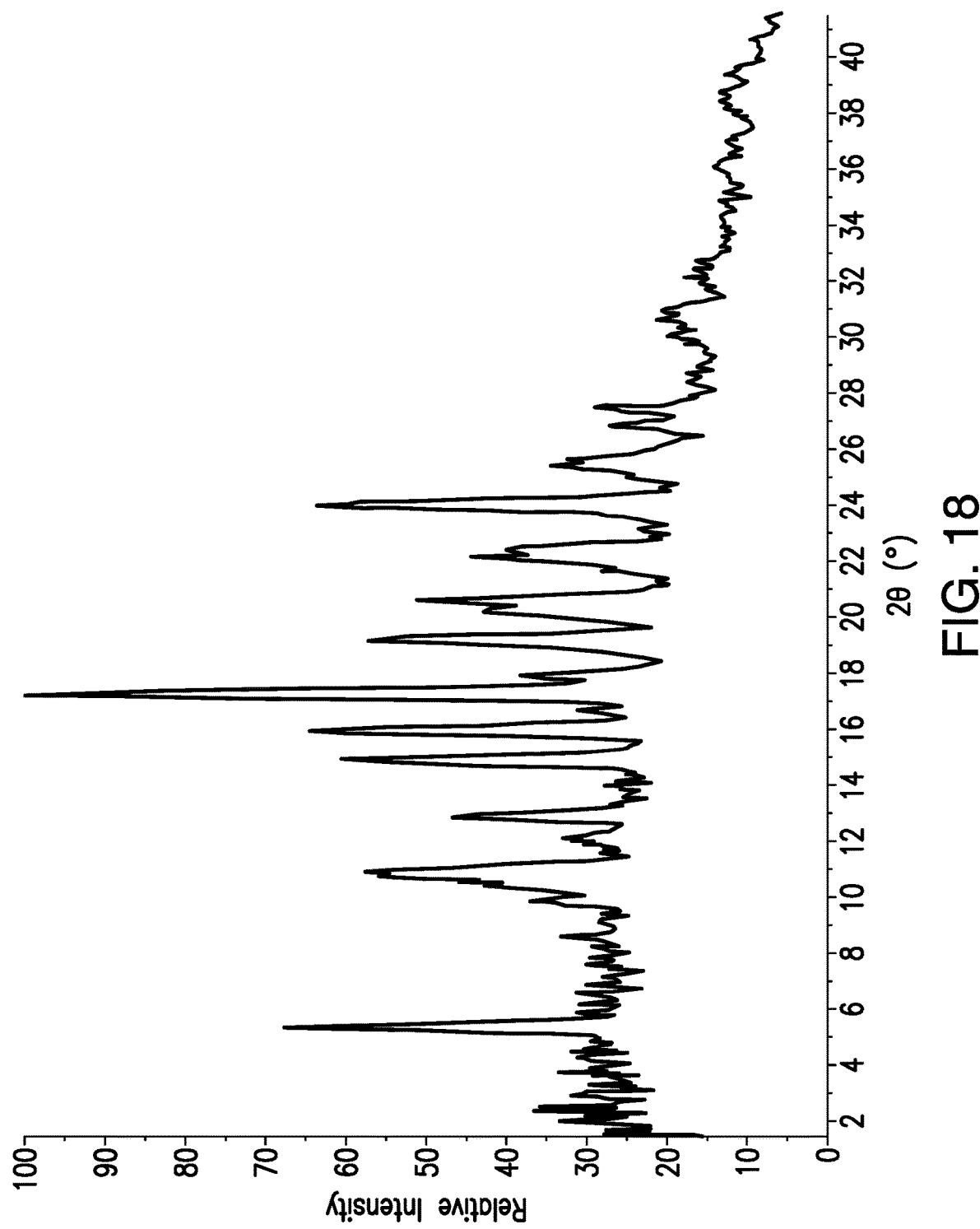
FIG. 18 is a X-Ray Powder Diffraction (XRPD) pattern obtained from a sample of brigatinib Form C. Relative Intensity (in counts) is shown on the vertical axis and the angle (in degrees two theta (° 2θ)) is shown on the horizontal axis.

Samples of Form C were analyzed by X-ray powder diffraction (XRPD). In some embodiments, the present disclosure relates to crystalline Form C having an x-ray powder diffraction pattern substantially as shown in FIG. 18.

In some embodiments, the XRPD pattern of crystalline Form C has at least one, at least two, at least three, at least four, at least five, at least six, at least seven, at least eight, at least nine, at least ten, at least eleven, at least twelve, at least thirteen, at least fourteen, at least fifteen, at least sixteen peaks expressed in degrees two-theta chosen from 2.1, 2.5, 5.4, 9.9, 10.9, 12.9, 14.9, 15.9, 16.6, 17.3, 17.9, 19.2, 20.6, 23.9, 26.8, and 27.4. As previously noted, in some embodiments, a variance of ±0.3° 2θ may be observed in one or more 2-θ peak positions.

In some embodiments, the XRPD pattern of crystalline Form C has at least one, at least two, at least three, at least four, at least five, at least six, at least seven, at least eight, at least nine, at least ten, at least eleven, at least twelve, at least thirteen, at least fourteen, at least fifteen, at least sixteen peaks expressed in degrees two-theta chosen from 2.1, 2.54, 5.42, 9.9, 10.9, 12.86, 14.86, 15.94, 16.62, 17.26, 17.9, 19.18, 20.58, 23.94, 26.82, and 27.42. In some embodiments, a variance of ±0.30° 2θ may be observed in one or more 2-θ peak positions.

In some embodiments, the XRPD pattern of crystalline Form C has at least one, at least two, at least three, at least four, at least five, at least six peaks expressed in degrees two-theta chosen from 5.4, 14.9, 15.9, 17.3, 19.2, and 23.9. In some embodiments, a variance of ±0.3° 2θ may be observed in one or more 2-θ peak positions.

Form D:

Form D is a heptahydrate that can be obtained directly from crystallization with methnol as the solvent and water as the anti-solvent. Form D can also be obtained from Form B, via Form C, upon slurries in aqueous media and exposure to high relative humidity (90% or higher, at 30° C.). Form D dehydrates (partially) to Form C at about 80% RH at 30° C. Upon temperature increase at ambient humidity, Form D dehydrates to Form C as measured by XRPD.

In some embodiments, the present disclosure relates to crystalline Form D of brigatinib. In some embodiments, the present disclosure relates to crystalline Form D of brigatinib, wherein the crystalline Form D of brigatinib is substantially pure.

Figure 19:
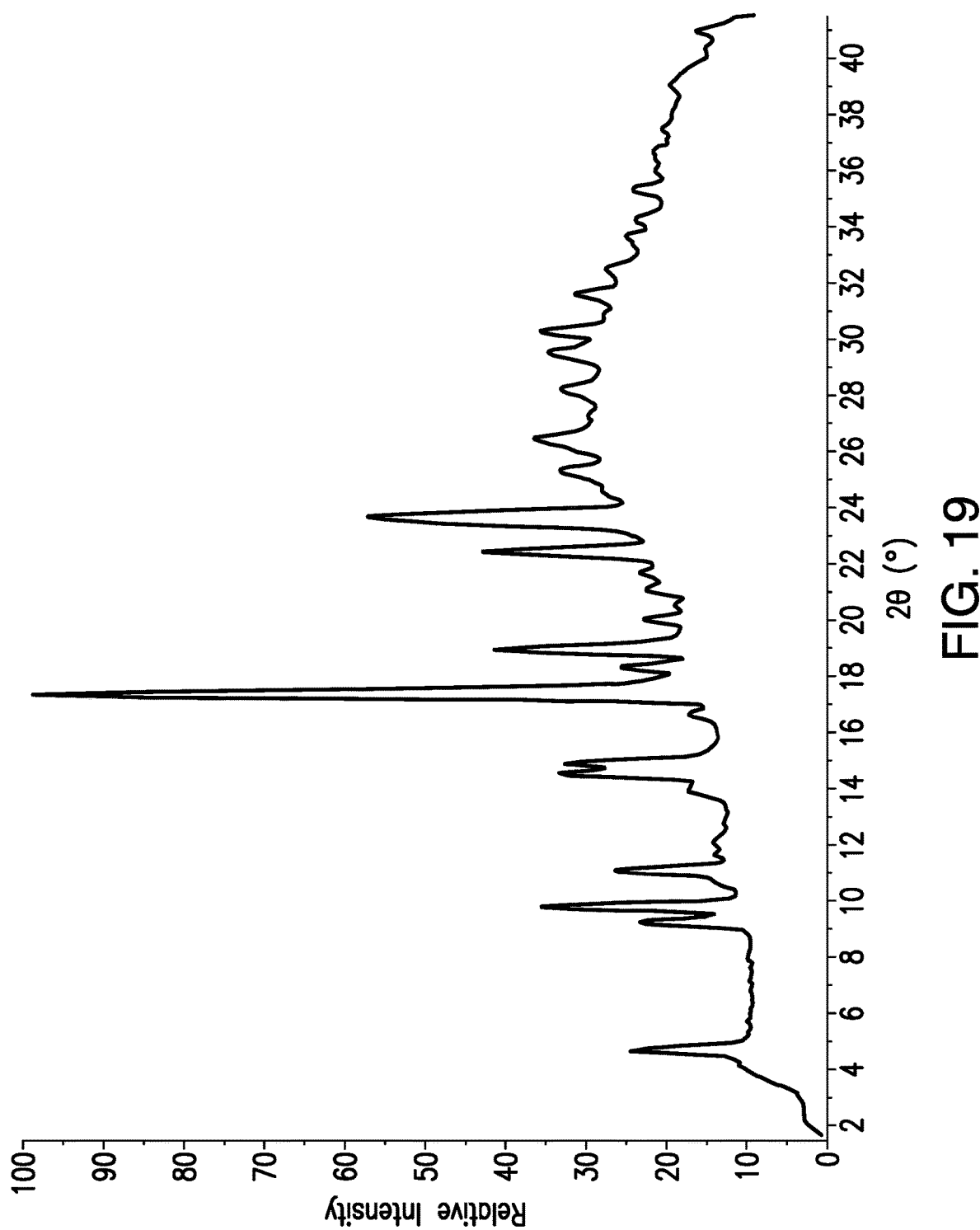
FIG. 19 is a X-Ray Powder Diffraction (XRPD) pattern obtained from a sample of brigatinib Form D. Relative Intensity (in counts) is shown on the vertical axis and the angle (in degrees two theta (° 2θ)) is shown on the horizontal axis.
Figure 19A:
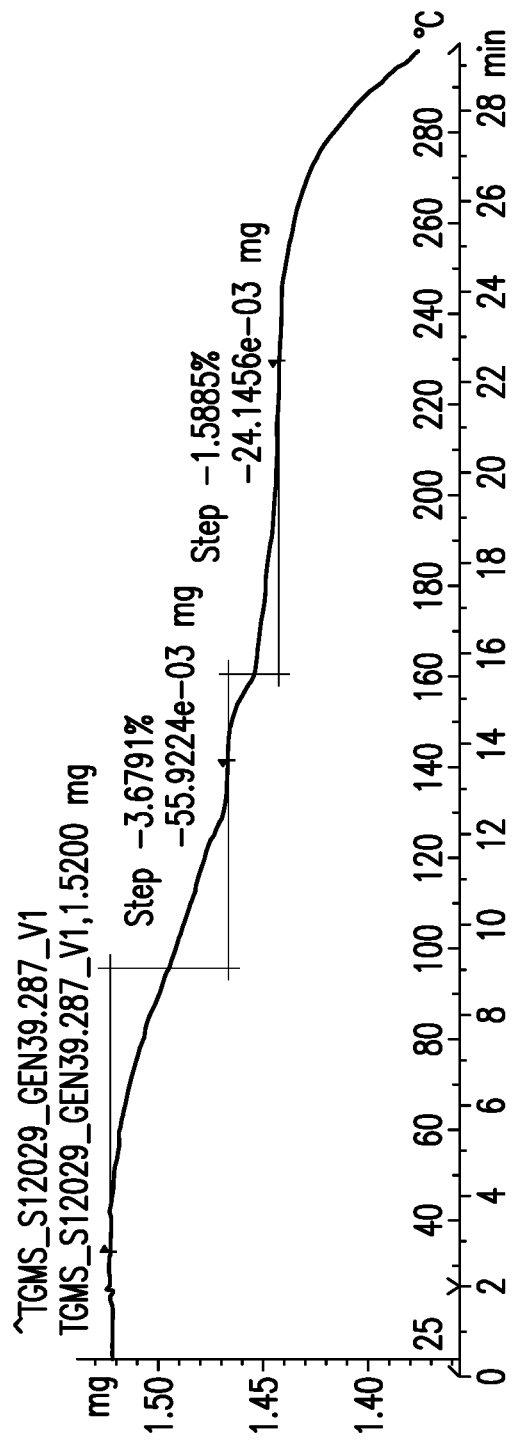
FIG. 19A is a thermogravimetric analysis/single differential thermal analysis thermogram (TGA/SDTA) for a sample of brigatinib Form D.
Figure 19B:
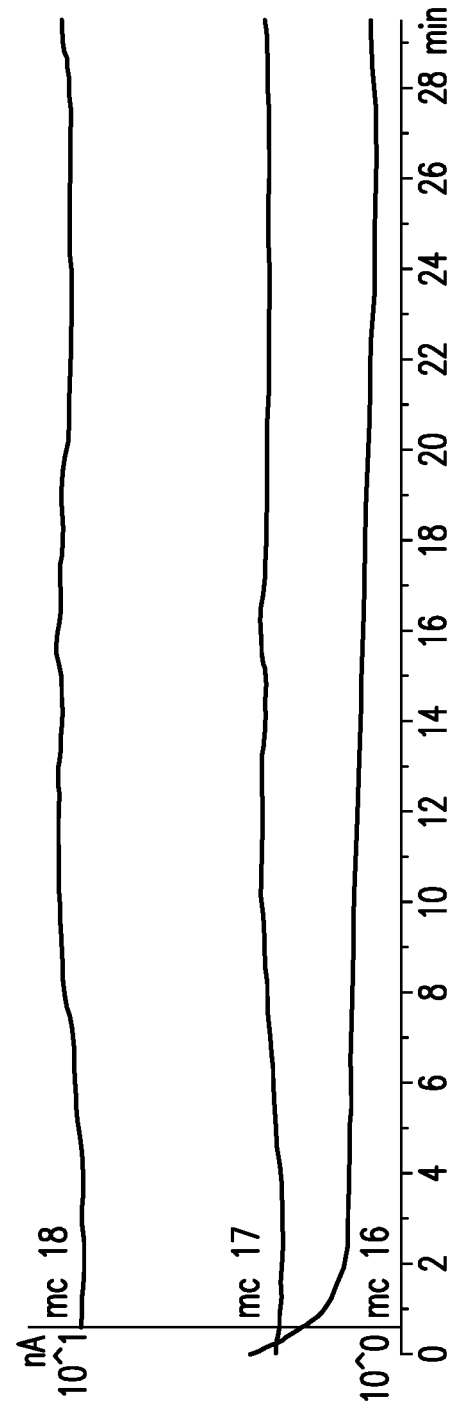
FIG. 19B is a thermogravimetric mass spectrometry (TGMS) thermogram for a sample of brigatinib Form D.

Samples of Form D were analyzed by X-ray powder diffraction (XRPD). In some embodiments, the present disclosure relates to crystalline Form D having an x-ray powder diffraction pattern substantially as shown in FIG. 19.

In some embodiments, the XRPD pattern of crystalline Form D has at least one, at least two, at least three, at least four, at least five, at least six, at least seven, at least eight, at least nine peaks expressed in degrees two-theta chosen from 4.7, 9.2, 9.7, 11.1, 14.5, 17.4, 18.9, 22.4, and 23.7. As previously noted, in some embodiments, a variance of ±0.3° 2θ may be observed in one or more 2-θ peak positions.

In some embodiments, the XRPD pattern of crystalline Form D has at least one, at least two, at least three, at least four, at least five, at least six, at least seven, at least eight, at least nine peaks expressed in degrees two-theta chosen from 4.66, 9.22, 9.74, 11.06, 14.54, 17.38, 18.94, 22.42, and 23.66. As previously noted, in some embodiments, a variance of ±0.30° 2θ may be observed in one or more 2-θ peak positions.

In some embodiments, the XRPD pattern of crystalline Form D has at least one, at least two, at least three, at least four, at least five peaks expressed in degrees two-theta chosen from 9.7, 11.1, 17.4, 18.9, and 23.7. As previously noted, in some embodiments, a variance of ±0.3° 2θ may be observed in one or more 2-θ peak positions.

In some embodiments, the XRPD pattern of crystalline Form D has at least one, at least two, at least three, at least four, at least five peaks expressed in degrees two-theta chosen from 9.74, 11.06, 17.38, 18.94, and 23.66. In some embodiments, a variance of ±0.3° 2θ may be observed in one or more 2-θ peak positions.

Conversion of Forms A-D:

Once Form A is obtained, no conventional method disclosed herein was found to convert this form to another form. Forms B, C and D, however, all interconverted depending on the temperature and relative humidity conditions.

At 30° C., increasing the humidity lead to hydration of Form B to Form C and eventually to Form D. The changes were reversible upon humidity decrease and occurred with a hysteresis: Form B converted to Form C at about 65% RH while Form C dehydrated to Form B at 25% RH. Similarly, Form C converted to Form D at about 90% RH while Form D partially dehydrated to Form C at 80% RH.

At ambient humidity, increasing the temperature lead to dehydration of Forms C and D to the anhydrous Form B (at about 40° C.) and to Form A via solid-solid transition at about 150° C. These conversions were not reversible: Form A remained stable upon temperature decrease.

Thermal stability and stability under moisture were assessed following storage for a maximum of 5 weeks at 50° C., 75° C. (for Form A) and 40° C./75% relative humidity (for both Forms A and B). Within this period samples were analyzed by XRPD and HPLC as follows: after 1 day, 3 days, 1 week, 2 weeks, 3 weeks, 4 weeks and 5 weeks. Form A was physically and chemically stable under all tested conditions. Form B, however, converted to the hydrated Form C after 1 day in the climate chamber and subsequently to Form A (partially) (data up to 3 weeks).

Figure 20A:
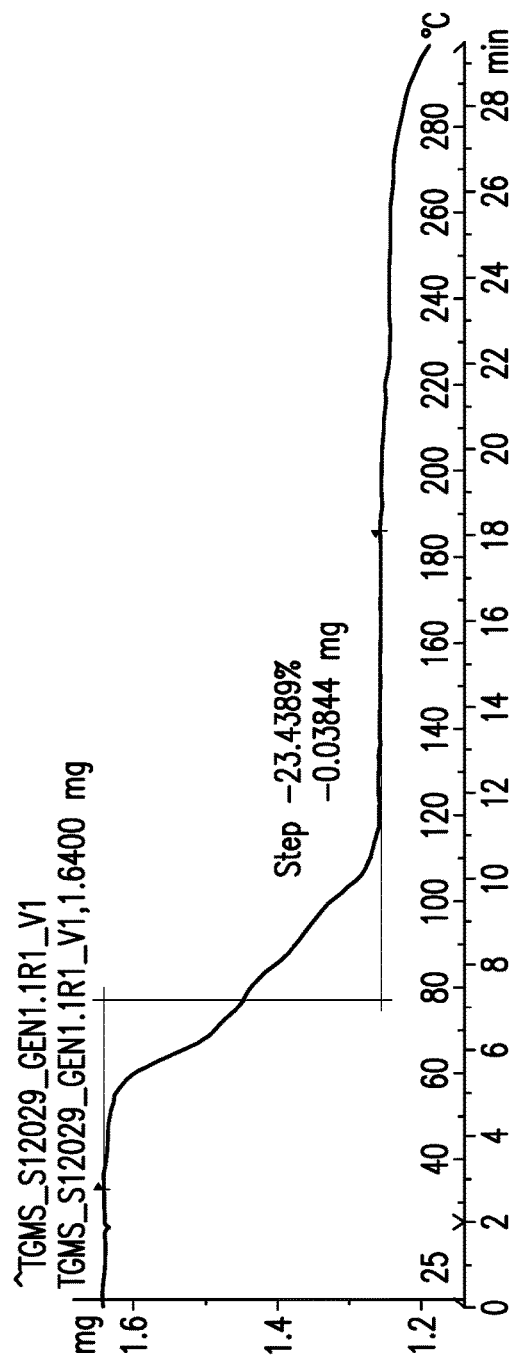
FIG. 20A is a thermogravimetric analysis/single differential thermal analysis (TGA/SDTA) of a sample of brigatinib Form E.
Figure 20B:
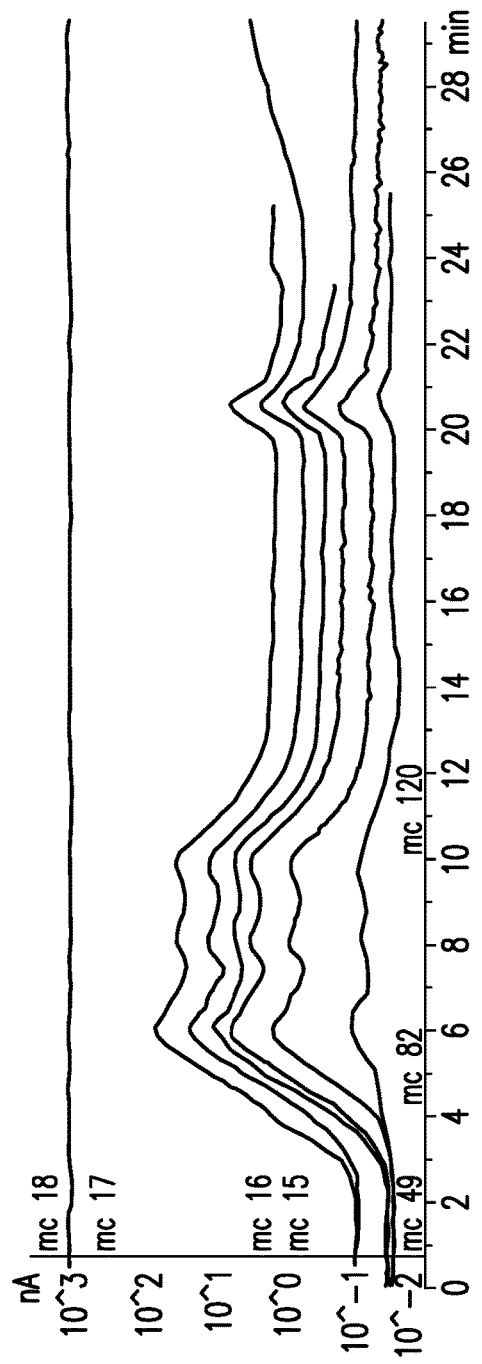
FIG. 20B is a thermogravimetric mass spectrometry (TGMS) thermogram of a sample of brigatinib Form E.

Form E:

Form E can be obtained from freeze-drying from chloroform, and is a chloroform solvate. Form E can also be obtained as a mixture with Form A by slurrying with chloroform. After several weeks at ambient temperature, Form E may revert to Form A as measured by XRPD. Analysis by TGA/SDTA (FIG. 20A) indicated a mass loss of 23.4% in the temperature range of 40-120° C., corresponding to 1.5 chloroform molecules per brigatinib molecule. According to the SDTA signal and the indicated melting point, the solid occurring upon desolvation is Form A.

In some embodiments, the present disclosure relates to crystalline Form E of brigatinib. In some embodiments, the present disclosure relates to crystalline Form E of brigatinib, wherein the crystalline Form E of brigatinib is substantially pure.

Figure 21:
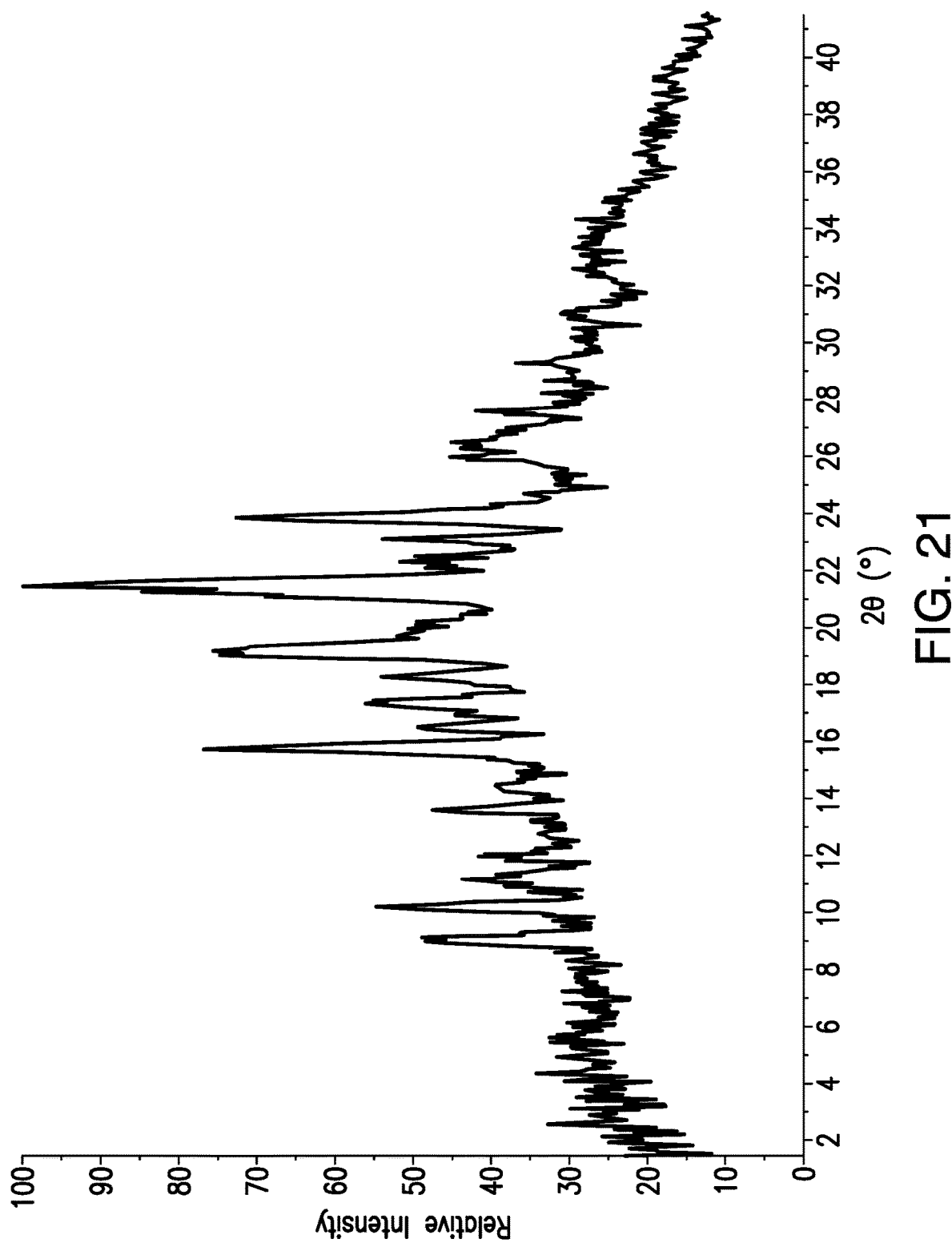
FIG. 21 is a X-Ray Powder Diffraction (XRPD) pattern obtained from a sample of brigatinib Form E. Relative Intensity (in counts) is shown on the vertical axis and the angle (in degrees two theta (° 2θ)) is shown on the horizontal axis.

Samples of Form E were analyzed by X-ray powder diffraction (XRPD). In some embodiments, the present disclosure relates to crystalline Form E having an x-ray powder diffraction pattern substantially as shown in FIG. 21.

In some embodiments, the XRPD pattern of crystalline Form E has at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen peaks expressed in degrees two-theta chosen from 9.1, 10.2, 11.2, 12.0, 13.7, 14.4, 15.8, 16.5, 17.4, 18.3, 19.2, 21.6, 22.3, 23.1, 23.9, 26.0, 26.4, 25.8, and 29.3. In some embodiments, a variance of ±0.3° 2θ may be observed in one or more 2-θ peak positions.

In some embodiments, the XRPD pattern of crystalline Form E has at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen peaks expressed in degrees two-theta chosen from 9.06, 10.22, 11.18, 11.98, 13.66, 14.42, 15.82, 16.54, 17.42, 18.34, 19.22, 21.62, 22.3, 23.14, 23.9, 26.02, 26.42, 25.78, and 29.34. In some embodiments, a variance of ±0.30° 2θ may be observed in one or more 2-θ peak positions.

In some embodiments, the XRPD pattern of crystalline Form E has at least one, at least two, at least three, at least four, at least five peaks expressed in degrees two-theta chosen from 9.1, 10.2, 15.8, 19.2, and 23.9. In some embodiments, a variance of ±0.3° 2θ may be observed in one or more 2-θ peak positions.

In some embodiments, the XRPD pattern of crystalline Form E has at least one, at least two, at least three, at least four, at least five peaks expressed in degrees two-theta chosen from 9.06, 10.22, 15.82, 19.22, and 23.9. In some embodiments, a variance of ±0.30° 2θ may be observed in one or more 2-θ peak positions.

Form F:

Form F was obtained from a freeze-drying experiment using TFE/water, and is a TFE solvate. Form F desolvated to give Form A upon heating or storage at ambient conditions for 8 weeks as measured by XRPD. Analysis by TGA/SDTA (FIG. 22) indicated a mass loss of 17.5% in the temperature range of 40-160° C., corresponding to 1.24 trifluoroethanol molecules per brigatinib molecule. According to the SDTA signal and the indicated melting point, the solid occurring upon desolvation is Form A.

In some embodiments, the present disclosure relates to crystalline Form F of brigatinib. In some embodiments, the present disclosure relates to crystalline Form F of brigatinib, wherein the crystalline Form F of brigatinib is substantially pure.

Figure 22:
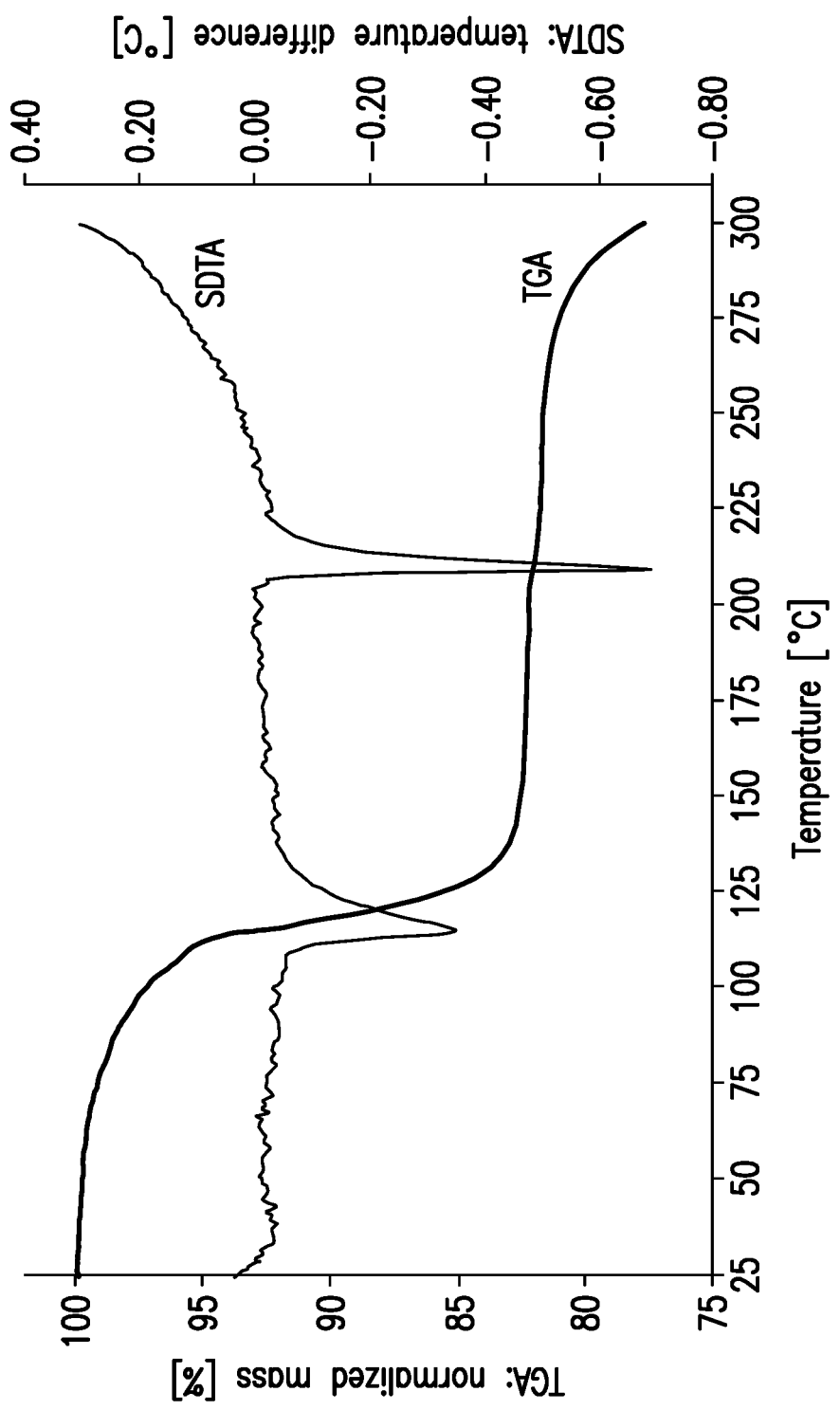
FIG. 22 is a thermogravimetric analysis/single differential thermal analysis (TGA/SDTA) of a sample of brigatinib Form F.
Figure 23:
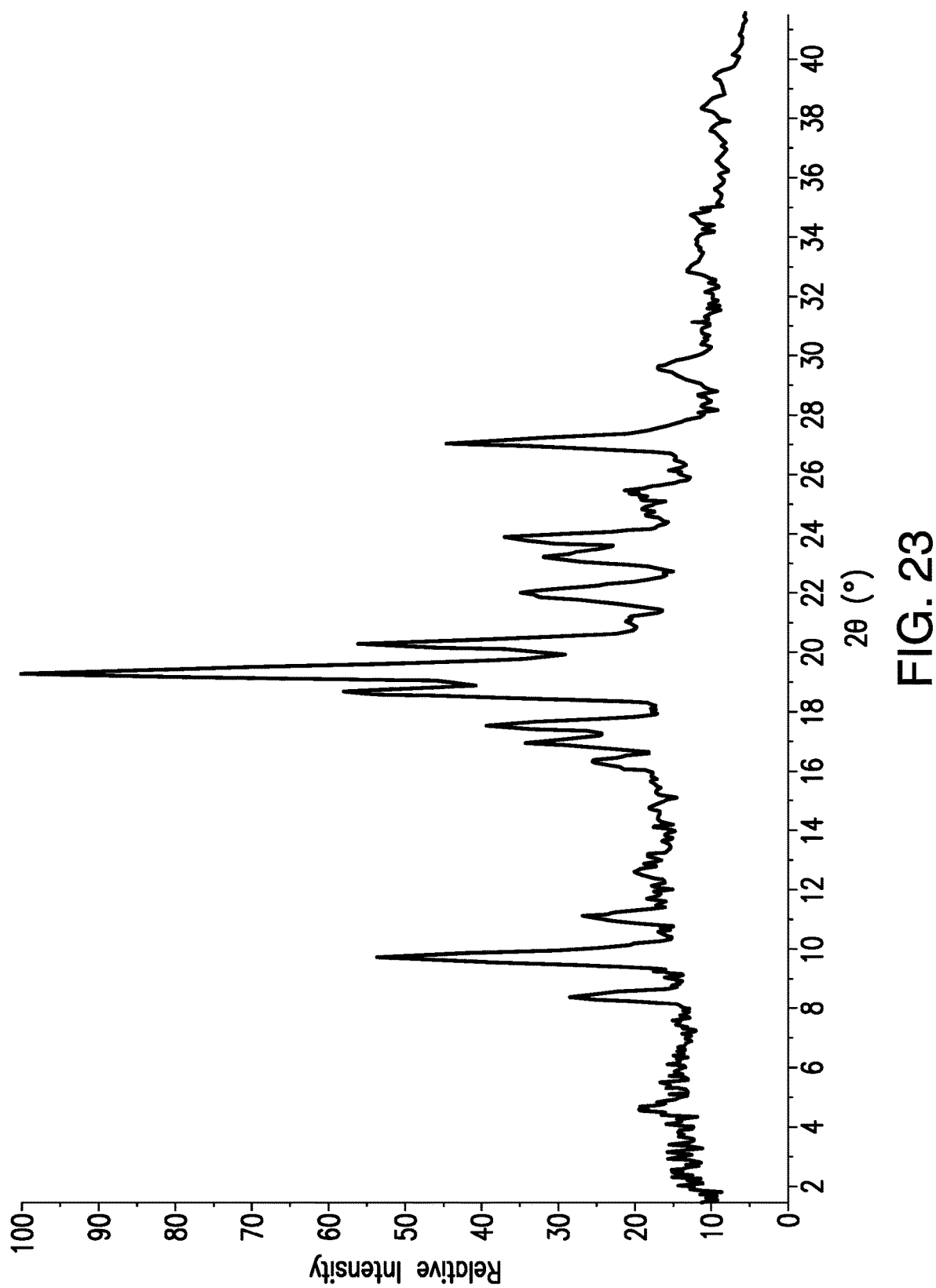
FIG. 23 is a X-Ray Powder Diffraction (XRPD) pattern obtained from a sample of brigatinib Form F. Relative Intensity (in counts) is shown on the vertical axis and the angle (in degrees two theta (° 2θ)) is shown on the horizontal axis.

Samples of Form F were analyzed by X-ray powder diffraction (XRPD). In some embodiments, the present disclosure relates to crystalline Form F having an x-ray powder diffraction pattern substantially as shown in FIG. 22.

In some embodiments, the XRPD pattern of crystalline Form F has at least one, at least two, at least three, at least four, at least five, at least six, at least seven, at least eight, at least nine, at least ten, at least eleven, at least twelve, at least thirteen peaks expressed in degrees two-theta chosen from 8.5, 9.8, 11.1, 16.3, 17.0, 17.6, 18.7, 19.4, 20.3, 22.0, 23.2, 23.9, and 27.1. In some embodiments, a variance of ±0.3° 2θ may be observed in one or more 2-θ peak positions.

In some embodiments, the XRPD pattern of crystalline Form F has at least one, at least two, at least three, at least four, at least five, at least six, at least seven, at least eight, at least nine, at least ten, at least eleven, at least twelve, at least thirteen peaks expressed in degrees two-theta chosen from 8.46, 9.78, 11.14, 16.34, 17.02, 17.58, 18.74, 19.38, 20.34, 22.02, 23.22, 23.86, and 27.1. In some embodiments, a variance of ±0.30° 2θ may be observed in one or more 2-θ peak positions.

In some embodiments, the XRPD pattern of crystalline Form F has at least one, at least two, at least three, at least four, at least five peaks expressed in degrees two-theta chosen from 9.8, 17.0, 19.4, 20.3, and 27.1. In some embodiments, a variance of ±0.3° 2θ may be observed in one or more 2-θ peak positions.

In some embodiments, the XRPD pattern of crystalline Form F has at least one, at least two, at least three, at least four, at least five peaks expressed in degrees two-theta chosen from 9.78, 17.02, 19.38, 20.34 and 27.1. In some embodiments, a variance of ±0.30° 2θ may be observed in one or more 2-θ peak positions.

Form G:

Form G was obtained from a crash crystallization experiment, with chloroform as solvent and acetonitrile as anti-solvent. Form G in mixture with Form A was also obtained from two other experiments using chloroform (anti-solvent addition and thermocycling). Remeasurement by XRPD of Form G, after storage of the measuring plate at ambient conditions for 5 weeks, showed that Form G had transformed to Form A. Form G may be an instable form, and may, for example, be a chloroform solvate, which desolvates and converts to Form A upon storage at ambient conditions.

In some embodiments, the present disclosure relates to crystalline Form G of brigatinib. In some embodiments, the present disclosure relates to crystalline Form G of brigatinib, wherein the crystalline Form G of brigatinib is substantially pure.

Figure 24:
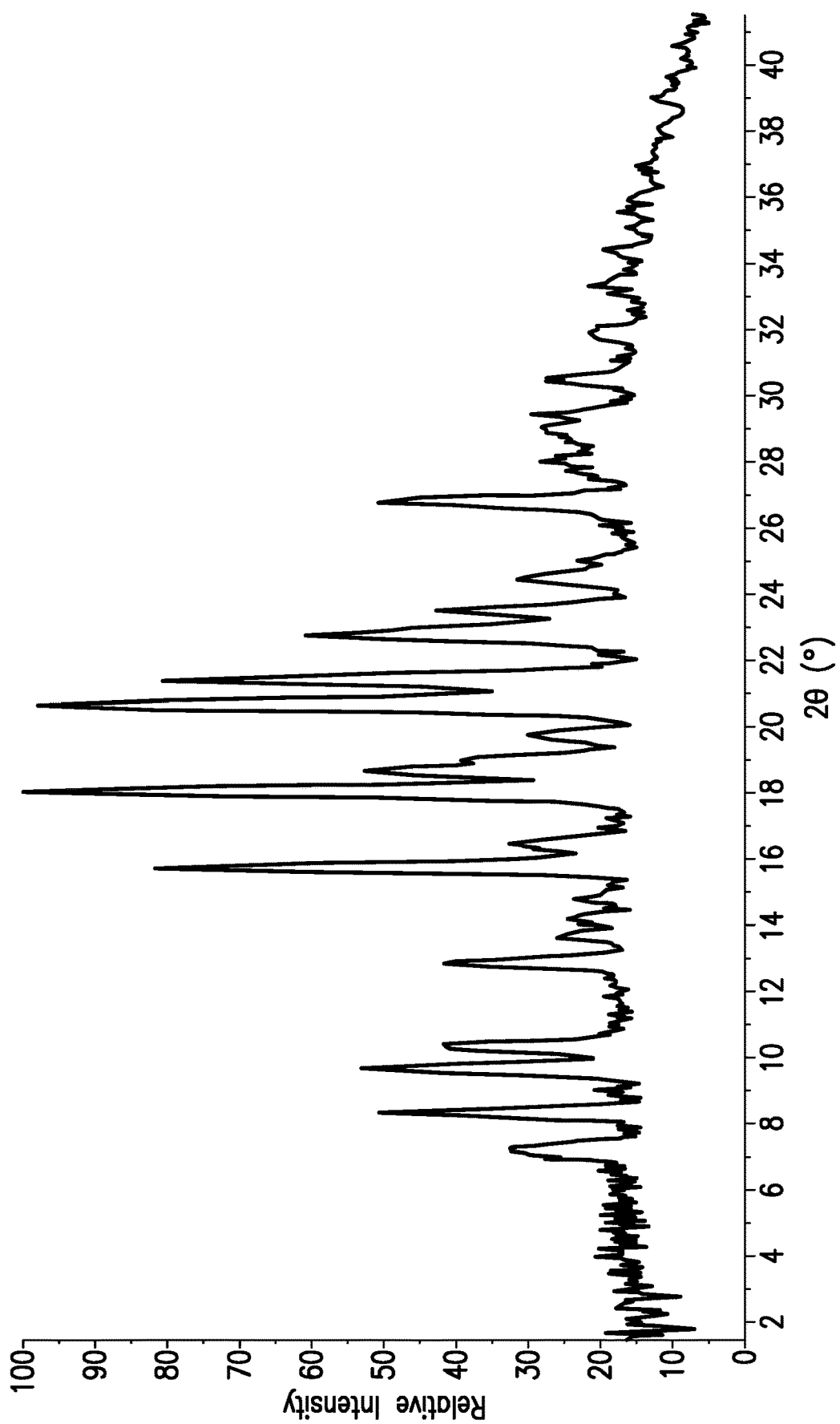
FIG. 24 is a X-Ray Powder Diffraction (XRPD) pattern obtained from a sample of brigatinib Form G. Relative Intensity (in counts) is shown on the vertical axis and the angle (in degrees two theta (° 2θ)) is shown on the horizontal axis.

Samples of Form G were analyzed by X-ray powder diffraction (XRPD). In some embodiments, the present disclosure relates to crystalline Form G having an x-ray powder diffraction pattern substantially as shown in FIG. 24.

In some embodiments, the XRPD pattern of crystalline Form G has at least one, at least two, at least three, at least four, at least five, at least six, at least seven, at least eight, at least nine, at least ten, at least eleven, at least twelve, at least thirteen, at least fourteen peaks expressed in degrees two-theta chosen from 7.2, 8.3, 9.7, 10.4, 12.9, 15.8, 18.1, 18.7, 20.7, 21.5, 22.8, 23.5, 24.5, and 26.8. In some embodiments, a variance of ±0.3° 2θ may be observed in one or more 2-θ peak positions.

In some embodiments, the XRPD pattern of crystalline Form G has at least one, at least two, at least three, at least four, at least five, at least six, at least seven, at least eight, at least nine, at least ten, at least eleven, at least twelve, at least thirteen, at least fourteen peaks expressed in degrees two-theta chosen from 7.22, 8.34, 9.7, 10.38, 12.86, 15.78, 18.1, 18.7, 20.74, 21.46, 22.82, 23.54, 24.5, and 26.82. In some embodiments, a variance of ±0.30° 2θ may be observed in one or more 2-θ peak positions.

In some embodiments, the XRPD pattern of crystalline Form G has at least one, at least two, at least three, at least four, at least five, at least six, at least seven, at least eight peaks expressed in degrees two-theta chosen from 8.3, 9.7, 12.9, 15.8, 18.1, 20.7, 22.8, and 26.8. In some embodiments, a variance of ±0.3° 2θ may be observed in one or more 2–θ peak positions.

In some embodiments, the XRPD pattern of crystalline Form G has at least one, at least two, at least three, at least four, at least five, at least six, at least seven, at least eight peaks expressed in degrees two-theta chosen from 8.34, 9.7, 12.86, 15.78, 18.1, 20.74, 22.82 and 26.82. In some embodiments, a variance of ±0.30° 2θ may be observed in one or more 2–θ peak positions.

Form H:

Form H can be obtained as a pure form or as a mixture with Form A through a cooling-evaporative method from a variety of solvents, such as for example ethanol/water, 1,4 dioxane/water, methanol, methanol/chloroform, and methanol/acetonitrile. Form H may be a solvate that accommodates small alcohols such as methanol, ethanol, and 1,4-dioxane. After storage at ambient conditions for 1-3 weeks, Form H had partially transformed to Form A as determined by XRPD.

In some embodiments, the present disclosure relates to crystalline Form H of brigatinib. In some embodiments, the present disclosure relates to crystalline Form H of brigatinib, wherein the crystalline Form H of brigatinib is substantially pure.

Figure 25:
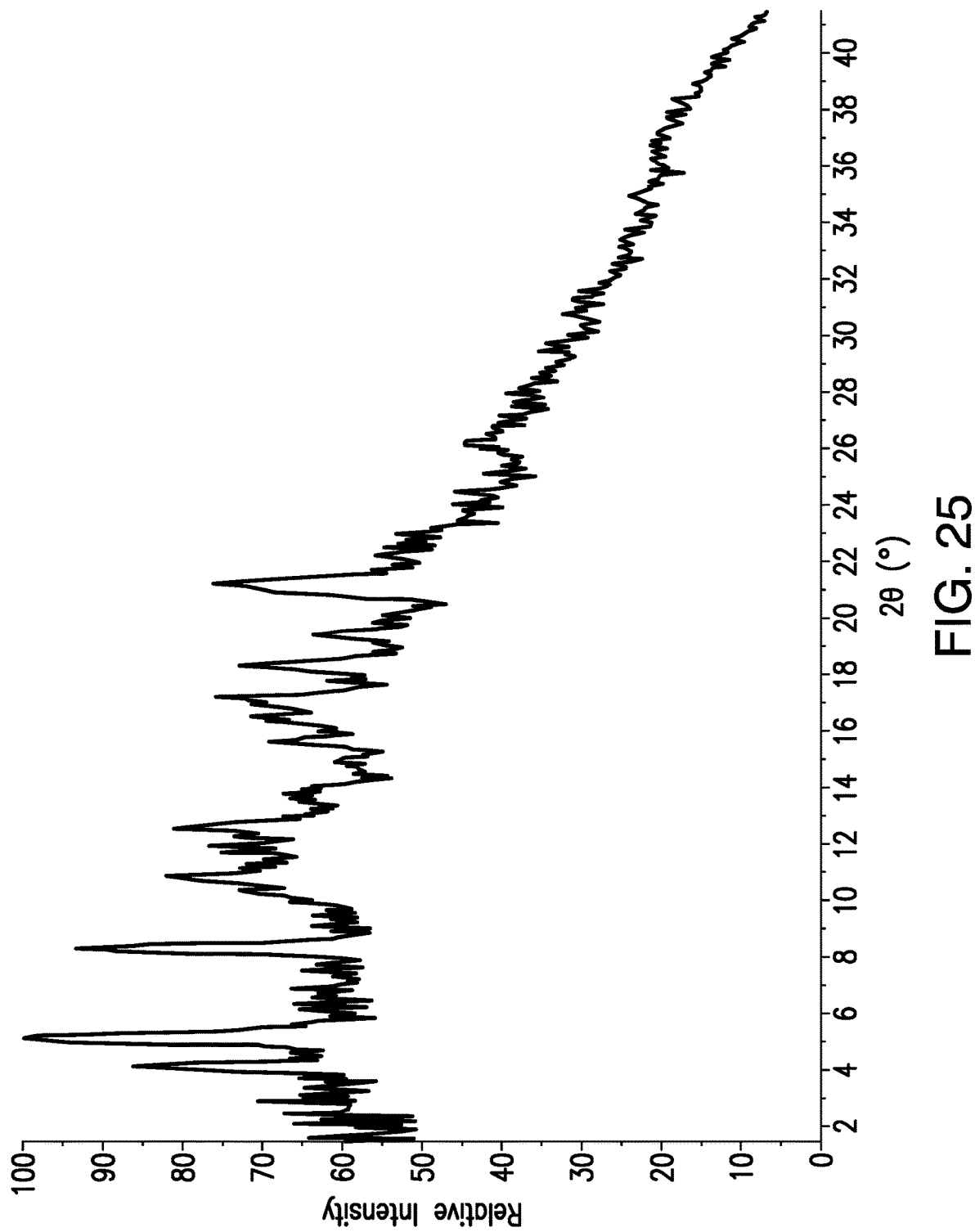
FIG. 25 is a X-Ray Powder Diffraction (XRPD) pattern obtained from a sample of brigatinib Form H. Relative Intensity (in counts) is shown on the vertical axis and the angle (in degrees two theta (° 2θ)) is shown on the horizontal axis.

Samples of Form H were analyzed by X-ray powder diffraction (XRPD). In some embodiments, the present disclosure relates to crystalline Form H having an x-ray powder diffraction pattern substantially as shown in FIG. 25.

In some embodiments, the XRPD pattern of crystalline Form H has at least one, at least two, at least three, at least four, at least five, at least six, at least seven, at least eight, at least nine, at least ten, at least eleven, at least twelve peaks expressed in degrees two-theta chosen from 4.2, 5.2, 8.4, 10.9, 12.7, 15.0, 15.7, 16.5, 17.2, 18.4, 19.5, and 21.3. In some embodiments, a variance of ±0.3° 2θ may be observed in one or more 2–θ peak positions.

In some embodiments, the XRPD pattern of crystalline Form H has at least one, at least two, at least three, at least four, at least five, at least six, at least seven, at least eight, at least nine, at least ten, at least eleven, at least twelve peaks expressed in degrees two-theta chosen from 4.22, 5.22, 8.38, 10.86, 12.66, 14.98, 15.74, 16.5, 17.18, 18.42, 19.5, and 21.3. In some embodiments, a variance of ±0.30° 2θ may be observed in one or more 2–θ peak positions.

In some embodiments, the XRPD pattern of crystalline Form H has at least one, at least two, at least three, at least four, at least five, at least six peaks expressed in degrees two-theta chosen from 4.2, 5.2, 8.4, 10.9, 12.7, and 21.3. In some embodiments, a variance of ±0.3° 2θ may be observed in one or more 2–θ peak positions.

In some embodiments, the XRPD pattern of crystalline Form H has at least one, at least two, at least three, at least four, at least five, at least six peaks expressed in degrees two-theta chosen from 4.22, 5.22, 8.38, 10.86, 12.66, and 21.30. In some embodiments, a variance of ±0.30° 2θ may be observed in one or more 2–θ peak positions.

Form J:

Form J was obtained as a mixture with Form A from 2-methoxyethanol in a cooling evaporative experiment at µL scale. Remeasurement by XRPD of the mixture of Forms A+J, after storage of the measuring plate at ambient conditions for 3 weeks, showed that the material was still a mixture of Forms A+J; however, the component of Form A was clearly larger.

Figure 26:
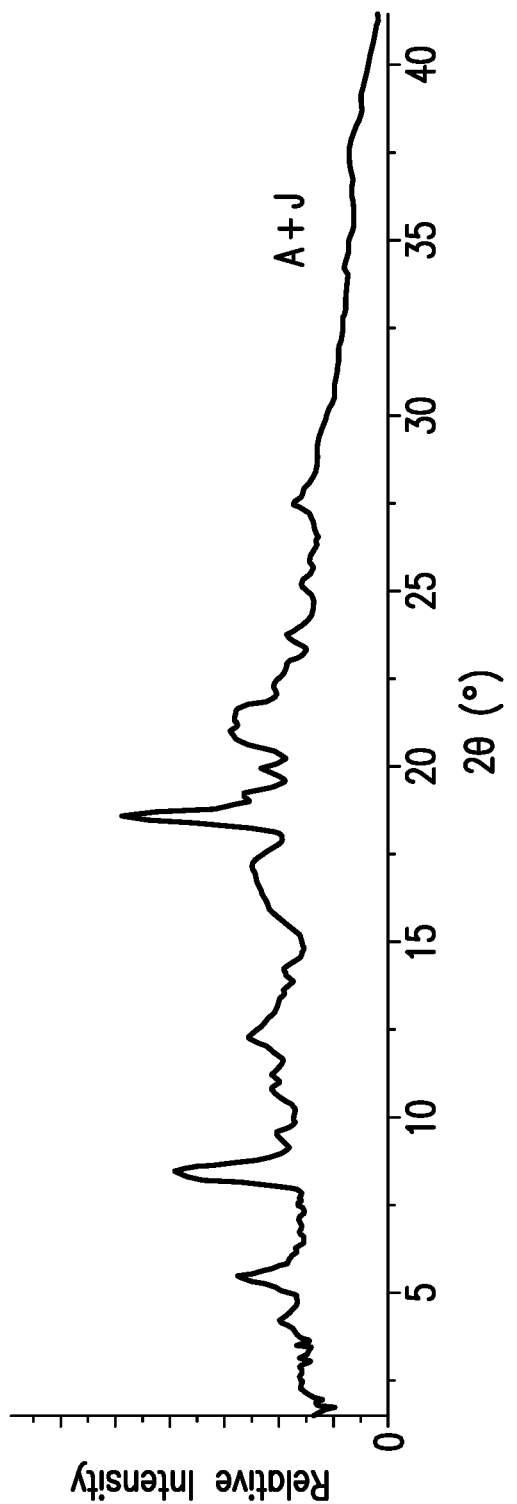
FIG. 26 is a X-Ray Powder Diffraction (XRPD) pattern obtained from the mixture of a sample of brigatinib Form A and Form J. Relative Intensity (in counts) is shown on the vertical axis and the angle (in degrees two theta (° 2θ)) is shown on the horizontal axis.

The mixture of Form A and Form J was analyzed by X-ray powder diffraction (XRPD) and the pattern is shown in FIG. 26. The XRPD pattern has at least one or all of the following peaks in degrees two theta (2θ) is shown for Forms A+J: 5.3, 7.6, 11.2, 17.6, 18.5, 19.8, and 21.3. In certain embodiments, the mixture of Forms A+J is characterized by a XRPD pattern comprising one or more of the following peaks in degrees two theta (2θ): 7.6, 17.6, and 21.3. In certain embodiments, the XRPD pattern of the mixture of Forms A+J can have two peaks or three peaks of the above-listed peaks.

Forms K and L:

Forms K and L were obtained as mixtures with Form A and their XRPD patterns exhibit only minor differences with that of Form A. Form K was obtained as a mixture with Form A from THF/NMP mixture in a cooling evaporative experiment at µL scale. Remeasurement by XRPD of the mixture of Forms A+K, after storage of the measuring plate at ambient conditions for 3 weeks, showed that the material was still a mixture of Forms A+K.

Form L was also obtained as a mixture with Form A from slurry experiments with n-heptane, hexane or methylcyclohexane. Remeasurement by XRPD of the mixtures A+L, after storage of the measuring plate at ambient conditions for 3 weeks, showed that the solids were still a mixture of A+L.

Figure 27A:
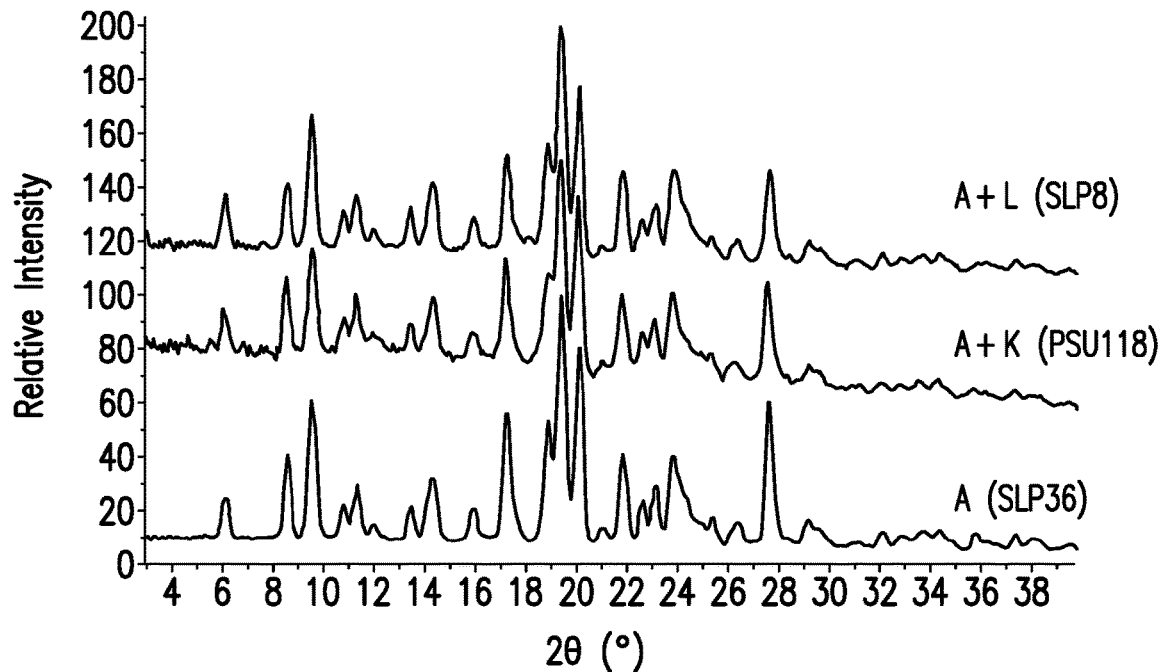
FIG. 27A is a X-Ray Powder Diffraction (XRPD) overlay pattern obtained from a sample of a mixture of brigatinib Form A and Form K, a sample of a mixture of brigatinib Form A and Form L, and a sample of brigatinib Form A. Relative Intensity (in counts) is shown on the vertical axis and the angle (in degrees two theta (° 2θ)) is shown on the horizontal axis.
Figure 27B:
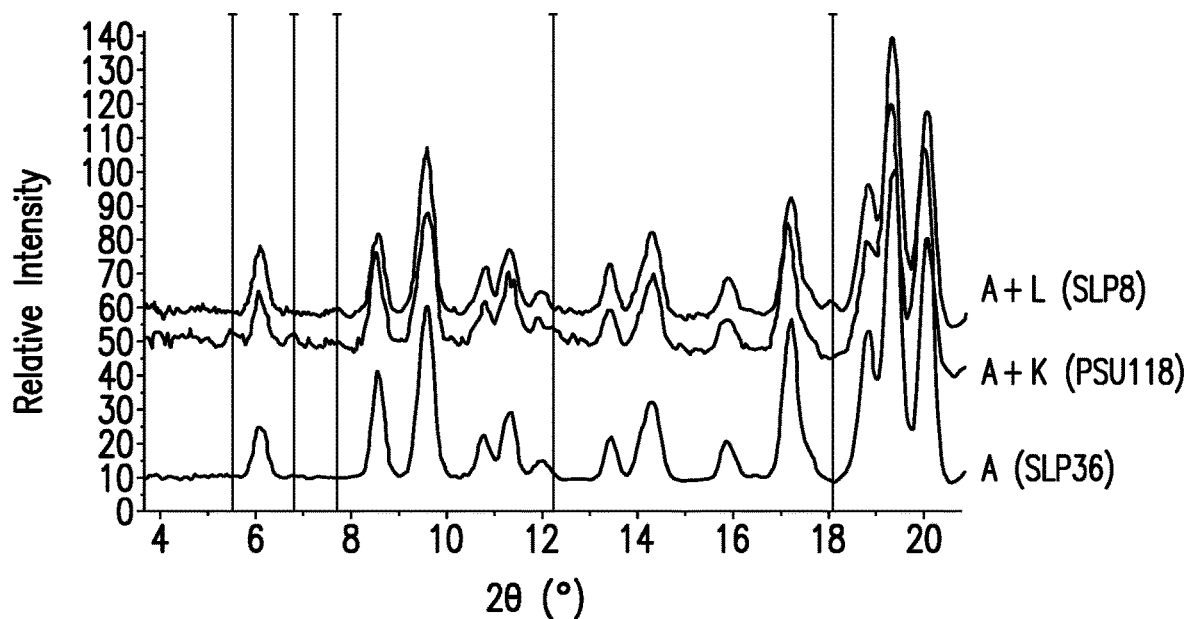
FIG. 27B is an expansion of FIG. 27A.

FIGS. 27A and 27B show the XRPD patterns observed for the mixtures A+K and A+L. The markers indicate the 2θ positions where the additional intensity peaks appear. For Form K, the peaks that are additional to Form A, as described above, include in degrees two theta (2θ): 5.5, 7.7, and 12.3. For Form L, the peak that is additional to Form A, as described above, in degrees two theta (2θ): 18.2. In certain embodiments, the XRPD patterns of either Form K or Form L can show two peaks or three peaks of the above-listed peaks.

Amorphous Form of Brigatinib

Figure 28:
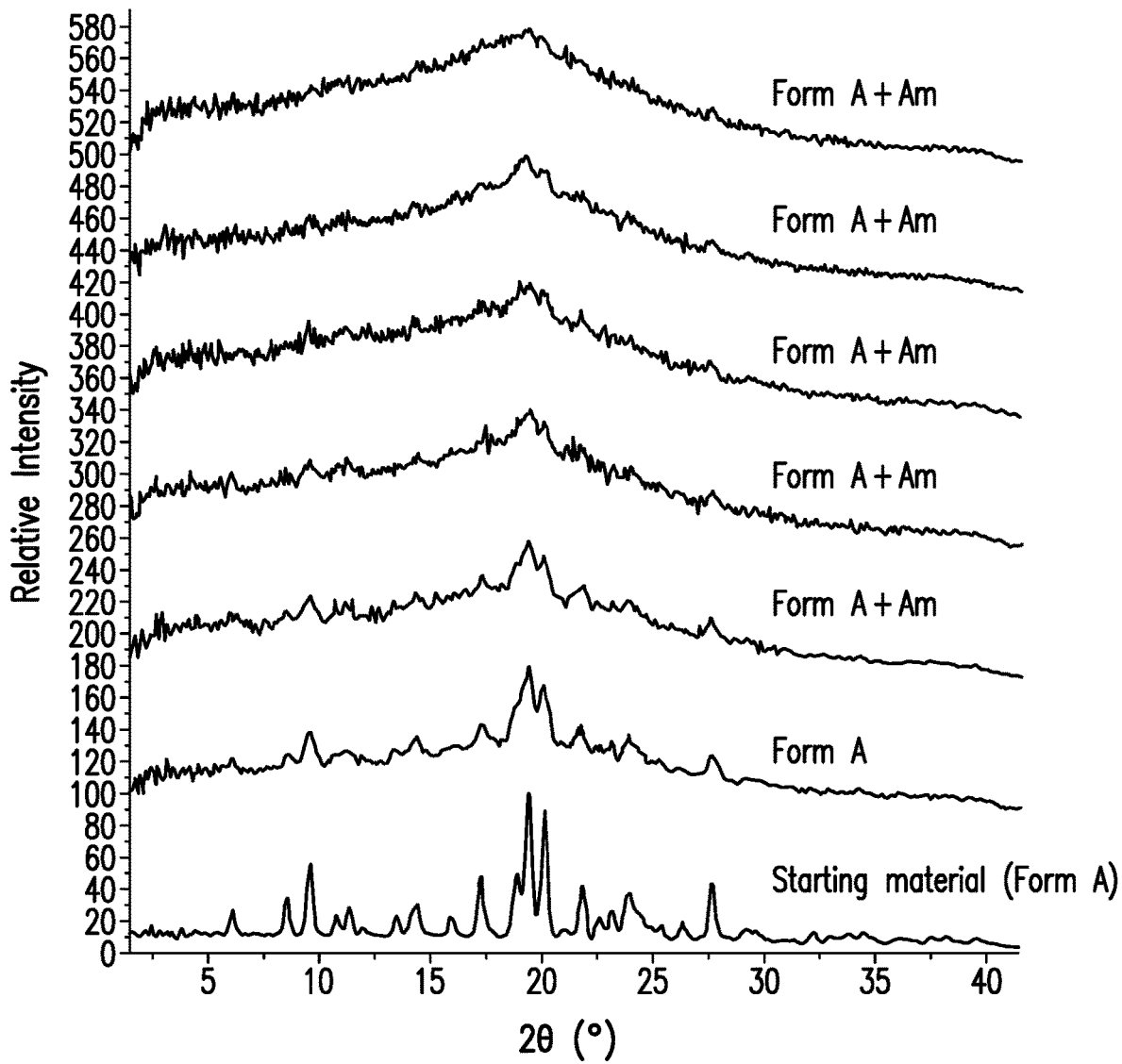
FIG. 28 contains overlaid X-Ray Powder Diffraction (XRPD) patterns of brigatinib Form A that has been subjected to grinding experiments for various lengths. Relative intensity (in counts) is shown on the vertical axis and the angle (in degrees two theta (° 2θ)) is shown on the horizontal axis.

Grinding experiments were performed to obtain amorphous brigatinib. After grinding a sample of Form A for 30 and 60 minutes, XRPD studies indicated an increase in amorphous content as shown in FIG. 28. Purity was assessed by HPLC and confirmed that chemical degradation did not occur during the grinding process. In a mechanical stress test via grinding, a sample of Form A was ground for 2, 3, 4 and 5 hours. Recovered solids were analyzed by XRPD and HPLC. By 5 hours, the sample was almost completely amorphous.

II. EXPERIMENTS IDENTIFYING BRIGATINIB POLYMORPHIC FORMS

Initial efforts to identify polymorphic forms of brigatinib were divided into two phases. Phase 1 included starting-material characterization, feasibility testing, solubility studies, compression studies, and intrinsic dissolution rate to provide data for the solvent selection for Phase 2. Phase 2 included polymorph screening experiments at milliliter (mL) and microliter (µL) scales. These efforts led to the identification of 10 polymorphic forms: Form A, Form B, Form C, Form D, Form E, Form F, Form G, Form H, Form J, and Form K.

Phase 1: Starting Material Characterization

The starting material, brigatinib, was provided as an off-white solid and its chemical purity was assessed by HPLC as 99.9%. Mass spectral data confirmed the molecular weight of brigatinib to be 584 g/mol. TGA and TGMS analyses showed 0.23% of mass loss (corresponding to about 0.08 water molecules per Form A molecule) in the temperature interval of 30° C.-100° C. DSC analysis showed an endothermic event with $T_{peak}$=214.5° C., related to melting of the compound, brigatinib. The water content of Form A was determined by coulometric Karl Fischer method. The average water content from two determinations was found to be 0.32%. Representative residual heavy metals in brigatinib Form A were determined by ICP-MS. The detected elements included cadmium (0.02 ppm), copper (0.14 ppm), molybdenum (0.10 ppm), palladium (0.087 ppm) and silver (0.03 ppm). The following metals were not detected: antimony, arsenic, bismuth, lead, mercury and tin.

NaOH titration experiments were performed to investigate the influence of the NaOH addition rate and crystallization temperature on the isolated crystal form. A stock solution of brigatinib Form A was prepared by weighing in 450 mg of Form A and slurrying in 9 mL water for 10 min. A quantity of 4.5 mL of 1M HCl was added to dissolve the brigatinib (final API concentration 33.3 mg/mL). For each experiment, 3 mL of stock solution was added in an 8 mL vial, containing a stirring bar, pH probe and tubing connected to the titrator (Titrino). The vial was placed in the Crystalline and brought to temperature before initiating NaOH titration. A volume of 3 mL 0.1M NaOH solution was titrated at a predefined rate. During the experiment, bottom stirring at 500 rpm was applied. While brown solids appeared during titration; upon stirring (10 min) the color changed to pink. Subsequently, all solids were separated from the solution by centrifugation, washed two times with 5 mL of water and then dried.

Four sets of NaOH addition rate (mL/min) and temperature ° C. conditions were evaluated: 0.02 mL/min at 25° C., 20 mL/min at 60° C., 0.05 mL/min at 25° C., and 20 mL/min at 60° C. Direct formation of Form A is possible from aqueous media when the process occurs at 60° C. and a slow NaOH addition is applied. A fast NaOH addition led to a mixture of Form A and the hepta-hydrated Form D while at 25° C., the crystallized from was the heptahydrate independently of the NaOH addition rate.

Phase 1: Solubility Study

Quantitative solubility testing was performed on brigatinib starting material, employing a set of 24 solvents (DMSO, heptane and water were performed in triplicate). In a vial, about 40 mg of starting material, 400 μL of solvent and a stir bar were added. After stirring for 24 h at 20° C. for 24 hours, the liquid was retrieved, filtered, and analyzed for API content by HPLC. The residual solids were characterized by XRPD and found to be Form A. The results are summarized in Table 7.

TABLE 7

Solubility of Brigatinib

| Solvent name | Solubility (mg/mL) | XRPD Form[1] |
|---|---|---|
| Acetone | 0.69 | Form A |
| Acetonitrile | 0.36 | Form A |
| 1-Butanol | 17.74 | Form A |
| 2-Butanone | 1.11 | Form A |
| Butyl acetate | 0.32 | Form A |
| Chloroform[1] | >181.8 | — |
| Cyclohexane | UR[2], <0.01 | Form A |
| 1,2-Dichloroethane | 38.29 | Form A |
| Dichloromethane[1] | >196.87 | — |
| 1,2-Dimethoxyethane | 1.13 | Form A |

TABLE 7-continued

Solubility of Brigatinib

| Solvent name | Solubility (mg/mL) | XRPD Form[1] |
|---|---|---|
| Dimethyl Sulfoxide | 2.95 | Form A |
| Dimethyl Sulfoxide | 3.02 | Form A |
| Dimethyl Sulfoxide | 3.05 | Form A |
| N,N-Dimethylacetamide | 0.47 | Form A |
| 1,4-Dioxane | 4.01 | Form A |
| Ethanol | 6.71 | Form A |
| Ethyl Acetate | 0.42 | Form A |
| Ethyl Formate | 0.99 | Form A |
| n-Heptane | UR, <0.01 | Form A |
| n-Heptane | UR, <0.01 | Form A |
| n-Heptane | UR, <0.01 | Form A |
| Isopropyl acetate | UR, <0.01 | Form A |
| Methanol | 35.31 | Form A |
| Nitromethane | 0.41 | Form A |
| Isopropanol | 1.55 | Form A |
| Tetrahydrofuran | UR, <0.01 | Form A |
| Water | 0.09 | Form A |
| Water | 0.09 | Form A |
| Water | 0.09 | Form A |
| p-Xylene | 0.35 | Form A |
| 2,2,2-trifluoroethanol[3] | >224 | — |
| 2,2,2-trifluoroethanol/water (90:10)[3] | >172 | — |
| 2,2,2-trifluoroethanol/water (80:20)[3] | >159 | — |

[1]Samples were dissolved after 24 h equilibration time, no solids were harvested.
[2]Under Range, lower then detection limit, the concentration is lower than 0.22 mg/mL
[3]Data obtained from freeze drying experiment The solubility of Form A was also evaluated in Simulated Gastric Fluid and observed to be 52 mg/ml. At 37° C. in aqueous buffers, solubilities of Form A were observed to be 70 mg/mL (in pH 1.0), 26 mg/mL (in pH 4.5) and 6 mg/mL (in pH 6.5).

In a second solubility study, the solubility of Forms A and B were determined in triplicate at 25° C. and 37° C. in water, pH 1.0 buffer (0.1 N HCl), pH 4.5 acetate buffer, pH 6.5 phosphate buffer and simulated gastric fluid SGF at 37° C. For each medium, a standard 1.8 mL screw cap vial was charged with circa 40 mg of the starting material, 400 μl of solvent and a magnetic stirring bar (in the cases of chloroform and dichloromethane 200 μl of solvent were used). The vials were subsequently closed and equilibrated at the corresponding temperature for 24 h while stirring. The liquid part was retrieved with a syringe and filtered (0.5 micron filter); the isolated mother liquors were diluted to two dilutions selected according to the calibration curve. Quantities of the API in the diluted solutions were determined via HPLC analysis (DAD). The calibration curve was obtained from two independently prepared stock solutions of compound brigatinib in 50% water/50% acetonitrile/0.1% TFA. Subsequently, the separated solids were measured wet by XRPD to confirm the solid form of which the solubility was measured.

Figure 29:
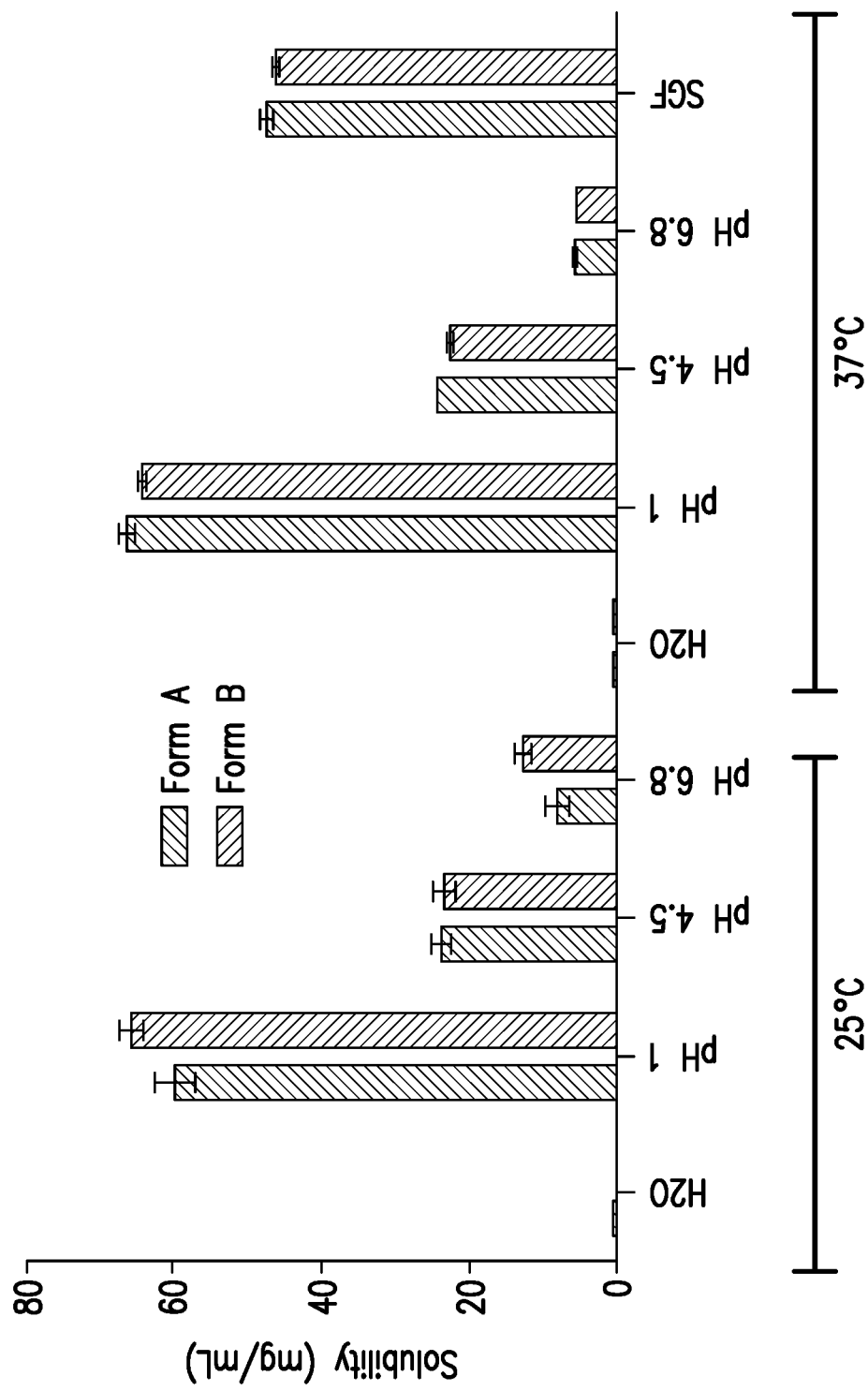
FIG. 29 depicts the solubility data for brigatinib Form A and Form B at 25° C. and 37° C., at varying pH values.

In Table 8, the solid forms of the separated slurries are listed. Form A remained stable in all media, while Form B converted to the hydrated Forms D and/or C in the experiments at 25° C. and to Form A in the experiments at 37° C. At the latter temperature and in water, Form B converted to the hydrates C and D and not to A as in the rest of the media. The solubility of Form B could not be measured as it converted to other solid forms. The average solubility values, shown in the same table, refer to the solid form to which the initially placed Form B was transformed. Hence, it was not possible to measure the solubility of Form B but rather that of Form C (and of C+D). The solubility values are plotted in FIG. 29. The solubility is greater in acidic media compared to basic ones.

TABLE 8

Form Attained at Solubility Study Conclusion

| | Initial Form | | | | | | | |
|---|---|---|---|---|---|---|---|---|
| | Form A | | | | Form B | | | |
| | Temp | | | | | | | |
| | 25° C. | | 37° C. | | 25° C. | | 37° C. | |
| Medium | Form | Solub (mg/mL) | Form | Solub (mg/mL) | Form | Solub (mg/mL) | Form | Solub (mg/mL) |
| water | A | 0.11 ± 0.0 | A | 0.1 ± 0.0 | C | 0.1 ± 0.0 | C + D | 0.3 ± 0.0 |
| pH 1.0 | A | 60.4 ± 2.9 | A | 70.6 ± 1.5 | C | 68.6 ± 2.0 | A | 70.7 ± 0.6 |
| pH 4.5 | A | 24.4 ± 1.2 | A | 26.0 ± 0.0 | C + D | 24.8 ± 1.4 | A | 25.1 ± 0.3 |
| pH 6.8 | A | 8.6 ± 1.4 | A | 6.2 ± 0.1 | C + D | 13.2 ± 1.3 | A | 6.0 ± 0.1 |
| SGF | — | — | A | 51.7 ± 0.6 | — | — | A | 51.3 ± 0.3 |

In a third solubility study, Form A was measured in different buffer solutions as shown in Table 9.

TABLE 9

Solubility Measurements of Form A in Buffers

| Slurry pH | Buffer | Conc. (mg/mL) |
|---|---|---|
| 1.7-2 | HCl/KCl | 177 |
| 2.4 | Potassium hydrogen phthalate/HCl | 329 |
| 3.6 | Potassium hydrogen phthalate/HCl | 173 |
| 6.2 | KH$_2$PO$_4$/NaOH | 8 |
| 7.2 | KH$_2$PO$_4$/NaOH | 11 |

Phase 1: Feasibility Study

Feasibility tests were performed to attempt to obtain amorphous starting material that could be employed in some crystallization techniques of the Phase 2 portion of the study. Two techniques were employed, i.e. grinding and freeze-drying. The results are presented below.

Grinding. Two grinding experiments were performed on samples of Form A with two different durations (30 and 60 min) at a frequency of 30 Hz. Their amorphous content increased with time, but their purity was stable at about 100%. Mechanical stress via grinding experiments were also performed, with grinding times of 2, 3, 4, and 5 hours. Similarly, amorphous content increased without degradation of chemical purity.

Freeze-drying. Six freeze-drying experiments were performed with samples of Form A as described in Table 10. Samples 1, 2, and 4 remained mostly crystalline, but samples 3 and 5 were amorphous and contained about 15-16% residual solvent. Sample 6 was amorphous and contained about 7% residual solvent. Forms E and F were produced using this method. However, due to the variable form and solvation, freeze-drying was not further employed to obtain amorphous brigatinib.

TABLE 10

Freeze-drying Feasibility Study of Brigatinib, Form A

| sample | Solvent | starting material (mg) | Solvent volume (µL) Concentration (mg/mL) | Form Obtained (XRPD) | Solvent content (%) |
|---|---|---|---|---|---|
| 1 | Chloroform | 19.9 | 100 199 | Form E | 23.4 |
| 2 | Dichloromethane | 19.9 | 100 199 | Form A | 2.23 |
| 3 | 2,2,2-Trifluoroethanol | 22.4 | 100 224 | Form A + amorphous | 15.0 |
| 4 | 2,2,2-Trifluoroethanol/Water 90/10 | 17.2 | 100 172 | Form F | 17.5 |
| 5 | 2,2,2-Trifluoroethanol/Water 80/20 | 15.9 | 100 159 | Form A + amorphous | 16.1 |
| 6 | 2,2,2-Trifluoroethanol/Water 50/50 | 20.2 | 500 40.4 | amorphous | 6.9 |

Phase 1: Compression

Compression tests were performed on brigatinib Form A in order to determine whether pressure-induced phase transformations or loss of crystallinity occurred. The press used was an Atlas Manual 25 Ton Hydraulic Press (from SPECAC). Experiments were carried out at 3 and 6 ton/cm$^2$ for one minute in each case. The pressed solids were measured by XRPD and no phase transitions or peak shifts in the XRPD patterns were revealed. The purity by HPLC of the two samples subjected to the compression tests were both determined to be comparable to that of the starting material.

Phase 1: Intrinsic Dissolution Rate

For measuring the intrinsic dissolution rate (IDR), the starting material was tableted using a mini-IDR compression system (pION/Heath Scientific). For preparation of the tablets, approximately 11 mg of material was pressed in the cylindrical hole of a passivated stainless steel die, to a uniform, flat surface, with an exposed area of 0.072 cm$^2$. The pressure applied was approximately 50 bar for 3-5 min. The sample die was inserted in a cylindrical Teflon rotating disk carrier containing an embedded magnetic stirring bar at its base. The die/stirrer assembly was placed in a flat bottomed glass vial, ready for dissolution analysis.

The dissolution rate was measured in 20 mL of solvent (medium) and the path length of the UV meter was 2 mm. Applied stirring speed during measurement was 100 rpm. Measurements were performed at 20° C. and 37° C.

For determining the dissolution rate from a powdered sample, approximately 5 mg of brigatinib (Form A or B) was weighed into a 5 mL dissolution vial and the dissolution probe was inserted into the vial. Subsequently, 4 mL of water was added at the same time the measurement was initiated. The concentration was recorded for 20 h.

In the first series, the IDR of Forms A and B were determined in monoplicate. The measurements were carried out in at 25° C. and 37° C. in water, pH 1.0 (0.1 N HCl) buffer, pH 6.8 phosphate buffer and in simulated gastric fluid SGF. In FIGS. 30-37, the IDRs are plotted for comparison between the forms and the same medium or between various media and the same form. The IDR of each of Forms A and B in the various media increases with increasingly acidic media (see FIGS. 34-37).

The intrinsic dissolution rate measurements of Form A in pH 1.0 and SGF shows that, within 5 min, roughly a concentration of 0.25 mg/ml could be reached. That indicates that, in the stomach, together with a 200 ml glass of water, about 50 mg of Form A could be dissolved (numbers are only indicative).

Furthermore, the IDR experiments show that Form A remains stable when slurried in water, SGF, and pH 1.0 aqueous buffer. Based on those results, no conversion would be expected to take place in the stomach.

In several cases, the results were counter-intuitive. These results were related to (1) the dissolution rate of the compound at 25° C. being higher compared to that at 37° C. (in the cases of Form A in water and pH 6.5 buffer—for the first 3-4 min—and of Form B in pH 6.5 buffer—in the whole range), while it is expected that the IDR at 37° C. would be the highest; and (2) the IDR of Form A being higher compared to that of Form B, at pH 6.5 buffer, while one would expect the opposite on the basis of the relative stability of Forms A and B. To further study these results, two additional series of experiments were performed: (a) the IDR's of Forms A and B were measured (in monoplicate) in water at 25° C. and in pH 6.5 buffer at 25° C. and 37° C.; and (b) the IDR's of Form A were measured in triplicate in water and pH 6.5 buffer at 25° C. The results of these additional experiments are plotted in FIGS. 38-42.

Figure 30A:
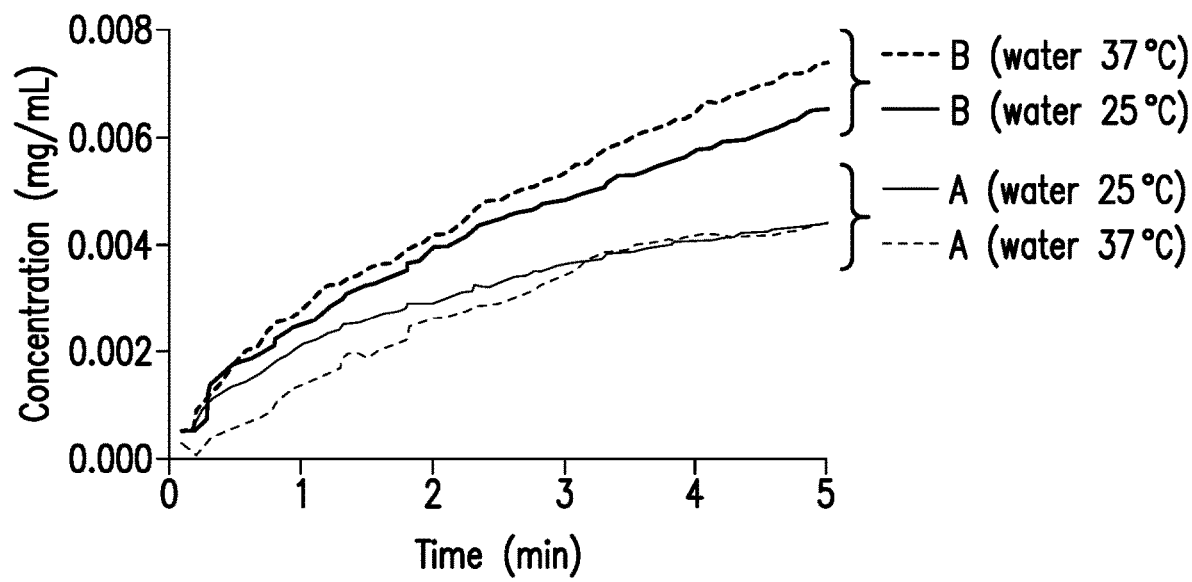
FIG. 30A is an expansion graph of FIG. 30B, showing the concentrations of brigatinib Forms A and B vs. time obtained from the intrinsic dissolution rate (IDR) experiments, where concentration (mg/mL) is plotted on the vertical axis and time (min) is plotted on the horizontal axis.
Figure 30B:
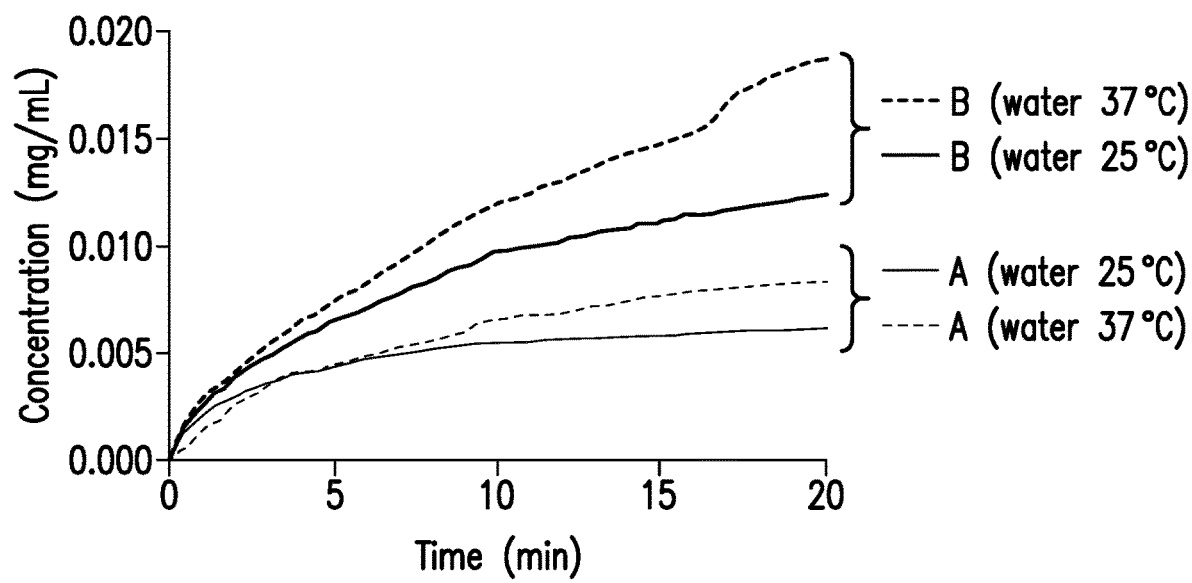
FIG. 30B is a plot of the concentrations of brigatinib Forms A and B vs. time obtained from the intrinsic dissolution rate (IDR) experiments, where concentration (mg/mL) is plotted on the vertical axis and time (min) is plotted on the horizontal axis.
Figure 38A:
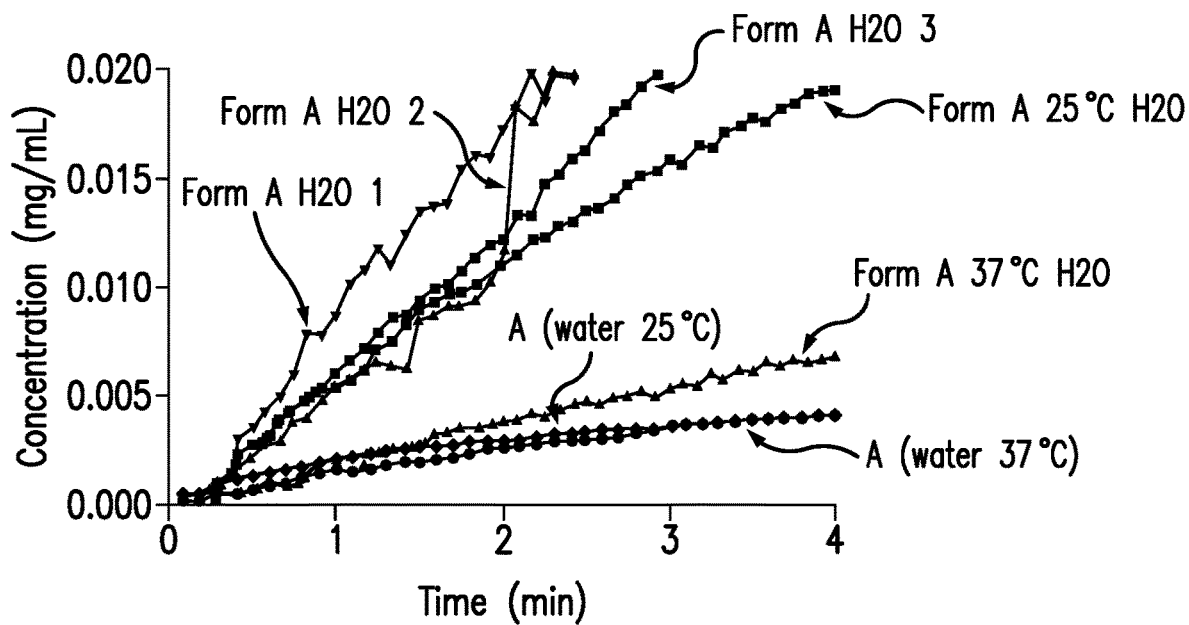
FIG. 38A is an expansion graph of FIG. 38B, showing the concentration of brigatinib Form A vs. time obtained from the IDR experiments in water at 25° C. and 37° C. Concentration (mg/mL) is plotted on the vertical axis and time (min) is plotted on the horizontal axis.
Figure 38B:
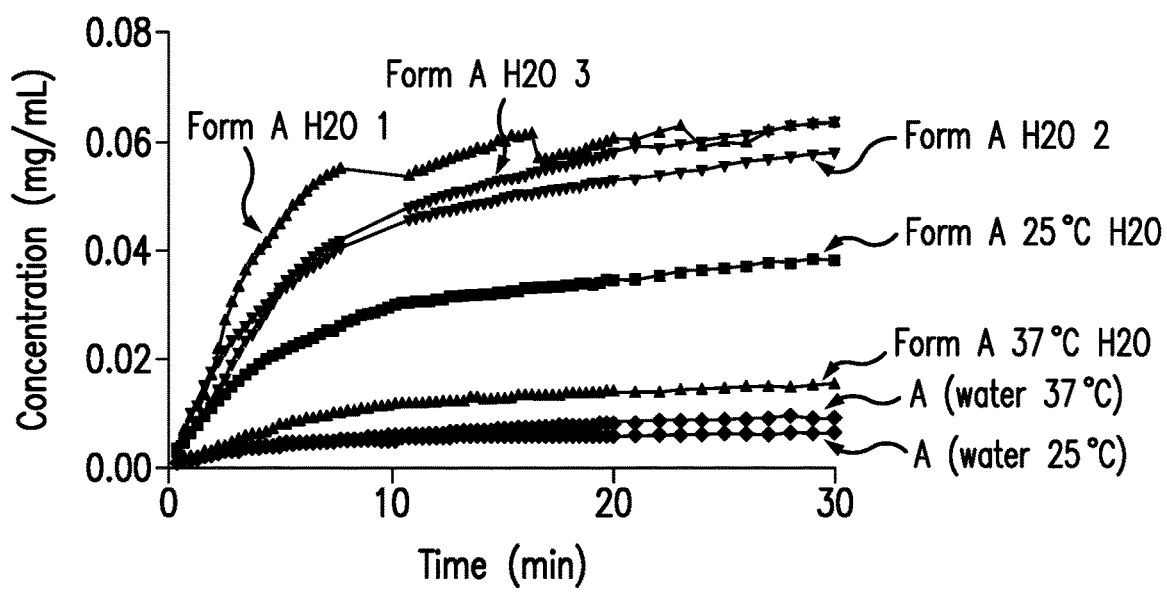
FIG. 38B is a plot of the concentration of brigatinib Form A vs. time obtained from the IDR experiments in water at 25° C. and 37° C. Concentration (mg/mL) is plotted on the vertical axis and time (min) is plotted on the horizontal axis.

With respect to the first observation (IDR of Form A higher at 25° C. compared to that at 37° C.), the following comments can be made:

FIG. 30: The IDR of Form A in water at 25° C. appears to be higher for the first 3 min. One possibility for this result is detachment of a tablet grain, which adds to the concentration. Thereafter, the concentrations of both Forms A and B are higher at 37° C., which is as expected. However, remeasurements of the IDR of Form A in water at both temperatures, showed considerable variability (FIGS. 38A/B). One possibility for this result is the low concentrations, which make the measurement more sensitive to measuring conditions.

Figure 31:
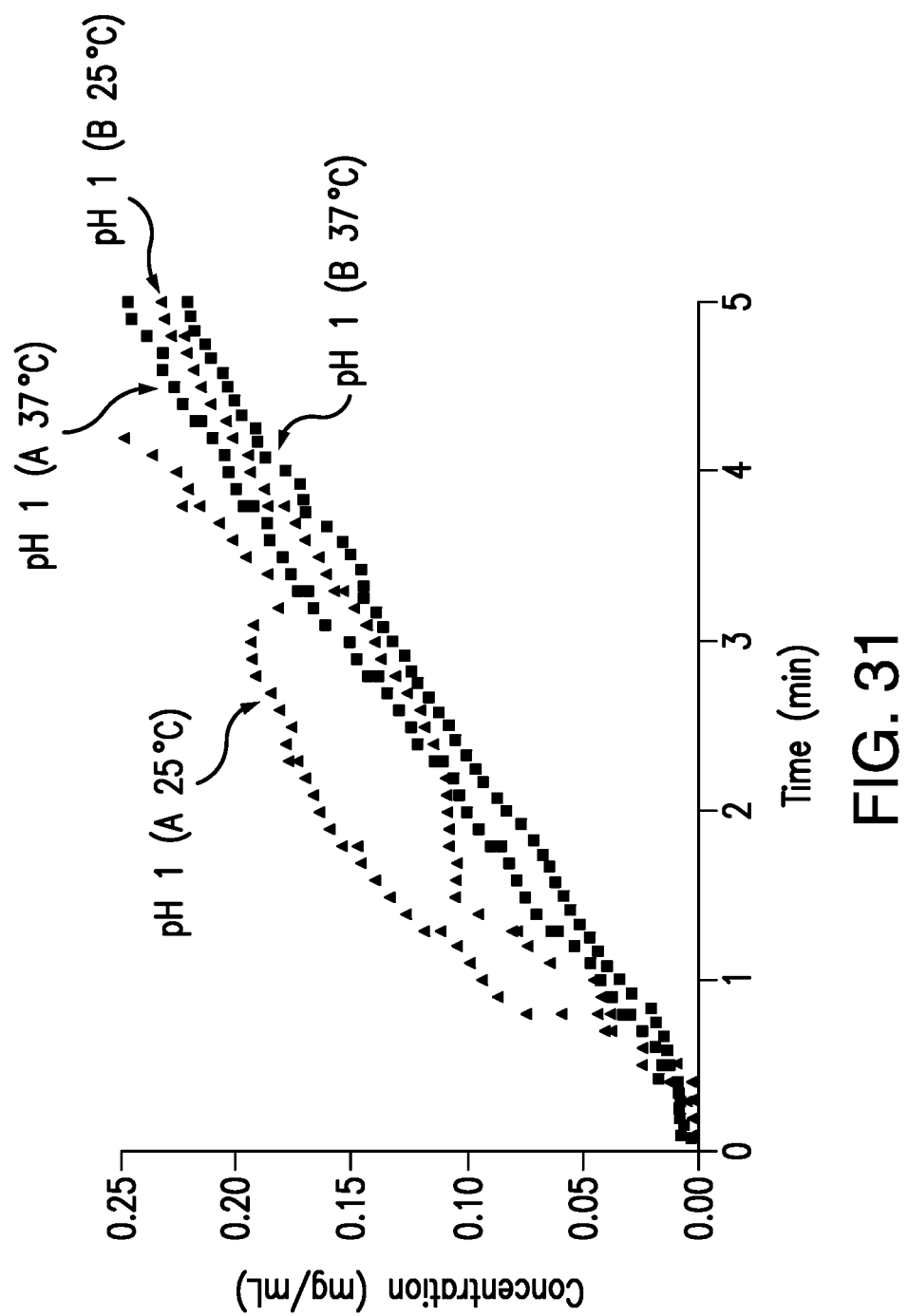
FIG. 31 is a plot of concentration of brigatinib Forms A and B vs. time obtained from the IDR experiments at 25° C. and 37° C. in pH 1.0 HCl buffer. Concentration (mg/mL) is shown on the vertical axis and time (min) is shown on the horizontal axis.

FIG. 31: Similarly, the IDRs in pH 1.0 buffer of both Forms A and B at 25° C. appear to be higher, one possibility is the detachment of tablet grains, as the large increase in concentration (at about 1 min) in both cases indicates. Concentrations higher than 0.25 mg/mL are not plotted as the detector reaches saturation at about these values.

Figure 32A:
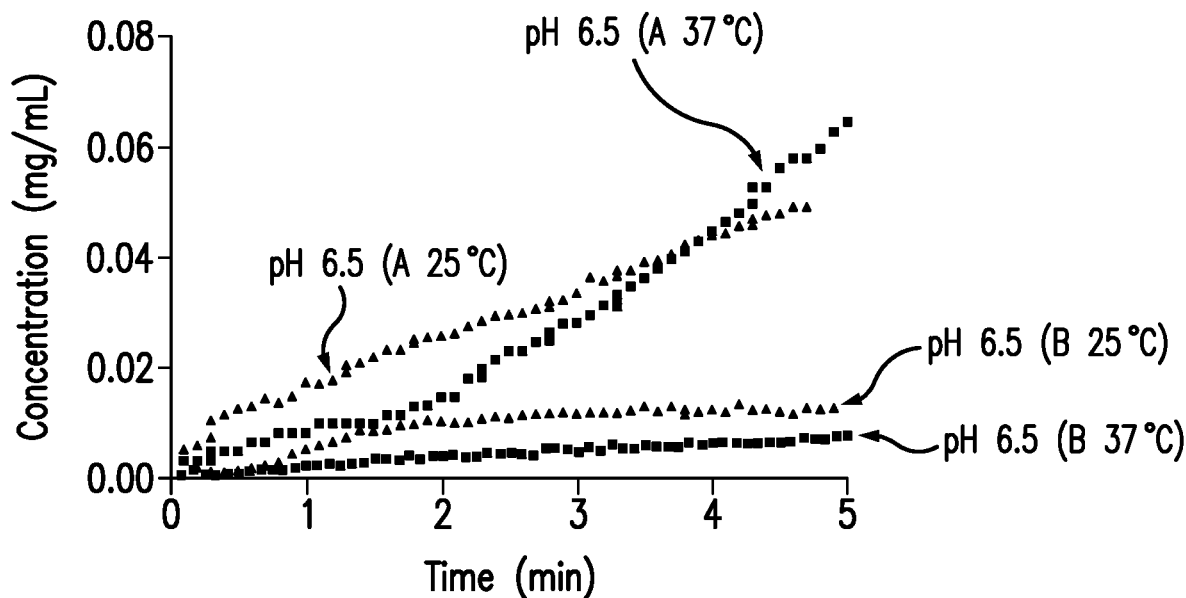
FIG. 32A is an expansion graph of FIG. 32B, showing the plot of the concentration of brigatinib Form A and Form B vs. time obtained from the IDR experiments at 25° C. and 37° C. in pH 6.5 buffer. Concentration (mg/mL) is plotted on the vertical axis and time (min) is plotted on the horizontal axis.
Figure 32B:
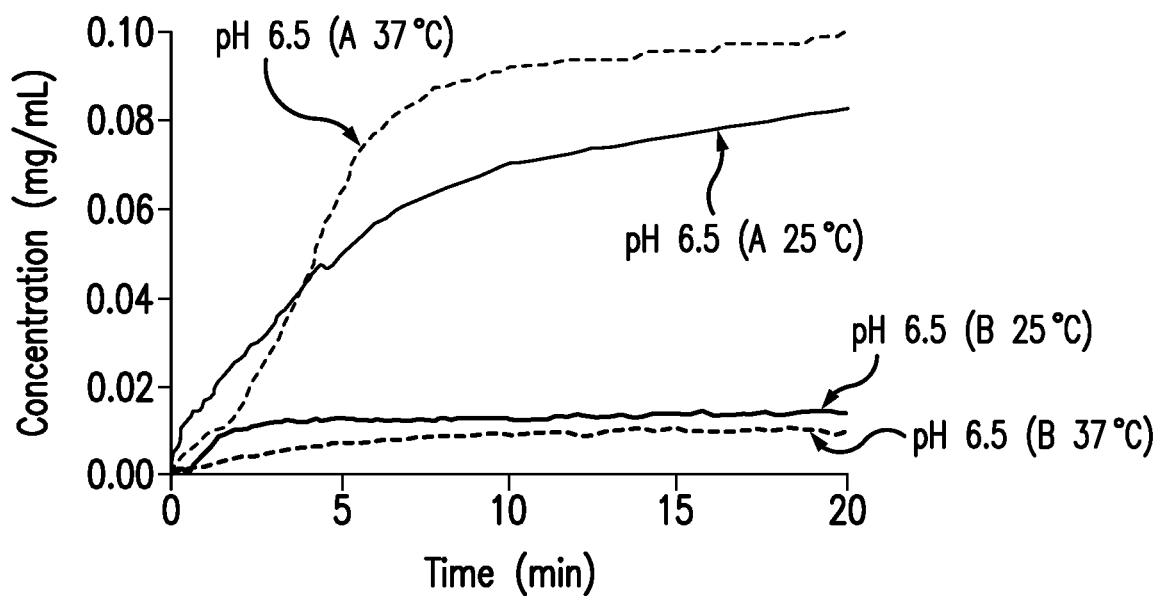
FIG. 32B is a plot of the concentration of brigatinib Form A and Form B vs. time obtained from the IDR experiments at 25° C. and 37° C. in pH 6.5 buffer. Concentration (mg/mL) is plotted on the vertical axis and time (min) is plotted on the horizontal axis.
Figure 39A:
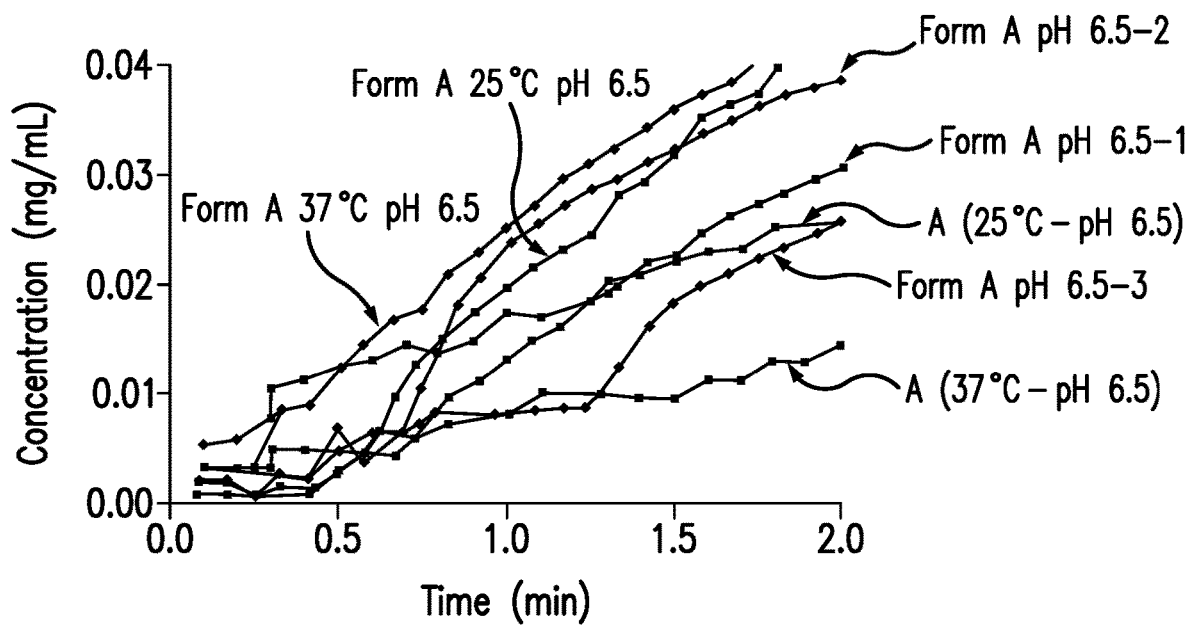
FIG. 39A is an expansion graph of FIG. 39B, showing the concentration of brigatinib Form A. vs. time obtained from the IDR experiments in pH 6.5 buffer at 25° C. and 37° C. Concentration (mg/mL) is plotted on the vertical axis and time (min) is plotted on the horizontal axis.
Figure 39B:
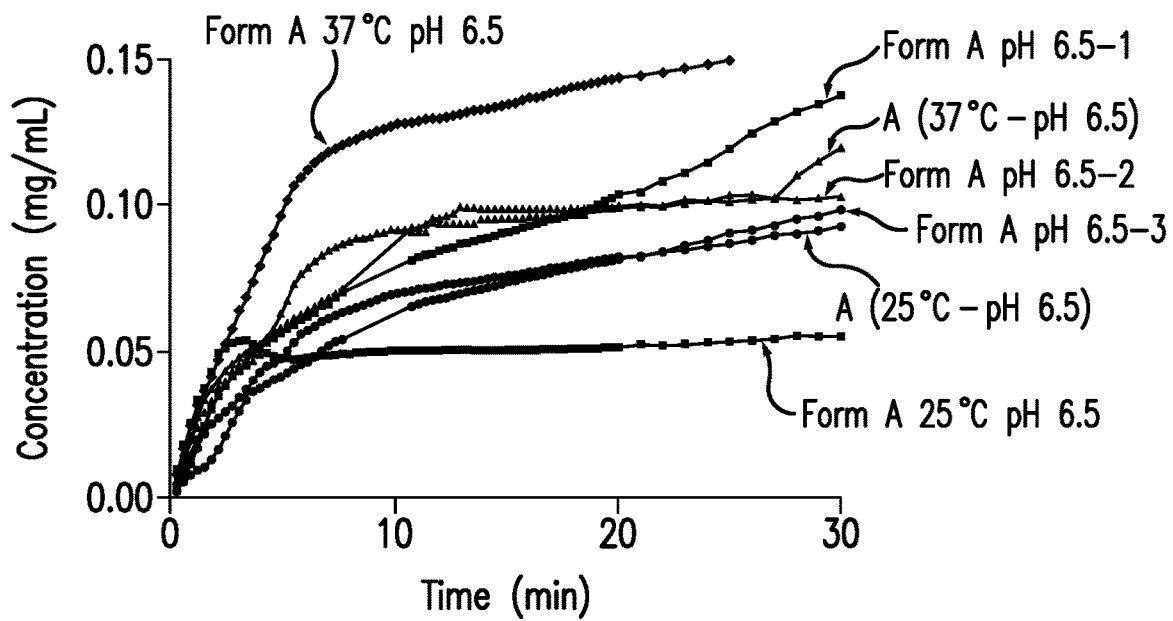
FIG. 39B is a plot of the concentration of brigatinib Form A vs. time obtained from the IDR experiments in pH 6.5 buffer at 25° C. and 37° C. Concentration (mg/mL) is plotted on the vertical axis and time (min) is plotted on the horizontal axis.
Figure 40A:
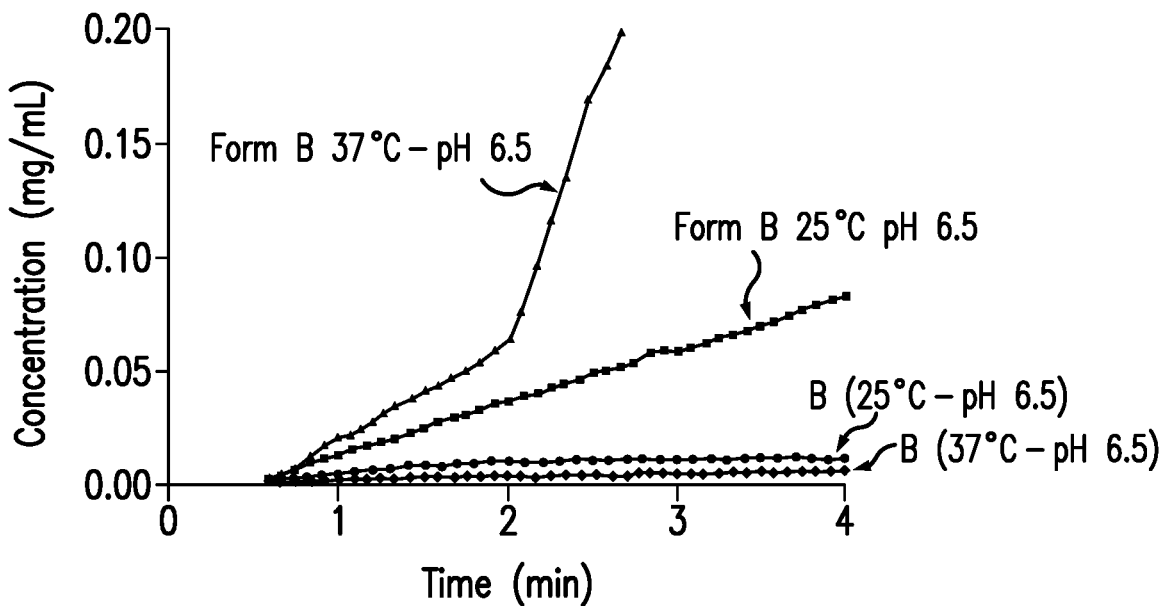
FIG. 40A is an expansion graph of FIG. 40B, showing the concentration of brigatinib Form B vs. time obtained from the IDR experiments in pH 6.5 buffer at 25° C. and 37° C. Concentration (mg/mL) is plotted on the vertical axis and time (min) is plotted on the horizontal axis.
Figure 40B:
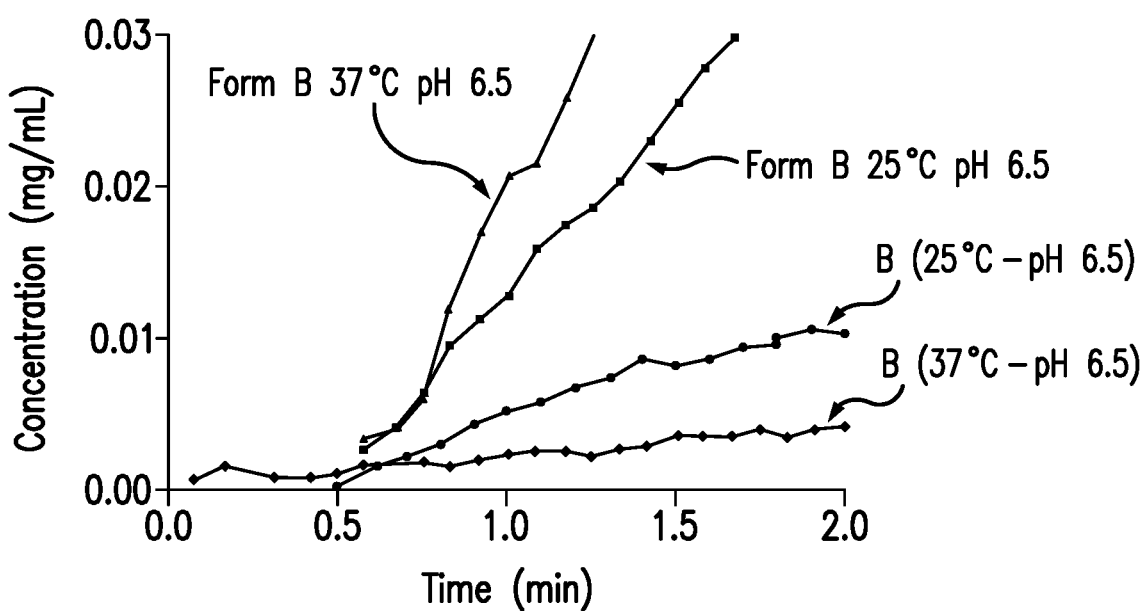
FIG. 40B is a plot of the concentration of brigatinib Form B vs. time obtained from the IDR experiments in pH 6.5 buffer at 25° C. and 37° C. Concentration (mg/mL) is plotted on the vertical axis and time (min) is plotted on the horizontal axis.

FIGS. 32A/B: The IDR of Form A in pH 6.5 buffer at 25° C. appears to be higher than that at 37° C. for the first 4 min, one possibility is the detachment of tablet grains; after 4 min, the IDR at 37° C. becomes higher. However, remeasurements of the IDR of Form A in pH 6.5 buffer, showed that the rate was higher at 37° C. compared to that at 25° C. (FIGS. 39A/B). The IDR of Form B appears to be higher at 25° C., however, the concentration of Form B at both temperatures appears to be stable. On a repetition of the IDR measurements of Form B in pH 6.5 buffer, in the second series of experiments, the results showed that the IDR at 37° C. was higher than that at 25° C. (FIGS. 40A/B). However, it is possible there was variability in the measurements, again likely due to the low concentrations, which make the measurement more sensitive to measuring conditions.

Figure 41A:
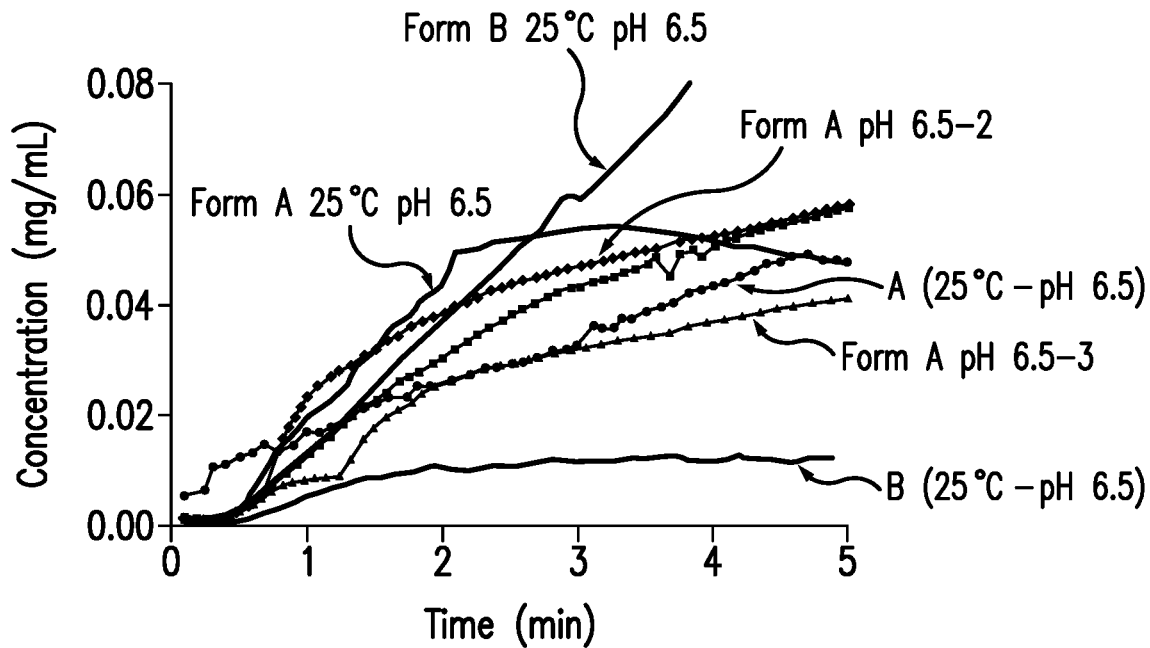
FIG. 41A is an expansion graph of FIG. 41B, showing the concentration of brigatinib Form A and Form B vs. time obtained from the IDR experiments at 25° C. in pH 6.5 buffer. Concentration (mg/mL) is plotted on the vertical axis and time (min) is plotted on the horizontal axis.
Figure 41B:
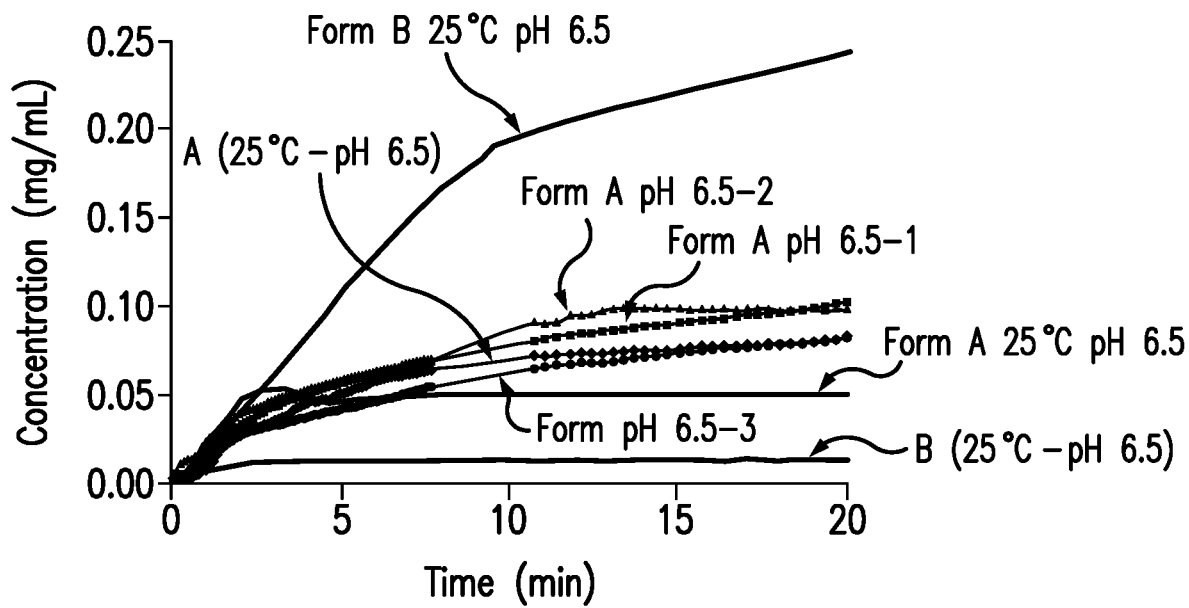
FIG. 41B is a plot of the concentration of brigatinib Form A and Form B vs. time obtained from the IDR experiments at 25° C. in pH 6.5 buffer. Concentration (mg/mL) is plotted on the vertical axis and time (min) is plotted on the horizontal axis.
Figure 42A:
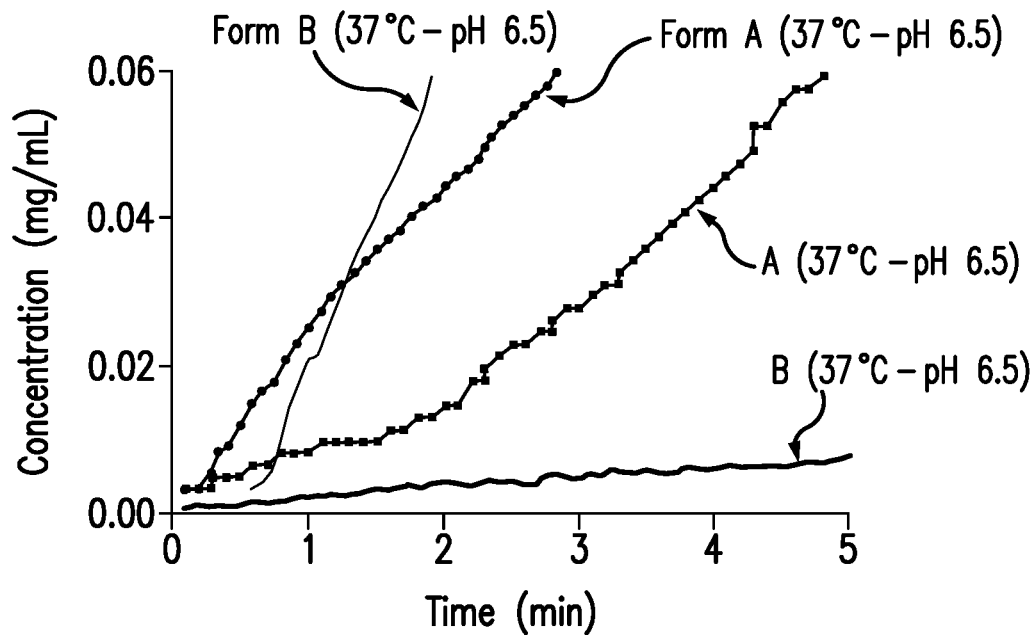
FIG. 42A is an expansion graph of FIG. 42B, showing the concentration of brigatinib Form A and Form B vs. time obtained from the IDR experiments at 37° C. in pH 6.5 buffer. Concentration (mg/mL) is plotted on the vertical axis and time (min) is plotted on the horizontal axis.
Figure 42B:
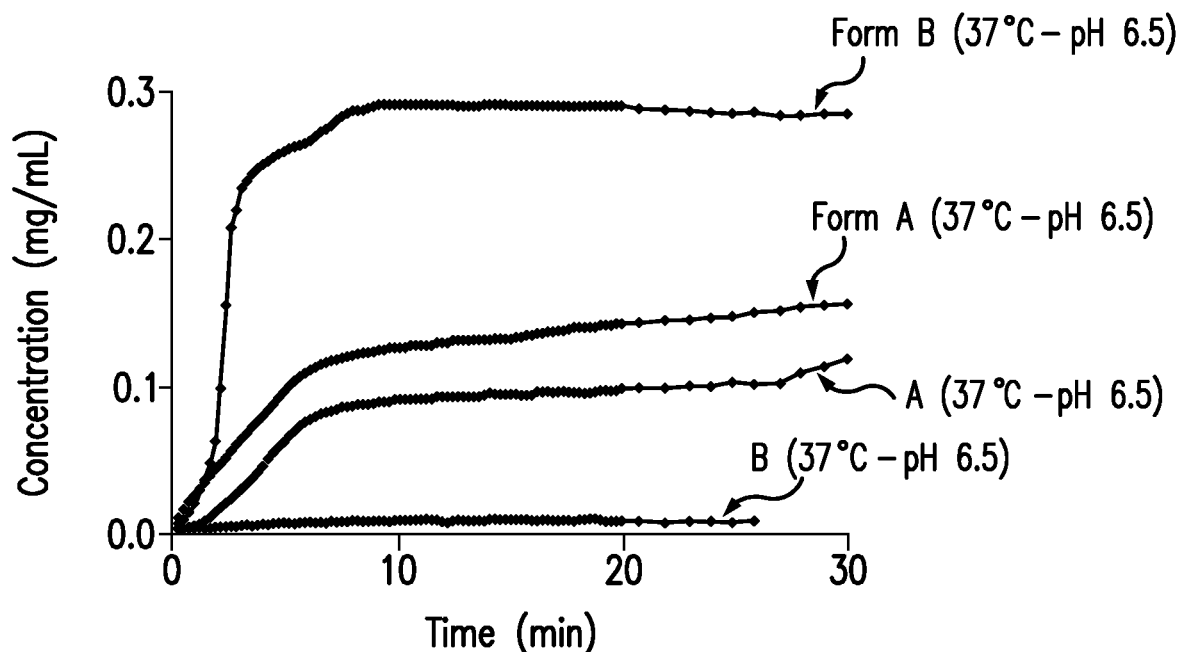
FIG. 42B is a plot of the concentration of brigatinib Form A and Form B vs. time obtained from the IDR experiments at 37° C. in pH 6.5 buffer. Concentration (mg/mL) is plotted on the vertical axis and time (min) is plotted on the horizontal axis.

The observation that Form A appeared to dissolve faster than Form B (FIGS. 32A/B) was investigated in a second series of IDR measurements. In FIG. 41, all IDR measurements of Forms A and B at 25° C. are plotted: the second series of experiments showed that after 3 min, the concentration of Form B is the highest, which is expected. Prior to 3 min, large increases of concentration are observed in several cases, indicating grain detachments from the tablets. In FIGS. 42A/B, all IDR measurements of Forms A and B at 37° C. are plotted: the second series of experiments showed that after about 1 min, the concentration of Form B was the highest.

It is noted that, in the cases of the IDR's of Forms A and B in water and pH 6.5 buffer, at both 25 and 37° C., the concentration values are very low, making the recorded values very sensitive to the measuring conditions. Measurements at these concentrations are prone to variability to a larger extent compared to measurements at higher concentrations. These values of IDR should be taken as indicative rather than absolute.

Figure 33A:
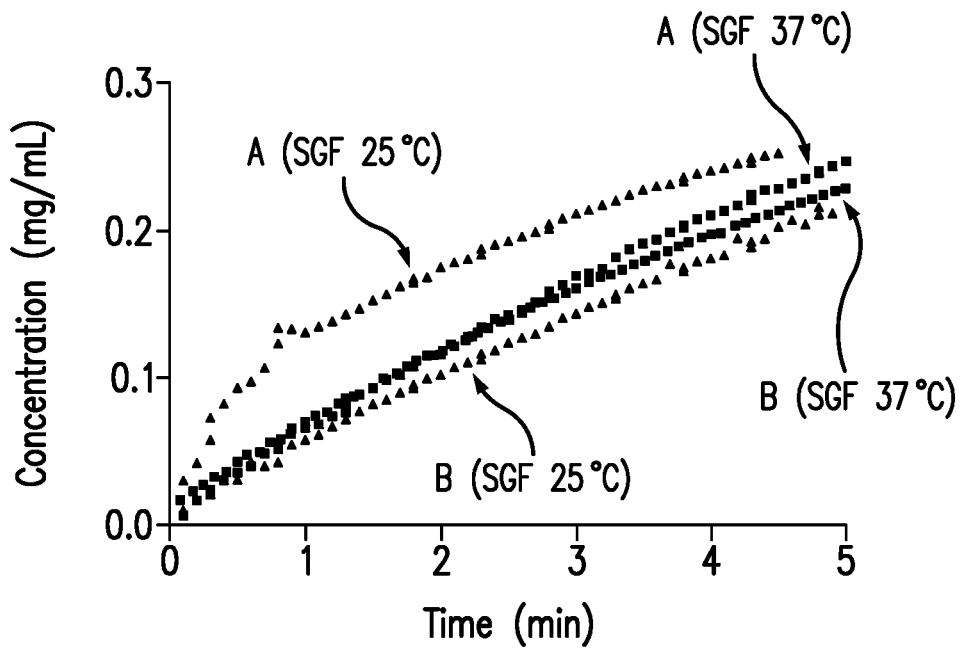
FIG. 33A is an expansion graph of FIG. 33B, showing the concentration of brigatinib Form A and Form B vs. time obtained from the IDR experiments at 25° C. and 37° C. in SGF. Concentration (mg/mL) is plotted on the vertical axis and time (min) is plotted on the horizontal axis.
Figure 33B:
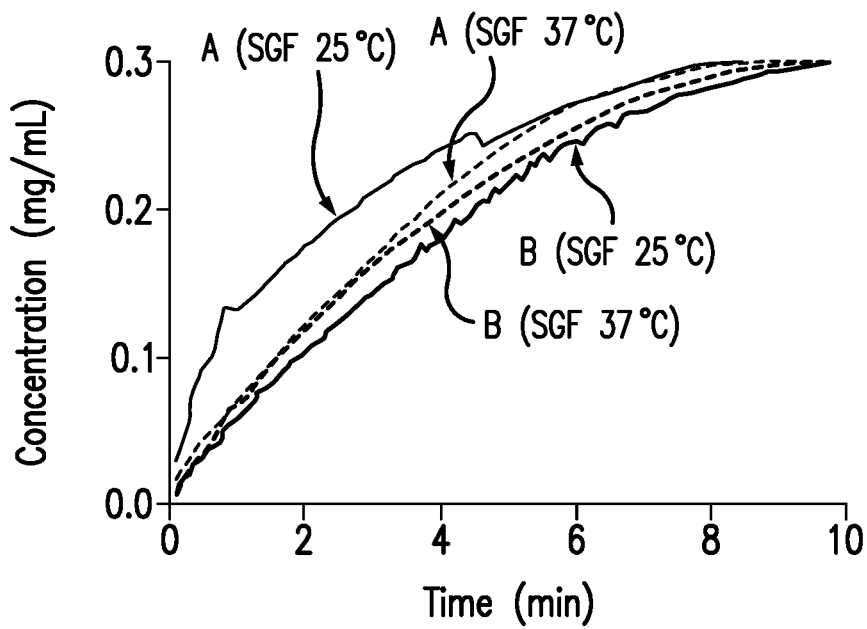
FIG. 33B is a plot of the concentration of brigatinib Form A and Form B vs. time obtained from the IDR experiments at 25° C. and 37° C. in SGF. Concentration (mg/mL) is plotted on the vertical axis and time (min) is plotted on the horizontal axis.

FIGS. 33 A/B: The IDR of Form A in SGF at 25° C. appears to be higher than that at 37° C. for the first 5 min, possibly from detachment of a tablet grain in the beginning of the measurement which adds to the concentration. Thereafter, the IDR's of Form A at both 25 and 37° C. appear similar. The IDR of Form B is higher at 37° C. than at 25° C., as expected. In pH 1.0 buffer and SGF, the IDRs of both Forms A and B and at both temperatures are comparable (see FIG. 31 and FIGS. 33A/B). At concentrations around 0.3 mg/mL, the detector is close to saturation.

Figure 34:
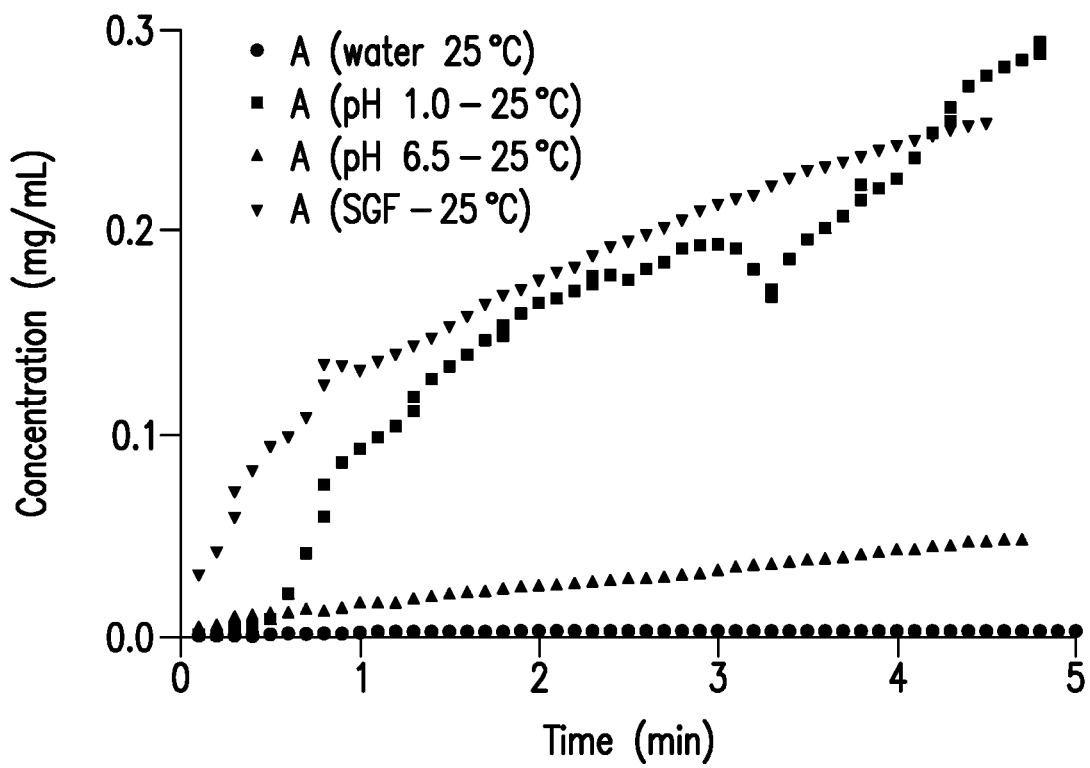
FIG. 34 is a plot of the concentration of brigatinib Form A vs. time obtained from the IDR experiments at 25° C. in water and aqueous buffers of pH 1.0, 4.5 and 6.5.

FIG. 34: Plots of increasing concentration of Form A vs. time from IDR experiments at 25° C. in water and aqueous buffers of pH 1.0, 4.5 and 6.5.

Figure 35:
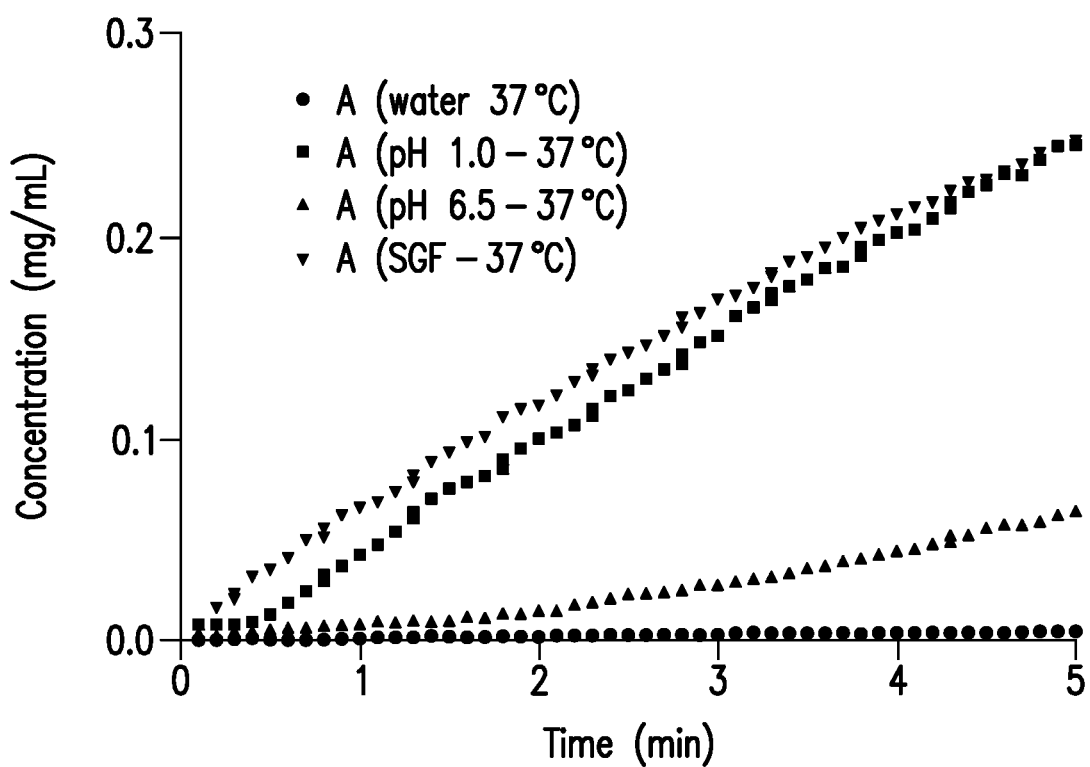
FIG. 35 is a plot of the concentration of brigatinib Form A vs. time obtained from the IDR experiments at 37° C. in water and aqueous buffers of pH 1.0, 4.5 and 6.5.

FIG. 35: Plots of increasing concentration of Form A vs. time from IDR experiments at 37° C. in water and aqueous buffers of pH 1.0, 4.5 and 6.5.

Figure 36:
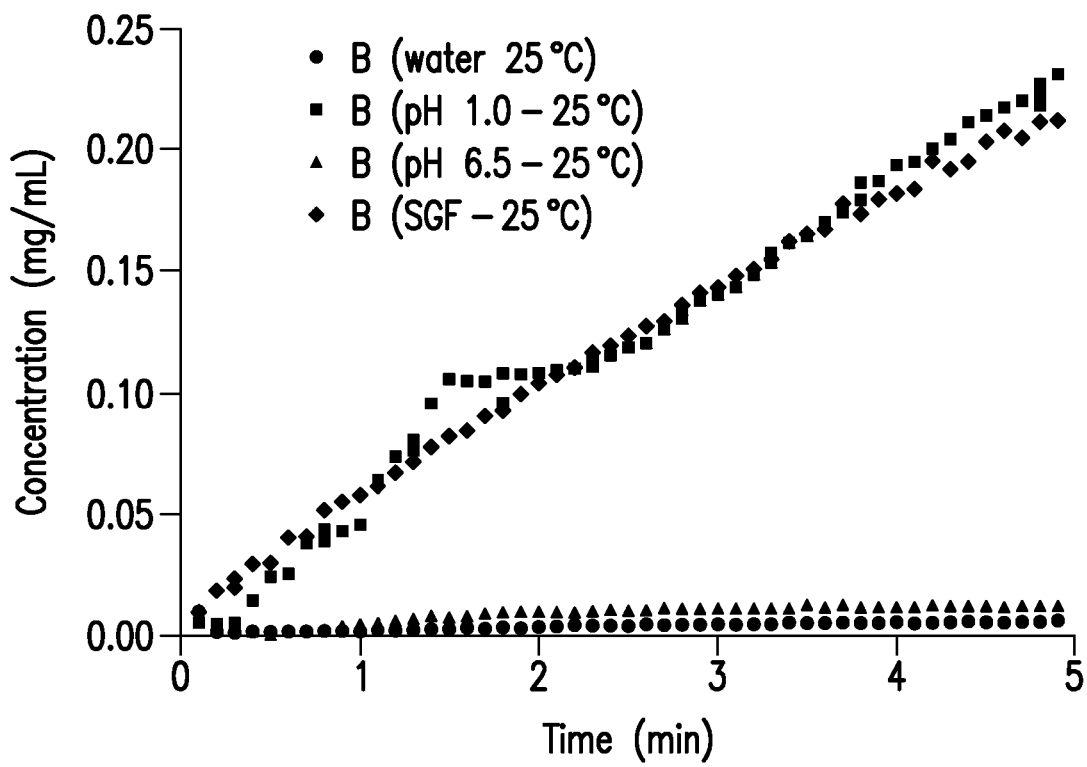
FIG. 36 is a plot of the concentration of brigatinib Form B vs. time obtained from the IDR experiments at 25° C. in water and aqueous buffers of pH 1.0, 4.5 and 6.5.

FIG. 36: Plots of increasing concentration of Form B vs. time from IDR experiments at 25° C. in water and aqueous buffers of pH 1.0, 4.5 and 6.5.

Figure 37:
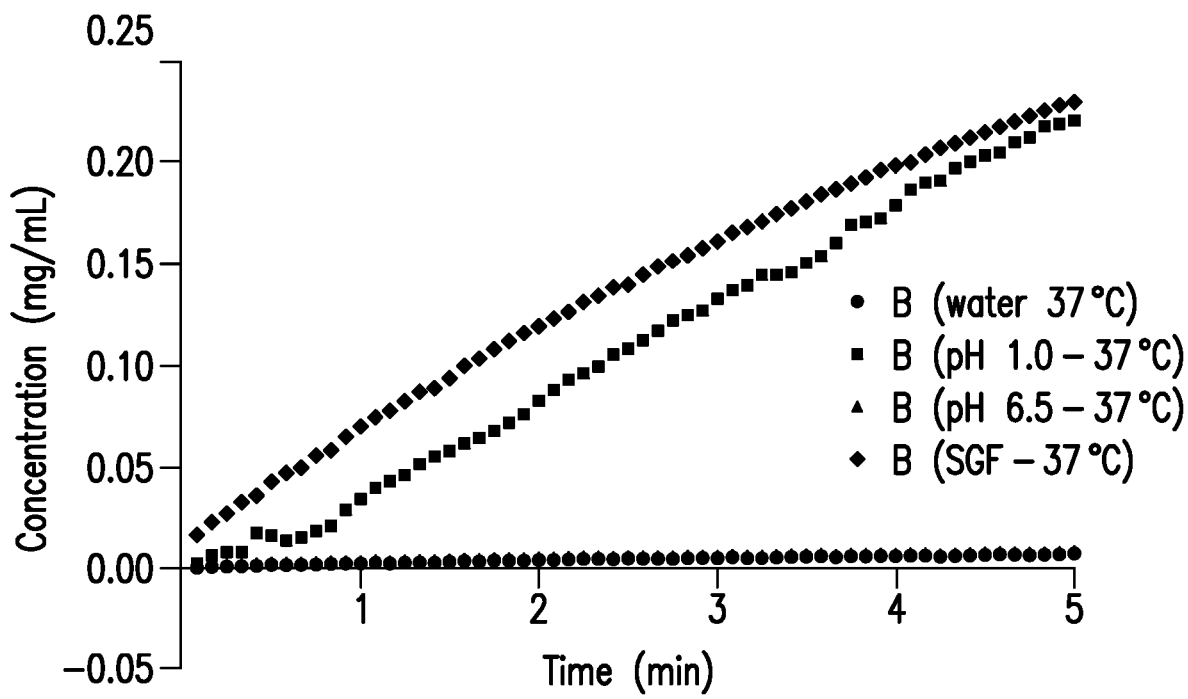
FIG. 37 is a plot of the concentration of brigatinib Form B vs. time obtained from the IDR experiments at 37° C. in water and aqueous buffers of pH 1.0, 4.5 and 6.5.

FIG. 37: Plots of increasing concentration of Form B vs. time from IDR experiments at 37° C. in water and aqueous buffers of pH 1.0, 4.5 and 6.5.

For measuring the dissolution rate from powder, the test was only performed in water for Forms A and B at 37° C., as the solubilities of Forms A and B were low enough to permit detection.

Figure 43A:
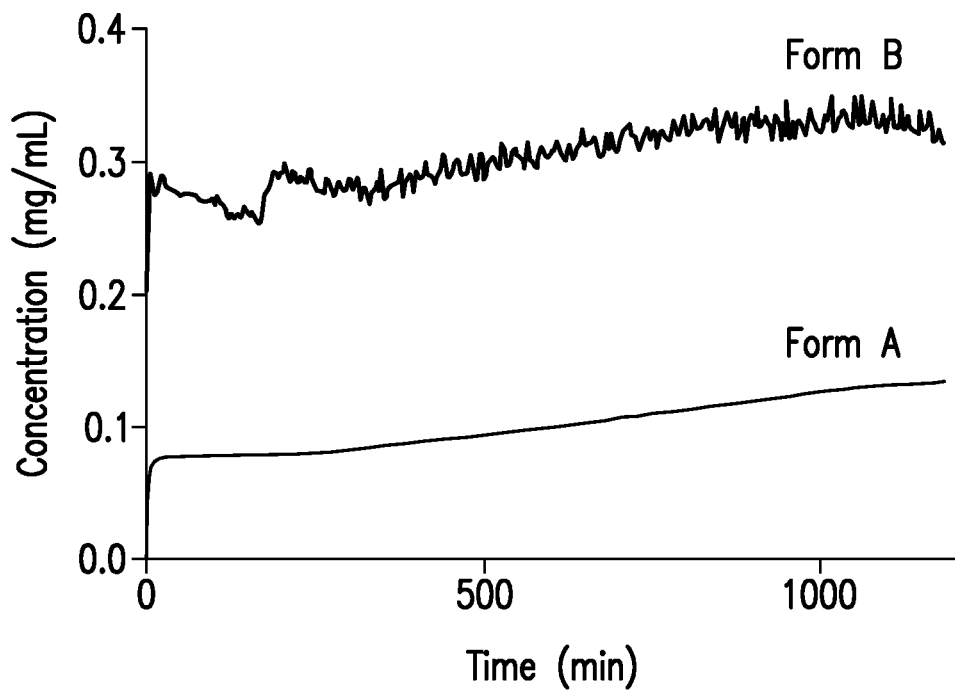
FIG. 43A is a plot of the concentration of brigatinib Form A and Form B vs. time obtained from the dissolution rate (IDR) experiment in water at 37° C. Concentration (mg/mL) is plotted on the vertical axis and time (min) is plotted on the horizontal axis.
Figure 43B:
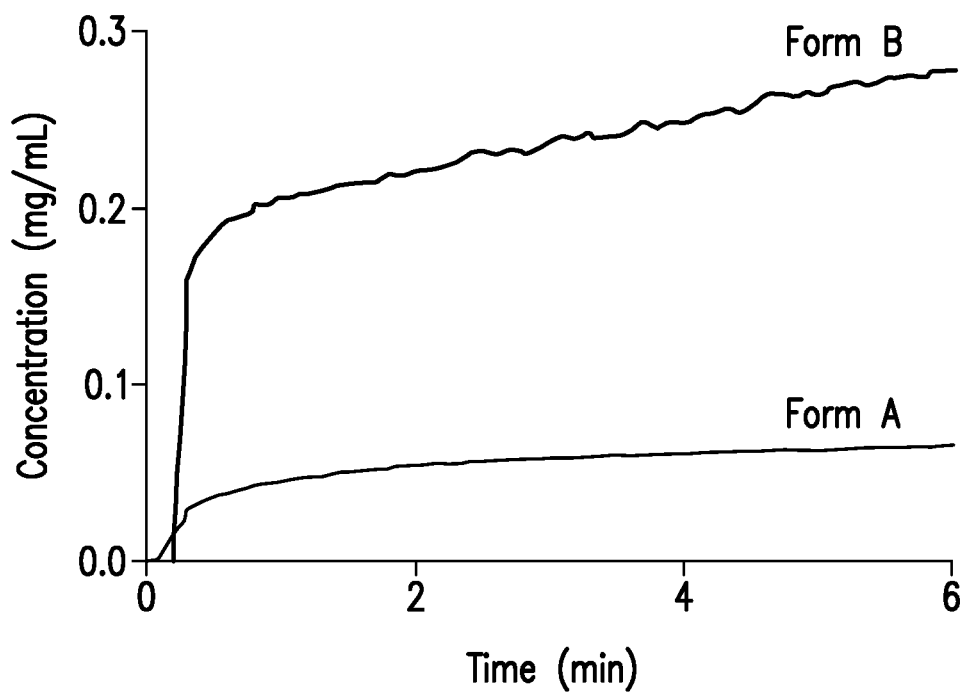
FIG. 43B is an expansion graph of FIG. 43A, showing the concentration of brigatinib Form A and Form B vs. time obtained from the dissolution rate (IDR) experiment in water at 37° C. Concentration (mg/mL) is plotted on the vertical axis and time (min) is plotted on the horizontal axis.

In FIGS. 43 A/B, the concentration of Forms A and B vs. time are plotted. In both cases, within about 10 min, the concentration reached a "maximum" and thereafter the dissolution was slowed down. Between 10 min and 20 h, the concentration of Form A almost doubled (from 0.07 to 0.14 mg/mL). For Form B, between 10 min and 260 min, a concentration decrease was observed; thereafter, the concentration increased again, to reach at the end of the experiment a value slightly higher compared to that at 10 min. The concentration increase might be connected to the transformation of Form B to Form D, which re-dissolved. Due to detector saturation at about 0.3 mg/mL, the maximum concentration of Form B was not conclusively determined.

Phase 2: Polymorph Identification

The polymorph screening experiments for brigatinib were carried out at milliliter (mL) scale using nearly 300 different conditions and also at microliter scale using nearly 200 different conditions. Six different crystallization procedures were applied: (1) cooling-evaporation; (2) evaporative crystallization; (3) vapor exposure; (4) cooling crystallization with hot filtration; (5) crash crystallization with anti-solvent addition; (6) slurry; (7) vapor diffusion into solution; (8) vapor diffusion onto solids; (9) grinding; (10) thermocycling; (11) VT-XRPD; (12) VH-XRPD; (13) DVS; and (14) dehydration. After the screening experiments were completed, the materials were collected and analyzed by XRPD and digital imaging.

Cooling-Evaporative Crystallization Experiments

The cooling-evaporative experiments shown at Tables 11-14 at μL scale were performed in 96-well plates, employing 24 different solvents and solvent mixtures, 2 concentrations, and 2 temperature profiles. In each well, 4 mg of Form A was weighed. Then, the screening solvent was added to reach a concentration of circa 40 mg/mL or 80 mg/mL. The plates, with each well individually sealed, were placed in a CrystalBreeder™ to undergo a temperature profile as described in Table 10 below. The plates were then placed under vacuum and evaporated for several days under 200 mbar and/or 5 mbar, then analyzed by XRPD and digital imaging. The final Form obtained is given in Tables 12-14.

TABLE 11

Cooling-evaporative crystallization parameters

| Experiment | T profile | $T^{initial}$ (° C.) | Hold (min) | Cooling rate (° C./h) | $T^{final}$ (° C.) | Ageing (h) |
|---|---|---|---|---|---|---|
| 1-48 | T1 | 60 | 60 | 1 | 5 | 48 |
| 49-96, 145-192 | T2 | 60 | 60 | 20 | 5 | 3 |
| 97-144 | T3 | 60 | 60 | 1 | 20 | 48 |
| 193-240 | T4 | 60 | 60 | 20 | 20 | 3 |

TABLE 12

Cooling-evaporative crystallization experimental results: T1 and T2 profiles

| | T profile 1 | | | | T profile 2 | | | |
|---|---|---|---|---|---|---|---|---|
| | Conc. (mg/mL) | | | | | | | |
| | 40 | | 80 | | 40 | | 80 | |
| Solvent | Expt. | Form | Expt. | Form | Expt. | Form | Expt. | Form |
| tert-Butyl methyl ether | 1 | A | 25 | A | 49 | A | 73 | A |
| Methyl acetate | 2 | A | 26 | A | 50 | A | 74 | A |
| Methanol | 3 | A + H | 27 | A + H | 51 | A + H | 75 | A |
| Tetrahydrofuran | 4 | A | 28 | A | 52 | A | 76 | A |
| Acetonitrile | 5 | A | 29 | A | 53 | A | 77 | A |
| 1,2-Dimethoxyethane | 6 | A | 30 | A | 54 | A | 78 | A |
| Isopropyl acetate | 7 | A | 31 | A | 55 | A | 79 | A |
| 1,4-Dioxane | 8 | A | 32 | A | 56 | A | 80 | A |
| 2-Methoxyethanol | 9 | A + J → A + J | 33 | A | 57 | A | 81 | A |
| 2-Hexanone | 10 | A | 34 | A | 58 | A | 82 | A |
| Heptane | 11 | A | 35 | A | 59 | A | 83 | A |
| 1-Pentanol | 12 | A | 36 | A | 60 | A | 84 | A |
| Acetone/Dichloromethane (50/50) | 13 | A | 37 | A | 61 | A | 85 | A |
| Methanol/Chloroform (50/50) | 14 | A + H | 38 | A | 62 | A + H | 86 | A |
| tert-Butyl methyl ether/Chloroform (50/50) | 15 | A | 39 | A | 63 | A | 87 | A |
| Methanol/Acetonitrile (50/50) | 16 | A | 40 | A | 64 | A | 88 | A |
| Acetonitrile/Chloroform (50/50) | 17 | A | 40 | A | 65 | A | 89 | A |
| Heptane/Ethyl formate (50/50) | 18 | A | 42 | A | 66 | A | 90 | A |
| 1,4-Dioxane/Cyclohexane (50/50) | 19 | A | 43 | A | 67 | A | 91 | A |
| Water/Methanol (50/50) | 20 | A | 44 | A | 68 | A | 92 | A |
| Cyclohexane/N-Methylpyrrolidone (50/50) | 21 | A | 45 | A | 69 | A | 93 | A |
| Tetrahydrofuran/N-Methylpyrrolidone (50/50) | 22 | A | 46 | A | 70 | A | 94 | A |
| 1,2,3,4-Tetrahydronaphthalene/Acetonitrile (50/50) | 23 | A | 47 | A | 71 | A | 95 | A |
| Chlorobenzene/N-Methylpyrrolidone (50/50) | 24 | A | 48 | A | 72 | A | 96 | A |

TABLE 13

Cooling-evaporative crystallization experimental results: T profile 3

| Solvent | T profile 3 Conc. (mg/mL) | | | | | | | |
|---|---|---|---|---|---|---|---|---|
| | 40 | | 80 | | 40 | | 80 | |
| | Expt. | Form | Expt. | Form | Expt. | Form | Expt. | Form |
| tert-Butyl methyl ether | 97 | A | 121 | A | 145 | A | 169 | A |
| Methyl acetate | 98 | A | 122 | A | 146 | A | 170 | A |
| Methanol | 99 | A + H | 123 | A + H | 147 | A + H | 171 | A + H |
| Tetrahydrofuran | 100 | A | 124 | A | 148 | A | 172 | A |
| Acetonitrile | 101 | A | 125 | A | 149 | A | 173 | A |
| 1,2-Dimethoxyethane | 102 | A | 126 | A | 150 | A | 174 | A |
| Isopropyl acetate | 103 | A | 127 | A | 151 | A | 175 | A |
| 1,4-Dioxane | 104 | A | 128 | A | 152 | A | 176 | A |
| 2-Methoxyethanol | 105 | A | 128 | A | 153 | A | 177 | A |
| 2-Hexanone | 106 | A | 130 | A | 154 | A | 178 | A |
| Heptane | 107 | A | 131 | A | 155 | A | 179 | A |
| 1-Pentanol | 108 | A | 132 | A | 156 | A | 180 | A |
| Acetone/Dichloromethane (50/50) | 109 | A | 133 | A | 157 | A | 181 | A |
| Methanol/Chloroform (50/50) | 110 | H → A + H | 134 | n | 158 | H → A + H | 182 | H → A + H |
| tert-Butyl methyl ether/Chloroform (50/50) | 111 | A | 135 | A | 159 | A | 183 | A |
| Methanol/Acetonitrile (50/50) | 112 | A | 136 | A | 160 | A | 184 | A + H |
| Acetonitrile/Chloroform (50/50) | 113 | A | 137 | A | 161 | A | 185 | A |
| Heptane/Ethyl formate (50/50) | 114 | A | 138 | A | 162 | A | 186 | A |
| 1,4-Dioxane/Cyclohexane (50/50) | 115 | A | 139 | A | 163 | A | 187 | A |
| Water/Methanol (50/50) | 116 | A | 140 | A | 164 | A | 188 | A |
| Cyclohexane/N-Methylpyrrolidone (50/50) | 117 | A | 141 | A | 165 | A | 189 | A |
| Tetrahydrofuran/N-Methylpyrrolidone (50/50) | 118 | A + K → A + K | 142 | A | 166 | A | 190 | A |
| 1,2,3,4-Tetrahydronaphthalene/Acetonitrile (50/50) | 119 | A | 143 | A | 167 | A | 191 | A |
| Chlorobenzene/N-Methylpyrrolidone (50/50) | 120 | A | 144 | A | 168 | A | 192 | A |

TABLE 14

Cooling-evaporative crystallization experimental results: T profile 4

| Solvent | T profile 4 Conc. (mg/mL) | | | |
|---|---|---|---|---|
| | 40 | | 80 | |
| | Expt. | Form | Expt. | Form |
| tert-Butyl methyl ether | 193 | A | 217 | A |
| Methyl acetate | 194 | A | 218 | A |
| Methanol | 195 | — | 219 | A |
| Tetrahydrofuran | 196 | A | 220 | A |
| Acetonitrile | 197 | A | 221 | A |
| 1,2-Dimethoxyethane | 198 | A | 222 | A |
| Isopropyl acetate | 199 | A | 223 | A |
| 1,4-Dioxane | 200 | A | 224 | A |
| 2-Methoxyethanol | 201 | A | 225 | A |
| 2-Hexanone | 202 | A | 226 | A |
| Heptane | 203 | A | 227 | A |
| 1-Pentanol | 204 | A | 228 | A |
| Acetone/Dichloromethane (50/50) | 205 | A | 229 | A |
| Methanol/Chloroform (50/50) | 206 | H → A + H | 230 | H → A |
| tert-Butyl methyl ether/Chloroform (50/50) | 207 | A | 231 | A |
| Methanol/Acetonitrile (50/50) | 208 | A | 232 | A |
| Acetonitrile/Chloroform (50/50) | 209 | A | 233 | A |
| Heptane/Ethyl formate (50/50) | 210 | A | 234 | — |

TABLE 14-continued

Cooling-evaporative crystallization experimental results: T profile 4

| | T profile 4 Conc. (mg/mL) | | | |
|---|---|---|---|---|
| | 40 | | 80 | |
| Solvent | Expt. | Form | Expt. | Form |
| 1,4-Dioxane/Cyclohexane (50/50) | 211 | A | 235 | A |
| Water/Methanol (50/50) | 212 | A | 236 | A |
| Cyclohexane/N-Methylpyrrolidone (50/50) | 213 | A | 237 | A |
| Tetrahydrofuran/N-Methylpyrrolidone (50/50) | 214 | A | 238 | A |
| 1,2,3,4-Tetrahydronaphthalene/Acetonitrile (50/50) | 215 | A | 239 | A |
| Chlorobenzene/N-Methylpyrrolidone (50/50) | 216 | A | 240 | A |

Evaporative Crystallization Experiments

Brigatinib Form A and 30 different solutions were employed. In a vial, 20 mg of material was weighed and 1000 μL of the given solvent was added. After stirring at rt for a maximum of 3 hours, the solvents were evaporated at rt (at 200 mbar for 120 h, then 5 mbar for 48 hours). Solids obtained were analyzed dry by XRPD and digital imaging as shown in Table 15.

TABLE 15

Evaporative crystallization experiments

| Mass (g) | Solvent | Dissolved? | Form (XRPD) |
|---|---|---|---|
| 19.8 | Acetone | N | A |
| 21.4 | Cyclohexane | N | A |
| 21.7 | Acetonitrile | N | A |
| 23.3 | Isopropyl Acetate | N | A |
| 19.4 | n-Heptane | N | A |
| 21.7 | Cyclohexanone | N | A |
| 19.7 | Ethyl formate | N | A |
| 21.3 | tert-Butyl methyl ether | N | A |
| 20.6 | Chloroform | Y | A |
| 19.8 | Methanol | Y | A |
| 21.8 | Hexane | N | A |
| 21.2 | Ethyl acetate | N | A |
| 20.3 | Ethanol | N | A |
| 20.9 | 2-Butanone | N | A |
| 21.6 | Isopropanol | N | A |
| 20.8 | Ethylene Glycol Dimethyl Ether | N | A |
| 21.4 | 2-Butanol | N | A |
| 21.3 | 1,4-Dioxane | N | A |
| 20.2 | Toluene | N | A |
| 20.3 | Butyl acetate | N | A |
| 19.7 | 2-Hexanone | N | A |
| 20.8 | Anisole | N | A |
| 20 | N,N-Dimethylacetamide | N | A |
| 20.2 | Dichloromethane | Y | A |
| 20.8 | Acetone/Water (50/50) | N | A + C |
| 19.8 | Cyclohexane/Tetrahydrofuran (50/50) | N | A |
| 20.1 | Water/Methanol (50/50) | N | A |
| 20.3 | Cyclohexane/1,4-Dioxane (50/50) | N | A |
| 20.4 | Water/Ethanol (50/50) | Y | A |
| 20.5 | Cyclohexane/Cyclohexanone (50/50) | N | A |
| 20.3 | 2,2,4-Trimethylpentane/3,3-Dimethyl-2-butanone (50/50) | N | A |
| 20.5 | Water/1,2-Propanediol | N | A |
| 20.6 | Water/Formamide | N | A |
| 20.2 | Cyclohexanone/cis-Decalin | N | A |

Vapor Exposure Experiments

The stability of Form A upon exposure to solvent vapors was investigated in twenty solvents as shown in Table 16. Approximately 20 mg of brigatinib Form A was weighed in 1.8 mL vials. The vials were left open and placed in closed 40 mL vials containing 2 mL of solvent. The material was exposed to solvent vapours at room temperature for two weeks. At the end of the experiment time, the solids were harvested wet and dry and analyzed by XRPD and digital imaging.

TABLE 16

Vapor exposure experiments

| Form A weight (mg) | Solvent | Form |
|---|---|---|
| 20.9 | Water | A |
| 21.5 | Acetone | A |
| 20.8 | Acetonitrile | A |
| 19.9 | n-Heptane | A |
| 20.7 | Isopropyl Acetate | A |
| 20 | 2-Methyltetrahydrofuran | A |
| 21.5 | Tetrahydrofuran | A |
| 20 | Methanol | A |
| 20.5 | Ethanol | A |
| 20.8 | Isopropanol | A |
| 19.5 | Isobutanol | A |
| 19.6 | Methyl acetate | A |
| 19.6 | Ethyl acetate | A |
| 21.1 | Propyl acetate | A |
| 21.2 | 2-Butanone | A |
| 21.6 | Ethyl Formate | A |
| 20.2 | tert-Butyl methyl ether | A |
| 20.8 | cyclohexane | A |

Cooling Crystallization with Hot Filtration Experiments

The cooling crystallization method with hot filtration included 34 solvents and solvent mixtures. Supersaturated solutions were prepared by stirring slurries of brigatinib in 1300 μL of a given solvent or mixture at 60° C. for one hour. Subsequently, the liquids were separated from the solids by filtration. The solutions were placed in a Crystal16™ instrument to undergo the following cooling profile. Samples were warmed to 60° C. and held for 60 min, then cooled at a rate of 1° C./hr until reaching 5° C. The samples were then held at that temperature for 48 hrs. In each experiment, precipitation was not observed at the end of the thermal profile. The solvents were evaporated, at 200 mbar for 104 hours and at 5 mbar for 70 hours. In several cases, evaporation at 5 mbar continued for about 400 hours while in some other cases, no yield was obtained after evaporation of the solvent. All obtained solids were analyzed by XRPD and digital imaging. Table 17 provides the applied crystallization conditions and corresponding obtained solid forms.

TABLE 17

Cooling crystallization with hot filtration experiments

| Solvent | Slurry conc. (mg/mL) | Slurry at 60° C.? | Solid after thermal cycle? | Form (XRPD) |
|---|---|---|---|---|
| Methanol/Acetonitrile | 86 | N | N | A |
| Acetone/Water | 45 | N | N | A + C |
| Acetonitrile/Chloroform | 67 | N | N | A |
| Cyclohexane/Tetrahydrofuran | 23 | Y | Y | A |
| tert-Butyl methyl ether/1,2-Propanediol | 31 | Y | N | A |
| Isoamyl acetate/Chloroform | 46 | N | N | A |
| Isopropyl ether/Diethoxymethane | 22 | Y | N | — |
| 2,2,4-Trimethylpentane/Isopropyl ether | 21 | Y | N | — |
| Water/Methanol | 45 | Y | N | A + C |
| Cyclohexane/1,4-Dioxane | 21 | Y | N | A |
| Water/Ethanol | 131 | Y | N | A |
| Cyclohexanone/Tetrahydrofuran | 43 | Y | N | A |
| Water/1,4-Dioxane | 66 | Y | Y | A + C |
| Isopropyl ether/p-Xylene | 19 | Y | N | A |
| Cyclohexane/Cyclohexanone | 19 | Y | N | A |
| 2,2,4-Trimethylpentane/Pinacolone | 25 | Y | N | Am |
| Cyclohexane/cis-Decahydronaphthalene | 23 | Y | N | — |
| Water/Isopropyl Acetate | 22 | Y | N | A |
| Water/1,2-Propanediol | 24 | Y | N | A |
| Water/Formamide | 22 | Y | N | — |
| n-Heptane/p-Xylene | 26 | Y | N | — |
| 2,2,4-Trimethylpentane/Mesitylene | 24 | N | N | — |
| cis-Decahydronaphthalene/MethylCyclohexane | 18 | Y | N | — |
| 2,2,4-Trimethylpentane/cis-Decahydronaphthalene | 26 | Y | N | — |
| p-Xylene/Anisole | 23 | Y | N | A |
| n-Nonane/1-Octanol | 22 | Y | N | — |
| n-Amyl acetate/1-Octanol | 20 | Y | N | A |
| 1,2,3,4-Tetrahydronaphthalene/Cumene | 21 | Y | N | A |
| Cyclohexanone/cis-Decahydronaphthalene | 23 | Y | N | A |
| Cumene/cis-Decahydronaphthalene | 21 | Y | N | — |
| Anisole/Nitrobenzene | 44 | Y | N | A |
| Cyclohexanone/N-Methyl-2-pyrrolidone | 87 | Y | N | A |
| Ethyleneglycol diacetate/Bis(2-methoxy ethyl)ether | 25 | Y | N | A |
| Cyclohexanone/Nitrobenzene | 22 | Y | N | A |

Crash Crystallization with Anti-Solvent Addition

In the crash-crystallization experiments, 34 different crystallization conditions were applied, using 6 different solvents and 24 different anti-solvents (see Table 17). The anti-solvent addition experiments were performed forward. For each solvent, a stock solution was prepared, the concentration of brigatinib in each case being that attained at saturation at ambient temperature after equilibration for 24 hours before filtering.

For each experiment, the anti-solvent was added to each solvent vial, with a solvent to anti-solvent ratio of 1:0.25. In the cases where no precipitation occurred, this ratio was increased to 1:1, and if again no precipitation occurred the ratio was increased to 1:4, with a waiting time of 60 minutes between the additions (up to the third addition) and 35 minutes between the third addition and fourth addition. When no crystallization occurred or not enough solids precipitated for separation, samples were kept at 5° C. for 17 hours. The precipitated solids were separated from the liquids by centrifugation and decantation. When decantation could not be applied, the liquid was carefully removed using Pasteur's pipettes. The solids were dried at 200 mbar for 17 hours and analyzed by XRPD and digital imaging. In the cases where no precipitation occurred, the solvents were evaporated at 200 mbar for 17 hours prior to lowering the vacuum to 5 mbar. All obtained solids were analyzed by XRPD and digital imaging. The measuring plates containing the final solid were stored at ambient temperature for 5 weeks. The solid form was assessed again by XRPD. The arrows in Table 18 indicate if the form changed during storage.

TABLE 18

Crash crystallization with anti-solvent addition experiments

| Solvent | Vol (μL) | Anti-solvent | Ratio S:AS Forward (1:x) | Precipitation | Form (XRPD) |
|---|---|---|---|---|---|
| Chloroform | 150 | tert-Butyl methyl ether | 4 | Yes | A + G (wet), A (dry, ML*) |
| Methanol | 900 | Acetonitrile | 4 | No | A |
| Acetone | 7400 | Water | 4 | No** | — |
| Chloroform | 150 | Acetonitrile | 1 | Yes | G (wet) → A, A (dry, ML*) |
| Cyclohexane | 7400 | Tetrahydrofuran | 4 | No** | — |
| tert-Butyl methyl ether | 7400 | 1,2-Propane diol | 4 | No** | — |
| Diisopropyl ether | 7400 | Diethoxyme ane | 4 | No** | — |
| 2,2,4-Trimethylpentane | 7400 | Isopropyl ether | 4 | No** | — |
| Methanol | 900 | Water | 4 | No | D**** |
| 1,4-Dioxane | 3900 | Cyclohexane | 4 | No | A |
| Ethanol | 4900 | Water | 4 | No | A + H |

TABLE 18-continued

Crash crystallization with anti-solvent addition experiments

| Solvent | Vol (μL) | Anti-solvent | Ratio S:AS Forward (1:x) | Precipitation | Form (XRPD) |
|---|---|---|---|---|---|
| Tetrahydrofuran | 3900 | Cyclohexanone | 4 | No | A |
| n-Heptane | 7400 | Cyclohexane | 4 | No** | — |
| 1,4-Dioxane | 3900 | Water | 4 | No | A + H |
| Cyclohexane | 7400 | Cyclohexanone | 4 | No** | — |
| 3,3-Dimethyl-2-butanone | 7400 | 2,2,4-Trimethylpentane | 1 | Yes** | — |
| Cyclohexane | 7400 | Cis-Decahydronaphthatene | 1*** | No** | — |
| Isopropyl Acetate | 7400 | Water | 4 | No** | — |
| 1,2-Propanediol | 7400 | Water | 4 | No** | — |
| Formamide | 7400 | Water | 4 | No** | — |
| n-Heptane, | 7400 | P-Xylene | 4 | No** | — |
| Cis-Decahydronaphthalene | 7400 | Methylcyclohexane | 4 | No** | — |
| 2,2,4-Trimethylpentane | 7400 | Cis-Decahydronaphthatene | 4*** | No** | — |
| Anisole | 7400 | P-Xylene | 4 | No | A |
| 1-Octanol | 7400 | n-Nonane | 4*** | No | A |
| 1-Octanol | 7400 | N-Amyl acetate | 4 | No | A |
| 1,2,3,4-Tetrahydronaphthalene | 7400 | Cumene | 4 | No** | — |
| Cyclohexanone | 7400 | Cis-Decahydronaphthalene | 4*** | No | A |
| N-Amyl acetate | 7400 | Ethyleneglycol diacetate | 4 | No** | — |
| Cumene | 7400 | Cis-Decahydronaphthalene | 4*** | No** | — |
| Isoamyl acetate | 7400 | Nitrobenzene | 4 | No** | — |
| Anisole | 7400 | Nitrobenzene | 4 | No** | — |
| Cyclohexanone | 7400 | N-Methyl-2-pyrrolidone | 4 | No** | — |
| Ethylene glycol diacetate | 7400 | Bis(2-methoxy ethyl) ether | 4 | No** | — |

*ML = From mother liquour;
**No yield;
***Two additions applied;
****Single crystal picked from liquid Slurry Experiments A total of 68 slurry experiments were performed with brigatinib both at room temperature (20° C.) and 40° C., using 34 solvents. In all cases, a solvent volume of 250 μL was used. The slurries were stirred for two weeks. At the end of the slurry time, the vials were centrifuged and solids and mother liquids separated. The solids were analyzed wet and dry by XRPD and digital imaging. The measuring plates were then stored at ambient conditions for 3-4 weeks and another XRPD was obtained of the solid, any form change is shown by an arrow. Tables 19a and 19b summarizes the experimental conditions and obtained solid forms TABLE 19a Slurry experiments at 20° C.

| Mass (mg) | Solvent | Conc. (mg/mL) | Form wet (XRPD) | Form dry (XRPD) |
|---|---|---|---|---|
| 22.6 | Ethyl formate | 90.4 | A | A |
| 22.4 | tert-Butyl methyl ether | 89.6 | A | A |
| 26.3 | Acetone | 105.2 | A | A |
| 23.8 | Methyl acetate | 95.2 | A | A |
| 22.6 | Chloroform* | 90.4 | — | A + E |
| 19.5 | Methanol | 78 | A | A |
| 23.9 | Tetrahydrofuran | 95.6 | A | A |
| 19.2 | Hexane | 76.8 | A + L→A + L | A + L→A + L |
| 19.9 | Ethyl acetate | 79.6 | A | A |
| 20.5 | Ethanol | 82 | A | A |
| 23.0 | Cyclohexane | 92 | A | A |
| 20.5 | Acetonitrile | 82 | A | A |
| 20.9 | 2-Propanol | 83.6 | A | A |
| 24.0 | 1,2-Dimethoxyethane | 96 | A | A |
| 20.8 | Isopropyl acetate | 83.2 | A | A |
| 20.0 | Hepta e | 80 | A + L→A + L | A |
| 25.8 | 2-Butanol | 103.2 | A | A |
| 24.6 | Water | 98.4 | A | A |
| 23.3 | Methylcyclohexane | 93.2 | A + L→A + L | A |
| 18.4 | 1,4-Dioxane | 73.6 | A | A |
| 18.6 | N-propyl acetate | 74.4 | A | A |
| 21.7 | Isobutanol | 86.8 | A | A |
| 23.9 | Toluene | 95.6 | A | A |
| 24.0 | Isobutylac ta e | 96 | A | A |
| 23.3 | 2-Methoxyethanol | 93.2 | A | A |
| 24.9 | n-Butyl acetate | 99.6 | A | A |
| 26.6 | 2-Hexanone | 106.4 | A | A |
| 19.1 | Chlorobenzene | 76.4 | A | A |
| 18.9 | 2-Ethoxyethanol | 75.6 | A | A |
| 24.8 | 1-Pentanol | 99.2 | A | A |
| 21.2 | m-Xylene | 84.8 | A | A |
| 19.7 | Cumene | 78.8 | A | A |
| 23.2 | N,N-Dimethylformamide | 92.8 | A | A |
| 18.5 | Anisole | 74 | A | A |

*in this experiment, the solids dissolved after 14 days

TABLE 19b

Slurry experiments at 40° C.

| Mass (mg) | Solvent | Conc. (mg/mL) | Form wet (XRPD) | Form dry (XRPD) |
|---|---|---|---|---|
| 33.8 | Ethyl formate | 135.2 | A | A |
| 33.9 | tert-Butyl methyl ether | 135.6 | A | A |
| 35.8 | Acetone | 143.2 | A | A |
| 34.9 | Methyl acetate | 139.6 | A | A |

TABLE 19b-continued

Slurry experiments at 40° C.

| Mass (mg) | Solvent | Conc. (mg/mL) | Form wet (XRPD) | Form dry (XRPD) |
|---|---|---|---|---|
| 35.9 | Chloroform* | 143.6 | — | A + E |
| 33.3 | Methanol | 133.2 | A | A |
| 37.6 | Tetrahydrofuran | 150.4 | A | A |
| 33.6 | Hexane | 134.4 | A | A |
| 31.6 | Ethyl acetate | 126.4 | A | A |
| 33.2 | Ethanol | 132.8 | A | A |
| 31.5 | Cyclohexane | 126 | A | A |
| 36.5 | Acetonitrile | 146 | A | A |
| 35.9 | 2-Propanol | 143.6 | A | A |
| 37.7 | 1,2-Dimethoxyethane | 150.8 | A | A |
| 37.1 | Isopropyl acetate | 148.4 | A | A |
| 32.9 | Heptane | 131.6 | A | A |
| 41.3 | 2-Butanol | 165.2 | A | A |
| 32.2 | Water | 128.8 | A | A |
| 32.0 | Methylcyclohexane | 128 | A | A |
| 36.4 | 1,4-Dioxane | 145.6 | A | A |
| 37.9 | N-propyl acetate | 151.6 | A | A |
| 36.1 | Isobutanol | 144.4 | A | A |
| 30.3 | Toluene | 121.2 | | A |
| 33.7 | Isobutylacetate | 134.8 | A | A |
| 31.0 | 2-Methoxyethanol | 124 | A | A |
| 34.1 | n-Butyl acetate | 136.4 | A | A |
| 33.5 | 2-Hexanone | 134 | A | A |
| 35.9 | Chlorobenzene | 143.6 | A | A |
| 33.2 | 2-Ethoxyethanol | 132.8 | A | A |
| 39.2 | 1-Pentanol | 156.8 | A | A |
| 33.2 | m-Xylene | 132.8 | A | A |
| 41.1 | Cumene | 164.4 | A | A |
| 34.1 | N,N-Dimethylformamide | 136.4 | A | A |
| 33.3 | Anisole | 133.2 | A | A |

*in this experiment, the solids dissolved after 14 days

In a second set of slurry experiments, the same amounts of Form A and Form B were weighed into 1.8 mL vials, and charged with a stirring bar. After addition of the solvent, the slurries were placed at 25° C. and 50° C., under stirring. Material from the slurries was sampled at the time points of 2, 4 and 14 days (sampling from the same vial per solvent and per temperature). These materials were analyzed wet by XRPD and digital imaging. As seen in Table 20, Form B converted to Form A in all organic solvents and in water at 37° C. The sampling after 2 and 4 days in water at 25° C. showed that the solids were a mixture of Form A and the hepta-hydrated Form D. This observation indicated that Form B converted to Form D in an aqueous environment and that Form A remained stable. In the sampling on the 14th day, only Form A was present, indicating its higher stability in water, compared to Form D.

TABLE 20

Slurry experiments

| | | | 2 Days | | 4 days | | 2 weeks | |
|---|---|---|---|---|---|---|---|---|
| Weight (mg) | Form A/B | Solvent | 25° C. | 60° C. | 25° C. | 60° C. | 25° C. | 60° C. |
| 15 | A | Water | A + D | A | A + D | A | A | A |
| 16.5 | A | n-Heptane | A | A | A | A | A | A |
| 17 | A | 1-Butanol | A | A | A | A | A | A |
| 18 | A | Methanol | A | A | A | A | A | A |
| 18.5 | A | Acetone | A | A | A | A | A | A |
| 28.7 | B | Water | A | A | A | A | A | A |
| 34.7 | B | n-Heptane | A | A | A | A | A | A |
| 27.4 | B | 1-Butanol | A | A | A | A | A | A |
| 28.4 | B | Methanol | A | A | A | A | A | A |
| 27.6 | B | Acetone | A | A | A | A | A | A |

Vapor Diffusion into Solution Experiments

For the vapor diffusion into solution experiments, saturated solutions of brigatinib were exposed to anti-solvent vapors at room temperature for two weeks. An aliquot of saturated solution was transferred to a vial which was left open and placed in a closed container with anti solvent (see Table 20). After two weeks, the samples were evaluated for solid formation. Where solids were present, the liquids were separated from the solids, which were then dried at full vacuum. In the cases where no precipitation was observed, the solvents were placed overnight at 5° C. to promote precipitation. If no solids were present, the liquids were evaporated at 200 mbar for 75 hours, or, if still no solids were present, the liquids were further evaporated at 10 mbar for a maximum of 10 days. All obtained solids were analyzed dry by XRPD and digital imaging. Table 21 provides the experimental conditions and corresponding solid forms obtained.

TABLE 21

Vapor diffusion into solution experiments

| Solvent | Volume (µL) | Anti-solvent | Solid after 2 weeks? | Form (XRPD) |
|---|---|---|---|---|
| Anisole | 8000 | Nitrobenzene | N | A |
| P-Xylene | 30000 | Anisole | N | A |
| Diisopropyl ether* | 5000 | Diethoxymethane | N | — |
| Isopropyl Acetate | 40000 | Water | N | A |
| Cyclohexanone | 40000 | Cis-Decahydronaphthalene | N | A |
| Cyclohexanone | 40000 | N-Methyl-2-pyrrolidone | N | A |
| Ethyl Formate | 8000 | n-Hexane | N | A |
| Ethyl Formate | 8000 | Cyclohexane | N | A |

TABLE 21-continued

Vapor diffusion into solution experiments

| Solvent | Volume (µL) | Anti-solvent | Solid after 2 weeks? | Form (XRPD) |
|---|---|---|---|---|
| Ethyl Formate | 8000 | 2,2,4-Trimethylpentane | N | A |
| Ethyl Formate | 8000 | n-Heptane | N | A |
| Tetrahydrofuran | 40000 | Cyclohexanone | N | A |
| Ethylene Glycol Dimethyl Ether | 8000 | n-Pentane | N | A |
| Ethylene Glycol Dimethyl Ether | 8000 | 2-Methylpentane | N | A |
| Ethylene Glycol Dimethyl Ether | 8000 | n-Hexane | N | A |
| Ethylene Glycol Dimethyl Ether | 8000 | Cyclohexane | N | A |
| Ethylene Glycol Dimethyl Ether | 8000 | n-Heptane | N | A |
| Ethylene glycol diacetate* | 8000 | Bis(2-methoxyethyl) ether | N | — |
| n-Nonane* | 40000 | 1-Octanol | N | — |
| 1,2,3,4-Tetrahydronaphthalene* | 8000 | Cumene | N | — |
| Dioxane, 1,4- (Extra dry) | 2000 | Cyclohexane | N | A |
| Isoamyl acetate* | 4000 | Nitrobenzene | N | A |
| n-Heptane | 40000 | P-Xylene | N | A |
| Cis-Decahydronaphthalene | 8000 | MethylCyclohexane | N | Am |
| 2,2,4-Trimethylpentane | 8000 | Cis-Decahydronaphthalene | N | A |
| 1,2-Propanediol* | 8000 | tert-Butylmethyl ether | N | — |
| 1,2-Propanediol* | 8000 | Water | N | — |
| N-Amyl acetate | 8000 | 1-Octanol | N | A |
| N-Amyl acetate* | 8000 | Ethyleneglycol diacetate | N | — |
| Ethanol | 2000 | Water | N | A |
| Methanol | 600 | Water | Y | A |
| Acetone* | 8000 | Water | N | — |
| Chloroform* | 200 | tert-Butylmethyl ether | N | — |
| Chloroform* | 200 | Acetonitrile | Y | — |
| Cumene | 8000 | Cis-Decahydronaphthalene | N | A |

*No yield after evaporation

Vapor Diffusion onto Solids Experiments

For the 34 vapor diffusion onto solids experiments, amorphous brigatinib was prepared by grinding the starting material for 4 hours. The vials containing the amorphous brigatinib were left open and placed in closed 40 mL vials containing 2 mL of solvent (see Table 21). The amorphous brigatinib was exposed to solvent vapors at room temperature for two weeks. At the end of the experiment time, the solids were harvested wet and dry and analyzed by XRPD and digital imaging. For the applied crystallization conditions and corresponding obtained solid forms see Table 22.

TABLE 22

Vapor diffusion onto solids

| Solvent | Weight (mg) | Solids after 2 weeks? | Form wet (XRPD) | Form dry (XRPD) |
|---|---|---|---|---|
| Ethyl ether | 30.7 | Y | A | A |
| N-pentane | 34.8 | Y | A | A |
| Dichloromethane | 30.1 | N | — | Am |
| Ethyl formate | 29.8 | Y | A | A |
| tert-Butylmethyl ether | 30.5 | Y | A | A |
| Acetone | 33.7 | Y | A | A |
| Methyl acetate | 31.2 | Y | A | A |
| Chloroform | 28.6 | N | — | A + Am |
| Methanol | 27.6 | Y | A | A |
| Tetrahydrofuran | 31.7 | Y | A | A |
| Hexane | 29.3 | Y | A | A |
| Ethyl acetate | 35.9 | Y | A | A |
| Ethanol | 30.7 | Y | A | A |
| 2-Butanone | 28.8 | Y | A | A |
| Cyclohexane | 29.2 | Y | A | A |
| Acetonitrile | 29.1 | Y | A | A |
| 2-Propanol | 29.8 | Y | A | A |
| 1,2-Dimethoxyethane | 36.1 | Y | A | A |
| Isopropyl acetate | 30.3 | Y | A | A |
| 1-Propanol | 30.1 | Y | A | A |
| Heptane | 39.1 | Y | A | A |
| 2-Butanol | 29.7 | Y | A | A |
| MethylCyclohexane | 29.9 | Y | A | A |
| N-propyl acetate | 34.8 | Y | A | A |
| 1,4-Dioxane | 35.1 | Y | A | A |
| Isobutanol | 31.3 | Y | A | A |
| Toluene | 37.5 | Y | A | A |
| Isobutylacetate | 33.1 | Y | A | A |
| 1-Butanol | 38.1 | Y | A | A |
| Water | 37.6 | Y | A | A + B + C |
| n-Butyl acetate | 35.4 | Y | A | A |
| 2-Hexanone | 31.9 | Y | A | A |
| Chlorobenzene | 33.8 | Y | A | A |
| 2-Ethoxyethanol | 32.0 | Y | A | A |

Solvent Assisted Grinding Experiments

In the solvent assisted grinding experiments, a small amount of solvent was added to solid brigatinib which had been mechanically ground in a stainless steel vial containing 2 stainless steel grinding balls. In this manner, 17 different solvents were investigated. Typically, 30 mg of starting material was weighed into the grinding vial and 10 µL of solvent was added to the vial. The grinding experiments were performed at 30 Hz for 60 min. Subsequently, the samples were collected and analyzed (wet) by XRPD and digital imaging. For the applied crystallization conditions and corresponding obtained solid forms see Table 23.

TABLE 23

Solvent assisted grinding experiments

| Solvent | Weight (mg) | Volume (µL) | Form (XHPD) |
|---|---|---|---|
| Ethanol | 30.7 | 10 | A |
| Cyclohexane | 30.8 | 10 | A |
| Acetonitrile | 34.1 | 10 | A |
| 2-propanol | 35.0 | 10 | A |
| Ethylene Glycol Dimethyl Ether | 31.5 | 10 | A |
| Isopropyl Acetate | 30.3 | 10 | A |
| n-Heptane | 32.1 | 10 | A |
| Water | 32.5 | 10 | A |
| 1,4-Dioxane | 32.0 | 10 | A |
| Isobutanol | 31.5 | 10 | A |
| Toluene | 31.8 | 10 | A |
| Butyl acetate | 33.0 | 10 | A |
| 2-Hexanone | 30.7 | 10 | A |
| Chlorobenzene | 30.8 | 10 | A |
| Acetone | 30.3 | 10 | A |
| Cumene | 31.0 | 10 | A |
| Anisole | 31.8 | 10 | A |

Thermocycling Experiments

A total of 33 slurries and 1 solution (chloroform) of starting material in solvents were prepared at room temperature. The mixtures were placed in a Crystal16™ to undergo the following temperature profile:

1. Heating at a rate of 5° C./h until reaching 40° C., with stirring (500 rpm)
2. Cooling at a rate of 5° C./h until 5° C., with stirring (200 rpm)
3. Aging for 30 min at 5° C.
4. Repeat 8 cycles After completion of the cycling program, the solids were separated from the mother liquids by centrifugation, dried under 200 mbar for 48 hours (2-ethoxyethanol for 283 hours) and analyzed by XRPD and digital imaging. For the applied crystallization conditions and corresponding obtained solid forms, see Table 24. Solid form (or mixture) following the arrow (→) was obtained upon remeasurement by XRPD after storage of the measuring plates at ambient conditions for 5 weeks.

TABLE 24

Thermocycling experiments

| Solvent | Weight (mg) | Volume (μL) | Solids after last cycle? | Form dry (XRPD) | Form mother liquid (XRPD) |
| --- | --- | --- | --- | --- | --- |
| Ethyl Formate | 20.5 | 750 | Y | A | — |
| tert-Butylmethyl ether | 20.1 | 750 | Y | A | — |
| Acetone | 20.0 | 750 | Y | A | — |
| Methyl acetate | 21.9 | 750 | Y | A | — |
| Chloroform | 173.3 | 400 | Y | A | A + G |
| Methanol | 20.6 | 500 | N | A | — |
| Tetrahydrofuran | 20.6 | 750 | Y | A | A |
| Hexane | 20.4 | 750 | Y | A | — |
| Ethyl acetate | 22.0 | 750 | Y | A | — |
| Ethanol | 19.2 | 750 | Y | A | A |
| Cyclohexane | 19.8 | 750 | Y | A | — |
| Acetonitrile | 19.8 | 750 | Y | A | — |
| Isoprapanol | 21.4 | 750 | Y | A | — |
| Ethylene Glycol Dimethyl Ether | 23.4 | 750 | Y | A | — |
| Isopropyl Acetate | 20.0 | 750 | Y | A | — |
| n-Heptane | 19.2 | 750 | Y | A | A + L → A |
| 2-Butanol | 17.9 | 750 | Y | A | — |
| Water | 21.7 | 750 | Y | A | — |
| MethylCyclohexane | 18.9 | 750 | Y | A | — |
| 1,4-Dioxane | 21.7 | 750 | Y | A | — |
| Propyl acetate | 23.7 | 750 | Y | A | — |
| Isobutanol | 21.3 | 750 | Y | A | A |
| Toluene | 20.5 | 750 | Y | A | — |
| Isobutyl aceta | 21.0 | 750 | Y | A | — |
| 2-Methoxyethanol | 56.5 | 750 | Y | A | A |
| Butyl acetate | 18.9 | 750 | Y | A | — |
| 2-Hexanone | 22.1 | 750 | Y | A | — |
| Chlorobenzene | 20.0 | 750 | Y | A | A |
| 2-Ethoxyethanol | 20.1 | 750 | N | A | — |
| 1-Pentanol | 19.4 | 750 | Y | A | A |
| m-Xylene | 20.4 | 750 | Y | A | — |
| Cumene | 19.7 | 750 | Y | A | — |
| N,N-Dimethylformamide | 20.0 | 750 | Y | A | A |
| Anisole | 18.8 | 750 | Y | A | A |

Variable Temperature XRPD Experiments

Data was collected for Forms A, B, C, and D almost immediately after reaching the target temperature (within approximately 10 min).

For Form A, the temperatures used in the experiment were 25, 40, 60, 100, 120, 140, 150, 160, 170, 180, 190, and 200° C. Data collection lasted 20 min per temperature and the stabilization time in between was 10 min. The variable temperature XRPD data collected for Form A did not reveal any phase transformation. The only peak shifts observed were attributed to thermal expansion.

For Form B, the temperatures used in the experiment were 25, 40, 60, 100, 120, 140, 150, 155, 160, 165, 170, 180, and 190° C. Data collection lasted 45 min per temperature and the stabilization time in between was 10 min. At 150° C., partial conversion to Form A was observed and at 155° C. the conversion was complete. Thereafter, Form A remained stable for the rest of the temperature profile.

For Form C, the temperatures used in the experiment were 25, 40, 60, 70, 80, 100, 120, 140, 150, 155, 160, 165, 170, 175, 180, 190, and 200° C. Data collection lasted 40 min per temperature and the stabilization time in between was 10 min. Form C is instable at temperatures higher than 25° C. By the first measurement, the material had already partially converted to the dehydrated Form B. Thereafter, the solid form transformations resembled those observed in the VT-XRPD experiments of Form B, with the difference that the transformation of Form B to Form A was initiated already at 120° C. The conversion was completed though at the same temperature (155° C.). Again, no phase transition was observed upon cooling.

For Form D, the temperatures used in the experiment were 25, 35, 45, 55, 65, 75, 85, 100, 120, 140, 150, 155, 160, 165, 170, 175, 180, 190, and 200° C. Data collection lasted 10 min for temperatures 25-85° C. with a stabilization time of 1 min, and 40 min for temperatures 100-25° C. with a stabilization time of 10 min. The variable temperature XRPD confirmed that the hepta-hydrated Form D is unstable at temperatures higher than 25° C. Indeed, after the first measurement, Form D had already converted (partially) to the hydrated Form C (at 35° C.) and to the dehydrated Form B at 45° C. Thereafter, the solid form transformations resembled those observed in the VT-XRPD experiments of Form C: Form B converted (partially) to Form A at 120° C. The conversion was completed at 150° C. No phase transition was observed upon cooling.

Variable Humidity-XRPD Experiments

The relative humidity was increased from the starting amount, brought up to the maximum, then dried back to the minimum value. The data collection time was 41 min at each step, time starting after equilibration of the relative humidity.

For Form A, the collected XRPD patterns of Form A did not show any phase transition, neither at 30 nor at 60° C. Only some minor, but clear, peak shifts of the order of 0.03° 2θ were observed in specific peaks, starting at about 60% RH. The peaks shifts were reversible at RH of about 30%. A sample of Form A was then exposed to 80% RH for 15 h. The peaks shifts had occurred after 90 min, and the extent of the shifts remained constant throughout the exposure at 80% RH for 15 h. Upon return to 10% RH, the peaks shifted to their original position. To investigate the amount of water adsorbed, a new sample of Form A was exposed for 2 h at 80% and a TGMS of this sample was measured. The TGMS thermogram showed a mass loss of 0.35% corresponding to 0.1 water molecules.

For Form B, the relative humidity was measured at 30° C. The RH % values measured were 10, 30, 50, 60, 65, 70, 75, and 80%. Upon sorption, Form B converts to the hydrated Form C, starting at about 65% RH. At 80% RH the conversion to Form C was completed. Upon desorption, Form C dehydrates to Form B, starting at about 30% RH. At 10% RH the conversion to Form B was completed.

For Form C, a hydrate, the relative humidity was measured at 30° C. The experiment was performed starting at the maximum RH and dehydrated, then rehydrated back up to the maximum value. The RH % values measured were 10, 15, 20, 25, 30, 35, 40, 60, and 80%. Upon desorption, Form C dehydrated to Form B, starting at about 25% RH. At 10% RH, the conversion to Form B was complete. Upon sorption, Form B converted to Form C, starting at about 60% RH. At 80% RH the conversion to Form C was complete. The results are consistent with the corresponding experiments of Form B.

For Form D, a hydrate, the relative humidity was measured at 30° C. The experiment was performed starting at the maximum RH and dehydrated, then rehydrated back up to the maximum value. The RH % values measured were 10, 15, 20, 25, 30, 35, 40, 60, and 80%. Despite attempts to have freshly prepared Form D, even the first measurements at 80% RH showed that the solid had already partially transformed to Form C. Thereafter, the solid transformed to the hydrated Form C and eventually to the anhydrous Form B, as already observed in the VH-XRPD measurements of Forms B and C. Upon desorption, the hepta-hydrated Form D converted to the hydrated Form C. Form C dehydrated to Form B, starting at about 20% RH. At 10% RH, the conversion to Form B was complete. Upon sorption, Form B converted to Form C, starting at about 40% RH. At 80% RH, the conversion to Form C was complete. The solid did not hydrate to Form D as a relative humidity of 80% is not sufficient; for the conversion to Form D, an exposure at relative humidity of 95% can be employed.

Dynamic Vapor Sorption Experiments

Figure 44:
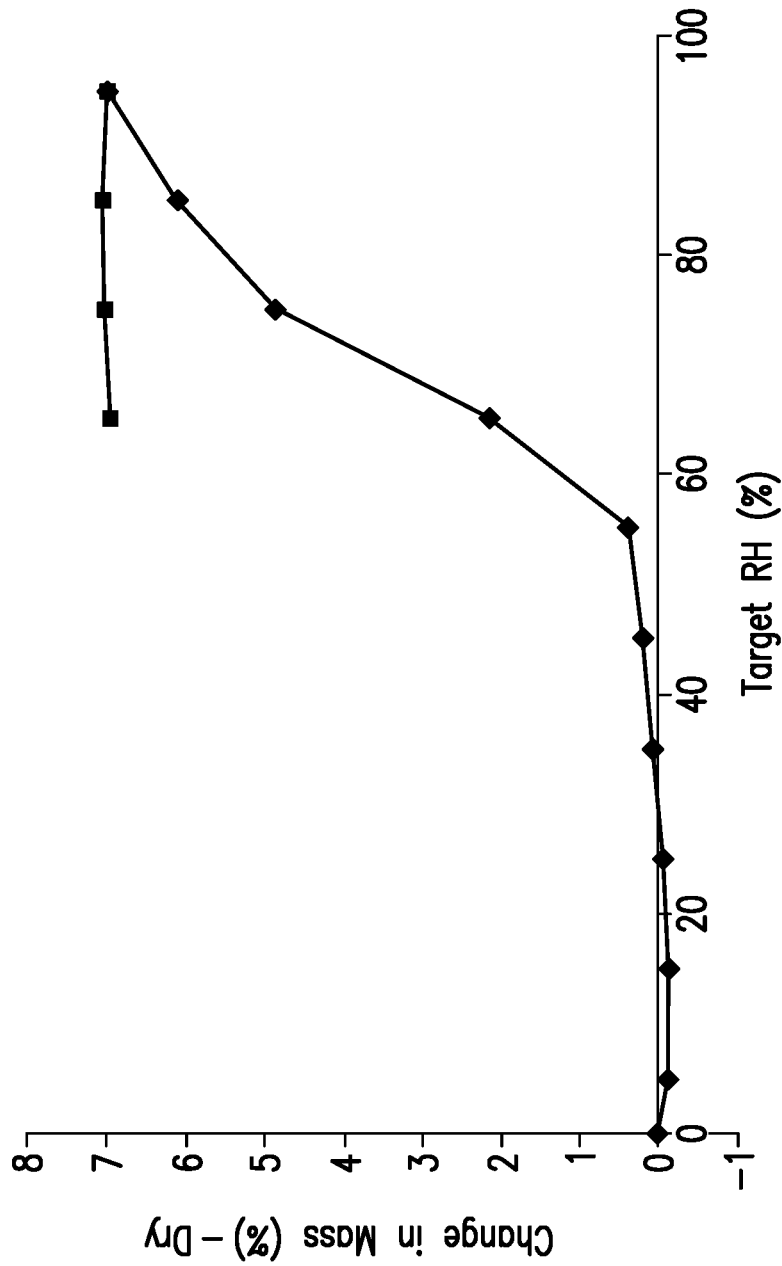
FIG. 44 is a DVS plot of Form B, wherein the total gain in mass at 95% RH corresponded to 2.26 water molecules.

In three DVS experiments, the relative humidity was varied as follows:
Expt. 1: 5%→95%→65% RH
Expt. 2: 5%→95%→5% RH
Expt. 3: 5%→95% RH
Expt. 4: 0% for 6h→5% for 1h→15% for 1 h→25-85% gradient over 2 h→95 for 5 h RH For Expt. 1, during sorption, Form B adsorbed water mass corresponding to 2.26 molecules of water between 45-95% RH, as shown in FIG. 44. Upon desorption to 65% RH, the gained water mass remained almost constant. XRPD measurement of the solid showed that it was the hydrated Form C. The additional gained water mass can be attributed to adsorption on the surface of the material.

Figure 45:
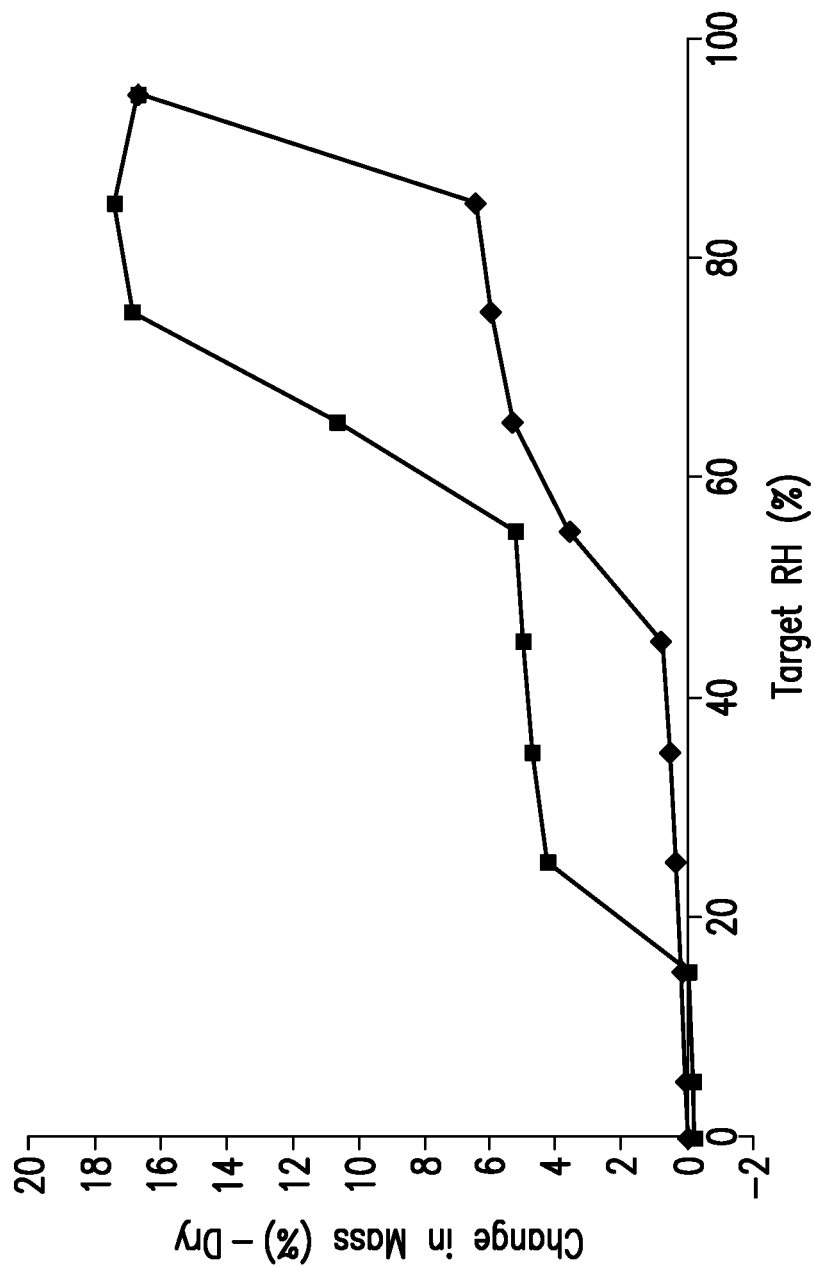
FIG. 45 is a DVS plot of Form B, wherein the total gain in mass at 85% RH corresponded to 5.6 water molecules.

For Expt. 2, during sorption, a two-step water mass gain was observed, as shown in FIG. 45. In the first step, between 45-85% RH, a mass change of 6.45% was observed corresponding to 2.1 water molecules. The data are consistent with the hydrated Form C being formed at this stage. In the second step, between 85% and 95% RH, a total change in mass of 16.7% was reached. A further mass increase of 17.4% was observed at 85% RH during desorption. The increasing mass gain during desorption indicates that no equilibrium was reached within one hour at 95% RH, and the water adsorption continued at least until 85% RH, during humidity decrease. The maximum change in mass corresponded to 5.6 water molecules. The data are consistent with the hepta-hydrated Form D being (partially) formed at the maximum RH. During the two-step desorption, the change in mass was roughly stable up to about 75% RH and it, thereafter, reduced to about 5.2%. The latter change in mass corresponded to about 1.7 water molecules. At this stage, the data was consistent with the hydrated Form C being formed. Thereafter, and until about 25% RH, the gained mass decreased to 4.2%, corresponding to 1.4 water molecules. The data is consistent with a mixture of the hydrated Form C with the anhydrous Form B being formed. Thereafter, the gained water was lost in one step, between 25% and 15% RH. The XRPD of the material at the end of the sorption-desorption cycle showed that it was a mixture of Forms B and C.

Figure 46:
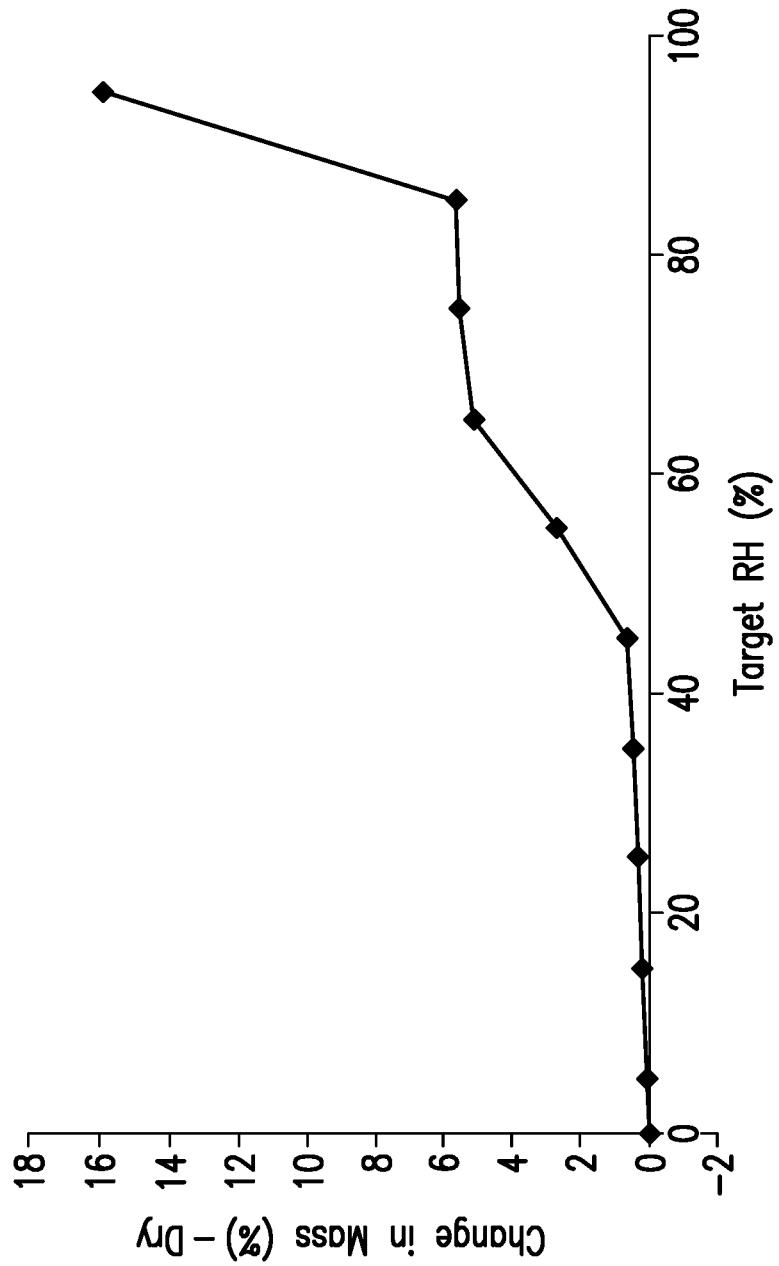
FIG. 46 is a DVS plot of Form B, wherein the total gain in mass at 95% RH corresponded to 5.15 water molecules.

For Expt. 3, the DVS indicated a two-step water adsorption as shown in FIG. 46. The change in mass during the first step (between 45-85% RH) was 5.59% corresponding to 1.8 water molecules. The total change in mass at 95% RH was 15.88% corresponding to 5.15 water molecules. XRPD measurement of the solid after the cycle showed that it was Forms B+C.

Figure 47:
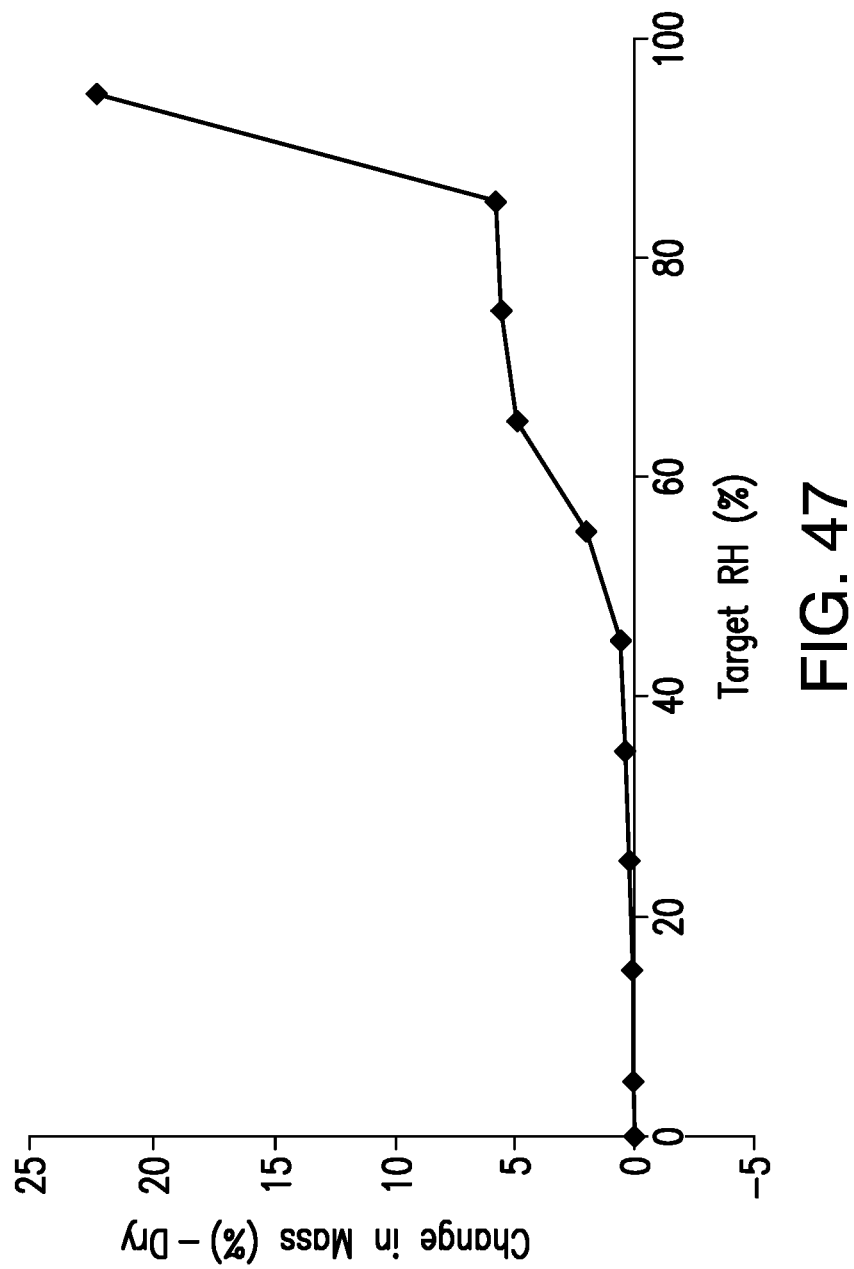
FIG. 47 is a DVS plot of Form B, wherein the total gain in mass at 95% RH corresponded to 7.2 water molecules.
Figure 48:
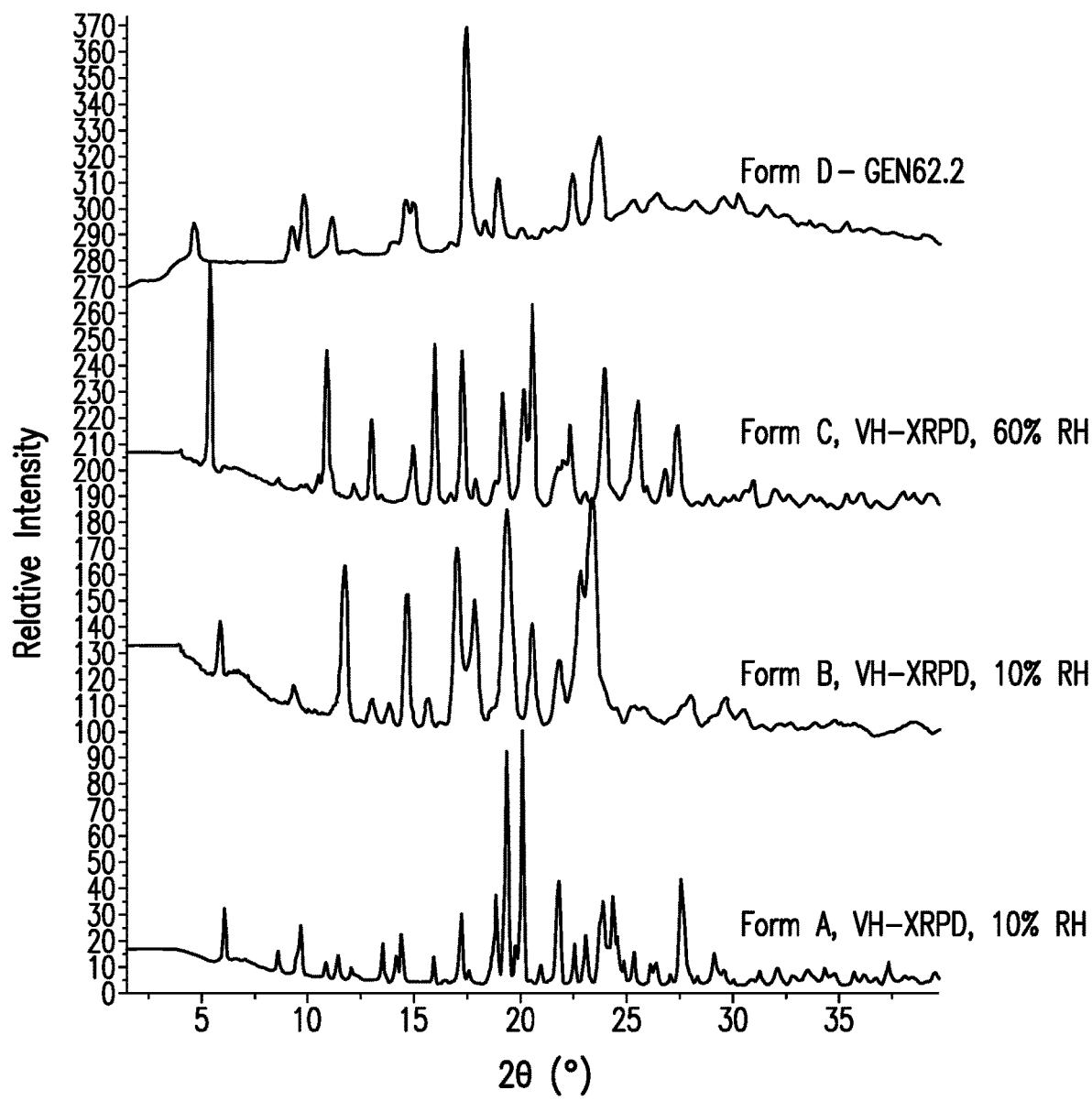
FIG. 48 is an overlay of XRPD patterns of Forms A, B, C and D.
Figure 49:
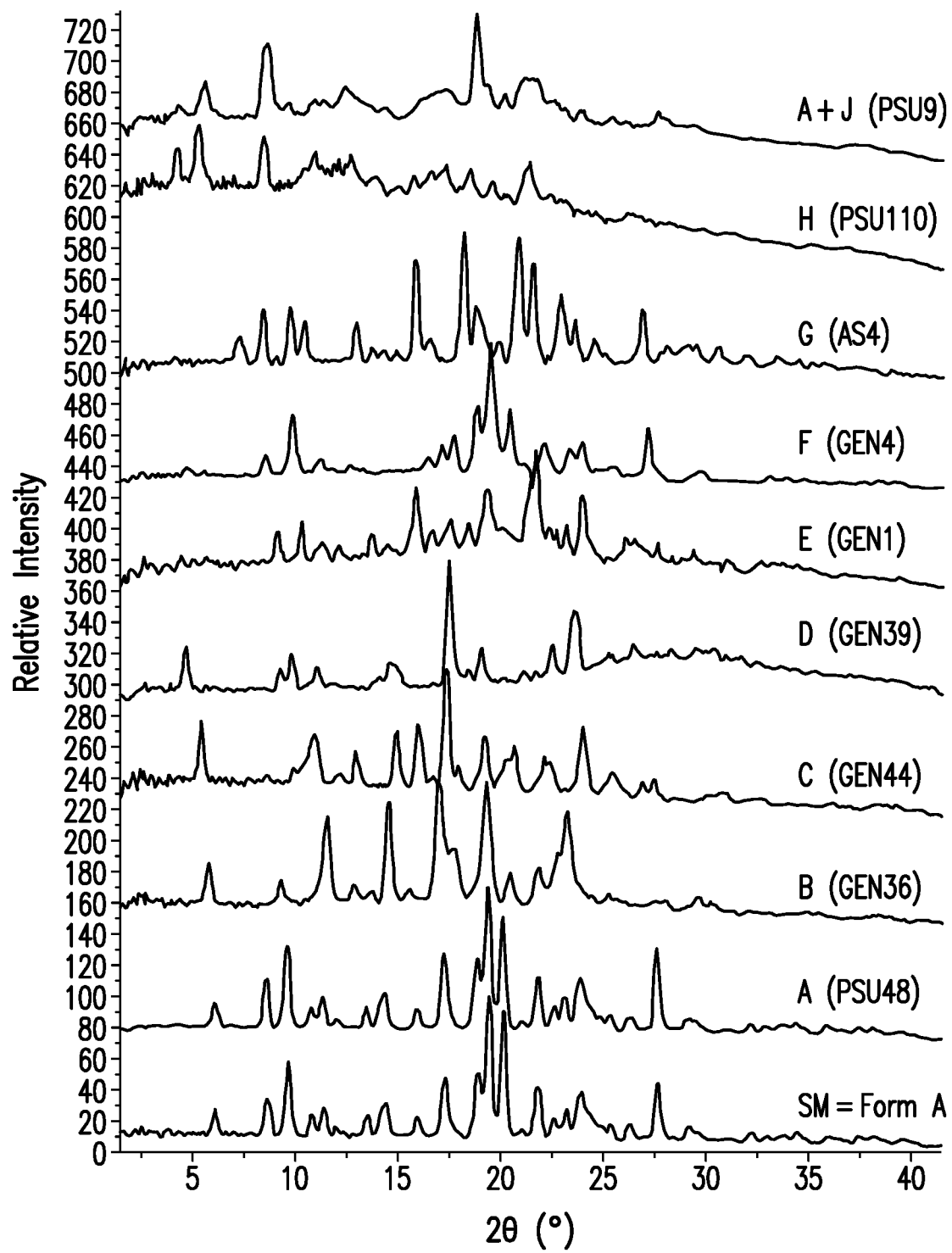
FIG. 49 is an overlay of XRPD patterns of Forms A, B, C, D, E, F, G, H, and A mixed with J.
Figure 50:
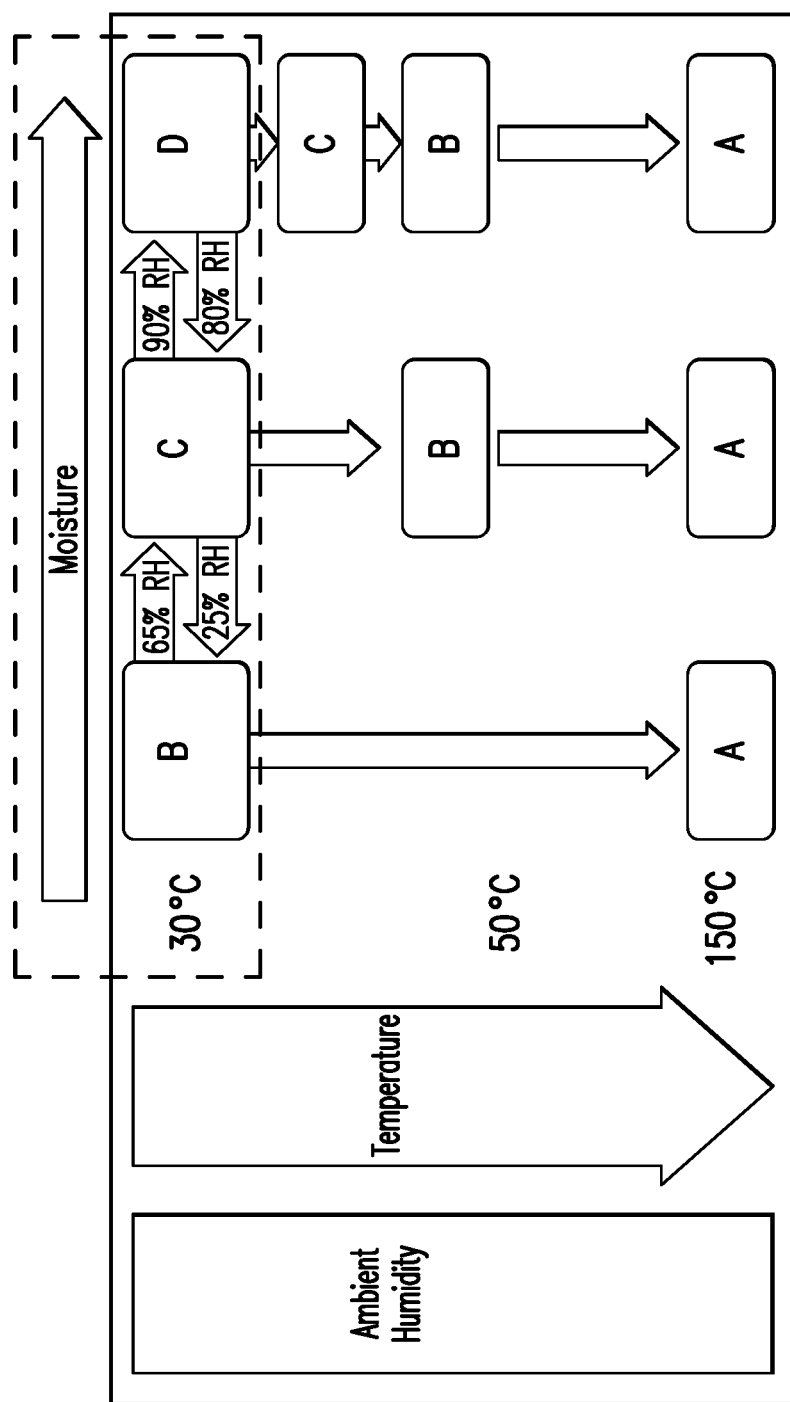
FIG. 50 is an inter-conversion scheme for Forms A, B, C and D based on experiments. The dashed box shows that, at 30° C., increasing the humidity lead to hydration of Form B to Form C and eventually to Form D. The changes are reversible upon humidity decrease. The solid-line box shows that, at ambient humidity, increasing the temperature lead to dehydration of Form C and Form D to Form B (at about 40° C.) and to Form A via solid-solid transition at about 150° C. These conversions are not reversible: Form A remains stable upon temperature decrease Disclosed herein are various crystalline forms of brigatinib. As used herein, the terms "crystalline form," "polymorphic form," and "polymorph" are used interchangeably, and refer to a solid form of brigatinib that is distinct from the amorphous form of brigatinib and from other solid form(s) of brigatinib as evidenced by certain properties such as, for example, kinetic and/or thermodynamic stability, certain physical parameters, X-ray crystal structure, DSC, and/or preparation processes. Polymorphic forms of a compound can have different chemical and/or physical properties, including, for example, stabilities, solubilities, dissolution rates, optical properties, melting points, chemical reactivities, mechanical properties, vapor pressures, and/or densities. These properties can affect, for example, the ability to process and/or manufacture the drug substance and the drug product, stability, dissolution, and/or bioavailability. Thus, polymorphism may affect at least one property of a drug including, but not limited to, quality, safety, and/or efficacy.

For Expt. 4, deviations between the measured values of water mass gain or losses and the expected corresponding water molecules can be attributed to the fact that the measurements were performed prior to reaching the equilibrium of an event. Therefore, in this experiment, the Relative Humidity profile was modified in order to investigate the impact of longer equilibration time at each step. As seen in FIG. 47, the maximum change in mass was 22.2% corresponding to 7.2 water molecules. The XRPD pattern of the material after the cycle was Forms C+D.

Hydration Studies of Forms A and B

Slurrying of Forms A and B (separately) was performed at room temperature in water, HCl buffer of pH 1.0 (0.1N HCl) and SGF (for Form A). The solids were harvested and measured wet by XRPD after 45 min, 1.5 h, 15 h, 48 h and 10 days (not in SGF). Form A remained stable even after 10 days slurrying in water and the HCl buffer or 1.5 h in SGF. Form B converted to the heptahydrate Form D after 45 min, which remained stable, at least for 10 days. In a separate experiment, where Form B was exposed to 90% RH for one day, the material converted to a mixture of Forms C and D.

Dehydration of Forms C and D

In Table 25, a list of drying conditions for Form C are presented together with the final solid form. At ambient pressure, Form C appears to be stable after 1.5 hours at 30° C. while at 40° C. it converted to Form B within one hour.

In Table 26, a list of drying processes of Form D are presented. Form D under 5 mbar pressure and at 60° C. led to the formation of Form B after 24 h. In some instances, small quantities of Form C were visible on the XRPD patterns, even after 5 days of drying. This observation could be attributed to different particle morphology (fine particles vs. agglomerates/aggregates). At 60° C. and at 50 mbar pressure, Form D converted to a mixture of Forms B+C after 86 h and to Form B after 110 h. In general, depending on the time and pressure, Forms B and C occur.

TABLE 25

Dehydration of Form C.

| Temp (° C.) | 0.5 h | 1 h | 1.5 h | 4.5 h |
|---|---|---|---|---|
| 20 | C | — | C | — |
| 30 | C | — | C | — |
| 40 | — | B | — | B |

TABLE 26

Dehydration of Form D

| Time (h) at 60° C. | 50 mbar | 5 mbar | ambient pressure |
|---|---|---|---|
| 24 | — | B | — |
| 28 | — | B + C | — |
| 5 days | — | B + C | — |
| 6 days | — | B | — |
| 15 (RT) | — | C | — |
| 20 (RT) | — | B + C | — |
| 15 | — | C + D | — |

TABLE 26-continued

Dehydration of Form D

| Time (h) at 60° C. | 50 mbar | 5 mbar | ambient pressure |
|---|---|---|---|
| 20 | — | B + C | — |
| 86 | B + C | — | — |
| 110 | B | — | — |
| 65 | B + C | — | — |
| 86 | B | — | — |
| 8 days, closed vial at RT | — | — | B + C |

In Table 27, the occurrence of solid forms of brigatinib is given, together with the crystallization methods from which they crystallized and the related solvents. The table provides the results of over 600 experiments with solid forms measured by XRPD wet and/or dry (wet and dry count as separate experiments). In eight cases, no form assignment was made due to low yield. The solid form(s) following the arrow was/were obtained upon remeasurement by XRPD after storage of the measuring plates at ambient conditions for several weeks (2-5 weeks).

TABLE 27

Summary of Brigatinib Solid Forms

| Obtained Form | Occurrence | Crystallization Methods | Solvent, Anti-Solvent |
|---|---|---|---|
| Am | 3 | Hot filtration, 1; Vapor diffusion onto solids, 1; Vapor dissusion onto liquids, 1 | 2,2,4-trimethylpentane/ Pinacolone (50/50); Cis-Decahydronaphthalene/ Methylcyclohexane (50/50); Dichloromethane |
| A | 562 | All methods | All solvents |
| D | 1 | Anti-solvent | Methanol (S)/water(AS) |
| E | 1 | Freeze-drying | Chloroform |
| F | 1 | Freeze-drying | Trifluoroethanol/water (90:10) |
| G → A | 1 | Anti-solvent | Chloroform (S)/ acetonitrile (AS) |
| H → A + H, A | 5 | Cooling-evaporative (µL scale) | Methanol/Chloroform (50/50) |
| A + Am | 1 | Vapor diffusion on onto solids | Chloroform |
| A + B + C | 1 | Vapor diffusion onto solids | Water |
| A + C | 4 | Hot filtration, 3 Evaporative, 1 | Acetone/Water (50/50) Water/Methanol (50/50) Water/1,4-Dioxane (50/50) Acetone/Water (50/50) |
| A + E | 2 | Slurry | Chloroform |
| A + G | 2 | Anti-solvent, 1 Thermocycling, 1 | Chloroform (S)/tert- Butyl methyl ether (AS) Chloroform |
| A + H | 12 | AS, 2 Cooling-evaporative (µL scale), 10 | Ethanol (S)/Water(AS) 1,4-Dioxane(S)/Water(AS) Methanol Methanol/Chloroform (50/50) Methanol/Acetonitrile (50/50) |
| A + J → A + J | 1 | Cooling-evaporative (µL scale) | 2-Methoxyethanol |
| A + K → A + K | 1 | Cooling-evaporative (µL scale) | Tetrahydrofuran/N-Methyl- 2-pyrrolidone (50/50) |
| A + L → A + L, A | 4 | Slurry | Hexane; n-Heptane; Methylcyclohexane |

III. PHARMACEUTICAL COMPOSITIONS

In some embodiments, the present disclosure provides pharmaceutical compositions comprising at least one crystalline form of brigatinib and at least one component chosen from pharmaceutically acceptable carriers, pharmaceutically acceptable vehicles, and pharmaceutically acceptable excipients. In some embodiments, the at least one crystalline form of brigatinib is present in a therapeutically effective amount. In some embodiments, the at least one crystalline form of brigatinib is substantially pure. In some embodiments, the at least one crystalline form of brigatinib is chosen from Form A, Form B, Form C, Form D, Form E, Form F, Form G, and Form H. In some embodiments, the crystalline brigatinib is Form A.

In some embodiments, a unit dosage form of a pharmaceutical composition comprises a single crystal form of brigatinib as the API. In some embodiments, the present disclosure provides pharmaceutical compositions consisting of one crystalline form of brigatinib. In some embodiments, the present disclosure provides pharmaceutical compositions consisting of one crystalline form of brigatinib and at least one component chosen from pharmaceutically acceptable carriers, pharmaceutically acceptable vehicles, and pharmaceutically acceptable excipients. In some embodiments, the present disclosure provides pharmaceutical compositions consisting essentially of one crystalline form of brigatinib and optionally at least one component chosen from pharmaceutically acceptable carriers, pharmaceutically acceptable vehicles, and pharmaceutically acceptable excipients.

In some embodiments, the present disclosure provides pharmaceutical compositions produced by combining at least one crystalline form of brigatinib and at least one component chosen from pharmaceutically acceptable carriers, pharmaceutically acceptable vehicles, and pharmaceutically acceptable excipients.

In some embodiments, a unit dosage form of a pharmaceutical composition comprises more than one crystal form of brigatinib. In some embodiments, more than 50%, more than 70%, more than 80%, more than 90%, more than 95%, or more than 99%, of brigatinib in the composition is in a single crystalline form. In some embodiments, the single crystalline form of brigatinib is chosen from Form A, Form B, Form C, Form D, Form E, Form F, Form G, and Form H. In some embodiments, the single crystalline form of brigatinib is Form A.

In some embodiments, one or all of the crystalline forms is substantially pure. For example, in some embodiments, the pharmaceutical composition comprises substantially pure Form A of brigatinib and at least one component chosen from pharmaceutically acceptable carriers, pharmaceutically acceptable vehicles, and pharmaceutically acceptable excipients. In some embodiments, a pharmaceutical composition comprises Form A and Form B of brigatinib and at least one component chosen from pharmaceutically acceptable carriers, pharmaceutically acceptable vehicles, and pharmaceutically acceptable excipients. Other embodiments are variations of this theme that will be readily apparent to those of ordinary skill in the art reading this disclosure. For example, in some embodiments, a pharmaceutical composition can comprise Form A and at least one additional crystalline form of brigatinib chosen from Forms B, C, D, E, F, G, H, J, and K, and at least one component chosen from pharmaceutically acceptable carriers, pharmaceutically acceptable vehicles, and pharmaceutically acceptable excipients.

The at least one component may be readily chosen by one of ordinary skill in the art and may be determined by the mode of administration. Illustrative and non-limiting examples of suitable modes of administration include oral, nasal, parenteral, topical, transdermal, and rectal. The pharmaceutical compositions disclosed herein can take any pharmaceutical form recognizable to the skilled artisan as being suitable. Non-limiting examples of suitable pharmaceutical forms include solid, semisolid, liquid, and lyophilized formulations, such as tablets, powders, capsules, suppositories, suspensions, liposomes, and aerosols.

In some embodiments, the pharmaceutical compositions optionally further comprise at least one additional therapeutic agent. In some embodiments, a compound as disclosed herein can be administered to a subject undergoing one or more other therapeutic interventions (e.g. Crizotinib or other kinase inhibitors, interferon, bone marrow transplant, farnesyl transferase inhibitors, bisphosphonates, thalidomide, cancer vaccines, hormonal therapy, antibodies, radiation, etc). For example, in some embodiments, the compound as disclosed herein can be used as a component of a combination therapy with at least one additional therapeutic agent (such as, for example, an anticancer agent), the at least one additional therapeutic agent being formulated together with or separately from the compound as disclosed herein.

As used herein, the term "compound as disclosed herein" refers to at least one crystalline form of brigatinib chosen from those disclosed herein, namely Forms A, B, C, D, E, F, G, H, J, and K, and amorphous brigatinib. A compound as disclosed herein can be present in a pharmaceutical composition as the single active agent or can be combined with at least one additional active agent which may be another form or amorphous brigatinib, or another non-brigatinib compound.

In some embodiments, a pharmaceutical composition disclosed herein can be specially formulated for administration in solid or liquid form, including as non-limiting examples those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution, a sterile suspension, or a sustained-release formulation; topical application, for example, as a cream, an ointment, a controlled-release patch, or spray applied to the skin; intravaginally or intrarectally, for example, as a pessary, cream, stent or foam; sublingually; jocularly; pulmonarily; local delivery by catheter or stent; intrathecally, or nasally.

Non-limiting examples of suitable carriers that can be employed in pharmaceutical compositions disclosed herein include water, ethanol, polyols (such as glycerol, propylene glycol, polyethylene glycol, and the like), vegetable oils (such as olive oil), injectable organic esters (such as ethyl oleate) and mixtures thereof. Proper fluidity can be maintained, for example, by the use of coating materials, such as lecithin, by the maintenance of the required particle size in the case of dispersions, and by the use of surfactants.

In some embodiments, the compositions disclosed herein also comprise at least one adjuvant chosen from preservatives, wetting agents, emulsifying agents, dispersing agents, lubricants, antioxidants, antibacterial agents, antifungal agents (e.g., paraben, chlorobutanol, phenol sorbic acid, and the like), isotonic agents (e.g., sugars, sodium chloride, and the like), and agents capable of delaying absorption (e.g., aluminum monostearate, gelatin, and the like).

Methods of preparing the compositions disclosed herein may, for example, comprise bringing into association at least one compound as disclosed herein and other component(s), such as, for example, chemotherapeutic agent(s) and/or carrier(s). In some embodiments, the compositions are prepared by uniformly and intimately bringing into association a compound as disclosed herein with at least one carrier chosen from liquid carriers and finely divided solid carriers, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 2003; Goodman and Gilman, eds., *The Pharmacological Basis of Therapeutics*, Tenth Edition, McGraw Hill, 2001; *Remington's Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of brigatinib in the disclosed pharmaceutical compositions is less than 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v or v/v. As used herein, "about" means±10% of the value being modified.

In some embodiments, the concentration of brigatinib in the disclosed pharmaceutical compositions is greater than about 90%, about 80%, about 70%, about 60%, about 50%, about 40%, about 30%, about 20%, about 19.75%, about 19.50%, about 19.25% about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v, or v/v. As used herein, "about" means±10% of the value being modified.

In some embodiments, the concentration of brigatinib in the disclosed pharmaceutical compositions is ranges from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.68% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v, v/v. As used herein, "approximately" means±10% of the value being modified.

In some embodiments, the concentration of brigatinib in the disclosed pharmaceutical compositions ranges from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v. As used herein, "approximately" means±10% of the value being modified.

In some embodiments, the amount of brigatinib in the disclosed pharmaceutical compositions is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g. In some embodiments, the amount of one or more of the compounds as disclosed herein can be more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g. about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5, about 3 g, about 3.5, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g. As used herein, "about" means±10% of the value being modified.

In some embodiments, the amount of brigatinib in the disclosed pharmaceutical compositions ranges from about 0.0001 to about 10 g, about 0.0005 g to about 9 g, about 0.001 g to about 0.5 g, about 0.001 g to about 2 g, about 0.001 g to about 8 g, about 0.005 g to about 2 g, about 0.005 g to about 7 g, about 0.01 g to about 6 g, about 0.05 g to about 5 g, about 0.1 g to about 4 g, about 0.5 g to about 4 g, or about 1 g to about 3 g. As used herein, "about" means±10% of the value being modified.

In some embodiments, the present disclosure provides pharmaceutical compositions for oral administration comprising at least one compound as disclosed herein and at least one pharmaceutically acceptable excipient suitable for oral administration. In some embodiments, the present disclosure provides pharmaceutical compositions for oral administration comprising: (i) a therapeutically effective amount of at least one compound as disclosed herein; optionally (ii) an effective amount of at least one second agent; and (iii) at least one pharmaceutically acceptable excipient suitable for oral administration. In some embodiments, the pharmaceutical composition further comprises (iv) an effective amount of at least one third agent.

In some embodiments, the pharmaceutical composition can be a liquid pharmaceutical composition suitable for oral consumption. Pharmaceutical compositions suitable for oral administration can be presented, for example, as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent.

Molded tablets can be made by molding in a suitable machine a mixture of the powdered compound moistened with an inert liquid diluent.

The tablets can be uncoated or coated by known techniques to delay disintegration and absorption in the gastro-intestinal tract and thereby provide a sustained action over a longer period. For example, a time delay material such as glyceryl monostearate or glyceryl distearate can be employed. Formulations for oral use can also be presented as hard gelatin capsules wherein the active ingredient can be mixed with an inert solid diluent, for example, calcium carbonate, calcium phosphate or kaolin, or as soft gelatin capsules wherein the active ingredient can be mixed with water or an oil medium, for example, peanut oil, liquid paraffin or olive oil.

The present disclosure further encompasses in some embodiments anhydrous pharmaceutical compositions and dosage forms comprising at least one active ingredient. Water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. In some embodiments, compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol for subsequent formulation. For example, suitable carriers include powders, capsules, and tablets, with the solid oral preparations. In some embodiments, tablets can be coated by standard aqueous or nonaqueous techniques.

Non-limiting examples of binders suitable for use in pharmaceutical compositions and dosage forms disclosed herein include, but are not limited to, corn starch, potato starch, and other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Non-limiting examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions and dosage forms disclosed herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to prepare the pharmaceutical compositions and the dosage forms disclosed herein. The amount of disintegrant can vary based upon the type of formulation and mode of administration, and can be readily discernible to those of ordinary skill in the art. For example, in some embodiments, about 0.5 to about 15 total weight percent of at least one disintegrant may be used. In some embodiments, about 1 to about 5 total weight percent of at least disintegrant can be used in the pharmaceutical composition. Disintegrants that can be used include, but are not limited to, agaragar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants which can be used in pharmaceutical compositions and dosage forms disclosed herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, syloid silica gel, coagulated aerosol of synthetic silica, and mixtures thereof. A lubricant can optionally be added in an amount of less than about 1 total weight percent of the pharmaceutical composition.

When aqueous suspensions and/or elixirs are chosen for oral administration, the pharmaceutical compositions may further comprise at least one additional agent chosen from sweetening agents, flavoring agents, coloring matters, dyes, emulsifying agents, suspending agents, and diluents (e.g., water, ethanol, propylene glycol, glycerin and the like).

Surfactants which can be included in the pharmaceutical compositions and dosage forms disclosed herein include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

In some embodiments, hydrophilic surfactant(s) has an HLB value of at least about 10, while lipophilic surfactant(s) has an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or nonionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, but are not limited to, lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Other non-limiting examples of ionic surfactants include ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-1actylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

No-limiting examples of hydrophilic non-ionic surfactants include alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, but are not limited to, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, but are not limited to, fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In some embodiments, the pharmaceutical compositions and dosage forms disclosed herein can include at least one solubilizer to ensure good solubilization and/or dissolution of a compound as disclosed herein and to minimize precipitation of the compound. This may be useful for pharmaceutical compositions for nonoral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydxoxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers can also be used. Examples include, but are not limited to, triacetin, triethylcitrate, ethyl oleate, ethyl caprylate, dimethylacetamide, N-methylpyrrolidone, N-hydxoxyethylpyrrolidone, polyvinylpyrrolidone, hydroxypropyl methylcellulose, hydxoxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol, and propylene glycol.

The amount of solubilizer that can be included can vary with the composition. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be present in an amount of about 10%, about 25%, about 50%, about 100%, or up to about 200% by weight based on the total weight of the composition. In some embodiments, solubilizer can be present in an amount of about 5%, about 2%, about 1% or even less. In some embodiments, solubilizer can be present in an amount of about 1% to about 100%, such as from about 5% to about 25% by weight.

The pharmaceutical composition can further comprise at least one pharmaceutically acceptable excipient. Such excipients include, but are not limited to, detackifiers, antifoaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Non-limiting examples of preservatives include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Non-limiting examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, betacarotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative can be an anti-oxidant. In other embodiments, the preservative can be a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukni nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean; sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In some embodiments, the composition disclosed herein may be oil/aqueous formulations. Oil/aqueous emulsion formulations can comprise at least one emulsifier optionally with at least one fat and/oil. In some embodiments, at least one hydrophilic emulsifier can be included in the compositions disclosed herein, optionally together with at least one lipophilic emulsifier, which may acts as a stabilizer. In some embodiments, both an oil and a fat can be used. The at least one emulsifier optionally with at least one stabilizer may create at least one emulsifying wax, which may form an emulsifying ointment base. This ointment base may form an oily dispersed phase of cream formulations. Emulsifiers and emulsion stabilizers suitable for use in the disclosed formulations include, but are not limited to, Tween 60, Span 80, cetostearyl alcohol, myristyl alcohol, glyceryl monostearate, sodium lauryl sulfate, glyceryl distearate alone or with a wax, and other materials well known in the art. In some cases, the solubility of the active compound in the oil(s) likely to be used in the pharmaceutical emulsion formulations can be low. Straight or branched chain, mono- or dibasic alkyl esters can aid solubility, such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters can be used. These can be used alone or in combination depending on the properties required. Alternatively, high melting point lipids such as white soft paraffin and/or liquid paraffin or other mineral oils can be used.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Non-limiting examples of suitable acids are pharmaceutically acceptable organic or inorganic acids. Examples of suitable inorganic acids include, but are not limited to, hydrochloric acid, hydrobromic acid, hydriodic acid, sulfuric acid, nitric acid, boric acid, phosphoric acid, and the like. Examples of suitable organic acids include, but are not limited to, acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like.

In some embodiments, provided herein are pharmaceutical compositions for parenteral administration containing at least one compound as disclosed herein and at least one pharmaceutically acceptable excipient suitable for parenteral administration. In some embodiments, provided herein are pharmaceutical compositions for parenteral administration comprising: (i) an effective amount of at least one compound disclosed herein; optionally (ii) an effective amount of at least one second agent; and (iii) at least one pharmaceutically acceptable excipient suitable for parenteral administration. In some embodiments, the pharmaceutical composition further comprises (iv) an effective amount of at least one third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, benzyl alcohol, and the like (and suitable mixtures thereof), cyclodextrin derivatives, sodium chloride, tragacanth gum, buffers, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

In some embodiments, the active ingredient can also be administered by injection as a composition with suitable carriers including, but not limited to, saline, dextrose, or water, or with cyclodextrin (e.g., Captisol), cosolvent solubilization (e.g., propylene glycol) or micellar solubilization (e.g., Tween 80).

Sterile injectable solutions can be prepared by incorporating a compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, including synthetic mono- or diglycerides. In addition, fatty acids such as oleic acid find use in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1% to about 5% w/w of a compound as disclosed herein.

In some embodiments, provided herein are pharmaceutical compositions for topical (e.g., transdermal) administration comprising at least one compound as disclosed herein and at least one pharmaceutically acceptable excipient suitable for topical administration. In some embodiments, provided herein are pharmaceutical compositions for topical administration comprising (i) an effective amount of at least one compound disclosed herein; optionally (ii) an effective amount of at least one second agent; and (iii) at least one pharmaceutically acceptable excipients suitable for topical administration. In some embodiments, the pharmaceutically acceptable composition further comprises (iv) an effective amount of at least one third agent.

Pharmaceutical compositions provided herein can be formulated into preparations in solid, semi-solid, or liquid forms suitable for local or topical administration, such as gels, water soluble jellies, linements, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area. For example, an ointment formulation can have either a paraffinic or a water-miscible base. Alternatively, the active ingredient can be formulated in a cream with an oil-in-water cream base. The aqueous phase of the cream base can include, for example at least about 30% w/w of a polyhydric alcohol such as propylene glycol, butane-1,3-diol, mannitol, sorbitol, glycerol, polyethylene glycol and mixtures thereof.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent. Patchs can be either of the reservoir and porous membrane type or of a solid matrix variety. In either case, the active agent can be delivered continuously from the reservoir or microcapsules through a membrane into the active agent permeable adhesive, which is in contact with the skin or mucosa of the recipient. If the active agent is absorbed through the skin, a controlled and predetermined flow of the active agent can be administered to the recipient. In the case of microcapsules, the encapsulating agent can also function as the membrane.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288;

4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid et injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a disclosed compound, although the concentration of the compound of Formula I can be as high as the solubility limit of the compound in the solvent. In some embodiments, topically-administrable formulations can, for example, include from about 0.001% to about 10% (w/w) compound, about 1% to about 9% (w/w) compound, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), further such as from about 1% to about 2% (w/w), and further such as from about 0.1% to about 1% (w/w) compound. In some embodiments, the topical formulation includes about 0.1 mg to about 150 mg administered one to four, such as one or two times daily. Formulations for topical administration can further comprise one or more of the additional pharmaceutically acceptable excipients described herein.

In some embodiments, provided herein are pharmaceutical compositions for inhalation administration comprising at least one compound as disclosed herein and at least one pharmaceutically acceptable excipients suitable for topical administration. In some embodiments, provided herein are pharmaceutical compositions for inhalation administration comprising: (i) an effective amount of at least one compound disclosed herein; optionally (ii) an effective amount of at least one second agent; and (iii) at least one pharmaceutically acceptable excipient suitable for inhalation administration. In some embodiments, the pharmaceutical composition further comprises: (iv) an effective amount of at least one third agent.

Pharmaceutical compositions for inhalation or insufflation include solutions and suspensions in pharmaceutically acceptable, aqueous or organic solvents, or mixtures thereof and powders. The liquid or solid pharmaceutical compositions can contain suitable pharmaceutically acceptable excipients as described herein. For example, suitable excipients include, but are not limited to, saline, benzyl alcohol and fluorocarbons. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

In some embodiments, provided herein are pharmaceutical compositions for opthalmic administration comprising at least one compound as disclosed herein and at least one pharmaceutically acceptable excipient suitable for ophthalmic administration. Pharmaceutical compositions suitable for ocular administration can be presented as discrete dosage forms, such as drops or sprays each containing a predetermined amount of an active ingredient, a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as disclosed herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to, intravenous, subcutaneous, and oral delivery. An exemplary method of administration can be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chiorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondritin sulfate, etc.; e.g., sodium polyacrylate, carboxyvinyl polymer, crosslinked polyacrylate, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art).

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate.

In some cases, the cationic agent can be selected from an alkylamine, a tertiary alkyl amine, a quarternary ammonium compound, a cationiclipid, an amino alcohol, a biguanidine salt, a cationic compound or a mixture thereof. In some cases, the cationic agent can be a biguanidine salt such as chlorhexidine, polyaminopropyl biguanidine, phenformin, alkylbiguanidine, or a mixture thereof. In some cases, the quaternary ammonium compound can be a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chiorallyl methenamine halide, myristylalkonium halide, stearalkonium halide or a mixture of two or more thereof. In some cases, cationic agent can be a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase can be mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

In some embodiments, the amount of a compound as disclosed herein in the formulation can be about 0.5% to about 20%, 0.5% to about 10%, or about 1.5% w/w.

In some embodiments, provided herein are pharmaceutical compositions for controlled release administration comprising at least one compound as disclosed herein and at least one pharmaceutically acceptable excipient suitable for controlled release administration. In some embodiments, provided herein are pharmaceutical compositions for controlled release administration comprising: (i) an effective amount of at least one compound disclosed herein; optionally (ii) an effective amount of at least one second agent; and (iii) at least one pharmaceutically acceptable excipient suitable for controlled release administration. In some embodiments, the pharmaceutical composition further comprises: (iv) an effective amount of at least one third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment can be characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as disclosed herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In some embodiments, a pump can be used (see, Sefton, *CRC Crit. Ref Biomed. Eng.* 14:201 (1987); Buchwald et al., *Surgery* 88:507 (1980); Sandek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release,* 115-138 (vol. 2, 1984). Other controlled release systems are discussed in the review by Langer, *Science* 249:1527-1533 (1990). The at least one active agent can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydxogels of esters of acrylic and methacrylic acid, collagen, cross-linked polyvinylalcohol and cross-linked partially hydxolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The at least one active agent then diffuses through the outer polymeric membrane in a release rate controlling step. The percentage of at least one active agent in such parenteral compositions can depend on the specific nature thereof, as well as the needs of the subject.

A compound described herein can be delivered in the form of pharmaceutically acceptable compositions which comprise a therapeutically effective amount of at least one compound disclosed herein and/or at least one additional therapeutic agent, such as a chemotherapeutic, formulated together with at least one pharmaceutically acceptable excipient. In some embodiments, only a compound provided herein without an additional therapeutic agent can be included in the dosage form. In some instances, the compound described herein and the additional therapeutic agent are administered in separate pharmaceutical compositions and can (e.g., because of different physical and/or chemical characteristics) be administered by different routes (e.g., one therapeutic can be administered orally, while the other can be administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the severity of the condition, the route of administration, the time of administration, the rate of excretion or metabolism of the particular compound being employed, the rate and extent of absorption, the duration of the treatment, administration of other drugs, compounds and/or materials used in combination with the particular compound employed, the age, sex, weight, condition, general health and prior medical history of the patient being treated, and like factors well known in the medical arts.

The dosage level can also be informed by in vitro or in vivo assays which can optionally be employed to help identify optimal dosage ranges. One guide to effective doses can be extrapolated from dose-response curves derived from in vitro or animal model test systems. Furthermore, after formulation with an appropriate pharmaceutically acceptable carrier in a desired dosage, the compositions as disclosed herein can be administered to humans and other animals orally, rectally, parenterally, intracisternally, intravaginally, intraperitoneally, topically (as by transdermal patch, powders, ointments, or drops), sublingually, bucally, as an oral or nasal spray, or the like.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. In some embodiments, the dose of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.1 mg to about 125 mg per day, or about 0.0001 mg to about 500 mg per day, or about 0.001 mg to about 500 mg per day, or about 0.01 mg to about 1000 mg per day, or about 0.01 mg to about 500 mg per day, or about 0.1 mg to about 500 mg per day, or about 1 mg to about 25 mg per day, or about 1 mg to about 50 mg per day, or about 5 mg to about 40 mg per day. An exemplary dosage can be about 10 to about 30 mg per day. In some embodiments, for a 70 kg human, a suitable dose would be about 0.05 to about 7 g/day, such as about 0.05 to about 2 g/day. In some embodiments, the daily oral dose is about 30 mg, about 90 mg, about 150 mg, or about 180 mg. As used herein, "about" means±5% of the value being modified. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, bi-weekly, or another intermittent schedule. The dosing schedule can include a "drug holiday," i.e., the drug can be administered for two weeks on, one week off, or three weeks on, one week on, or four weeks on, one week off, etc., or continuously, without a drug holiday.

In some embodiments, a compound as provided herein can be administered in multiple doses. Dosing can be about once, twice, three times, four times, five times, six times, or more than six times per day. Dosing can be about once a month, about once every two weeks, about once a week, or about once every other day. In another embodiment, a compound as disclosed herein and another agent are administered together about once per day to about 6 times per day. For example, the compound can be administered one or more times per day on a weekly basis (e.g., every Monday) indefinitely or for a period of weeks, e.g., 4-10 weeks. Alternatively, it can be administered daily for a period of days (e.g., 2-10 days) followed by a period of days (e.g., 1-30 days) without administration of the compound, with that cycle repeated indefinitely or for a given number of repititions, e.g., 4-10 cycles. As an example, a compound provided herein can be administered daily for 5 days, then discontinued for 9 days, then administered daily for another 5 day period, then discontinued for 9 days, and so on, repeating the cycle indefinitely, or for a total of 4-10 times. In another embodiment, the administration of a compound as provided herein and an agent continues for less than about 7 days. In yet another embodiment, the administration continues for more than about 6, about 10, about 14, about 28 days, about two months, about six months, or about one year. In some cases, continuous dosing can be achieved and maintained as long as necessary.

Administration of the pharmaceutical compositions as disclosed herein can continue as long as necessary. In some embodiments, an agent as disclosed herein can be administered for more than about 1, about 2, about 3, about 4, about 5, about 6, about 7, about 14, or about 28 days. In some embodiments, an agent as disclosed herein can be administered for less than about 28, about 14, about 7, about 6, about 5, about 4, about 3, about 2, or about 1 day. In some embodiments, an agent as disclosed herein can be administered chronically on an ongoing basis, e.g., for the treatment of chronic effects.

When administered for the treatment or inhibition of a particular disease state or disorder, the effective dosage of the compound as disclosed herein can vary depending upon the particular compound utilized, the mode of administration, the condition, and severity thereof, of the condition being treated, as well as the various physical factors related to the individual being treated. In some embodiments, the effective systemic dose of the compound will typically be in the range of about 0.01 to about 500 mg of compound per kg of patient body weight, such as about 0.1 to about 125 mg/kg, and in some cases about 1 to about 25 mg/kg, administered in single or multiple doses. The projected daily dosages are expected to vary with route of administration. Thus, parenteral dosing will often be at levels of about 10% to about 20% of oral dosing levels. Generally, the compound can be administered to patients in need of such treatment in a daily dose range of about 50 to about 2000 mg per patient. Administration can be once or multiple times daily, weekly (or at some other multiple-day interval) or on an intermittent schedule.

In some embodiments, the dose of a compound as disclosed herein can be selected from 30, 60, 90, 120, 180, and 240 mg administered orally once daily. Another dosing regimen can include 90 mg administered orally once daily, or an oral 90 mg dose each day for 7 days followed by a 180 mg dose each day. In some embodiments, the compound being dosed is brigatinib Form A.

Since the compounds described herein can be administered in combination with other treatments (such as additional chemotherapeutics, radiation or surgery), the doses of each agent or therapy can be lower than the corresponding dose for single-agent therapy. The dose for single agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When a compound provided herein is administered in a pharmaceutical composition that comprises one or more agents, and one or more of the agents has a shorter half-life than the compound provided herein, unit dose forms of the agent(s) and the compound provided herein can be adjusted accordingly.

In some embodiments, provided herein are kits. The kits can include a compound or pharmaceutical composition as described herein, in suitable packaging, and written material that can include instructions for use, discussion of clinical studies, listing of side effects, and the like. Kits are well suited for the delivery of solid oral dosage forms such as tablets or capsules. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid can be provided with the kit, e.g., in the form of numbers next to the tablets or capsules whereby the numbers correspond with the days of the regimen which the tablets or capsules so specified should be ingested. Another example of such a memory aid can be a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day.

The kit can further contain another agent. In some embodiments, the compound as disclosed herein and the agent are provided as separate pharmaceutical compositions in separate containers within the kit. In some embodiments, the compound as disclosed herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a usually transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but

IV. THERAPEUTIC METHODS

In some embodiments, pharmaceutical compositions comprising at least one crystalline form of brigatinib can be used for treating cancer, by the administration of a therapeutically effective amount of the pharmaceutical composition to the subject in need thereof. In some embodiments, the cancer is an ALK+-driven cancer. In some embodiments, the cancer is non-small cell lung cancer.

A "therapeutically effective amount" is that amount effective for detectable killing or inhibition of the growth or spread of cancer cells; the size or number of tumors; or other measure of the level, stage, progression or severity of the cancer. The exact amount required can vary from subject to subject, depending on the species, age, and general condition of the subject, the severity of the disease, the particular anticancer agent, its mode of administration, combination treatment with other therapies, and the like.

Disclosed herein are compounds having biological properties which make them of interest for treating or modulating disease in which kinases can be involved, symptoms of such disease, or the effect of other physiological events mediated by kinases. For instance, a number of compounds as disclosed herein have been shown to inhibit tyrosine kinase activity of ALK, fak and c-met, among other tyrosine kinases which are believed to mediate the growth, development and/or metastasis of cancer. A number of compounds as disclosed herein have also been found to possess potent in vitro activity against cancer cell lines, including among others karpas 299 cells. Such compounds are thus of interest for the treatment of cancers, including solid tumors as well as lymphomas and including cancers which are resistant to other therapies.

In some embodiments, the cancer is an ALK+-driven cancer. In some embodiments, the cancer is non-small cell lung cancer. In some embodiments, the cancer is ALK-positive NSCLC. In some embodiments, the cancer is locally advanced or metastatic ALK-positive NSCLC. In some embodiments, the cancer/patient has previously been treated with crizotinib or another tyrosine kinase inhibitor. In some embodiments, the cancer/patient has not previously been treated with an ALK inhibitor.

Such cancers include, but are not limited to, cancers of the breast, non small cell lung cancer (NSCLC), neural tumors such as glioblastomas and neuroblastomas; esophaegeal carcinomas, soft tissue cancers such as rhabdomyosarcomas, among others; various forms of lymphoma such as a non-Hodgkin's lymphoma (NHL) known as anaplastic large-cell lymphoma (ALCL), various forms of leukemia; and including cancers which are ALK or c-met mediated.

Anaplastic Lymphoma Kinase (ALK) is a cell membrane-spannning receptor tyrosine kinase, which belong to the insulin receptor subfamily. ALK receptor tyrosine kinase (RTK) was initially identified due to its involvement in the human non-Hodgkin lymphoma subtype known as anaplastic large-cell lymphoma (ALCL). ALK normally has a restricted distribution in mammalian cells, being found at significant levels only in nervous system during embryonic development, suggesting a possible role for ALK in brain development (Duyster, J. Et al., *Oncogene*, 2001, 20, 5623-5637).

In addition to its role in normal development, expression of the full-length normal ALK has also been detected in cell lines derived from a variety of tumors such as neuroblastomas, neuroectodermal tumors (Lamant L. Et al., *Am. J. Pathol.*, 2000, 156, 1711-1721; Osajima-Hakomori Y., et al., *Am. J. Pathol.* 2005, 167, 213-222) and glioblastoma (Powers C. et al., *J. Biol. Chem.* 2002, 277, 14153-14158; Grzelinski M. et al., *Int. J. Cancer*, 2005, 117, 942-951; Mentlein, R. Et al., *J. Neurochem.*, 2002, 83, 747-753) as well as breast cancer and melanoma lines (Dirk W G. Et al., *Int. J. Cancer*, 2002, 100, 49-56).

In common with other RTKs, translocations affect the ALK gene, resulting in expression of oncogenic fusion kinases, the most common of which is NPM-ALK. For example, approximately sixty percent of anaplastic large cell lymphomas (ALCL) are associated with a chromosome mutation that generates a fusion protein consisting of nucleophosmin (NMP) and the intracellular domain of ALK. (Armitage, J. O. et al., Cancer: principle and practice of oncology, $6^{th}$ Edition, 2001, 2256-2316; kutok, J. L. & Aster J. C., *J. Clin. Oncol.*, 2002, 20, 3691-3702; Wan, W. et al., *Blood*, 2006, 107, 1617-1623. This mutant protein, NPM-ALK, possesses a constitutively active tyrosine kinase domain that is responsible for its oncogenic property through activation of downstream effectors (Falini, B and al., *Blood*, 1999, 94, 3509-3515; Morris, S. W. et al., *Brit. J. Haematol.*, 2001, 113, 275-295). Experimental data have demonstrated that the aberrant expression of constitutuvely active ALK is directly implicated in the pathogenesis of ALCL and that inhibition of ALK can markedly impair the growth of ALK positive lymphoma cells (Kuefer, Mu et al., *Blood*, 1997, 90, 2901-2910; Bai, R. Y. et al., *Exp. Hematol.*, 2001, 29, 1082-1090; Slupianek, A. et al., *Cancer Res.*, 2001, 61, 2194-2199; Turturro, F. et al., *Clin. Cancer. Res.*, 2002, 8, 240-245). The constitutively activated chimeric ALK has also been demonstrated in about 60% of inflammatory myofibroblastic tumors (IMTs), a slow growing sarcoma that mainly affects children and young adults (Lawrence, B. et al., Am. J. Pathol., 2000, 157, 377-384). Furthermore, recent reports have also described the occurrence of a variant ALK fusion, TPM4-ALK, in cases of squamous cell carcinoma (SCC) of the esophagus (Jazzi fr., et al., *World J. Gastroenterol.*, 2006, 12, 7104-7112; Du X., et al., *J. Mol. Med.*, 2007, 85, 863-875; Aklilu M., *Semin. Radiat. Oncol*, 2007, 17, 62-69). Thus, ALK is one of the few examples of an RTK implicated in oncogenesis in both non-hematopoietic and hematopoietic malignancies. More recently, it has been shown that a small inversion within chromosome 2p results in the formation of a fusion gene comprising portions of the echinoderm microtubule-associated protein-like 4 (EML4) gene and the anaplastic lymphoma kinase (ALK) gene in non-small-cell lung cancer (NSCLC) cells (Soda M., et al., Nature, 2007, 448, 561-567).

In some embodiments, an ALK inhibitor can create durable cures when used as a single therapeutic agent or combined with current chemotherapy for ALCL, IMT, proliferative disorders, glioblastoma and other possible solid tumors cited herein, or, as a single therapeutic agent, could be used in a maintenance role to prevent recurrence in patients in need of such a treatment.

Compounds as disclosed herein can be administered as part of a treatment regimen in which the compound is the sole active pharmaceutical agent, or used in combination with one or more other therapeutic agents as part of a combination therapy. When administered as one component of a a combination therapy, the therapeutic agents being administered can be formulated as separate compositions that are administered at the same time or sequentially at different times (e.g., within 72 hours, 48 hours, or 24 hours are not limited to, hermetically sealed foils, plastic or the like, unit dose containers, blister packs, and strip packs.

of one another), or the therapeutic agents can be formulated together in a single pharmaceutical composition and administered simultaneously.

Thus, the administration of brigatinib in a form disclosed herein can be in conjunction with at least one additional therapeutic agent known to those skilled in the art in the prevention or treatment of cancer, such as radiation therapy or cytostatic agents, cytotoxic agents, other anti-cancer agents and other drugs to ameliorate symptoms of the cancer or side effects of any of the drugs. Non-limiting examples additional therapeutic agents include agents suitable for immunotherapy (such as, for example, PD-1 and PDL-1 inhibitors), antiangiogenesis (such as, for example, bevacizumab), and/or chemotherapy.

If formulated as a fixed dose, such combination products employ compounds as disclosed herein within the accepted dosage ranges. Compounds as disclosed herein can also be administered sequentially with other anticancer or cytotoxic agents when a combination formulation is inappropriate. Compounds as disclosed herein can be administered prior to, simultaneously with, or after administration of the other anticancer or cytotoxic agent.

Currently, standard treatment of primary tumors consists of surgical excision, when appropriate, followed by either radiation or chemotherapy, and typically administered intravenously (IV). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, hormonal agents, immunological agents, interferon-type agents and a category of miscellaneous agents.

A first family of antineoplastic agents which can be used in combination with compounds as disclosed herein includes antimetabolite-type/thymidilate synthase inhibitor antineoplastic agents. Suitable antimetabolite antineoplastic agents can be selected from, but not limited to, 5-FU-fibrinogen, acanthifolic acid, aminothiadiazole, brequinar sodium, carmofur, CibaGeigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co., EX-015, fazarabine, floxuridine, fludarabine phosphate, 5fluorouracil, N-(21-furanidyl) fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC788, thioguanine, tiazofurin, Erbamont TIF, trimetrexate, tyrosine kinase inhibitors, Taiho UFT and uricytin.

A second family of antineoplastic agents which can be used in combination with compounds as disclosed herein consists of alkylating-type antineoplastic agents. Suitable alkylating-type antineoplastic agents can be selected from, but not limited to, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D 384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G M, Chinoin GYKI-17230, hepsulfam, ifosfamide, iproplatin, lomustine, mafosfamide, mitolactolf Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which can be used in combination with compounds as disclosed herein includes antibiotic-type antineoplastic agents. Suitable antibiotic-type antineoplastic agents can be selected from, but not limited to, Taiho 4181-A, aclarubicin, actinomycin D, actinoplanone, Erbamont ADR-456, aeroplysinin derivative, Ajinomoto AN II, Ajinomoto AN3, Nippon Soda anisomycins, anthracycline, azino-mycin-A, bisucaberin, Bristol-Myers BL-6859, Bristol-Myers BMY-25067, Bristol-Myers BNY-25551, Bristol-Myers BNY-26605 IBristolMyers BNY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko, DC89-AI, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AI, esperamicin-Alb, Erbamont FCE21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which can be used in combination with compounds as disclosed herein includes a miscellaneous family of antineoplastic agents, such as tubulin interacting agents, topoisomerase II inhibitors, topoisomerase I inhibitors and hormonal agents, selected from, but not limited to, xcarotene, X-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1F Henkel APD, aphidicolin glycinate, asparaginase, Avarol, baccharin, batracylin, benfluron, benzotript, Ipsen-Beaufour BIM-23015, bisantrene, BristoMyers BNY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, WarnerLambert CI-937, Warner-Lambert CI-941, Warner-Lambert C1958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704t gallium nitrate, genkwadaphnin, Chugai GLA-43, Glaxo GR-63178, grifolan NMF5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76OOONa, Kureha Chemical K-AM, MECT Corp KI-8110, American Cyanamid L-623, leukoregulin, lonidamine, Lundbeck LU 1121 Lilly LY-186641, NCI (US) MAP, marycin, Merrel Dow MDL-27048, Medco MEDR-340, merbarone, merocyanlne derivatives, methylanilinoacridine, Molecular Genetics MG1136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, WarnerLambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, with anolides and Yamanouchi YM.

Alternatively, the present compounds can also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glyco-pine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon1, interferon alpha, natural, interferon beta, interferon beta-Ia, interferon beta-b, interferon gamma, natural interferon gamma-Ia, interferon gamma-Ib, interleukin-I beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama. vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinidel filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM iodine 131 MAb (Techniclone), polymorphic epithelial mucin-yttrium 90 MAb (Antisoma), marimastat, menogaril, mitumomab, motexafin, gadolinium, MX 6 (Galderma), nelarabine, nolatrexed, P 30 protein, pegvisomant, pemetrexed, porfiromycin, prinomastat, RL 0903 (Shire), rubitecan; satraplatin, sodium phenylacetate, sparfosic acid, SRL 172 (SR Pharma), SU 5416 (SUGEN)y SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

V. SYNTHESIS OF BRIGATINIB FORM A

The following representative synthesis of brigatinib Form A contains additional information, exemplification and guidance which can be adapted to the practice of the invention in its various embodiments and the equivalents thereof.

Examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein.

The contents of those cited references are incorporated herein by reference to help illustrate the state of the art. In addition, for purposes of the invention, the chemical elements are identified in accordance with the Periodic Table of the Elements, CAS version, Handbook of Chemistry and Physics, 75$^{th}$ Ed., inside cover. Additionally, general principles of organic chemistry, as well as specific functional moieties and reactivity, are described in "Organic Chemistry", Thomas Sorrell, University Science Books, Sausalito: 1999, and "Organic Chemistry", Morrison & Boyd (3d Ed), the entire contents of both of which are incorporated herein by reference.

Step 1: (2-aminophenyl)dimethylphosphine oxide

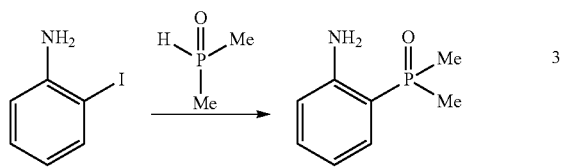

A mixture of 2-iodoaniline (86 g, 0.393 mol, 1.0 eq.), dimethyl phosphine oxide (36.4 g, 0.466 mol, 1.19 eq.), potassium phosphate (92.4 g, 0.423 mol, 1.1 eq.), palladium (II) acetate (4.56 g, 0.02 mol, 0.05 eq.), and Xantphos (11.6 g, 0.02 mol, 0.05 eq.) in DMF (700 mL) was stirred at ~120° C. for ~6 h. The color of the mixture turned dark brown. Upon cooling to rt, celite (30 g) was added to the mixture. The mixture was then filtered and the filter cake was rinsed with EtOAc (2×250 mL). The filtrate was then concentrated in vacuo to afford a residue.

Another batch of (2-aminophenyl)dimethylphosphine oxide was synthesized at the same scale as performed above, and the residue obtained from both batches were combined and purified as discussed below.

To the combined residues was added EtOAc (1 L), and the resulting mixture was stirred at rt for ~1 h. The mixture was filtered, and the collected residue was washed with EtOAc (2×250 mL). The combined filtrate was dried over sodium sulfate, filtered and concentrated in vacuo to afford an oil. The resulting oil was dissolved in a mixture of water/concentrated hydrochloric acid (1.2 L/300 mL) with agitation at rt, and stirred for 30 min. The resulting mixture was filtered, and the collected residue was washed with aqueous hydrochloric acid (10%, 300 mL). The combined aqueous filtrate was washed with EtOAc (2×1 L washes, followed by a 500 mL wash). The aqueous layer was cooled in an ice bath (less than 10° C. internal mixture temperature) and the pH of the solution was adjusted to ~12 (as determined by pH paper) by adding aqueous sodium hydroxide (30% w/w), while maintaining an internal solution temperature of less than 20° C. throughout the addition. The resulting solution was extracted with IPA/DCM (1/3 v/v, 4×1 L), and the combined organic layers were dried over sodium sulfate, filtered, and concentrated in vacuo to afford a viscous oil, which crystallized upon standing at rt. The resulting solids were triturated with EtOAc/heptane (1/10 v/v, 2×150 mL) to afford (2-aminophenyl)dimethylphosphine oxide as a light brown solid.

Step 2: (2-((2,5-dichloropyrimidin-4-yl)amino)phenyl)dimethylphosphine oxide

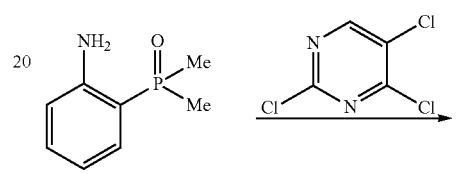

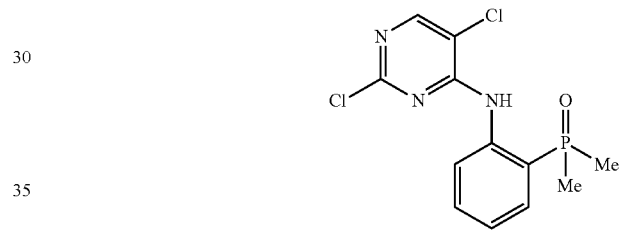

2,4,5-trichloropyrimidine (54.2 g, 0.296 mol, 1.0 eq.), (2-aminophenyl)dimethyl-phosphine oxide (50.0 g, 0.296 mole, 1.0 eq.), potassium carbonate (49.1 g, 0.355 mol, 1.2 eq.) and tetrabutylammonium bisulfate (10.2 g, 0.03 mole, 0.1 eq.) were combined in DMF (1050 mL), and heated at 65° C. for ~8.0-8.5 h. During the course of heating, an off-white suspension formed. Upon cooling, the mixture was cooled to rt and filtered. The collected solids were rinsed with DMF (2×50 mL), and the combined filtrates were concentrated in vacuo. The resulting residue was dissolved in EtOAc (1.3 L) and water (350 mL). The aqueous layer was isolated and extracted with EtOAc (2×250 mL). The combined organic layers were washed with brine (20% w/w, 500 mL), dried over sodium sulfate, filtered, and concentrated in vacuo to afford (2-((2,5-dichloropyrimidin-4-yl)amino)phenyl)dimethylphosphine oxide as an off-white solid.

Alternative Synthesis of (2-((2,5-dichloropyrimidin-4-yl)amino)phenyl)-dimethylphosphine oxide (2-((2,5-dichloropyrimidin-4-yl)amino)phenyl)dimethylphosphine oxide can be synthesized using the conditions in Table 28 according to the previously described procedure.

TABLE 28

Reaction Conditions for the Synthesis of (2-((2,5-dichloropyrimidin-4-yl)amino)phenyl)dimethylphosphine oxide

| Entry | Amount of (2-aminophenyl)-dimethylphosphine oxide | Amount of 2,4,5-trichloropyrimidine | Base (equivalents) | Phase Transfer Catalyst (mole %) | Solvent(s), Conditions |
|---|---|---|---|---|---|
| 1 | 1.0 eq. | 1.1 eq. | $K_2CO_3$ (3 eq.) | N/A | DMF<br>120° C., 6-8 h |
| 2 | 1.0 eq. | 1.1 eq. | $Cs_2CO_3$ (2.5 eq.) | N/A | Acetone<br>Reflux |
| 3 | 1.0 eq. | 1.2 eq. | $K_2CO_3$ (2.5 eq.) | N/A | Acetone<br>Reflux |
| 4 | 1.0 eq. | 1.1 eq. | $Et_3N$ (2.5 eq.) | N/A | MeCN<br>rt, then<br>80° C. for 6-8 h |
| 5 | 1.0 eq. | 1.1 eq. | $Et_3N$ (2.5 eq.) | $n\text{-}Bu_4I$ (10 mole-%) | MeCN<br>80° C., 6-8 h |
| 6 | 1.0 eq. | 1.1 eq. | $KHCO_3$ (1.2 eq.) | $n\text{-}Bu_4I$ (5 mole-%) | $PhMe/H_2O$<br>(1/1, v/v)<br>rt to reflux |
| 7 | 1.0 eq. | 1.1 eq. | $KHCO_3$ (1.2 eq.) | $n\text{-}Bu_4I$ (5 mole-%) | $THF/H_2O$<br>(1/1, v/v)<br>rt to reflux |
| 8 | 1.0 eq. | 1.2 eq. | $KHCO_3$ (1.2 eq.) | $n\text{-}Bu_4I$ (5 mole-%) | 2-Me—$THF/H_2O$<br>(1/1, v/v)<br>rt to reflux |
| 9 | 1.0 eq. | 1.1 eq. | LiHMDS (2M solution in THF, 2.1 eq.) | N/A | −60° C. |
| 10 | 1.0 eq. | 1.0 eq. | $K_2CO_3$ (1.2 eq.) | $n\text{-}Bu_4NHSO_4$ (10 mole-%) | 2-Me—THF<br>65-70° C., 7-8 h |
| 11 | 1.0 eq. | 1.0 eq. | $K_2CO_3$ (1.2 eq.) | $n\text{-}Bu_4NHSO_4$ (10 mole-%) | DMF<br>60° C., 4-6 h |

Step 3: 1-(1-(3-methoxy-4-nitrophenyl)piperidin-4-yl)-4-methylpiperazine

Step 4: 2-methoxy-4-(4-(4-methylpiperazin-1-yl)piperidin-1-yl)aniline

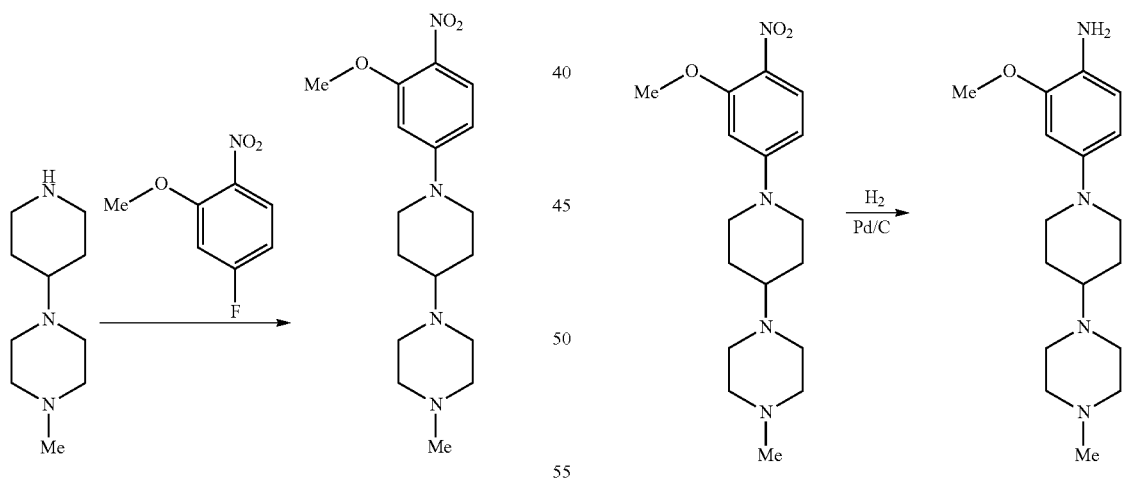

A mixture of 5-fluoro-2-nitroanisole (85.6 g, 0.5 mol, 1.0 eq.), 1-methyl-4-(piperidin-4-yl)piperazine (91.7 g, 0.5 mol, 1.0 eq.), and potassium carbonate (138.5 g, 1.0 mol, 2.0 eq.) in MeCN (500 mL) was stirred at reflux for ~13 h. Upon cooling to rt, DCM (1 L) was added to the mixture and the resulting mixture was filtered. The collected residue was washed with DCM (500 mL). The combined filtrates were washed with water (400 mL) and brine (20% w/w, 300 mL), dried over sodium sulfate, filtered, and concentrated in vacuo to afford 1-(1-(3-methoxy-4-nitrophenyl)piperidin-4-yl)-4-methylpiperazine as a yellow solid.

A mixture of 1-(1-(3-methoxy-4-nitrophenyl)piperidin-4-yl)-4-methylpiperazine (78 g, 0.233 mol) and Pd/C (10% loading, 50% wet, 4 g, ~2.5 wt-%) in EtOH (800 mL) was stirred under a hydrogen atmosphere (~20 p.s.i.) for ~2.5 h. Subsequently, the mixture was filtered through a pad of Celite (50 g), and the Celite pad was rinsed with EtOH (2×50 mL).

The combined filtrates were concentrated in vacuo to afford 2-methoxy-4-(4-(4-methylpiperazin-1-yl)piperidin-1-yl)aniline as a purple solid.

Step 5: (2-((5-chloro-2-((2-methoxy-4-(4-(4-methylpiperazin-1-yl)piperidin-1-yl)phenyl)amino)pyrimidin-4-yl)amino)phenyl)dimethylphosphine oxide

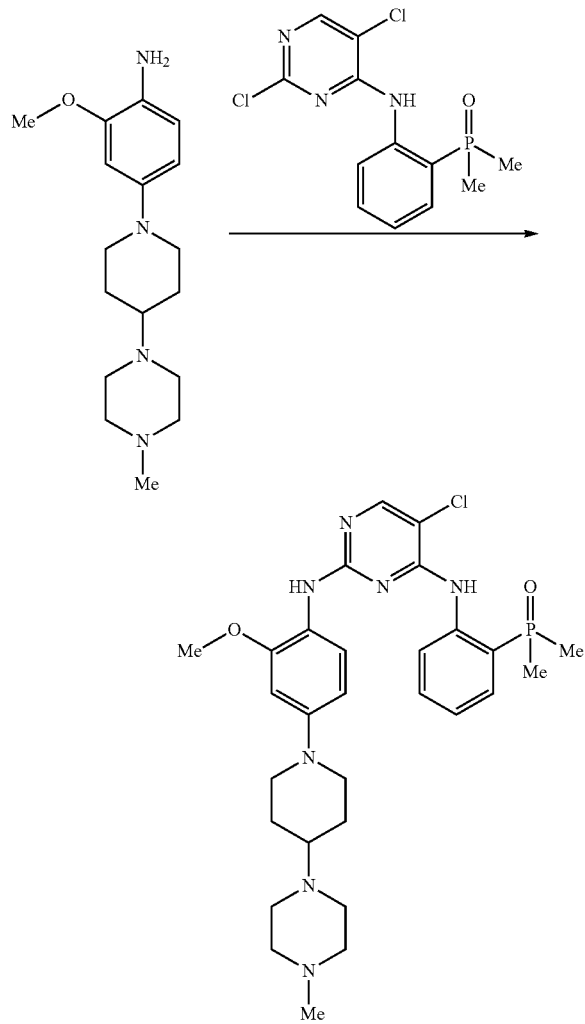 [SMILES: COc1cc(N2CCC(N3CCN(C)CC3)CC2)ccc1N ; CP(C)(=O)c1ccccc1Nc1nc(Cl)ncc1Cl ; COc1cc(N2CCC(N3CCN(C)CC3)CC2)ccc1Nc1ncc(Cl)c(Nc2ccccc2P(C)(C)=O)n1]

A mixture of (2-((2,5-dichloropyrimidin-4-yl)amino)phenyl)-dimethylphosphine oxide (55 g, 0.174 mol, 1.0 eq.), 2-methoxy-4-(4-(4-methylpiperazin-1-yl)piperidin-1-yl) aniline (74.2 g, 0.244 mol, 1.4 eq.), and HCl in EtOH (2.5 M, 175 mL) in 2-methoxyethanol (750 mL) was stirred at 120° C. for ~6 h. Upon cooling to rt, the mixture was concentrated in vacuo, and the resulting residue was dissolved in water (400 mL), and washed with EtOAc (500 mL). Aqueous sodium hydroxide (20% w/w) was added to the aqueous layer until the pH was ~12 (as determined by pH paper). The aqueous layer was extracted with DCM (3×500 mL), and the combined organic layers were concentrated in vacuo. The residue was triturated with EtOAc/MeOH (9/1 v/v, 250 mL) and EtOAc/heptane (1/2 v/v, 300 mL), sequentially, at rt for ~1 h, and then filtered to afford a light color solid (Batch A).

Another batch of (2-((5-chloro-2-((2-methoxy-4-(4-(4-methylpiperazin-1-yl)piperidin-1-yl)phenyl)amino)pyrimidin-4-yl)amino)phenyl)dimethyl-phosphine oxide was prepared using (2-((2,5-dichloropyrimidin-4-yl)amino)phenyl) dimethylphosphine oxide (50.8 g, 0.161 mol, 1.0 eq.), 2-methoxy-4-(4-(4-methylpiperazin-1-yl)piperidin-1-yl) aniline (68.4 g, 0.225 mol, 1.4 eq.), and HCl in EtOH (2.5 M, 160 mL) in 2-methoxyethanol (650 mL). After the previously described workup, a solid was obtained (Batch B).

The two batches (Batch A and Batch B) were combined and triturated with MeOH/EtOAc (1% v/v, 500 mL) and MeOH/EtOAc (2.5% v/v, 500 mL) at rt for ~30 min, and then filtered. The isolated solids were then triturated with hot EtOAc (500 mL) for 15 minutes followed by cooling to rt, and then filtration. The isolated solids were then triturated in hot MeOH/EtOAc (2% v/v, 500 mL) for 15 minutes followed by cooling to room temperature and filtration. Then the isolated solids were triturated in DCM (750 mL) at room temperature. The resulting solution was filtered and the collected solid was dried in vacuo to afford (2-((5-chloro-2-((2-methoxy-4-(4-(4-methylpiperazin-1-yl)piperidin-1-yl) phenyl)amino)pyrimidin-4-yl)amino)phenyl)dimethylphosphine oxide as a beige solid. 127 g, 65% yield. $^1$H NMR: refer to Table 2. ESI-MS m/s: 584.2 [M+H]$^+$.

VI. PHARMACEUTICAL COMPOSITION EXAMPLES

Representative pharmaceutical compositions and dosage forms of compounds as disclosed herein (the active ingredient being referred to as "Compound") for therapeutic or prophylactic use in humans may be as follows:

| (a) Tablet I | |
|---|---|
| | mg/tablet |
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | |
|---|---|
| | mg/tablet |
| Compound | 50 |
| Lactose Ph. Eur | 223.75 |
| Croscarmellose sodium | 6.0 |
| Maize starch | 15.0 |
| Polyvinvylpyffolidone (5% w/v paste) | 2.25 |
| Magnesium stearate | 3.0 |

| (c) Tablet III | |
|---|---|
| | mg/tablet |
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0-76 |

(d) Capsule

| | mg/capsule |
|---|---|
| Compound | 10 |
| Lactose Ph. Eur | 488.5 |
| Magnesium | 1.5 |

(e) Injection I

| | (50 mg/mL) |
|---|---|
| Compound | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection to 100% | |

(f) Injection II

| | (10 mg/mL) |
|---|---|
| Compound | 1.0% w/v |
| Sodium phosphate BP | 3.6% w/v |
| 0.1M Sodium hydroxide solution | 15.0% v/v |
| Water for injection to 100% | |

(g) Injection III

| | (1 mg/mL, buffered to pH 6) |
|---|---|
| Compound | 0.1% w/v |
| Sodium phosphate BP | 2.26% w/v |
| Citric acid | 0.38% w/v |
| Polyethylene glycol 400 | 3.5% w/v |
| Water for injection to 100% | |

(h) Aerosol I

| | mg/mL |
|---|---|
| Compound | 10.0 |
| Sorbitan trioleate | 13.5 |
| Trichlorofluoromethane | 910.0 |
| Dichlorodifluoromethane | 490.0 |

(i) Aerosol II

| | mg/mL |
|---|---|
| Compound | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j) Aerosol III

| | mg/mL |
|---|---|
| Compound | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

(k) Aerosol IV

| | mg/mL |
|---|---|
| Compound | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l) Ointment

| | unit/mL |
|---|---|
| Compound | 40 mg |
| Ethanol | 300 μL |
| Water | 300 μL |
| 1-Dodecylazacycloheptan one | 50 μL |
| Propylene glycol | to 1 mL |

These formulations can be prepared using conventional procedures well known in the pharmaceutical art. The tablets (a)-(c) can be enteric coated by conventional means, if desired to provide a coating of cellulose acetate phthalate, for example. In certain embodiments, tablets suitable for oral administration contain about 30 mg, about 90 mg, about 150 mg, or about 180 mg of substantially pure Form A of brigatinib, together with one or more pharmaceutically acceptable excipients such as are described herein. As used herein, "about" means±5% of the value being modified. The aerosol formulations (h)-(k) can be used in conjunction with standard, metered dose aerosol dispensers, and the suspending agents sorbitan trioleate and soya lecithin can be replaced by an alternative suspending agent such as sorbitan monooleate, sorbitan sesquioleate, polysorbate 80, polyglycerol oleate or oleic acid.

VII. KINASE INHIBITION

Compounds as described herein were screened for kinase inhibition activity as follows. Kinases suitable for use in the following protocol include, but are not limited to: ALK, Jak2, b-Raf, c-Met, Tie-2, FLT3, Abl, Lck, Lyn, Src, Fyn, Syk, Zap-70, Itk, Tec, Btk, EGFR, ErbB2, Kdr, FLT1, Tek, InsR, and AKT.

Kinases are expressed as either kinase domains or full length constructs fused to glutathione S-transferase (GST) or polyHistidine tagged fusion proteins in either E. coli or Baculovirus-High Five expression systems. They are purified to near homogeneity by affinity chromatography as previously described (Lehr et al., 1996; Gish et al., 1995). In some instances, kinases are co-expressed or mixed with purified or partially purified regulatory polypeptides prior to measurement of activity.

Kinase activity and inhibition can be measured by established protocols (see e.g., Braunwalder et al., 1996). In such cases, the transfer of $^{33}PO_4$ from ATP to the synthetic substrates poly(Glu, Tyr) 4:1 or poly(Arg, Ser) 3:1 attached to the bioactive surface of microtiter plates is taken as a measure of enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{33}P$ incorporated onto the substrate bound to the plate.

Other methods relying upon the transfer of phosphate to peptide or polypeptide substrate containing tyrosine, serine, threonine or histidine, alone, in combination with each other, or in combination with other amino acids, in solution or immobilized (i.e., solid phase) are also useful.

For example, transfer of phosphate to a peptide or polypeptide can also be detected using scintillation proximity, Fluorescence Polarization and homogeneous time-resolved fluorescence. Alternatively, kinase activity can be measured using antibody-based methods in which an antibody or polypeptide can used as a reagent to detect phosphorylated target polypeptide.

For additional background information on such assay methodologies, see e.g., Braunwalder et al., 1996, Anal. Biochem. 234(I):23; Cleaveland et al., 1990, Anal Biochem. 190(2):249; Gish et al. (1995). Protein Eng. 8(6):609; Kolb et al. (1998). Drug Discov. Toda V. 3:333; Lehr et al. (1996). Gene 169(2):27527-87; Seethala et al. (1998). Anal Biochem. 255(2):257; Wu et al. (2000).

The inhibition of ALK tyrosine kinase activity can be demonstrated using known methods. For example, in one method, compounds can be tested for their ability to inhibit kinase activity of baculovirus-expressed ALK using a modification of the ELISA protocol reported for trkA in Angeles, T. S. et al., *Anal. Biochem.* 1996, 236, 49-55, which is incorporated herein by reference. Phosphorylation of the substrate, phopholipase C-gamma (PLC-γ) generated as a fusion protein with glutathione-S-transferase (GST) as reported in rotin, D. et al., *EMBO J.* 1992, 11, 559-567, which is incorporated by reference, can be detected with europium-labeled anti-phosphotyrosine antibody and measured by time-resolved fluorescence (TRF). In this assay, 96-well plate is coated with 100 μL/well of 10 μg/mL substrate (phospholipase C-γ in tris-buffered saline (TBS). The assay mixture (total volume=100 μL/well) consisting of 20 nM HEPES (pH 7.2, 1 μM ATP ($K_m$ level), 5 nM $MnCl_2$, 0.1% BSA, 2.5% DMSO, and various concentrations of test compound is then added to the assay plate. The reaction is initiated by adding the enzyme (30 ng/mL ALK) and is allowed to proceed at 37 degrees C. for 15 minutes. Detection of the phosphorylated product can be performed by adding 100 μL/well of Eu-N1 labeled PT66 antibody (Perkim Elmer #AD0041). Incubation at 37.degrees C. then proceeds for one hour, followed by addition of 100 μL enhancement solution (for example Wallac #1244-105). The plate is gently agitated and after thirty minutes, the fluorescence of the resulting solution can be measured (for example using EnVision 2100 (or 2102) multilabel plate reader from Perkin Elmer).

Data analysis can then be performed. $IC_{50}$ values can be calculated by plotting percent inhibition versus $\log_{10}$ of concentration of compound.

The inhibition of ALK tyrosine kinase activity can also be measured using the recombinant kinase domain of the ALK in analogy to VEDG-R kinase assay described in J. Wood et al., *Cancer Res* 2000, 60, 2178-2189. In vitro enzyme assays using GST-ALK protein tyrosine kinase can be performed in 96-well plate as a filter binding assay in 20 mM Tris.HCl, pH 7.5, 3 mM $MgCl_2$, 10 mM $MnCl_2$, 1 nM DTT, 0.1 μCi/assay (=30 μL) [γ-$^{33}$P]-ATP, 2 μM ATP, 3 μg/mL poly (Glu, tyr 4:1) Poly-EY (sigma P-0275), 1% DMSO, 25 ng ALK enzyme. Assays tan be incubated for 10 min, at ambient temperature. Reactions can be terminated by adding 50 μL of 125 mM EDTA, and the reaction mixture can be transferred onto a MAIP Multiscreen plate (Millipore, Bedford, Mass.) previously wet with methanol, and rehydrated for 5 minutes with water. Following washing (0.5% $H_3PO_4$), plates can be counted in a liquid scintillation counter. $IC_{50}$ values are calculated by linear regression analysis of the percentage inhibition.

Certain compounds as disclosed herein have also been demonstrated cytotoxic or growth inhibitory effects on tumor and other cancer cell lines and thus can be useful in the treatment of cancer and other cell proliferative diseases. Compounds are assayed for anti-tumor activity using in vivo and in vitro assays which are well known to those skilled in the art. Generally, initial screens of compounds to identify candidate anti-cancer drugs are performed in cellular assays. Compounds identified as having anti-proliferative activity in such cell-based assays can then be subsequently assayed in whole organisms for anti-tumor activity and toxicity. Generally speaking, cell-based screens can be performed more rapidly and cost-effectively relative to assays that use whole organisms. As disclosed herein, the terms "anti-tumor" and "anti-cancer" activity are used interchangeably.

Cell-based methods for measuring antiproliferative activity are well known and can be used for comparative characterization of compounds as disclosed herein. In general, cell proliferation and cell viability assays are designed to provide a detectable signal when cells are metabolically active. Compounds can be tested for antiproliferative activity by measuring any observed decrease in metabolic activity of the cells after exposure of the cells to compound. Commonly used methods include, for example, measurement of membrane integrity (as a measure of cell viability) (e.g. using trypan blue exclusion) or measurement of DNA synthesis (e.g. by measuring incorporation of BrdU or 3H-thymidine).

Some methods for assaying cell proliferation use a reagent that is converted into a detectable compound during cell proliferation. Such reagents are tetrazolium salts and include without limitation MTT (3-(4, 5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bemas et al. Biochim Biophys Acta 1451(1):73-81, 1999). More commonly used assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55-63, 1983).

Other methods for assaying cell proliferation involve incubating cells in a given growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999, both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

In addition, a wide variety of cell types can be used to screen compounds for antiproliferative activity, including the following cell lines, among others: COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

While the cell line is can be mammalian, lower order eukaryotic cells such as yeast can also be used to screen compounds. Mammalian cell lines are derived from humans, rats, mice, rabbits, monkeys, hamsters, and guinea pigs since cells lines from these organisms are well-studied and characterized. However, others can be used as well.

Suitable mammalian cell lines are often derived from tumors. For example, the following tumor cell-types can be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1/EBNA-1.

Other cellular assays can be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem Biol. 6:541-51; incorporated herein by reference) used HeLa cells containing an inducible variant of GFP to detect compounds that inhibited expression of the GFP, and thus inhibited cell proliferation.

An example of a cell-based assay is shown below. The cell lines that can be used in the assay are Ba/F3, a murine pro-B cell line, which has been stably transfected with an expression vector pCIneo™ (Promega Corp., Madison Wis.) coding for NPM-ALK and subsequent selection of G418 resistant cells. Non-transfected Ba/F3 cells depend on IL-3 for cell survival. In contrast NPM-ALK expressing Ba/F3 cells (named Ba/F3-NPM-ALK) can proliferate in the absence of IL-3 because they obtain proliferative signal through NPM-ALK kinase. Putative inhibitors of NPM-ALK kinase therefore abolish the growth signal and result in antiproliferative activity. The antiproliferative activity of inhibitors of the NPM-ALK kinase can however be overcome by addition of IL-3 which provides growth signals through an NPM-ALK independent mechanism. For an analogous cell system using FLT3 kinase, see E. Weisberg et al. Cancer cell, 2002, 1, 433-443. The inhibitory activity of compounds as disclosed herein can be determined as follows: BaF3-NPM-ALK cells (15,000/microtitre plate well) can be transferred to a 96-well microtitre plates. The test compound (dissolved in DMSO) is then added in a series of concentrations (dilution series) in such a manner that the final concentration of DMSO is not greater than 1% (v/v). After the addition, the plates can be incubated for two days during which the control cultures without test compound are able to undergo two cell-division cycles. The growth of BaF3-NPM-ALK cells can be measured by means of Yopro™ staining (T Idziorek et al., J. Immunol. Methods 1995, 185, 249-258). Then, 25 µL of lysis buffer consisting of 20 mM sodium citrate, pH 4.0, 26.8 nM sodium chloride, 0.4% NP40, 20 mM EDTA and 20 mM is added into each well. Cell lysis is completed within 60 minutes at room temperature and total amount of Yopro bound to DNA is determined by measurement using for example a CytoFluor II 96-well reader (PerSeptive Biosystems). The $IC_{50}$ can be determined by a computer aided system using the formula:

$$IC_{50}=[(ABS_{test}-ABS_{start})/(ABS_{control}-ABS_{start})]\times 100$$

in which ABS is absorption. The $IC_{50}$ value in such an experiment is given as that concentration of the test compound in question that results in a cell count that is 50% lower than that obtained using the control without inhibitor.

The antiproliferative action of compounds as disclosed herein can also be determined in the human KARPAS-299 lymphoma cell line by means of an immunoblot as described in W G Dirks et al. Int. J. Cancer 2002, 100, 49-56, using the methodology described above for the BaF3-NPM-ALK cell line.

In another example, antiproliferative activity can be determined using KARPAS-299 lumphoma cell line in the following procedure: Compounds as disclosed herein were incubated with the cells for 3 days, and the number of viable cells in each well was measured indirectly using an MTS tetrazolium assay (Promega). This assay is a colorimetric method for determining the number of viable cells through measurement of their metabolic activity. For example the detection of the product of the enzymatic conversion of tetrazolium salts into blue formazan derivatives is achieved by measuring absorbance at 490 nm using a plate reader. 40 µL of the MTS reagent was added to all wells except the edge wells and then the plates were returned to the incubator at 37° C. for 2 hours. The absorbance in each well was then measured at 490 nm using a Wallac Victor$^2$V plate reader. The $IC_{50}$ was calculated by determining the concentration of compound required to decrease the MTS signal by 50% in best-fit curves using Microsoft XLfit software, by comparing with baseline, the DMSO control, as 0% inhibition.

Compounds identified by such cellular assays as having anti-cell proliferation activity can then be tested for anti-tumor activity in whole organisms, such as mammalian species. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice can be used in the present assays (see for example U.S. Pat. Nos. 4,736,866 and 5,175,383). For a review and discussion on the use of rodent models for antitumor drug testing, see Kerbel (Cancer Metastasis Rev. 17:301-304, 1998-99).

In general, the tumors of interest are implanted in a test organism subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds, see Corbett et al. (Invest New Drugs. 15:207-218, 1997; incorporated herein by reference).

The compounds disclosed herein have inhibitory activity against a wild type or mutant (especially a clinically relevant mutant) kinase, especially a kinase such as ALK, Met, Jak2, bRaf, EGFR, Tie-2, FLT3 or another kinase of interest with an $IC_{50}$ value of 1 μM or less (as determined using any scientifically acceptable kinase inhibition assay), such as with an $IC_{50}$ of 500 nM or better, and further such as an $IC_{50}$ value of 250 nM or better; or inhibitory activity against a given kinase with an $IC_{50}$ value at least 100-fold lower than their $IC_{50}$ values for other kinases of interest; or inhibitory activity for ALK, Met, Jak2 or B-Raf with a 1 μM or better $IC_{50}$ value against each; or a cytotoxic or growth inhibitory effect on cancer cell lines maintained in vitro, or in animal studies using a scientifically acceptable cancer cell xenograft model, (such as Ba/F3 NPM-ALK, Ba/F3 EML4-ALK, Karpas 299 and/or SU-DHL-1 cells with a potency at least as great as the potency of known ALK inhibitors such as NVP-TAE684 and PF2341066 among others, or with a potency at least twice that of known ALK inhibitors, or with a potency at least 10 times that of known ALK inhibitors as determined by comparative studies.

Compounds disclosed herein were found to potently inhibit a number of important kinase targets. Compounds exhibited $IC_{50}$'s under 100 nM, and in many cases under 10 nM and in some cases under 1 nM when tested as inhibitors of the kinase, ALK, for instance. Some compounds were single digit nanomolar inhibitors of a panel of kinases including kinaseslike ALK, FER, FLT3, FES/FPS, FAK/PTK2, BRK and others.

What is claimed is:
1. Crystalline Form B of brigatinib having the structure:

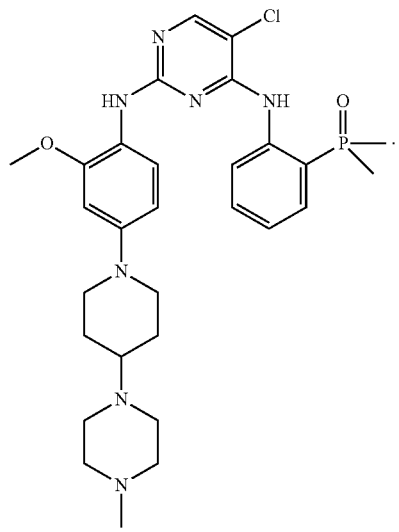

wherein the crystalline form has an x-ray powder diffraction pattern with peaks at 11.5, 14.5, 16.9, 19.2, and 23.2° 2θ, with a variance of ±0.2° 2θ.

2. The crystalline form of claim 1, having an x-ray powder diffraction pattern as shown in FIG. 14.

3. The crystalline form of claim 1, having an x-ray powder diffraction pattern with peaks at 5.7, 9.2, 11.5, 12.8, 14.5, 15.5, 16.9, 17.7, 19.2, 20.4, 21.8, 23.2, and 29.5° 2θ, with a variance of 0.2° 2θ.

4. Crystalline Form C of brigatinib having the structure:

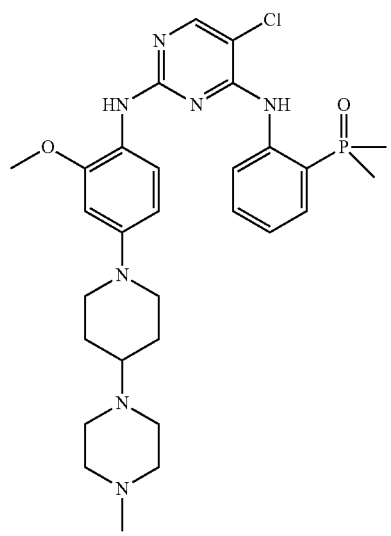

wherein the crystalline form has an x-ray powder diffraction pattern with peaks at 5.4, 14.9, 15.9, 17.3, 19.2, and 23.9° 2θ, with a variance of 0.2° 2θ.

5. Crystalline Form D of brigatinib having the structure:

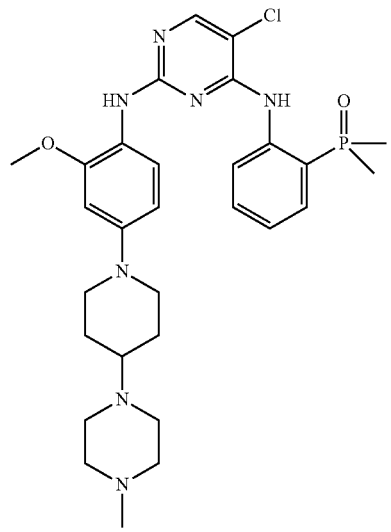

wherein the crystalline form has an x-ray powder diffraction pattern with peaks at 9.7, 11.1, 17.4, 18.9, and 23.7° 2θ, with a variance of 0.2° 2θ.

6. Crystalline Form E of brigatinib having the structure:

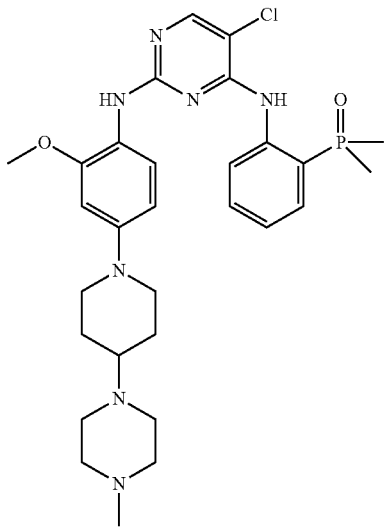

which is a chloroform solvate,
wherein the crystalline form has an x-ray powder diffraction pattern with peaks at 9.1, 10.2, 15.8, 19.2, and 23.9° 2θ, with a variance of 0.2° 2θ.

7. Crystalline Form F of brigatinib having the structure:

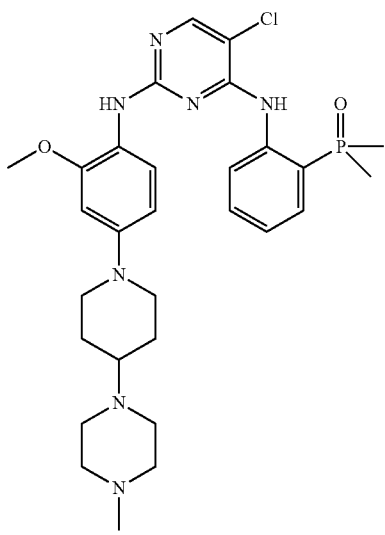

which is a TFE solvate,
wherein the crystalline form has an x-ray powder diffraction pattern with peaks at 9.8, 17.0, 19.4, 20.3, and 27.1° 2θ, with a variance of 0.2° 2θ.

8. Crystalline Form G of brigatinib having the structure:

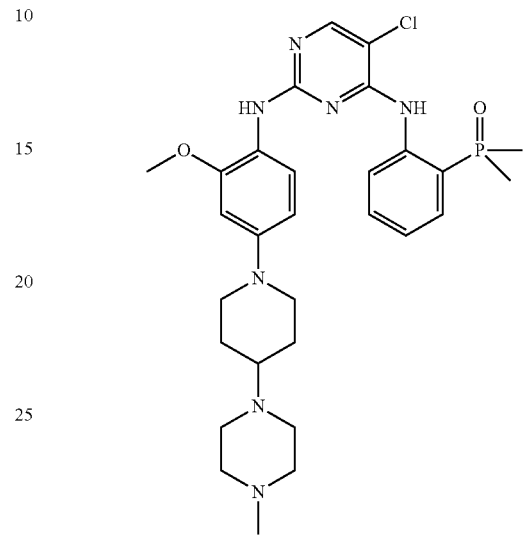

which is a chloroform solvate,
wherein the crystalline form has an x-ray powder diffraction pattern with peaks at 8.3, 9.7, 12.9, 15.8, 18.1, 20.7, 22.8, and 26.8° 2θ, with a variance of 0.2° 2θ.

9. A pharmaceutical composition comprising the Crystalline Form B of brigatinib of claim 1 and at least one component chosen from pharmaceutically acceptable carriers, pharmaceutically acceptable vehicles, and pharmaceutically acceptable excipients.

10. A method for treating non-small cell lung cancer in a subject in need thereof comprising administering to the subject the Crystalline Form B of brigatinib of claim 1.

11. The method of claim 10, wherein the non-small cell lung cancer is ALK-positive non-small cell lung cancer.

12. The method of claim 11, wherein the non-small cell lung cancer is ALK-positive metastatic non-small cell lung cancer.

13. The method of claim 12, wherein the subject has been previously treated with crizotinib.

* * * * *